US010809271B2

(12) United States Patent
Van Keuren-Jensen et al.

(10) Patent No.: US 10,809,271 B2
(45) Date of Patent: Oct. 20, 2020

(54) BIOMARKERS AND METHODS OF DIAGNOSING AND PROGNOSING MILD TRAUMATIC BRAIN INJURIES

(71) Applicant: THE TRANSLATIONAL GENOMICS RESEARCH INSTITUTE, Phoenix, AZ (US)

(72) Inventors: Kendall Van Keuren-Jensen, Phoenix, AZ (US); Matthew Huentelman, Phoenix, AZ (US); Ashish Yeri, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 0 days.

(21) Appl. No.: 15/559,001

(22) PCT Filed: Mar. 28, 2016

(86) PCT No.: PCT/US2016/024588
§ 371 (c)(1),
(2) Date: Sep. 15, 2017

(87) PCT Pub. No.: WO2016/160742
PCT Pub. Date: Oct. 6, 2016

(65) Prior Publication Data
US 2018/0306806 A1    Oct. 25, 2018

Related U.S. Application Data

(60) Provisional application No. 62/139,328, filed on Mar. 27, 2015.

(51) Int. Cl.
| *A61K 38/00* | (2006.01) |
| *C12Q 1/68* | (2018.01) |
| *G01N 33/567* | (2006.01) |
| *G01N 33/68* | (2006.01) |
| *G16B 20/00* | (2019.01) |
| *G16H 50/30* | (2018.01) |

(52) U.S. Cl.
CPC ......... *G01N 33/6893* (2013.01); *G01N 33/68* (2013.01); *G16B 20/00* (2019.02); *G16H 50/30* (2018.01); *G01N 2800/50* (2013.01)

(58) Field of Classification Search
None
See application file for complete search history.

(56) References Cited

U.S. PATENT DOCUMENTS

2013/0060168 A1    3/2013  Chu et al.

FOREIGN PATENT DOCUMENTS

| WO | 2013/090285 A1 | 6/2013 |
| WO | 2014/152773 A1 | 9/2014 |

OTHER PUBLICATIONS

Wang et al., Nature Rev, 2009, 10(1):57-63.*
Chu et al., Nucleic Acid Therapeutics, 2012, 22(4):271-4.*
Redell et al., "Analysis of functional pathways altered after mild traumatic brain injury", J. Neurotrauma, 30 (9):752-764 (May 7, 2013).
Jordan, B., "The clinical spectrum of sport-related traumatic brain injury", Nat Rev Neurol., 9(4)122-230 (Mar. 12, 2013).
Love, M. I., et al. Moderated estimation of fold change and dispersion for RNA-seq data with DESeq2. Genome Biology 2014; 15:550.
Freitas, T., et al. Accurate read-based metagenome characterization using a hierarchical suite of unique signatures. Nucleic Acids Res 2015; 43:e69.
Burgos, K. L., et al. Identification of extracellular miRNA in human cerebrospinal fluid by next-generation sequencing. RNA 2013; 19:712-722.
Hackenberg, M., et al. miRanalyzer: an update on the detection and analysis of microRNAs in high-throughput sequencing experiments. Nucl Acids Res 2011; 39:W132-W138.
Langlois, J. A., et al. The epidemiology and impact of traumatic brain injury: a brief overview. J Head Trauma Rehabil 2006; 21(5):375-378.
Alla, S., et al. Self-report scales/checklists for the measurement of concussion symptoms: a systematic review. Br J Sports Med 2009; 43(Suppl 1):i3-12.
Hutchison, J. S., et al. Impact of hypotension and low cerebral perfusion pressure on outcomes in children treated with hypothermia therapy following sever traumatic brain injury: a post hoc analysis of the Hypothermia Pediatric Head Injury Trial. Dev Neurosci 2010; 32(5-6):406-412.
Hutchison, M., et al. Differential emotional responses of varsity athletes to concussion and musculoskeletal injuries. Clin J Sport Med 2009; 19(1):13-19.
Gosselin, N., et al. Sleep following sport-related concussions. Sleep Med 2009; 10(1):35-46.
Gosselin, D., et al. MyD88 signaling in brain endothelial cells is essential for the neuronal activity and glucocorticoid release during systemic inflammation. Mol Psychiatry 2008; 13(5):480-497.
Wilusz, J. E., et al. Long noncoding-RNAs: functional surprises from the RNA world. Genes Dev 2009; 23 (13):1494-1504.
Wilusz, J. RNA stability: is it the endo' the world as we know it? Nat Struct Mol Biol 2009; 16(1):9-10.
Moran, A., et al. Re-imagining motor imagery: building bridges between cognitive neuroscience and sport psychology. Br J Psychol 2012; 103(2):224-247.

(Continued)

*Primary Examiner* — Olga N Chernyshev
(74) *Attorney, Agent, or Firm* — Rodney J. Fuller; Booth Udall Fuller, PLC

(57) ABSTRACT

The invention provides biomarkers and methods for determining the risk of a subject for developing mild traumatic brain injuries (mTBI). In some aspects, the methods of the invention also determine the fitness of a subject for participating in an activity with increased chances of receiving a head impact. Some embodiments of the invention are directed to kits for determining the risk of a subject for developing mTBI or the fitness of a subject for participating in an activity with increased chances of receiving a head impact.

7 Claims, No Drawings

(56) References Cited

OTHER PUBLICATIONS

Taft, R. J., et al. Non-coding RNAs: regulators of disease. J Pathol 2010; 220(2):126-139.

Casalini, P., et al. MicroRNAs and future therapeutic applications in cancer. J BUON 2009; 14(Suppl 1):S17-22.

Iorio, L., et al. N-terminal pro-brain natriuretic peptide determination as possible marker of cardiac dysfunction in patients with adrenal disorders. J Endocrinol Invest 2010; 33(7):509-510.

Iorio, L., et al. Neurological picture. Pseudoperipheral tongue weakness. J Neurol Neurosurg Psychiatry 2010; 81 (9):1024-1025.

Iorio, M. V., et al. Interplay between microRNAs and the epigenetic machinery: an intricate network. Biochimica et Biophysica Acta 2010; 1799(10-12):694-701 doi: 10.1016/j.bbagrm.2010.05.005. Epub May 20, 2010.

Schratt, G. microRNAs at the synapse. Nat Rev Neurosci 2009; 10(12):842-849.

Schratt, G. Fine-tuning neural gene expression with microRNAs. Curr Opin Neurobiol 2009; 19(2):213-219.

Rosa, A., et al. MicroRNAs in early vertebrate development. Cell Cycle 2009; 8(21):3513-3520.

Rosa, A., et al. The miR-430/427/302 family controls mesendodermal fate specification via species-specific target selection. Dev Cell 2009; 16(4):517-527.

Mercer, S. L., et al. Study designs for effectiveness and translation research: identifying trade-offs. Am J Prev Med 2007; 33(2):139-154.

Mercer, A., et al. Characterization of neurons in the CA2 subfield of the adult rat hippocampus. J Neurosci 2007; 27 (27):7329-7338.

Barbato, C., et al. Searching for MIND: microRNAs in neurodegenerative diseases. J Biomed Biotechnol 2009; 2009:871313.

Li, Y., et al. Brain anatomical network and intelligence. PLoS Comput Biol 2009; 5(5):e1000395.

Olsen, L., et al. MicroRNAs show mutually exclusive expression patterns in the brain of adult male rats. PLoS One 2009: 4(10):e7225.

Taft, R.J., et al. Nuclear-localized tiny RNAs are associated with transcription initiation and splice sites in metazoans. Nat Struct Mol Biol 2010; 17(8):1030-1034.

Yin, X., et al. Brain endothelial cells synthesize neurotoxic thrombin in Alzheimer's disease. Am J Pathol 2010; 176 (4):1600-1606.

Lei, H., et al. Evolution of the neurochemical profile after transient focal cerebral ischemia in the mouse brain. J Cereb Blood Flow Metab 2009; 29(4):811-819.

Lei, P., et al. Microarray based analysis of microRNA expression in rat cerebral cortex after traumatic brain injury. Brain Res 2009; 12884:191-201.

Lei, B., et al. Effects of midazolam on brain injury after transient focal cerebral ischemia in rats. J Neurosurg Anesthesiol 2009; 21(2):131-139.

Breiman, L. Random Forests. Machine Learning 2001; 45(1): 5-32.

Tan, A. A., et al. Strain differences in response to traumatic brain injury in Long-Evans compared to Sprague-Dawley rats. J Neurotrauma 2009; 26(4):539-548.

Tan, Z. Neural protection by naturopathic compounds—an example f tetramethylpyrazine from retina to brain. J Ocul Biol Dis Infor 2009; 2(2):57-64.

McCrory, P., et al. Consensus Statement on Concussion in Sport—the 3rd International Conference on Concussion in sport held in Zurich, Nov. 2008. SAJSM 2009; 21(2)36-46.

Broglio, S. P., et al. The effect of sport concussion on neurocognitive function, self-report symptoms and postural control: a meta-analysis. Sports Med 2008; 38(1):53-67.

Guskiewicz, Kevin M. Postural Stability Assessment Following Concussion: One Piece of the Puzzle. Clinical Journal of Sport Medicine 2001; 11:182-189.

McCrea, M., et al. Acute effects and recovery time following concussion in collegiate football players; the NCAA Concussion Study. JAMA 2003; 290(19):2556-2563.

Guskiewicz, K. M., et al. Recurrent concussion and risk of depression in retired professional football players. Med Sci Sports Exerc 2007; 39(6):903-909.

Van Donkelaar, P., et al. Attentional deficits in concussion. Brain Injury 2005; 19(12):1031-1039.

Kosik, Kenneth S. The neuronal microRNA system. Nature Reviews Neuroscience 2006; 7:911-920.

Nelson, P. T., et al. In situ hybridization is a necessary experimental complement to microRNA (miRNA) expression profiling in the human brain. Neuroscience Letters 2009; 466(2):69-72.

Fineberg, S. K., et al. MicroRNAs Potentiate Neural Development. Neuron 2009; 64(3):303-309.

Eacker, S. M., et al. Understanding microRNAs in neurodegeneration. Nat Rev Neurosci 2009; 10(12):837-841.

Dharap, A., et al. Transient Focal Ischemia Induces Extensive Temporal Changes in Rate Cerebral MicroRNAome. Journal of Cerebral Blood Flow & Metabolism 2009; 29(4):675-687.

Rowson, et al. Brain Injury Prediction: Assessing the Combined Probability of Concussion Using Linear and Rotational Head Acceleration. Ann of Biomed. Engg 2013; 41(5):873-882.

Raposo, G., et al. Extracellular vesicles: exosomes, microvesicles, and friends. J Cell Biol 2013; 200(4):373-383.

Colombo, M., et al. Biogenesis, secretion, and intercellular interactions of exosomes and other extracellular vesicles. Annu Rev Cell Dev Biol 2014; 30:255-289.

Yanez-Mo, M., et al. Biological properties of extracellular vesicles and their physiological functions. J Extracell Vesicles 2015: 4:27066.

Minciacchi, V., et al. Extracellular vesicles in cancer: exosomes, microvesicles and emerging role of large oncosomes. Semin Cell Dev Biol 2015; 40:41-51.

Vickers, K., et al. MicroRNAs are transported in plasma and delivered to recipient cells by high-density lipoproteins. Nat Cell Biol 201; 13:423-433.

Arroyo, J., et al. Argonaute2 complexes carry a population of circulating microRNAs independent of vesicles in human plasma. Proc Natl Acad Sci 2011; 108:5003-5008.

Turchinovich, A., et al. Characterization of extracellular circulating microRNA. Nucleic Acids Res 2011; 39:7223-7233.

Margue, C., et al. Comparison of a healthy miRNome with melanoma patient miRNomes: are microRNAs suitable serum biomarkers for cancer? Oncotarget 2015; 6(14):12110-12127.

Yuan, T., et al. Plasma extracellular RNA profiles in healthy and cancer patients. Sci Rep 2016; 20:19413.

Freedman, J., et al. Diverse human extracellular RNAs are widely detected in human plasma. Nat Commun 2016; 7:11106.

Ben-Dov, I., et al. Cell and Microvesicle Urine microRNA Deep Sequencing Profiles from Healthy Individuals: Observations with Potential Impact on Biomarker Studies. PLoS One 2016; 11:e0147249.

Fehlmann, T., et al. Distribution of microRNA biomarker candidates in solid tissues and body fluids. RNA Biol 2016; 13:1084-1088.

Hecksteden, A., et al. miRNAs and sports: tracking training status and potentially confounding diagnoses. J Transl Med 2016; 14:219.

Meiri, E, et al. Discovery of microRNAs and other small RNAs in solid tumors. Nucleic Acids Res 2010; 38:6234-6246.

Dhahbi, J. 5' tRNA Halves: The Next Generation of Immune Signaling Molecules. Front Immunol 2015; 6:74.

Dhahbi, J., et al. Deep Sequencing of Serum Small RNAs Identifies Patterns of 5' tRNA Half and YRNA Fragment Expression Associated with Breast Cancer. Biomark Cancer 2014; 6:37-47.

Dhahbi, J., et al. 5'-YRNA fragments derived by processing of transcripts from specific YRNA genes and pseudogenes are abundant in human serum and plasma. Physiol Genomics 2013; 45:990-998.

Chakrabortty, S., et al. Extracellular vesicle-mediated transfer of processed and functional RNY5 RNA. RNA 2015; 21:1966-1979.

Tosar, J., et al. Assessment of small RNA sorting into different extracellular fractions revealed by high-throughput sequencing of breast cell lines. Nucleic Acids Res 2015; 43:5601-5616.

Van Balkom, B. W., et al. Quantitative and qualitative analysis of small RNAs in human endothelial cells and exosomes provides insights into localized RNA processing, degradation and sorting. J Extracell Vesicles 2015; 4:26760.

(56) References Cited

OTHER PUBLICATIONS

Nicolas, F. E., et al. Biogenesis of Y RNA-derived small RNAs is independent of the microRNA pathway. FEBS Lett 2012; 586:1226-1230.

Fritz, J. V. et al. Sources and Functions of Extracellular Small RNAs in Human Circulation. Annu Rev Nutr 2016; 36:301-336.

Stein, A. J., et al. Structural insights into RNA quality control: the Ro autoantigen binds misfolded RNAs via its central cavity. Cell 2015; 121:529-539.

Zhang, A. T., et al. Dynamic interaction of Y RNAs with chromatin and initiation proteins during human DNA replication. J Cell Sci 2011; 124:2058-2069.

Kirchner, S., et al. Emerging roles of tRNA in adaptive translation, signalling dynamics and disease. Nat Rev Genet 2015; 16:98-112.

Goodarzi, H., et al. Endogenous tRNA-Derived Fragments Suppress Breast Cancer Progression via YBX1 Displacement. Cell 2015; 161:790-802.

Cozen, A., et al. ARM-seq: AlkB-facilitated RNA methylation sequencing reveals a complex landscape of modified tRNA fragments. Nat Methods 2015; 12:879-884.

Zheng, G., et al. Efficient and quantitative high-throughput tRNA sequencing. Nat Methods 2015; 12:835-837.

Patton, J. G., et al. Biogenesis, delivery, and function of extracellular RNA. J Extracell Vesicles 2015; 4:27494.

Siomi, M. C., et al. PIWI-interacting small RNAs: the vanguard of genome defence. Nat Rev Mol Cell Biol 2011; 12:246-258.

Morris, K. V., et al. The rise of regulatory RNA. Nat Rev Genet 2014; 15:423-437.

Thompson, D., et al. tRNA cleavage is a conserved response to oxidative stress in eukaryotes. RNA 2008; 14:2095-2103.

Thompson, D. M., et al. Stressing out over tRNA cleavage. Cell 2009; 138:215-219.

Ivanov, P., et al. Angiogenin-Induced tRNA Fragments Inhibit Translation Initiation. Molecular Cell 2011; 43:613-623.

Anderson, P., et al. tRNA fragments in human health and disease. FEBS Letters 2014; 588:4297-4304.

Pang, Y., et al. Diverse cell stresses induce unique patterns of tRNA up- and down-regulation: tRNA-seq for quantifying changes in tRNA copy number. Nucleic Acids Research 2014; 42:e170.

Lee, Y. S., et al. A novel class of small RNAs: tRNA-derived RNA fragments (tRFs). Genes and Dev 2009; 23:2639-2649.

Kumar, P., et al. tRFdb: a database for transfer RNA fragments. Nucl Acids Res 2015; 43:D141-D145.

Sinasac, David S. et al., "Slc25a13-Knockout Mice Harbor Metabolic Deficits but Fail to Display Hallmarks of Adult-Onset Type II Citrullinemia", Molecular and Cellular Biology, 24(2):527-536 (Jan. 2004).

Di Pietro, Valentina et al., "Potentially neuroprotective gene modulation in an in vitro model of mild traumatic brain injury", Molecular and Cellular Biochemistry, 375:185-198 (Mar. 2013).

Satrustegui, Jorgina et al., "Role of aralar, the mitochondrial transporter of aspartate-glutamate, in brain N-acetylasparate formation and Ca(2+) signaling in neuronal mitochondria", Journal of Neuroscience Research, 85:3359-3366 (Nov. 15, 2007).

Dienel, Gerald A., "Lactate shuttling and lactate use as fuel after traumatic brain injury: metabolic considerations", Journal of Cerebral Blood Flow and Metabolism, 34:1736-1748 (Nov. 2014).

Scafidi, Susanna et al., "Delayed cerebral oxidative glucose metabolism after traumatic brain injury in young rats", Journal of Neurochemistry, 109(1):189-197 (May 2009).

* cited by examiner

BIOMARKERS AND METHODS OF DIAGNOSING AND PROGNOSING MILD TRAUMATIC BRAIN INJURIES

RELATED APPLICATION DATA

This application is the U.S. National Stage of International Application No. PCT/US2016/024588 filed on Mar. 28, 2016, which claims priority to and the benefit of U.S. Provisional Application No. 62/139,328 filed on Mar. 27, 2015, the contents of each of which are hereby incorporated by reference in their entireties.

FIELD OF THE INVENTION

The present invention is related to biomarkers and methods for determining the risk of a subject for developing mild traumatic brain injuries (mTBI). In some aspects, embodiments of the invention are directed to kits and apparatuses.

BACKGROUND OF THE INVENTION

Despite significant benefits to the physical, mental, and social development of adolescents and young adults participating athletics, sport-related injuries are a significant risk in this population. Particularly, playing contact sports such as football and hockey involves a significant risk of brain injury due to impact to the head. During such physical activity, the head or other body part of the individual is often subjected to direct contact to the head, which results in impact to the skull and brain of the individual as well as movement of the head or body part itself. Sport-related concussion is the most commonly cited athletic injury in the lay and professional literature during the past decade. These injuries are a significant public health issue because of concerns with the developing brain following head trauma, recurrent and cumulative effects of concussion, recovery following concussion, as well as more global issues concerning academic performance and psychosocial issues.

The Center for Disease Control and Prevention (CDC) estimates estimated that 1.6 to 3.8 million sport-related concussion injuries occurring annually and that the incidence of sports-related mild traumatic brain injury (mTBI) approaches 300,000 annually in the United States. It is not uncommon that a typical range of concussions per year for a football team of 90 players is 4-6 (7%) and for a hockey team with 28 players is 6 (21%). In rugby, concussion can affect as many as 40% of players on a team each year. Approximately a third of these injuries occur in football. Head injuries accounted for 13.3% of all football injuries to boys and 4.4% of all soccer injuries to both boys and girls in a large study of high school sports injuries. Approximately 62,800 mTBI cases occur annually among high school varsity athletes, with football accounting for about 63% of cases. Concussions in hockey affect 10% of the athletes and make up 12%-14% of all injuries.

The CDC statistics on mTBI does not even include such incidences in the United States Armed Forces. In the army, the incidence of TBI in the armed forces is around 20,000 annually, and for the Navy, Airforce, and the Marines, the incidence of TBI for each branch is around 2,500 annually.

Concussions, particularly when repeated multiple times, significantly threaten the long-term health of the person. The health care costs associated with mTBI in sports are estimated to be in the hundreds of millions annually. The National Center for Injury Prevention and Control considers sports-related traumatic brain injury (mild and severe) an important public health problem because of the high incidence of these injuries, the relative youth of those being injured with possible long term disability, and the danger of cumulative effects from repeat incidences.

Sport-related concussion has been linked to various markers of health, including an increase in symptom reports, cognitive deficits, balance impairments, as well as depression, mood disturbances, sleep disturbances, and attention/concentration issues, which are all mediators that may affect one's perception of their quality of life. While there have been great strides in the evaluation of clinical assessment tools for evaluating the concussed athlete, concussion remains a clinical diagnosis based primarily on self-reported signs and symptoms, cognitive deficits, and balance impairments. These tools are helpful in tracking recovery post-injury, but they rely on self-reporting by an individual who is motivate to remain participating in sport and lack the sensitivity to be a diagnostic tool.

The health risks of subsequent head impact increases significantly, for example subsequent impacts following an initial concussion (mTBI) may be 4-6 times more likely to result in a second, often more severe, brain injury. Although increased brain tissue strain, pressure waves, and pressure gradients within the skull have been linked with specific brain injury mechanisms, much remains unknown about the response of the brain to head impacts. There is even less known about the correspondence between specific impact forces and injury, particularly with respect to injuries caused by repeated exposure to impact forces of a lower level than those that result in a catastrophic injury or fatality.

Detecting changes that are a direct result of head impact and mild traumatic brain injury are challenging. Conventional imaging techniques are usually insufficient to identify damage associated with mTBI. However, the presence of lingering symptoms indicates that functional changes resulting from repeated and/or acute exposure to head impact do occur and can typically last several days. These functional changes possibly result from structural damage to torn axons and synaptic connections and inflammation. Therefore, there is an opportunity to detect either physical injury and/or repair processes going on in the brain as a head impact that do not result in a concussion diagnosis or only result in mTBI. Unfortunately, there is limited data on the molecular changes associated with mTBI or from the effect repeated head impacts that do not result in a diagnosis of concussion such as those that occur during routine practices and games of contact sports.

SUMMARY OF THE INVENTION

Embodiments of the invention provide methods for determining the risk of a subject for developing mTBI. The methods comprise obtaining a biological sample from a subject; measuring the biological sample for an amount of at least one biomarker selected from the group consisting of the biomarkers selected from biomarkers listed in any one of Tables 1-53; and comparing the amount of the at least biomarker with the amount of the at least one biomarker in a control biological sample, wherein a change in the amount of the at least one biomarker from the subject compared with the control is indicative of the subject having an increased risk for mTBI.

Embodiments of the invention further provides methods for determining the fitness of a subject for participating in an activity with increased chances of receiving a head impact comprising: obtaining a biological sample from a subject; measuring the biological sample for an amount of at least one biomarker selected from biomarkers listed in any one of Tables 1-53; and comparing the amount of the at least one biomarker with the amount of the at least one biomarker in a control sample; and wherein a change in the amount of the at least one biomarker from the subject compared with the control is indicative of the subject being unfit for participating in the activity with increased chances of receiving a head impact.

The amount of the at least one biomarker is preferably the amount of biomarkers' extracellular RNA expression in the biological sample. Some implementations of the methods of the invention comprise measuring the biological sample for for an amount of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or at least twenty biomarkers selected from biomarkers listed in any one of Tables 1-53.

In some embodiments, the methods of the invention provide that a subject has an increased risk for developing mTBI or is not fit for participating in an activity with increased chances of receiving a head impact when the change in amount of the amount of at least one biomarker selected from biomarkers listed in any one of Tables 6-32 and 53 corresponds with the indicated change in expression of the at least one biomarker shown in Tables 6-32 and 53.

In some aspects, the biological sample is obtained after the subject has received a head impact incident, for example within 48 hours, within 24 hours, within 12 hours, or within 6 hours of the subject having had a head impact incident or is suspected of having a head impact incident.

The invention also provides kits for determining the risk of a subject for developing mTBI or for determining the fitness of a subject for participating in an activity with increased chances of receiving a head impact, wherein the kits detect the expression of at least one biomarker selected from the biomarkers listed in any one of Tables 1-53. In some embodiments, the kit comprises a primer or probe that specifically determines the expression level of at least one biomarker selected from any one of Tables 6-53 in the subject. The kits may further comprise a dataset comprising the expression level of the at least one biomarker in normal subjects and/or a control sample.

The kits may further comprise instructions listing the direction of change in the expression of the at least one biomarker in the subject in relation to the dataset or the control that demonstrates the subject has increased risk of the subject for developing mTBI. In some embodiments, the direction of change in the expression corresponds to the changes as depicted in any one of Tables 6-53.

In some embodiments, the kits determine the probability score for a subject's exposure to potentially injurious head impact. Such kits comprise a primer or probe that specifically determines the expression level of at least one biomarker selected from any one of Tables 31 and 32 and a control sample or a dataset comprising the expression level of the at least one biomarker in normal subjects. Correlating the change in the expression of the at least one biomarker with the changes as depicted in any one of Tables 31 and 32 determines the subject's probability score for a subject's risk for concussion.

Additional objectives, advantages and novel features will be set forth in the description which follows or will become apparent to those skilled in the art upon examination of the drawings and detailed description which follows.

DETAILED DESCRIPTION

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article article "a" or "an" thus usually means "at least one."

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some implementations, the subject may be a mammal, preferably a human.

As used herein, the term "acute head injury" refers to head injury received by subjects who do not have a history chronic cumulative head impact exposure. For example, the subject may play non-contract sports.

As used herein, the term "biological sample" or "biofluid" includes blood samples, salivary samples, and urine samples. However, other biological samples are also contemplated, for example, cerebral spinal fluid samples, plasma samples, and tear samples. Thus biological sample, as used herein, refers to biological fluids (biofluids) of the subject.

As used herein, the term "head impact," refers generally to measurable impact to the head. Determination that head impact has occurred may, for example, be based on readings from protective headgear, such as helmets made by Riddell (Chicago, Ill., USA).

As used herein, the term "expression" in relation to biomarkers refers both genetic expression and protein expression. Measuring genetic expression includes measuring the expression of DNA and/or RNA, including measuring non-coding RNA molecules, such as microRNAs. Such measurements include measuring extracellular RNA expression. Measuring protein expression includes measuring the presence of whole proteins and/or peptides. For RNA expression, a biomarker is considered expressed if a sample has at least 10 read counts of the mRNA.

As referenced herein, ENSEMBL ID described contain the sequences of ENSEMBL 75, Gencode release 19, the contents of which are incorporated herein.

The invention relates to the discovery that subjects who are contact sports athletes (e.g. football or baseball players) and subject who are not contact sports athletes (e.g. track and field athletes or swimmers) have unique transcriptomes. The invention also relates to the discovery that the transcriptomes of contact sports athletes who recently had or did not have any head impact incidents are unique. Furthermore, the uniqueness of the transcriptome can distinguish based on the force of the head impact (as measured by linear or rotational acceleration or an impact score such as HITsp from helmets made by Riddell), the number of hits, and the frequency of the head impact. Thus, the invention provides biomarkers for determining the risk of a subject for developing mTBI and for concussion. In some aspects, the disclosed biomarkers have been found to be significant in at least four comparisons.

Table 1 lists the biomarkers that differentiate (based on linear regression analysis, differential expression analysis, or random forest algorithm) various case and control samples. For linear regression, simple linear regression was performed where the players' impact data from the helmets were regressed were on the gene expression measured in counts which have been normalized for sequencing depth between the samples. The impact data from the helmets are the total number of all head impacts sustained by the player in the game (Total Hits or the number of hits), the highest impact sustained by the player in the game, where the impact can be measured by linear acceleration sustained by the head (Max_Lin_acc), the rotational acceleration (Max_Rot_acc) and a combined score of the location of impact, linear and rotational acceleration (HITsp), and the sum of all impacts sustained by the player in the game (Cum_Lin_acc, Cum_Rot_acc, or Cum HITsp). Genes with a |slope|>0.1 and a p-value <0.05 were considered significant and included in Table 1. In some aspects, the biomarkers of Table 1 were determined based comparisons between the following pairs of samples:

- A subject who is a contact sport athlete and experienced the most forceful head impact (Max_HITsp) and the subject's baseline;
- Subjects who are contact sport athletes and experienced the most forceful head impact (Max_HITsp) and subjects who are contact sport athletes and experienced the least forceful head impact (Min_HITsp);
- Subjects who are contact sport athletes and experienced the most forceful head impact (Max_HITsp) and subjects with normal exposure to head impact (e.g. athletes who do not play contact sports) (Track_field_control);
- A subject who is a contact sport athlete and experienced the least forceful head impact (Min_HITsp) and the subject's baseline;
- A subject who is a contact sport athlete and experienced the most frequent head impact (Max_freq_hits) and the subject's baseline;
- Subject who are contact sport athletes and experienced the most frequent head impact (Max_freq_hits) and subjects who are a contact sport athletes and experienced the least frequent head impact (Min_freq_hits);
- Subjects who are contact sport athletes and experienced the most frequent head impact (Max_freq_hits) and subjects with normal exposure to head impact (e.g. athletes who do not play contact sports) (Track_field_control);
- Subjects who experienced most frequent head impact (Max_freq_hits) and the subject's baseline or subjects who are not contact sport athletes (Track_field_control);
- A subject who is a contact sport athlete and experienced the least frequent head impact (Min_freq_hits) and the subject's baseline;
- Subjects who experienced the least frequent head impact (Min_freq_hits) and the subject's baseline or subjects who are not contact sport athletes (Track_field_control);
- Subjects who are contact sport athletes (baseline) and subjects who are not contact sport athletes (Track_field_control);
- A subject who is a contact sport athlete and experienced the least forceful head impact (Min_HITsp) and the subject's baseline;
- Subjects who experienced least forceful head impact (Min_HITsp) and the subject's baseline or subjects who are not contact sport athletes (Track_field_control);
- Subjects with mild exposure to potentially injurious head impact (probability score of 0-0.1) and subjects with least exposure to potentially injurious head impact (probability score of 0);
- Subjects with moderate exposure potentially injurious head impact (probability score of 0.1-0.5) and subjects with least exposure potentially injurious head impact (probability score of 0);
- Subjects with moderate exposure potentially injurious head impact (probability score of 0.1-0.5) and subjects with mild exposure potentially injurious head impact (probability score of 0-0.1);
- Subjects with high exposure potentially injurious head impact (probability score of >0.5) and subjects with least exposure potentially injurious head impact (probability score of 0);
- Subjects with high exposure potentially injurious head impact (probability score of >0.5) and subjects with mild exposure potentially injurious head impact (probability score of 0-0.1); and
- Subjects with high exposure potentially injurious head impact (probability score of >0.5) and subject with moderate exposure potentially injurious head impact (probability score of 0.1-0.5).

In comparisons using the probability score for risk of concussion, the scores are calculated using the linear and rotational acceleration was studied previously by Rowson et. al ("Brain Injury Prediction: Assessing the Combined Probability of Concussion Using Linear and Rotational Head Acceleration." *Ann of Biomed. Engg* 2013).

Table 2 list the biomarkers that are differentially expressed, regardless of whether the biological sample is from blood, urine, or saliva, that can be used for determining the risk of a subject for developing mTBI and for concussion, Table 3 is a subset of the biomarkers that are differentially expressed in blood samples. Table 4 is a subset of the biomarkers that are differentially expressed in saliva samples. Table 5 is a subset of the biomarkers that are differentially expressed urine samples.

Tables 6-15 lists the significant genes from linear regression analysis with year 1 and year 2 samples. The analysis was performed with two levels of stringency: (1) only those genes which had measurable expression in at least 50% of the samples (Expr in 0.5 samples) and (2) only those genes which had expression in at least 80% of the samples (Expr in 0.8 samples). Genes with a |slope|>0.1 and a p-value<0.05 were considered significant. Tables 6-11 contain the significant genes in plasma samples. Tables 12-15 list the significant genes in urine samples.

Accordingly, the invention provides methods for determining the risk of a subject for developing mTBI. The methods comprise obtaining a biological sample from a subject; measuring the biological sample for an amount of at least one biomarker selected from the group consisting of the biomarkers listed in any one of Tables 1-15; and comparing the amount of the at least one biomarker in the biological sample with the amount of the at least one biomarker in a control sample, wherein a change in the amount of the at least one biomarker from the subject compared with the control sample is indicative of the subject being at an increased risk for developing mTBI. In some aspects, the biomarkers detect the risk of developing mTBI after a head impact incident.

The invention also provides methods for determining the fitness of a subject for participating in an activity with increased chances of receiving a head impact. The methods comprise obtaining a biological sample from a subject; measuring the biological sample for an amount of at least one biomarker selected from the group consisting of the biomarkers listed in any one of Tables 1-15; and comparing the amount of the at least one biomarker with the amount of the at least one biomarker in a control sample, wherein a change in the amount of the at least one biomarker from the subject compared with the control is indicative of the subject being unfit for participating in the activity with increased chances of receiving a head impact.

In some aspects, the methods of the invention further comprises determining, based on the biomarker measurement, whether the subject should be hospitalized for the head impact incident, whether the subject should be monitored while continuing or halting the activity that resulted in the head impact, or the whether the subject incurred no significant increases in risk for developing mTBI due to the head impact incident.

In some aspects, measuring the biological sample of the methods of the invention comprises measuring the biological sample for an amount of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or at least twenty biomarkers selected from the group consisting of the biomarkers listed in any one of Tables 1-15.

In some embodiments of the invention, the biological sample from a subject is obtained after known head impact, for example head impact that is detected by helmet, such as one by Riddell. In some aspects, the biological sample may be collected immediately after known head impact or within one hour, three hours, six hours, eight hours, 12 hours, 18 hours, 24 hours, or 48 hours after known head impact or the time of suspected head impact incident. The biological sample may also be collected at least one hour, at least three hours, at least six, at least eight hours, at least 12 hours, at least 18 hours, or at least 24 hours after known head impact the time of suspected head impact incident.

In some implementations, the control sample is the baseline sample of the subject. The baseline sample of the subject may be collected prior the immediate head trauma, which may or may not reflect a history of frequent head impacts, such as in athletes playing contact sports. For example, the baseline sample of a football player collected before the start of the athlete's competitive season or during the practice week may reflect a baseline comprising changes due to the subject having a history of frequent head impacts. Though if the baseline sample of a football player were collected before the start of the athlete's first competitive season or if the baseline sample were from a subject not participating in contact sports, the baseline sample would not reflect a baseline comprising such changes.

In other implementations, the control sample is not the baseline sample of the subject. For example, the control sample may be a matched sample (for example by age and sex) from a different subject or a predicted control sample calculated from the general population. The predicted control sample may be further made representative by characterizing the general population by age. Thus prepubescent athletes and post-pubescent athletes would have separate predicted control samples. The representative sample for the general population of post-pubescent athletes may be further refined by sex and additional age brackets, for example, for a population of males between the ages of 18 to 24, females between the ages of 18 to 24, males between the ages of 25 to 30, females between the ages of 25 to 30, males between the ages of 30 to 40, or females between the ages of 30 to 40.

Methods for measuring the biological sample for an amount of at least one biomarker are well established in the art. Such methods include detection of the at least one biomarker by reacting the biological sample with primers to detect gene expression or reaction the biological sample with antibodies to detect protein expression. Particular methods for measuring the biological sample for an amount of at least one biomarker include PCR, real-time PCR, immunoassays, gene or protein arrays, and western blotting. In some implementations, detection of protein biomarkers in the biological sample may be through mass spectrometry, protein arrays, antibody arrays, ELISA, and other forms of immunoassays.

When more than one biomarker is measured, the determination of the risk of a subject for developing mTBI may be based on a uniform increase in the expression of a set of biomarkers selected from the biomarkers listed in any one of Tables 1-53, a uniform decrease in the expression of a set of biomarkers selected from the biomarkers listed in any one of Tables 1-53, or a combination of increased expression of some biomarkers listed in any one of Tables 1-53 and decrease expression of other biomarkers listed in any one of Tables 1-53.

For example, an increased risk may be reflected by the detection of increased expression in the measured biomarkers. An increased risk may also be reflected by the detection of decreased expression in the measured biomarkers. An increased risk may additionally be reflected by the detection of decreased expression in some of the measured biomarkers in combination with the detection of increased expression in the other measured biomarkers. In some implementations, the determination of the risk of a subject for developing mTBI may be based a combination of biomarker listed in any one of Tables 1-53 having increased expression, decreased expression, and no change in expression.

Gradations of risk may also be determined by comparing the amount of the at least one biomarker in the biological sample with the amount of the at least one biomarker in a control sample. The magnitude of the change in expression is correlated to increased or decreased risk of the subject developing mTBI. The combination of particularly changes or lack of change in the expression of biomarker is also correlated is correlated to increased or decreased risk of the subject developing mTBI.

The invention further encompasses kits for determining the risk of a subject for developing mTBI or for determining the fitness of a subject for participating in an activity with increased chances of receiving a head impact, wherein the kits detect the expression of at least one biomarker selected from the biomarkers listed in any one of Tables 1-53. In some embodiments, the kit comprises a primer or probe that specifically determines the expression level of at least one biomarker selected from any one of Tables 1-53 in the subject. In some implementations, the probe is covalently attached to the surface of a solid support. The kits may further comprise a dataset comprising the expression level of the at least one biomarker in normal subjects and/or a control sample.

The kits may further comprise instructions listing the direction of change in the expression of the at least one biomarker in the subject in relation to the dataset or the control that demonstrates the subject has increased risk of the subject for developing mTBI. In some embodiments, the direction of change in the expression corresponds to the changes as depicted in any one of Tables 6-53.

In some embodiments, the kits determine the probability of a subject's exposure to potentially injurious head impact, for example least exposure (probability score of 0), mild exposure (probability score of 0-0.1), moderate exposure (probability score of 0.1-0.5), and high exposure (probability score of >0.5). Such kits comprise a primer or probe that specifically determines the expression level of at least one biomarker selected from Table 32 or 33 and a control sample or a dataset comprising the expression level of the at least one biomarker in normal subjects. Correlating the change in the expression of the at least one biomarker with the changes as depicted in Table 32 or 33 determines the subject's probability score exposure to potentially injurious head impact.

In some aspects, the kits provide rapid onsite determination of the risk of a subject for developing mTBI. An example of such a kit comprises a detection agent for at least one biomarker at least one biomarker selected from the group consisting of the biomarkers listed in any one of Tables 1-53 and reagents facilitating the detection of the at least one biomarker. The detection agent may be antibodies that recognize the at least one biomarker, which can be fluorescence-conjugated. The detection agent may also be a nucleotide sequence that recognize the at least one biomarker. Reagents facilitating the detection of the at least one biomarker by using the aforementioned detection agents are well known in the art. In some embodiments, the kits may comprise a DNA polymerase and a buffer.

EXAMPLES

It should be understood that while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

1. Identification of Biomarkers for Determining the Risk for Developing mTBI or Concussion A. Sample Collection:

Samples of saliva, urine and blood were collected from players on youth, high school, and collegiate football players and matched non-contact athletes. The samples were collected at baseline (prior to the first contact practice) and once each week of the season (from summer training camp to the Pac-12 championship game at the end of the season). Post-season, return to baseline, samples were also collected and stored. In order to correlate molecular changes with head impact exposure, the athletes were outfitted with the Riddell Sideline Response System (SRS) (U.S. patent application Ser. No. 13/603,319), which recorded the magnitude and frequency of every head impact during each practice and game in one season. Head injury samples were generally collected as soon after the head injury as possible. In cases were the samples were labeled "previous day," the samples were collected a day after a game took place. Thus the samples were collected a day after a head impact incident or suspected time of a head impact incident.

B. Sample Selection for RNASeq:

Sample selection for RNA sequencing was carried based on the following criteria:

a) Players who were hit more frequently between two sample collections/games than others. These constitute the groups Max_freq_hits and Min_freq_hits respectively. The number of hits between two games/sample collections range from 128-200 for the Max_freq_hits and 2-20 for the Min_freq_hits groups respectively.

b) Players who were hit with a high impact as evidenced by the HITSp values from the helmet data between two sample collections/games than others. These constitute the groups Max_hitsp and Min_hitsp respectively. The HITsp values take into account the linear and rotational acceleration and the location of impact amongst others. The HITSp values range from 120-200 for the Max_hitsp and 15-30 for the Min_hitsp groups respectively.

c) The baselines for the aforementioned players and other non-footballer athletes (track and field, swimmers, wrestlers, etc.) were sequenced.

2. Verification of Biomarkers for Determining the Risk for Developing mTBI or Concussion A. Analysis Methodology for Differential Expression The sequenced samples were aligned to the human genome (Gencode release 19, ENSEMBL 75) using the Spliced Transcripts Alignment to a Reference (STAR) software1. The aligned reads were then counted for gene features using htseq-count. The output from htseq-count, which is a list of genes and their corresponding counts for each sample, is then analyzed for differential expression by DESeq2. DESeq2 estimates variance-mean dependence in count data arising from the htseq-count in this case, and tests for differential expression based on a model using the negative binomial distribution. The raw counts for the samples were normalized using the median ratio method, which is used by the DESeq2 software by default to minimize the effect of large expression outliers across the samples. Only samples with a sufficient number of coding genes discovered (>10,000 coding genes with at least 10 counts) were allowed for further analysis.

The three major steps in the DESeq2 software are a) estimation of size factors; b) estimation of dispersion; and c) negative binomial GLM fitting and Wald statistics.

For year 1 samples, pairwise comparisons were performed for Max_freq_hits/Max_HITsp versus their baselines and Min_freq_hits/Min_HITsp. Comparisons were also made with non-footballer controls. Only genes with an adjusted p-value of less than 0.05 and a log 2foldchange >+2 or <−2 were deemed to be significantly over-expressed and under-expressed respectively for each pairwise comparison. This analysis was carried out for all three biofluids, namely blood, urine and saliva, separately owing to the difference in the constitution of the exRNA (extracellular RNA) present in them. Tables 16-26 depict the fold change in the expression of these markers in the pairwise comparisons. Positive values indicate increased expression while negative values indicate decreased expression.

Table 16 lists the markers that are differentially expressed when the blood sample of subjects who experienced most forceful head impact (Max_HITsp) as compared to the subject's baseline, subjects who experienced least forceful head impact (Min_HITsp), or subjects who are not contact sports athletes (Track_field_control). Table 17 lists markers that are differentially expressed when the urine or saliva sample of subjects who experienced most forceful head impact (Max_HITsp) as compared to the subject's baseline or subjects who are not contact sports athletes (Track_field_control).

Table 18 lists markers that are differentially expressed when the blood sample of subjects who experienced most frequent head impact (Max_freq_hits) are compared to the subjects' baseline or subjects who are not contact sports athletes (Track_field_control). Table 19 lists markers that are differentially expressed when the urine sample of subjects who experienced most frequent head impacts (Max_freq_hits) are compared to the subjects' baseline, subjects with least frequent head impacts (Min_freq_hits), or subjects who are not contact sports athletes (Track_field_control). Table 20 lists markers that are differentially expressed when the saliva sample of subjects who experienced most frequent head impact (Max_freq_hits) are compared to the subjects' baseline or subjects who experienced least frequent head impact (Min_freq_h its).

Table 21 lists markers that are differentially expressed when the blood sample of subjects who experienced least forceful head impact (Min_HITsp) are compared to the subject's baseline or subjects who are not contact sports athletes (Track_field_control). Table 22 lists markers that are differentially expressed when the urine sample of subjects who experienced least forceful head impact (Min_HITsp) are compared to subjects who are not contact sports athletes (Track_field_control).

Table 23 lists markers that are differentially expressed when the blood sample of subjects who experienced frequent head impact (Min_freq_hits) are compared to the subjects' baseline or subjects who are not contact sports athletes (Track_field_control). Table 24 lists markers that are differentially expressed when the urine sample of subjects who experienced frequent head impact (Min_freq_hits) are compared to the subjects who are not contact sports athletes (Track_field_control).

Table 25 lists markers that are differentially expressed when the baseline blood sample of subjects who are contact sport athletes (baseline) are compared to subjects who are not contact sports athletes (Track_field_control). Table 26 lists markers that are differentially expressed when the baseline urine sample of subjects who are contact sport athletes (baseline) are compared to the subjects who are not contact sports athletes (Track_field_control).

Another analysis was carried for the combination of year 1 and years 2 samples. In year 2, there were 240 samples sequenced in all for small RNA, which consisted of 91 plasma and 149 urine samples. The cut-off employed for sample selection was that each sample has at least 7500 protein coding genes with at least 10 read counts. Since no new saliva samples were sequenced from year 2, the analyses are restricted to plasma and urine only. All the analyses conducted were with respect to the player's hit data on the previous day. The analysis for the combination of year 1 and year 2 samples was performed in two ways.

The first way comprises dividing the sample set by sample source into various categories based on a single measurement: Number of hits sustained on the previous day or the highest impact sustained on the previous day (HITsp). The categories here are:

| SI no | Case | Control |
|---|---|---|
| 1 | Max_hitsp | Min_hitsp |
| 2 | Max_hitsp | Baseline |
| 3 | Min_hitsp | Baseline |
| 4 | High_freq_hits | Low_freq_hits |
| 5 | High_freq_hits | Baseline |
| 6 | Low_freq_hits | Baseline |

Max_HITsp represents players who sustain a hit greater than or equal to 85 the previous day. Min_HITsp represents payers who sustain a hit less than or equal to 30 the previous day. High_freq_hits represents players who were hit greater than or equal to 60 times the previous day. Low_freq_hits represents players who were hit less than or equal to 15 times the previous day. Baseline represents sample acquired from players before the season began. Concussion represents players with a diagnosed concussion.

Tables 27-30 list the differentially expressed biomarkers based on the above comparisons and depict the fold change in the expression of these markers in the pairwise comparisons. Positive values indicate increased expression while negative values indicate decreased expression.

Table 27 lists a subset of markers that are differentially expressed in plasma when considering the frequency of head impact. Table 28 lists a subset of markers that are differentially expressed in plasma when considering the level of head impact. The listed markers in Tables 27 and 28 are significant in at least four differential expression comparisons. Table 29 lists markers that are differentially expressed in urine when considering the frequency of head impact. Table 30 lists markers that are differentially expressed in urine when considering the level of head impact.

The second way comprises weighting each impact sustained the previous day by the linear and rotational acceleration for each impact to determine the probability for concussion using the algorithms of Rowson et. al ("Brain Injury Prediction: Assessing the Combined Probability of Concussion Using Linear and Rotational Head Acceleration." *Ann of Biomed. Engg* 2013). The methods of Rowson et al. was used to determine risk of exposure associated with each impact. Briefly, each impact sustained by the player is given a probability score that informs the risk of exposure to potentially injurious impacts. These probabilities are summed up for the previous day hit data to get a cumulative risk score. The players are then categorized as 0 (least risk: baseline samples), 1 (risk between 0-0.1), 2 (0.1-0.5) and 3 (0.5 and above). Differential expression analysis was then conducted for the following categories:

| SI no | Case | Control |
|---|---|---|
| 1 | 3 | 0 |
| 2 | 3 | 1 |
| 3 | 3 | 2 |
| 4 | 2 | 0 |
| 5 | 2 | 1 |
| 6 | 1 | 0 |

The above analysis therefore takes into account the number of impacts sustained by the player the previous day along with their corresponding impact information (linear and rotational acceleration associated with each hit). Tables 31 and 32 lists differentially expressed biomarkers based on the above comparisons in plasma and urine samples, respectively, and depict the fold change in the expression of these markers in the pairwise comparisons. Positive values indicate increased expression while negative values indicate decreased expression. The listed markers in Table 31 are a subset of differentially expressed biomarkers that are significant in at least four differential expression comparisons.

B. Analysis Methodology for Linear Regression

Simple linear regression was performed in year 1 and years 2 samples where the players' impact data from the helmets, in seven categories, were regressed up on the RNA expression. The categories are: the total number of all head impacts sustained by the player in the game (Total Hits), the highest impact sustained by the player in the game, where the impact can be measured by linear acceleration sustained by the head (Max_Lin_acc), the rotational acceleration (Max_Rot_acc), and a combined score of the location of impact, linear and rotational acceleration (HITsp) (Max HITsp), and sum of all impacts sustained by the player in the game (Cum_Lin_acc, Cum_Rot_acc, and Cum HITsp). These data were regressed on the gene expression measured in counts which have been normalized for sequencing depth between the samples.

The analysis was performed with two levels of stringency, firstly with only those genes which had measurable expression in at least 50% of the samples (Expr in 0.5 samples) and secondly with only those genes which had expression in at least 80% of the samples (Expr in 0.8 samples). Genes with a |slope|>0.1 and a p-value <0.05 were considered significant. Here expressed is defined as having at least 10 read counts of the mRNA. Tables 6-15 disclose the significant biomarkers from linear regression.

C. Methodology for Random Forest Machine Learning Algorithm

To arrive at the smallest set of genes that could comprehensively discriminate between cases and controls, random forests machine learning algorithm was used. Random forest is a machine learning technique for classification and regression which instead of using all predictors (genes) and all individuals (samples) to make a single classification tree, it uses a forest of many trees each based on a random selection of predictors and individuals. Each tree is fit using a bootstrap sample of data drawn with replacement and grown until each node is pure. The trees all act as weak classifiers and when there are ~10,000 weak classifiers, the average result from all these classifiers give a robust and accurate estimate of the data. Random forest gives us a set of genes ranked by their importance or discriminating power between the samples—case or control. This is especially useful when dealing with a large set of genes which are significantly differentially expressed or when too few are differentially expressed.

Tables 33-53 present the set of the genes that discriminate between various cases and controls using blood samples and urine samples. Tables 33 and 34 list markers that discriminate between contact sport athletes and non-contact sports athletes from their blood and urine samples, respectively. Tables 35-39 list the markers that differentiate subjects who had the most frequent head impact by using blood and urine samples. Tables 40-45 list markers that differentiate subjects who had the most forceful head impact from the subject by using blood and urine samples. Tables 46-49 lists the markers that differentiate subjects who had the least frequent head impact by using blood and urine samples. Tables 50-52 list the markers that differentiate subjects who had the lest frequent head impact by using blood and urine samples. Table 53 lists markers with expression that is significant different across the different biological samples.

Elevations or reductions in the expression of these RNA indicate frequent head contact and might increase risk for injury. In some implementations, an expression profile wherein the changes in marker expression completely corresponds with the changes depicted in Table 53 is indicative of the subject being at increased risk for mTBI. Though in other implementations, just decreased expression of ENSG00000113889, ENSG00000164825, ENSG00000165685, ENSG00000169344, ENSG00000184908, and ENSG00000270103 or just increased expression of ENSG00000125652, ENSG00000145113, ENSG00000153802, ENSG00000196352, ENSG00000197674, ENSG00000206652, ENSG00000210194, ENSG00000230140, ENSG00000254325, ENSG00000258406, ENSG00000267706, ENSG00000269364, and ENSG00000271043 is indicative of the subject being at increased risk for mTBI. Accordingly, in some embodiments, a change in the expression of at least 6 markers listed in Table 53 is indicative of the subject being at increased risk for mTBI.

TABLE 1

| Ensembl ID | Hgnc symbol | Description |
|---|---|---|
| ENSG00000004864 | SLC25A13 | solute carrier family 25 (aspartate/glutamate carrier), member 13 [Source:HGNC Symbol;Acc:HGNC:10983] |
| ENSG00000005175 | RPAP3 | RNA polymerase II associated protein 3 [Source:HGNC Symbol;Acc:HGNC:26151] |
| ENSG00000005249 | PRKAR2B | protein kinase, cAMP-dependent, regulatory, type II, beta [Source:HGNC Symbol;Acc:HGNC:9392] |
| ENSG00000005961 | ITGA2B | integrin, alpha 2b (platelet glycoprotein IIb of IIb/IIIa complex, antigen CD41) [Source:HGNC Symbol;Acc:HGNC:6138] |
| ENSG00000006432 | MAP3K9 | mitogen-activated protein kinase kinase kinase 9 [Source:HGNC Symbol;Acc:HGNC:6861] |
| ENSG00000006715 | VPS41 | vacuolar protein sorting 41 homolog (*S. cerevisiae*) [Source:HGNC Symbol;Acc:HGNC:12713] |
| ENSG00000010318 | PHF7 | PHD finger protein 7 [Source:HGNC Symbol;Acc:HGNC:18458] |
| ENSG00000011275 | RNF216 | ring finger protein 216 [Source:HGNC Symbol;Acc:HGNC:21698] |
| ENSG00000011638 | TMEM159 | transmembrane protein 159 [Source:HGNC Symbol;Acc:HGNC:30136] |
| ENSG00000012779 | ALOX5 | arachidonate 5-lipoxygenase [Source:HGNC Symbol;Acc:HGNC:435] |
| ENSG00000013016 | EHD3 | EH-domain containing 3 [Source:HGNC Symbol;Acc:HGNC:3244] |
| ENSG00000025293 | PHF20 | PHD finger protein 20 [Source:HGNC Symbol;Acc:HGNC:16098] |
| ENSG00000029725 | RABEP1 | rabaptin, RAB GTPase binding effector protein 1 [Source:HGNC Symbol;Acc:HGNC:17677] |
| ENSG00000031003 | FAM13B | family with sequence similarity 13, member B [Source:HGNC Symbol;Acc:HGNC:1335] |
| ENSG00000034677 | RNF19A | ring finger protein 19A, RBR E3 ubiquitin protein ligase [Source:HGNC Symbol;Acc:HGNC:13432] |
| ENSG00000035403 | VCL | vinculin [Source:HGNC Symbol;Acc:HGNC:12665] |
| ENSG00000041353 | RAB27B | RAB27B, member RAS oncogene family [Source:HGNC Symbol;Acc:HGNC:9767] |

TABLE 1-continued

| Ensembl ID | Hgnc symbol | Description |
|---|---|---|
| ENSG00000044090 | CUL7 | cullin 7 [Source:HGNC Symbol;Acc:HGNC:21024] |
| ENSG00000048405 | ZNF800 | zinc finger protein 800 [Source:HGNC Symbol;Acc:HGNC:27267] |
| ENSG00000064012 | CASP8 | caspase 8, apoptosis-related cysteine peptidase [Source:HGNC Symbol;Acc:HGNC:1509] |
| ENSG00000064102 | ASUN | asunder spermatogenesis regulator [Source:HGNC Symbol;Acc:HGNC:20174] |
| ENSG00000064313 | TAF2 | TAF2 RNA polymerase II, TATA box binding protein (TBP)-associated factor, 150 kDa [Source:HGNC Symbol;Acc:HGNC:11536] |
| ENSG00000065054 | SLC9A3R2 | solute carrier family 9, subfamily A (NHE3, cation proton antiporter 3), member 3 regulator 2 [Source:HGNC Symbol;Acc:HGNC:11076] |
| ENSG00000066322 | ELOVL1 | ELOVL fatty acid elongase 1 [Source:HGNC Symbol;Acc:HGNC:14418] |
| ENSG00000067369 | TP53BP1 | tumor protein p53 binding protein 1 [Source:HGNC Symbol;Acc:HGNC:11999] |
| ENSG00000068796 | KIF2A | kinesin heavy chain member 2A [Source:HGNC Symbol;Acc:HGNC:6318] |
| ENSG00000070190 | DAPP1 | dual adaptor of phosphotyrosine and 3-phosphoinositides [Source:HGNC Symbol;Acc:HGNC:16500] |
| ENSG00000074755 | ZZEF1 | zinc finger, ZZ-type with EF-hand domain 1 [Source:HGNC Symbol;Acc:HGNC:29027] |
| ENSG00000075624 | ACTB | actin, beta [Source:HGNC Symbol;Acc:HGNC:132] |
| ENSG00000078124 | ACER3 | alkaline ceramidase 3 [Source:HGNC Symbol;Acc:HGNC:16066] |
| ENSG00000079459 | FDFT1 | farnesyl-diphosphate farnesyltransferase 1 [Source:HGNC Symbol;Acc:HGNC:3629] |
| ENSG00000080608 | KIAA0020 | KIAA0020 [Source:HGNC Symbol;Acc:HGNC:29676] |
| ENSG00000081087 | OSTM1 | osteopetrosis associated transmembrane protein 1 [Source:HGNC Symbol;Acc:HGNC:21652] |
| ENSG00000081320 | STK17B | serine/threonine kinase 17b [Source:HGNC Symbol;Acc:HGNC:11396] |
| ENSG00000081791 | KIAA0141 | KIAA0141 [Source:HGNC Symbol;Acc:HGNC:28969] |
| ENSG00000081803 | CADPS2 | Ca++-dependent secretion activator 2 [Source:HGNC Symbol;Acc:HGNC:16018] |
| ENSG00000087494 | PTHLH | parathyroid hormone-like hormone [Source:HGNC Symbol;Acc:HGNC:9607] |
| ENSG00000100023 | PPIL2 | peptidylprolyl isomerase (cyclophilin)-like 2 [Source:HGNC Symbol;Acc:HGNC:9261] |
| ENSG00000100181 | TPTEP1 | transmembrane phosphatase with tensin homology pseudogene 1 [Source:HGNC Symbol;Acc:HGNC:43648] |
| ENSG00000100345 | MYH9 | myosin, heavy chain 9, non-muscle [Source:HGNC Symbol;Acc:HGNC:7579] |
| ENSG00000100580 | TMED8 | transmembrane emp24 protein transport domain containing 8 [Source:HGNC Symbol;Acc:HGNC:18633] |
| ENSG00000100592 | DAAM1 | dishevelled associated activator of morphogenesis 1 [Source:HGNC Symbol;Acc:HGNC:18142] |
| ENSG00000101210 | EEF1A2 | eukaryotic translation elongation factor 1 alpha 2 [Source:HGNC Symbol;Acc:HGNC:3192] |
| ENSG00000102243 | VGLL1 | vestigial-like family member 1 [Source:HGNC Symbol;Acc:HGNC:20985] |
| ENSG00000102572 | STK24 | serine/threonine kinase 24 [Source:HGNC Symbol;Acc:HGNC:11403] |
| ENSG00000102804 | TSC22D1 | TSC22 domain family, member 1 [Source:HGNC Symbol;Acc:HGNC:16826] |
| ENSG00000103194 | USP10 | ubiquitin specific peptidase 10 [Source:HGNC Symbol;Acc:HGNC:12608] |
| ENSG00000103569 | AQP9 | aquaporin 9 [Source:HGNC Symbol;Acc:HGNC:643] |
| ENSG00000104447 | TRPS1 | trichorhinophalangeal syndrome I [Source:HGNC Symbol;Acc:HGNC:12340] |
| ENSG00000105186 | ANKRD27 | ankyrin repeat domain 27 (VPS9 domain) [Source:HGNC Symbol;Acc:HGNC:25310] |
| ENSG00000105778 | AVL9 | AVL9 homolog (*S. cerevisiase*) [Source:HGNC Symbol;Acc:HGNC:28994] |
| ENSG00000106615 | RHEB | Ras homolog enriched in brain [Source:HGNC Symbol;Acc:HGNC:10011] |
| ENSG00000107438 | PDLIM1 | PDZ and LIM domain 1 [Source:HGNC Symbol;Acc:HGNC:2067] |
| ENSG00000107669 | ATE1 | arginyltransferase 1 [Source:HGNC Symbol;Acc:HGNC:782] |
| ENSG00000108094 | CUL2 | cullin 2 [Source:HGNC Symbol;Acc:HGNC:2552] |
| ENSG00000108389 | MTMR4 | myotubularin related protein 4 [Source:HGNC Symbol;Acc:HGNC:7452] |
| ENSG00000108883 | EFTUD2 | elongation factor Tu GTP binding domain containing 2 [Source:HGNC Symbol;Acc:HGNC:30858] |
| ENSG00000109084 | TMEM97 | transmembrane protein 97 [Source:HGNC Symbol;Acc:HGNC:28106] |
| ENSG00000109272 | PF4V1 | platelet factor 4 variant 1 [Source:HGNC Symbol;Acc:HGNC:8862] |
| ENSG00000109320 | NFKB1 | nuclear factor of kappa light polypeptide gene enhancer in B-cells 1 [Source:HGNC Symbol;Acc:HGNC:7794] |

TABLE 1-continued

| Ensembl ID | Hgnc symbol | Description |
|---|---|---|
| ENSG00000109854 | HTATIP2 | HIV-1 Tat interactive protein 2, 30 kDa [Source:HGNC Symbol;Acc:HGNC:16637] |
| ENSG00000110002 | VWA5A | von Willebrand factor A domain containing 5A [Source:HGNC Symbol;Acc:HGNC:6658] |
| ENSG00000110060 | PUS3 | pseudouridylate synthase 3 [Source:HGNC Symbol;Acc:HGNC:25461] |
| ENSG00000110906 | KCTD10 | potassium channel tetramerization domain containing 10 [Source:HGNC Symbol;Acc:HGNC:23236] |
| ENSG00000111215 | PRR4 | proline rich 4 (lacrimal) [Source:HGNC Symbol;Acc:HGNC:18020] |
| ENSG00000111237 | VPS29 | vacuolar protein sorting 29 homolog (*S. cerevisiae*) [Source:HGNC Symbol;Acc:HGNC:14340] |
| ENSG00000111348 | ARHGDIB | Rho GDP dissociation inhibitor (GDI) beta [Source:HGNC Symbol;Acc:HGNC:679] |
| ENSG00000112118 | MCM3 | minichromosome maintenance complex component 3 [Source:HGNC Symbol;Acc:HGNC:6945] |
| ENSG00000112541 | PDE10A | phosphodiesterase 10A [Source:HGNC Symbol;Acc:HGNC:8772] |
| ENSG00000112561 | TFEB | transcription factor EB [Source:HGNC Symbol;Acc:HGNC:11753] |
| ENSG00000112893 | MAN2A1 | mannosidase, alpha, class 2A, member 1 [Source:HGNC Symbol;Acc:HGNC:6824] |
| ENSG00000113494 | PRLR | prolactin receptor [Source:HGNC Symbol;Acc:HGNC:9446] |
| ENSG00000113649 | TCERG1 | transcription elongation regulator 1 [Source:HGNC Symbol;Acc:HGNC:15630] |
| ENSG00000113658 | SMAD5 | SMAD family member 5 [Source:HGNC Symbol;Acc:HGNC:6771] |
| ENSG00000114013 | CD86 | CD86 molecule [Source:HGNC Symbol;Acc:HGNC:1705] |
| ENSG00000114166 | KAT2B | K(lysine) acetyltransferase 2B [Source:HGNC Symbol;Acc:HGNC:8638] |
| ENSG00000114638 | UPK1B | uroplakin 1B [Source:HGNC Symbol;Acc:HGNC:12578] |
| ENSG00000114805 | PLCH1 | phospholipase C, eta 1 [Source:HGNC Symbol;Acc:HGNC:29185] |
| ENSG00000115159 | GPD2 | glycerol-3-phosphate dehydrogenase 2 (mitochondrial) [Source:HGNC Symbol;Acc:HGNC:4456] |
| ENSG00000115641 | FHL2 | four and a half LIM domains 2 [Source:HGNC Symbol;Acc:HGNC:3703] |
| ENSG00000116117 | PARD3B | par-3 family cell polarity regulator beta [Source:HGNC Symbol;Acc:HGNC:14446] |
| ENSG00000116191 | RALGPS2 | Ral GEF with PH domain and SH3 binding motif 2 [Source:HGNC Symbol;Acc:HGNC:30279] |
| ENSG00000116580 | GON4L | gon-4-like (*C. elegans*) [Source:HGNC Symbol;Acc:HGNC:25973] |
| ENSG00000116984 | MTR | 5-methyltetrahydrofolate-homocysteine methyltransferase [Source:HGNC Symbol;Acc:HGNC:7468] |
| ENSG00000117335 | CD46 | CD46 molecule, complement regulatory protein [Source:HGNC Symbol;Acc:HGNC:6953] |
| ENSG00000117461 | PIK3R3 | phosphoinositide-3-kinase, regulatory subunit 3 (gamma) [Source:HGNC Symbol;Acc:HGNC:8981] |
| ENSG00000119242 | CCDC92 | coiled-coil domain containing 92 [Source:HGNC Symbol;Acc:HGNC:29563] |
| ENSG00000119684 | MLH3 | mutL homolog 3 [Source:HGNC Symbol;Acc:HGNC:7128] |
| ENSG00000119888 | EPCAM | epithelial cell adhesion molecule [Source:HGNC Symbol;Acc:HGNC:11529] |
| ENSG00000119943 | PYROXD2 | pyridine nucleotide-disulphide oxidoreductase domain 2 [Source:HGNC Symbol;Acc:HGNC:23517] |
| ENSG00000120586 | NA | NA |
| ENSG00000120690 | ELF1 | E74-like factor 1 (ets domain transcription factor) [Source:HGNC Symbol;Acc:HGNC:3316] |
| ENSG00000120889 | TNFRSF10B | tumor necrosis factor receptor superfamily, member 10b [Source:HGNC Symbol;Acc:HGNC:11905] |
| ENSG00000121594 | CD80 | CD80 molecule [Source:HGNC Symbol;Acc:HGNC:1700] |
| ENSG00000121989 | ACVR2A | activin A receptor, type IIA [Source:HGNC Symbol;Acc:HGNC:173] |
| ENSG00000122779 | TRIM24 | tripartite motif containing 24 [Source:HGNC Symbol;Acc:HGNC:11812] |
| ENSG00000125676 | THOC2 | THO complex 2 [Source:HGNC Symbol;Acc:HGNC:19073] |
| ENSG00000125945 | ZNF436 | zinc finger protein 436 [Source:HGNC Symbol;Acc:HGNC:20814] |
| ENSG00000127588 | GNG13 | guanine nucleotide binding protein (G protein), gamma 13 [Source:HGNC Symbol;Acc:HGNC:14131] |
| ENSG00000127947 | PTPN12 | protein tyrosine phosphatase, non-receptor type 12 [Source:HGNC Symbol;Acc:HGNC:9645] |
| ENSG00000127952 | STYXL1 | serine/threonine/tyrosine interacting-like 1 [Source:HGNC Symbol;Acc:HGNC:18165] |
| ENSG00000128245 | YWHAH | tyrosine 3-monooxygenase/tryptophan 5-monooxygenase activation protein, eta [Source:HGNC Symbol;Acc:HGNC:12853] |
| ENSG00000128266 | GNAZ | guanine nucleotide binding protein (G protein), alpha z polypeptide [Source:HGNC Symbol;Acc:HGNC:4395] |
| ENSG00000128383 | APOBEC3A | apolipoprotein B mRNA editing enzyme, catalytic polypeptide-like 3A [Source:HGNC Symbol;Acc:HGNC:17343] |
| ENSG00000129315 | CCNT1 | cyclin T1 [Source:HGNC Symbol;Acc:HGNC:1599] |
| ENSG00000129353 | SLC44A2 | solute carrier family 44 (choline transporter), member 2 [Source:HGNC Symbol;Acc:HGNC:17292] |

TABLE 1-continued

| Ensembl ID | Hgnc symbol | Description |
| --- | --- | --- |
| ENSG00000129422 | MTUS1 | microtubule associated tumor suppressor 1 [Source:HGNC Symbol;Acc:HGNC:29789] |
| ENSG00000130600 | H19 | H19, imprinted maternally expressed transcript (non-protein coding) [Source:HGNC Symbol;Acc:HGNC:4713] |
| ENSG00000132530 | XAF1 | XIAP associated factor 1 [Source:HGNC Symbol;Acc:HGNC:30932] |
| ENSG00000133116 | KL | klotho [Source:HGNC Symbol;Acc:HGNC:6344] |
| ENSG00000133136 | GNG5P2 | guanine nucleotide binding protein (G protein), gamma 5 pseudogene 2 [Source:HGNC Symbol;Acc:HGNC:24826] |
| ENSG00000133606 | MKRN1 | makorin ring finger protein 1 [Source:HGNC Symbol;Acc:HGNC:7112] |
| ENSG00000134265 | NAPG | N-ethylmaleimide-sensitive factor attachment protein, gamma [Source:HGNC Symbol;Acc:HGNC:7642] |
| ENSG00000134627 | PIWIL4 | piwi-like RNA-mediated gene silencing 4 [Source:HGNC Symbol;Acc:HGNC:18444] |
| ENSG00000135365 | PHF21A | PHD finger protein 21A [Source:HGNC Symbol;Acc:HGNC:24156] |
| ENSG00000135521 | LTV1 | LTV1 ribosome biogenesis factor [Source:HGNC Symbol;Acc:HGNC:21173] |
| ENSG00000135677 | GNS | glucosamine (N-acetyl)-6-sulfatase [Source:HGNC Symbol;Acc:HGNC:4422] |
| ENSG00000135828 | RNASEL | ribonuclease L (2',5'-oligoisoadenylate synthetase-dependent) [Source:HGNC Symbol;Acc:HGNC:10050] |
| ENSG00000135966 | TGFBRAP1 | transforming growth factor, beta receptor associated protein 1 [Source:HGNC Symbol;Acc:HGNC:16836] |
| ENSG00000136193 | SCRN1 | secernin 1 [Source:HGNC Symbol;Acc:HGNC:22192] |
| ENSG00000136457 | CHAD | chondroadherin [Source:HGNC Symbol;Acc:HGNC:1909] |
| ENSG00000136689 | IL1RN | interleukin 1 receptor antagonist [Source:HGNC Symbol;Acc:HGNC:6000] |
| ENSG00000136715 | SAP130 | Sin3A-associated protein, 130 kDa [Source:HGNC Symbol;Acc:HGNC:29813] |
| ENSG00000136738 | STAM | signal transducing adaptor molecule (SH3 domain and ITAM motif) 1 [Source:HGNC Symbol;Acc:HGNC:11357] |
| ENSG00000136861 | CDK5RAP2 | CDK5 regulatory subunit associated protein 2 [Source:HGNC Symbol;Acc:HGNC:18672] |
| ENSG00000136872 | ALDOB | aldolase B, fructose-bisphosphate [Source:HGNC Symbol;Acc:HGNC:417] |
| ENSG00000136925 | TSTD2 | thiosulfate sulfurtransferase (rhodanese)-like domain containing 2 [Source:HGNC Symbol;Acc:HGNC:30087] |
| ENSG00000137073 | UBAP2 | ubiquitin associated protein 2 [Source:HGNC Symbol;Acc:HGNC:14185] |
| ENSG00000139055 | ERP27 | endoplasmic reticulum protein 27 [Source:HGNC Symbol;Acc:HGNC:26495] |
| ENSG00000139192 | TAPBPL | TAP binding protein-like [Source:HGNC Symbol;Acc:HGNC:30683] |
| ENSG00000140299 | BNIP2 | BCL2/adenovirus E1B 19 kDa interacting protein 2 [Source:HGNC Symbol;Acc:HGNC:1083] |
| ENSG00000140374 | ETFA | electron-transfer-flavoprotein, alpha polypeptide [Source:HGNC Symbol;Acc:HGNC:3481] |
| ENSG00000140740 | UQCRC2 | ubiquinol-cytochrome c reductase core protein II [Source:HGNC Symbol;Acc:HGNC:12586] |
| ENSG00000140750 | ARHGAP17 | Rho GTPase activating protein 17 [Source:HGNC Symbol;Acc:HGNC:18239] |
| ENSG00000141076 | CIRH1A | cirrhosis, autosomal recessive 1A (cirhin) [Source:HGNC Symbol;Acc:HGNC:1983] |
| ENSG00000141179 | PCTP | phosphatidylcholine transfer protein [Source:HGNC Symbol;Acc:HGNC:8752] |
| ENSG00000141194 | OR4D1 | olfactory receptor, family 4, subfamily D, member 1 [Source:HGNC Symbol;Acc:HGNC:8293] |
| ENSG00000142669 | SH3BGRL3 | SH3 domain binding glutamate-rich protein like 3 [Source:HGNC Symbol;Acc:HGNC:15568] |
| ENSG00000143179 | UCK2 | uridine-cytidine kinase 2 [Source:HGNC Symbol;Acc:HGNC:12562] |
| ENSG00000143409 | FAM63A | family with sequence similarity 63, member A [Source:HGNC Symbol;Acc:HGNC:25648] |
| ENSG00000145439 | CBR4 | carbonyl reductase 4 [Source:HGNC Symbol;Acc:HGNC:25891] |
| ENSG00000146192 | FGD2 | FYVE, RhoGEF and PH domain containing 2 [Source:HGNC Symbol;Acc:HGNC:3664] |
| ENSG00000147183 | CPXCR1 | CPX chromosome region, candidate 1 [Source:HGNC Symbol;Acc:HGNC:2332] |
| ENSG00000147394 | ZNF185 | zinc finger protein 185 (LIM domain) [Source:HGNC Symbol;Acc:HGNC:12976] |
| ENSG00000147419 | CCDC25 | coiled-coil domain containing 25 [Source:HGNC Symbol;Acc:HGNC:25591] |
| ENSG00000147606 | SLC26A7 | solute carrier family 26 (anion exchanger), member 7 [Source:HGNC Symbol;Acc:HGNC:14467] |
| ENSG00000148396 | SEC16A | SEC16 homolog A (*S. cerevisiae*) [Source:HGNC Symbol;Acc:HGNC:29006] |
| ENSG00000148498 | PARD3 | par-3 family cell polarity regulator [Source:HGNC Symbol;Acc:HGNC:16051] |

TABLE 1-continued

| Ensembl ID | Hgnc symbol | Description |
|---|---|---|
| ENSG00000148840 | PPRC1 | peroxisome proliferator-activated receptor gamma, coactivator-related 1 [Source:HGNC Symbol;Acc:HGNC:30025] |
| ENSG00000148848 | ADAM12 | ADAM metallopeptidase domain 12 [Source:HGNC Symbol;Acc:HGNC:190] |
| ENSG00000148908 | RGS10 | regulator of G-protein signaling 10 [Source:HGNC Symbol;Acc:HGNC:9992] |
| ENSG00000150054 | MPP7 | membrane protein, palmitoylated 7 (MAGUK p55 subfamily member 7) [Source:HGNC Symbol;Acc:HGNC:26542] |
| ENSG00000150093 | ITGB1 | integrin, beta 1 (fibronectin receptor, beta polypeptide, antigen CD29 includes MDF2, M5K12) [Source:HGNC Symbol;Acc:HGNC:6153] |
| ENSG00000152127 | MGAT5 | mannosyl (alpha-1,6-)-glycoprotein beta-1,6-N-acetyl-glucosaminyltransferase [Source:HGNC Symbol;Acc:HGNC:7049] |
| ENSG00000152457 | DCLRE1C | DNA cross-link repair 1C [Source:HGNC Symbol;Acc:HGNC:17642] |
| ENSG00000152601 | MBNL1 | muscleblind-like splicing regulator 1 [Source:HGNC Symbol;Acc:HGNC:6923] |
| ENSG00000153071 | DAB2 | Dab, mitogen-responsive phosphoprotein, homolog 2 (*Drosophila*) [Source:HGNC Symbol;Acc:HGNC:2662] |
| ENSG00000155827 | RNF20 | ring finger protein 20, E3 ubiquitin protein ligase [Source:HGNC Symbol;Acc:HGNC:10062] |
| ENSG00000155903 | RASA2 | RAS p21 protein activator 2 [Source:HGNC Symbol;Acc:HGNC:9872] |
| ENSG00000156650 | KAT6B | K(lysine) acetyltransferase 6B [Source:HGNC Symbol;Acc:HGNC:17582] |
| ENSG00000158710 | TAGLN2 | transgelin 2 [Source:HGNC Symbol;Acc:HGNC:11554] |
| ENSG00000158856 | DMTN | dematin actin binding protein [Source:HGNC Symbol;Acc:HGNC:3382] |
| ENSG00000159186 | | |
| ENSG00000159231 | CBR3 | carbonyl reductase 3 [Source:HGNC Symbol;Acc:HGNC:1549] |
| ENSG00000159256 | MORC3 | MORC family CW-type zinc finger 3 [Source:HGNC Symbol;Acc:HGNC:23572] |
| ENSG00000159267 | HLCS | holocarboxylase synthetase (biotin-(proprionyl-CoA-carboxylase (ATP-hydrolysing)) ligase) [Source:HGNC Symbol;Acc:HGNC:4976] |
| ENSG00000159840 | ZYX | zyxin [Source:HGNC Symbol;Acc:HGNC:13200] |
| ENSG00000160094 | ZNF362 | zinc finger protein 362 [Source:HGNC Symbol;Acc:HGNC:18079] |
| ENSG00000160584 | SIK3 | SIK family kinase 3 [Source:HGNC Symbol;Acc:HGNC:29165] |
| ENSG00000160917 | CPSF4 | cleavage and polyadenylation specific factor 4, 30 kDa [Source:HGNC Symbol;Acc:HGNC:2327] |
| ENSG00000161533 | ACOX1 | acyl-CoA oxidase 1, palmitoyl [Source:HGNC Symbol;Acc:HGNC:119] |
| ENSG00000162105 | SHANK2 | SH3 and multiple ankyrin repeat domains 2 [Source:HGNC Symbol;Acc:HGNC:14295] |
| ENSG00000162236 | STX5 | syntaxin 5 [Source:HGNC Symbol;Acc:HGNC:11440] |
| ENSG00000162434 | JAK1 | Janus kinase 1 [Source:HGNC Symbol;Acc:HGNC:6190] |
| ENSG00000162722 | TRIM58 | tripartite motif containing 58 [Source:HGNC Symbol;Acc:HGNC:24150] |
| ENSG00000162817 | C1orf115 | chromosome 1 open reading frame 115 [Source:HGNC Symbol;Acc:HGNC:25873] |
| ENSG00000163029 | SMC6 | structural maintenance of chromosomes 6 [Source:HGNC Symbol;Acc:HGNC:20466] |
| ENSG00000163602 | RYBP | RING1 and YY1 binding protein [Source:HGNC Symbol;Acc:HGNC:10480] |
| ENSG00000163793 | DNAJC5G | DnaJ (Hsp40) homolog, subfamily C, member 5 gamma [Source:HGNC Symbol;Acc:HGNC:24844] |
| ENSG00000163993 | S100P | S100 calcium binding protein P [Source:HGNC Symbol;Acc:HGNC:10504] |
| ENSG00000164056 | SPRY1 | sprouty homolog 1, antagonist of FGF signaling (*Drosophila*) [Source:HGNC Symbol;Acc:HGNC:11269] |
| ENSG00000164124 | TMEM144 | transmembrane protein 144 [Source:HGNC Symbol;Acc:HGNC:25633] |
| ENSG00000164134 | NAA15 | N(alpha)-acetyltransferase 15, NatA auxiliary subunit [Source:HGNC Symbol;Acc:HGNC:30782] |
| ENSG00000164181 | ELOVL7 | ELOVL fatty acid elongase 7 [Source:HGNC Symbol;Acc:HGNC:26292] |
| ENSG00000164237 | CMBL | carboxymethylenebutenolidase homolog (*Pseudomonas*) [Source:HGNC Symbol;Acc:HGNC:25090] |
| ENSG00000164266 | SPINK1 | serine peptidase inhibitor, Kazal type 1 [Source:HGNC Symbol;Acc:HGNC:11244] |
| ENSG00000164305 | CASP3 | caspase 3, apoptosis-related cysteine peptidase [Source:HGNC Symbol;Acc:HGNC:1504] |
| ENSG00000164402 | 8-Sep | septin 8 [Source:HGNC Symbol;Acc:HGNC:16511] |
| ENSG00000164691 | TAGAP | T-cell activation RhoGTPase activating protein [Source:HGNC Symbol;Acc:HGNC:15669] |
| ENSG00000164808 | SPIDR | scaffolding protein involved in DNA repair [Source:HGNC Symbol;Acc:HGNC:28971] |

TABLE 1-continued

| Ensembl ID | Hgnc symbol | Description |
|---|---|---|
| ENSG00000165406 | 8-Mar | membrane-associated ring finger (C3HC4) 8, E3 ubiquitin protein ligase [Source:HGNC Symbol;Acc:HGNC:23356] |
| ENSG00000165819 | METTL3 | methyltransferase like 3 [Source:HGNC Symbol;Acc:HGNC:17563] |
| ENSG00000165841 | CYP2C19 | cytochrome P450, family 2, subfamily C, polypeptide 19 [Source:HGNC Symbol;Acc:HGNC:2621] |
| ENSG00000166086 | JAM3 | junctional adhesion molecule 3 [Source:HGNC Symbol;Acc:HGNC:15532] |
| ENSG00000166387 | PPFIBP2 | PTPRF interacting protein, binding protein 2 (liprin beta 2) [Source:HGNC Symbol;Acc:HGNC:9250] |
| ENSG00000166428 | PLD4 | phospholipase D family, member 4 [Source:HGNC Symbol;Acc:HGNC:23792] |
| ENSG00000166478 | ZNF143 | zinc finger protein 143 [Source:HGNC Symbol;Acc:HGNC:12928] |
| ENSG00000166579 | NDEL1 | nudE neurodevelopment protein 1-like 1 [Source:HGNC Symbol;Acc:HGNC:17620] |
| ENSG00000166963 | MAP1A | microtubule-associated protein 1A [Source:HGNC Symbol;Acc:HGNC:6835] |
| ENSG00000167230 | NA | NA |
| ENSG00000167257 | RNF214 | ring finger protein 214 [Source:HGNC Symbol;Acc:HGNC:25335] |
| ENSG00000167258 | CDK12 | cyclin-dependent kinase 12 [Source:HGNC Symbol;Acc:HGNC:24224] |
| ENSG00000167491 | GATAD2A | GATA zinc finger domain containing 2A [Source:HGNC Symbol;Acc:HGNC:29989] |
| ENSG00000167671 | UBXN6 | UBX domain protein 6 [Source:HGNC Symbol;Acc:HGNC:14928] |
| ENSG00000167693 | NXN | nucleoredoxin [Source:HGNC Symbol;Acc:HGNC:18008] |
| ENSG00000167740 | CYB5D2 | cytochrome b5 domain containing 2 [Source:HGNC Symbol;Acc:HGNC:28471] |
| ENSG00000168067 | MAP4K2 | mitogen-activated protein kinase kinase kinase kinase 2 [Source:HGNC Symbol;Acc:HGNC:6864] |
| ENSG00000168394 | TAP1 | transporter 1, ATP-binding cassette, sub-family B (MDR/TAP) [Source:HGNC Symbol;Acc:HGNC:43] |
| ENSG00000168992 | OR7E102P | olfactory receptor, family 7, subfamily E, member 102 pseudogene [Source:HGNC Symbol;Acc:HGNC:15043] |
| ENSG00000170049 | KCNAB3 | potassium voltage-gated channel, shaker-related subfamily, beta member 3 [Source:HGNC Symbol;Acc:HGNC:6230] |
| ENSG00000170485 | NPAS2 | neuronal PAS domain protein 2 [Source:HGNC Symbol;Acc:HGNC:7895] |
| ENSG00000170606 | HSPA4 | heat shock 70 kDa protein 4 [Source:HGNC Symbol;Acc:HGNC:5237] |
| ENSG00000170802 | FOXN2 | forkhead box N2 [Source:HGNC Symbol;Acc:HGNC:5281] |
| ENSG00000171794 | UTF1 | undifferentiated embryonic cell transcription factor 1 [Source:HGNC Symbol;Acc:HGNC:12634] |
| ENSG00000172183 | ISG20 | interferon stimulated exonuclease gene 20 kDa [Source:HGNC Symbol;Acc:HGNC:6130] |
| ENSG00000172476 | RAB40A | RAB40A, member RAS oncogene family [Source:HGNC Symbol;Acc:HGNC:18283] |
| ENSG00000172594 | SMPDL3A | sphingomyelin phosphodiesterase, acid-like 3A [Source:HGNC Symbol;Acc:HGNC:17389] |
| ENSG00000172769 | OR5B3 | olfactory receptor, family 5, subfamily B, member 3 [Source:HGNC Symbol;Acc:HGNC:8324] |
| ENSG00000173210 | ABLIM3 | actin binding LIM protein family, member 3 [Source:HGNC Symbol;Acc:HGNC:29132] |
| ENSG00000173728 | C1orf100 | chromosome 1 open reading frame 100 [Source:HGNC Symbol;Acc:HGNC:30435] |
| ENSG00000175224 | ATG13 | autophagy related 13 [Source:HGNC Symbol;Acc:HGNC:29091] |
| ENSG00000175602 | CCDC85B | coiled-coil domain containing 85B [Source:HGNC Symbol;Acc:HGNC:24926] |
| ENSG00000176043 | | |
| ENSG00000176928 | GCNT4 | glucosaminyl (N-acetyl) transferase 4, core 2 [Source:HGNC Symbol;Acc:HGNC:17973] |
| ENSG00000177125 | ZBTB34 | zinc finger and BTB domain containing 34 [Source:HGNC Symbol;Acc:HGNC:31446] |
| ENSG00000177200 | CHD9 | chromodomain helicase DNA binding protein 9 [Source:HGNC Symbol;Acc:HGNC:25701] |
| ENSG00000177602 | GSG2 | germ cell associated 2 (haspin) [Source:HGNC Symbol;Acc:HGNC:19682] |
| ENSG00000177628 | GBA | glucosidase, beta, acid [Source:HGNC Symbol;Acc:HGNC:4177] |
| ENSG00000177685 | CRACR2B | calcium release activated channel regulator 2B [Source:HGNC Symbol;Acc:HGNC:28703] |
| ENSG00000177853 | ZNF518A | zinc finger protein 518A [Source:HGNC Symbol;Acc:HGNC:29009] |
| ENSG00000178222 | RNF212 | ring finger protein 212 [Source:HGNC Symbol;Acc:HGNC:27729] |
| ENSG00000179914 | ITLN1 | intelectin 1 (galactofuranose binding) [Source:HGNC Symbol;Acc:HGNC:18259] |
| ENSG00000180488 | FAM73A | family with sequence similarity 73, member A [Source:HGNC Symbol;Acc:HGNC:24741] |

TABLE 1-continued

| Ensembl ID | Hgnc symbol | Description |
|---|---|---|
| ENSG00000180694 | TMEM64 | transmembrane protein 64 [Source:HGNC Symbol;Acc:HGNC:25441] |
| ENSG00000181227 | | |
| ENSG00000182393 | IFNL1 | interferon, lambda 1 [Source:HGNC Symbol;Acc:HGNC:18363] |
| ENSG00000182446 | NPLOC4 | nuclear protein localization 4 homolog (*S. cerevisiae*) [Source:HGNC Symbol;Acc:HGNC:18261] |
| ENSG00000182606 | TRAK1 | trafficking protein, kinesin binding 1 [Source:HGNC Symbol;Acc:HGNC:29947] |
| ENSG00000183346 | C10orf107 | chromosome 10 open reading frame 107 [Source:HGNC Symbol;Acc:HGNC:28678] |
| ENSG00000184108 | TRIML1 | tripartite motif family-like 1 [Source:HGNC Symbol;Acc:HGNC:26698] |
| ENSG00000184319 | RPL23AP82 | ribosomal protein L23a pseudogene 82 [Source:HGNC Symbol;Acc:HGNC:33730] |
| ENSG00000184602 | SNN | stannin [Source:HGNC Symbol;Acc:HGNC:11149] |
| ENSG00000184674 | NA | NA |
| ENSG00000185008 | ROBO2 | roundabout, axon guidance receptor, homolog 2 (*Drosophila*) [Source:HGNC Symbol;Acc:HGNC:10250] |
| ENSG00000185187 | SIGIRR | single immunoglobulin and toll-interleukin 1 receptor (TIR) domain [Source:HGNC Symbol;Acc:HGNC:30575] |
| ENSG00000185296 | | |
| ENSG00000186038 | HTR3E | 5-hydroxytryptamine (serotonin) receptor 3E, ionotropic [Source:HGNC Symbol;Acc:HGNC:24005] |
| ENSG00000186298 | PPP1CC | protein phosphatase 1, catalytic subunit, gamma isozyme [Source:HGNC Symbol;Acc:HGNC:9283] |
| ENSG00000186453 | FAM228A | family with sequence similarity 228, member A [Source:HGNC Symbol;Acc:HGNC:34418] |
| ENSG00000187109 | NAP1L1 | nucleosome assembly protein 1-like 1 [Source:HGNC Symbol;Acc:HGNC:7637] |
| ENSG00000187689 | AMTN | amelotin [Source:HGNC Symbol;Acc:HGNC:33188] |
| ENSG00000187990 | NA | NA |
| ENSG00000188060 | RAB42 | RAB42, member RAS oncogene family [Source:HGNC Symbol;Acc:HGNC:28702] |
| ENSG00000188536 | HBA2 | hemoglobin, alpha 2 [Source:HGNC Symbol;Acc:HGNC:4824] |
| ENSG00000189339 | SLC35E2B | solute carrier family 35, member E2B [Source:HGNC Symbol;Acc:HGNC:33941] |
| ENSG00000189403 | HMGB1 | high mobility group box 1 [Source:HGNC Symbol;Acc:HGNC:4983] |
| ENSG00000196116 | TDRD7 | tudor domain containing 7 [Source:HGNC Symbol;Acc:HGNC:30831] |
| ENSG00000196565 | HBG2 | hemoglobin, gamma G [Source:HGNC Symbol;Acc:HGNC:4832] |
| ENSG00000196782 | MAML3 | mastermind-like 3 (*Drosophila*) [Source:HGNC Symbol;Acc:HGNC:16272] |
| ENSG00000197170 | PSMD12 | proteasome (prosome, macropain) 26S subunit, non-ATPase, 12 [Source:HGNC Symbol;Acc:HGNC:9557] |
| ENSG00000197417 | SHPK | sedoheptulokinase [Source:HGNC Symbol;Acc:HGNC:1492] |
| ENSG00000197568 | HHLA3 | HERV-H LTR-associating 3 [Source:HGNC Symbol;Acc:HGNC:4906] |
| ENSG00000197753 | LHFPL5 | lipoma HMGIC fusion partner-like 5 [Source:HGNC Symbol;Acc:HGNC:21253] |
| ENSG00000198466 | ZNF587 | zinc finger protein 587 [Source:HGNC Symbol;Acc:HGNC:30955] |
| ENSG00000198478 | SH3BGRL2 | SH3 domain binding glutamate-rich protein like 2 [Source:HGNC Symbol;Acc:HGNC:15567] |
| ENSG00000198682 | PAPSS2 | 3'-phosphoadenosine 5'-phosphosulfate synthase 2 [Source:HGNC Symbol;Acc:HGNC:8604] |
| ENSG00000198712 | MT-CO2 | mitochondrially encoded cytochrome c oxidase II [Source:HGNC Symbol;Acc:HGNC:7421] |
| ENSG00000198787 | OR4D12P | olfactory receptor, family 4, subfamily D, member 12 pseudogene [Source:HGNC Symbol;Acc:HGNC:19587] |
| ENSG00000198818 | SFT2D1 | SFT2 domain containing 1 [Source:HGNC Symbol;Acc:HGNC:21102] |
| ENSG00000198829 | SUCNR1 | succinate receptor 1 [Source:HGNC Symbol;Acc:HGNC:4542] |
| ENSG00000198840 | MT-ND3 | mitochondrially encoded NADH dehydrogenase 3 [Source:HGNC Symbol;Acc:HGNC:7458] |
| ENSG00000198938 | MT-CO3 | mitochondrially encoded cytochrome c oxidase III [Source:HGNC Symbol;Acc:HGNC:7422] |
| ENSG00000199287 | NA | NA |
| ENSG00000199470 | | Small nucleolar RNA SNORA64/SNORA10 family [Source:RFAM;Acc:RF00264] |
| ENSG00000200492 | | Small nucleolar RNA U3 [Source:RFAM;Acc:RF00012] |
| ENSG00000200510 | NA | NA |
| ENSG00000200702 | | Y RNA [Source:RFAM;Acc:RF00019] |
| ENSG00000200753 | | Small nucleolar RNA SNORD56 [Source:RFAM;Acc:RF00275] |
| ENSG00000200783 | RN7SKP180 | RNA, 7SK small nuclear pseudogene 180 [Source:HGNC Symbol;Acc:HGNC:45904] |
| ENSG00000201271 | RNU1-112P | RNA, U1 small nuclear 112, pseudogene [Source:HGNC Symbol;Acc:HGNC:48454] |

TABLE 1-continued

| Ensembl ID | Hgnc symbol | Description |
|---|---|---|
| ENSG00000201955 | RNY3P1 | RNA, Ro-associated Y3 pseudogene 1 [Source:HGNC Symbol;Acc:HGNC:42477] |
| ENSG00000203426 | NA | NA |
| ENSG00000203691 | NA | NA |
| ENSG00000203849 | NA | NA |
| ENSG00000204250 | LINC00587 | long intergenic non-protein coding RNA 587 [Source:HGNC Symbol;Acc:HGNC:31372] |
| ENSG00000204310 | AGPAT1 | 1-acylglycerol-3-phosphate O-acyltransferase 1 [Source:HGNC Symbol;Acc:HGNC:324] |
| ENSG00000204389 | HSPA1A | heat shock 70 kDa protein 1A [Source:HGNC Symbol;Acc:HGNC:5232] |
| ENSG00000206053 | HN1L | hematological and neurological expressed 1-like [Source:HGNC Symbol;Acc:HGNC:14137] |
| ENSG00000206637 | | Small nucleolar RNA SNORA70 [Source:RFAM;Acc:RF00156] |
| ENSG00000206848 | RNU6-890P | RNA, U6 small nuclear 890, pseudogene [Source:HGNC Symbol;Acc:HGNC:47853] |
| ENSG00000207712 | MIR627 | microRNA 627 [Source:HGNC Symbol;Acc:HGNC:32883] |
| ENSG00000209082 | MT-TL1 | mitochondrially encoded tRNA leucine 1 (UUA/G) [Source:HGNC Symbol;Acc:HGNC:7490] |
| ENSG00000210049 | MT-TF | mitochondrially encoded tRNA phenylalanine [Source:HGNC Symbol;Acc:HGNC:7481] |
| ENSG00000210077 | MT-TV | mitochondrially encoded tRNA valine [Source:HGNC Symbol;Acc:HGNC:7500] |
| ENSG00000210107 | MT-TQ | mitochondrially encoded tRNA glutamine [Source:HGNC Symbol;Acc:HGNC:7495] |
| ENSG00000210140 | MT-TC | mitochondrially encoded tRNA cysteine [Source:HGNC Symbol;Acc:HGNC:7477] |
| ENSG00000210156 | MT-TK | mitochondrially encoded tRNA lysine [Source:HGNC Symbol;Acc:HGNC:7489] |
| ENSG00000210176 | MT-TH | mitochondrially encoded tRNA histidine [Source:HGNC Symbol;Acc:HGNC:7487] |
| ENSG00000210191 | MT-TL2 | mitochondrially encoded tRNA leucine 2 (CUN) [Source:HGNC Symbol;Acc:HGNC:7491] |
| ENSG00000210194 | MT-TE | mitochondrially encoded tRNA glutamic acid [Source:HGNC Symbol;Acc:HGNC:7479] |
| ENSG00000210195 | MT-TT | mitochondrially encoded tRNA threonine [Source:HGNC Symbol;Acc:HGNC:7499] |
| ENSG00000210196 | MT-TP | mitochondrially encoded tRNA proline [Source:HGNC Symbol;Acc:HGNC:7494] |
| ENSG00000211538 | MIR501 | microRNA 501 [Source:HGNC Symbol;Acc:HGNC:32135] |
| ENSG00000211967 | IGHV3-53 | immunoglobulin heavy variable 3-53 [Source:HGNC Symbol;Acc:HGNC:5610] |
| ENSG00000212338 | | Small nucleolar RNA SNORA67 [Source:RFAM;Acc:RF00272] |
| ENSG00000212564 | RNU6-1326P | RNA, U6 small nuclear 1326, pseudogene [Source:HGNC Symbol;Acc:HGNC:48289] |
| ENSG00000213014 | VN2R17P | vomeronasal 2 receptor 17 pseudogene [Source:HGNC Symbol;Acc:HGNC:33223] |
| ENSG00000213023 | SYT3 | synaptotagmin III [Source:HGNC Symbol;Acc:HGNC:11511] |
| ENSG00000213048 | OR5S1P | olfactory receptor, family 5, subfamily S, member 1 pseudogene [Source:HGNC Symbol;Acc:HGNC:15040] |
| ENSG00000213144 | | |
| ENSG00000213401 | MAGEA12 | melanoma antigen family A, 12 [Source:HGNC Symbol;Acc:HGNC:6799] |
| ENSG00000213516 | RBMXL1 | RNA binding motif protein, X-linked-like 1 [Source:HGNC Symbol;Acc:HGNC:25073] |
| ENSG00000213626 | LBH | limb bud and heart development [Source:HGNC Symbol;Acc:HGNC:29532] |
| ENSG00000214049 | UCA1 | urothelial cancer associated 1 (non-protein coding) [Source:HGNC Symbol;Acc:HGNC:37126] |
| ENSG00000215030 | RPL13P12 | ribosomal protein L13 pseudogene 12 [Source:HGNC Symbol;Acc:HGNC:35701] |
| ENSG00000215089 | KRT18P11 | keratin 18 pseudogene 11 [Source:HGNC Symbol;Acc:HGNC:6431] |
| ENSG00000215271 | HOMEZ | homeobox and leucine zipper encoding [Source:HGNC Symbol;Acc:HGNC:20164] |
| ENSG00000215834 | FMO9P | flavin containing monooxygenase 9 pseudogene [Source:HGNC Symbol;Acc:HGNC:32210] |
| ENSG00000217557 | | |
| ENSG00000219188 | CACYBPP3 | calcyclin binding protein pseudogene 3 [Source:HGNC Symbol;Acc:HGNC:45124] |
| ENSG00000219368 | ZNF299P | zinc finger protein 299, pseudogene [Source:HGNC Symbol;Acc:HGNC:13088] |
| ENSG00000220505 | EIF4EBP2P3 | eukaryotic translation initiation factor 4E binding protein 2 pseudogene 3 [Source:HGNC Symbol;Acc:HGNC:49318] |

TABLE 1-continued

| Ensembl ID | Hgnc symbol | Description |
|---|---|---|
| ENSG00000221083 | | Small nucleolar RNA SNORA77 [Source:RFAM;Acc:RF00599] |
| ENSG00000221096 | NA | NA |
| ENSG00000221291 | | |
| ENSG00000222036 | POTEG | POTE ankyrin domain family, member G [Source:HGNC Symbol;Acc:HGNC:33896] |
| ENSG00000222524 | RN7SKP109 | RNA, 7SK small nuclear pseudogene 109 [Source:HGNC Symbol;Acc:HGNC:45833] |
| ENSG00000223026 | RN7SKP247 | RNA, 7SK small nuclear pseudogene 247 [Source:HGNC Symbol;Acc:HGNC:45971] |
| ENSG00000223554 | | |
| ENSG00000223783 | | |
| ENSG00000223881 | | |
| ENSG00000224288 | | |
| ENSG00000224418 | STK24-AS1 | STK24 antisense RNA 1 [Source:HGNC Symbol;Acc:HGNC:39935] |
| ENSG00000224618 | | |
| ENSG00000224924 | LINC00320 | long intergenic non-protein coding RNA 320 [Source:HGNC Symbol;Acc:HGNC:19690] |
| ENSG00000225112 | | |
| ENSG00000225181 | | |
| ENSG00000225216 | | |
| ENSG00000225630 | MTND2P28 | MT-ND2 pseudogene 28 [Source:HGNC Symbol;Acc:HGNC:42129] |
| ENSG00000225785 | | |
| ENSG00000225906 | | |
| ENSG00000225972 | MTND1P23 | MT-ND1 pseudogene 23 [Source:HGNC Symbol;Acc:HGNC:42092] |
| ENSG00000226104 | NA | NA |
| ENSG00000226272 | ARHGAP26-AS1 | ARHGAP26 antisense RNA 1 [Source:HGNC Symbol;Acc:HGNC:40792] |
| ENSG00000226659 | | |
| ENSG00000226801 | OSTCP8 | oligosaccharyltransferase complex subunit pseudogene 8 [Source:HGNC Symbol;Acc:HGNC:42869] |
| ENSG00000226939 | | |
| ENSG00000226981 | ABHD17AP6 | abhydrolase domain containing 17A pseudogene 6 [Source:HGNC Symbol;Acc:HGNC:34044] |
| ENSG00000227011 | C17orf112 | chromosome 17 open reading frame 112 [Source:HGNC Symbol;Acc:HGNC:42963] |
| ENSG00000227159 | DDX11L16 | DEAD/H (Asp-Glu-Ala-Asp/His) box helicase 11 like 16 [Source:HGNC Symbol;Acc:HGNC:37115] |
| ENSG00000227274 | | |
| ENSG00000227438 | | |
| ENSG00000227468 | | |
| ENSG00000227593 | | |
| ENSG00000227676 | LINC01068 | long intergenic non-protein coding RNA 1068 [Source:HGNC Symbol;Acc:HGNC:49106] |
| ENSG00000227790 | | |
| ENSG00000227970 | NR1H5P | nuclear receptor subfamily 1, group H, member 5, pseudogene [Source:HGNC Symbol;Acc:HGNC:32673] |
| ENSG00000228253 | MT-ATP8 | mitochondrially encoded ATP synthase 8 [Source:HGNC Symbol;Acc:HGNC:7415] |
| ENSG00000228513 | | |
| ENSG00000228648 | | |
| ENSG00000229031 | | |
| ENSG00000229196 | | |
| ENSG00000229338 | | |
| ENSG00000229344 | | |
| ENSG00000229485 | KSR1P1 | kinase suppressor of ras 1 pseudogene 1 [Source:HGNC Symbol;Acc:HGNC:44977] |
| ENSG00000229775 | | |
| ENSG00000230019 | YWHAQP9 | YWHAQ pseudogene 9 [Source:HGNC Symbol;Acc:HGNC:37688] |
| ENSG00000230022 | FNTAP2 | farnesyltransferase, CAAX box, alpha pseudogene 2 [Source:HGNC Symbol;Acc:HGNC:3784] |
| ENSG00000230495 | | |
| ENSG00000230515 | | |
| ENSG00000230528 | NOS2P3 | nitric oxide synthase 2 pseudogene 3 [Source:HGNC Symbol;Acc:HGNC:35124] |
| ENSG00000230589 | IMP3P1 | IMP3 pseudogene 1 [Source:HGNC Symbol;Acc:HGNC:49385] |
| ENSG00000230645 | | |
| ENSG00000230867 | | |
| ENSG00000231680 | | |
| ENSG00000231682 | | |
| ENSG00000231957 | GNAI2P2 | guanine nucleotide binding protein (G protein), alpha inhibiting activity polypeptide 2 pseudogene 2 [Source:HGNC Symbol;Acc:HGNC:45110] |
| ENSG00000232111 | | |
| ENSG00000232120 | | |
| ENSG00000232491 | | |
| ENSG00000232578 | | |
| ENSG00000232650 | | |

TABLE 1-continued

| Ensembl ID | Hgnc symbol | Description |
|---|---|---|
| ENSG00000233265 | MICF | MHC class I polypeptide-related sequence F (pseudogene) [Source:HGNC Symbol;Acc:HGNC:16801] |
| ENSG00000233545 | CYCSP33 | cytochrome c, somatic pseudogene 33 [Source:HGNC Symbol;Acc:HGNC:24407] |
| ENSG00000233614 | DDX11L10 | DEAD/H (Asp-Glu-Ala-Asp/His) box helicase 11 like 10 [Source:HGNC Symbol;Acc:HGNC:14125] |
| ENSG00000233643 | | |
| ENSG00000234113 | | |
| ENSG00000234420 | ZNF37BP | zinc finger protein 37B, pseudogene [Source:HGNC Symbol;Acc:HGNC:13103] |
| ENSG00000234456 | MAGI2-AS3 | MAGI2 antisense RNA 3 [Source:HGNC Symbol;Acc:HGNC:40862] |
| ENSG00000234619 | RPL7P11 | ribosomal protein L7 pseudogene 11 [Source:HGNC Symbol;Acc:HGNC:35667] |
| ENSG00000234683 | | |
| ENSG00000234713 | | |
| ENSG00000234723 | | |
| ENSG00000234724 | HDAC1P1 | histone deacetylase 1 pseudogene 1 [Source:HGNC Symbol;Acc:HGNC:45190] |
| ENSG00000234975 | FTH1P2 | ferritin, heavy polypeptide 1 pseudogene 2 [Source:HGNC Symbol;Acc:HGNC:3989] |
| ENSG00000235147 | | |
| ENSG00000235154 | | |
| ENSG00000235186 | | |
| ENSG00000235902 | | |
| ENSG00000235938 | NA | NA |
| ENSG00000236090 | LDHAP3 | lactate dehydrogenase A pseudogene 3 [Source:HGNC Symbol;Acc:HGNC:6538] |
| ENSG00000236852 | | |
| ENSG00000236876 | TMSB4XP1 | thymosin beta 4, X-linked pseudogene 1 [Source:HGNC Symbol;Acc:HGNC:11883] |
| ENSG00000237256 | PGAM3P | phosphoglycerate mutase 3, pseudogene [Source:HGNC Symbol;Acc:HGNC:16557] |
| ENSG00000237356 | | |
| ENSG00000237621 | OR9A1P | olfactory receptor, family 9, subfamily A, member 1 pseudogene [Source:HGNC Symbol;Acc:HGNC:8486] |
| ENSG00000237731 | RNGTTP1 | RNA guanylyltransferase and 5'-phosphatase pseudogene 1 [Source:HGNC Symbol;Acc:HGNC:39652] |
| ENSG00000237973 | MIR6723 | microRNA 6723 [Source:HGNC Symbol;Acc:HGNC:50152] |
| ENSG00000238083 | LRRC37A2 | leucine rich repeat containing 37, member A2 [Source:HGNC Symbol;Acc:HGNC:32404] |
| ENSG00000238460 | | |
| ENSG00000238617 | NA | NA |
| ENSG00000238754 | | Small nucleolar RNA U109 [Source:RFAM;Acc:RF01233] |
| ENSG00000238763 | NA | NA |
| ENSG00000238858 | NA | NA |
| ENSG00000239011 | NA | NA |
| ENSG00000239072 | NA | NA |
| ENSG00000239073 | NA | NA |
| ENSG00000239547 | RN7SL843P | RNA, 7SL, cytoplasmic 843, pseudogene [Source:HGNC Symbol;Acc:HGNC:46859] |
| ENSG00000239617 | | |
| ENSG00000239791 | | |
| ENSG00000240286 | MEAF6P1 | MYST/Esa1-associated factor 6 pseudogene 1 [Source:HGNC Symbol;Acc:HGNC:42660] |
| ENSG00000240545 | RN7SL492P | RNA, 7SL, cytoplasmic 492, pseudogene [Source:HGNC Symbol;Acc:HGNC:46508] |
| ENSG00000240808 | | |
| ENSG00000241468 | ATP5J2 | ATP synthase, H+ transporting, mitochondrial Fo complex, subunit F2 [Source:HGNC Symbol;Acc:HGNC:848] |
| ENSG00000241656 | UBA52P7 | ubiquitin A-52 residue ribosomal protein fusion product 1 pseudogene 7 [Source:HGNC Symbol;Acc:HGNC:36615] |
| ENSG00000241757 | RN7SL714P | RNA, 7SL, cytoplasmic 714, pseudogene [Source:HGNC Symbol;Acc:HGNC:46730] |
| ENSG00000241945 | PWP2 | PWP2 periodic tryptophan protein homolog (yeast) [Source:HGNC Symbol;Acc:HGNC:9711] |
| ENSG00000241954 | | |
| ENSG00000242716 | NA | NA |
| ENSG00000243136 | RN7SL22P | RNA, 7SL, cytoplasmic 22, pseudogene [Source:HGNC Symbol;Acc:HGNC:46038] |
| ENSG00000243290 | IGKV1-12 | immunoglobulin kappa variable 1-12 [Source:HGNC Symbol;Acc:HGNC:5730] |
| ENSG00000243370 | RN7SL775P | RNA, 7SL, cytoplasmic 775, pseudogene [Source:HGNC Symbol;Acc:HGNC:46791] |
| ENSG00000243824 | | |
| ENSG00000244414 | CFHR1 | complement factor H-related 1 [Source:HGNC Symbol;Acc:HGNC:4888] |

TABLE 1-continued

| Ensembl ID | Hgnc symbol | Description |
|---|---|---|
| ENSG00000244734 | HBB | hemoglobin, beta [Source:HGNC Symbol;Acc:HGNC:4827] |
| ENSG00000244921 | | |
| ENSG00000248360 | LINC00504 | long intergenic non-protein coding RNA 504 [Source:HGNC Symbol;Acc:HGNC:43555] |
| ENSG00000248538 | | |
| ENSG00000248891 | | |
| ENSG00000248898 | | |
| ENSG00000249072 | | |
| ENSG00000249307 | LINC01088 | long intergenic non-protein coding RNA 1088 [Source:HGNC Symbol;Acc:HGNC:49148] |
| ENSG00000249429 | | |
| ENSG00000249465 | RBMXP4 | RNA binding motif protein, X-linked pseudogene 4 [Source:HGNC Symbol;Acc:HGNC:34028] |
| ENSG00000249941 | | |
| ENSG00000250067 | YJEFN3 | YjeF N-terminal domain containing 3 [Source:HGNC Symbol;Acc:HGNC:24785] |
| ENSG00000250256 | | |
| ENSG00000250347 | | |
| ENSG00000250360 | | |
| ENSG00000250392 | | |
| ENSG00000250461 | | |
| ENSG00000250508 | | |
| ENSG00000250519 | | |
| ENSG00000250612 | | |
| ENSG00000250770 | | |
| ENSG00000251062 | | |
| ENSG00000251354 | | |
| ENSG00000251751 | RN7SKP46 | RNA, 7SK small nuclear pseudogene 46 [Source:HGNC Symbol;Acc:HGNC:45770] |
| ENSG00000251983 | RN7SKP157 | RNA, 7SK small nuclear pseudogene 157 [Source:HGNC Symbol;Acc:HGNC:45881] |
| ENSG00000252164 | RNA5SP282 | RNA, 5S ribosomal pseudogene 282 [Source:HGNC Symbol;Acc:HGNC:43182] |
| ENSG00000252180 | NA | NA |
| ENSG00000252343 | RNU2-34P | RNA, U2 small nuclear 34, pseudogene [Source:HGNC Symbol;Acc:HGNC:48527] |
| ENSG00000252497 | RPPH1-2P | ribonuclease P RNA component H1, 2 pseudogene [Source:HGNC Symbol;Acc:HGNC:47029] |
| ENSG00000252596 | NA | NA |
| ENSG00000252670 | NA | NA |
| ENSG00000252672 | NA | NA |
| ENSG00000252863 | RNU6-1183P | RNA, U6 small nuclear 1183, pseudogene [Source:HGNC Symbol;Acc:HGNC:48146] |
| ENSG00000252904 | | Small nucleolar RNA SNORA76 [Source:RFAM;Acc:RF00598] |
| ENSG00000253008 | MIR2355 | microRNA 2355 [Source:HGNC Symbol;Acc:HGNC:38328] |
| ENSG00000253377 | | |
| ENSG00000253603 | | |
| ENSG00000253729 | PRKDC | protein kinase, DNA-activated, catalytic polypeptide [Source:HGNC Symbol;Acc:HGNC:9413] |
| ENSG00000253780 | IGHVIII-2-1 | immunoglobulin heavy variable (III)-2-1 (pseudogene) [Source:HGNC Symbol;Acc:HGNC:5695] |
| ENSG00000253784 | | |
| ENSG00000253849 | | |
| ENSG00000254070 | | |
| ENSG00000254273 | | |
| ENSG00000254683 | SNRPCP6 | small nuclear ribonucleoprotein polypeptide C pseudogene 6 [Source:HGNC Symbol;Acc:HGNC:49821] |
| ENSG00000254845 | NA | NA |
| ENSG00000255003 | CYCSP28 | cytochrome c, somatic pseudogene 28 [Source:HGNC Symbol;Acc:HGNC:24402] |
| ENSG00000255031 | | |
| ENSG00000255408 | PCDHA3 | protocadherin alpha 3 [Source:HGNC Symbol;Acc:HGNC:8669] |
| ENSG00000256257 | CACNA1C-IT2 | CACNA1C intronic transcript 2 (non-protein coding) [Source:HGNC Symbol;Acc:HGNC:41313] |
| ENSG00000256972 | | |
| ENSG00000257004 | | |
| ENSG00000257519 | | |
| ENSG00000257723 | CHCHD3P2 | coiled-coil-helix-coiled-coil-helix domain containing 3 pseudogene 2 [Source:HGNC Symbol;Acc:HGNC:44698] |
| ENSG00000257777 | | |
| ENSG00000257915 | GLULP5 | glutamate-ammonia ligase (glutamine synthetase) pseudogene 5 [Source:HGNC Symbol;Acc:HGNC:37989] |
| ENSG00000258088 | | |
| ENSG00000258273 | | |
| ENSG00000258642 | | |
| ENSG00000258790 | KIAA0391 | KIAA0391 [Source:HGNC Symbol;Acc:HGNC:19958] |

TABLE 1-continued

| Ensembl ID | Hgnc symbol | Description |
|---|---|---|
| ENSG00000258828 | KRT8P2 | keratin 8 pseudogene 2 [Source:HGNC Symbol;Acc:HGNC:20282] |
| ENSG00000258845 | | |
| ENSG00000259045 | | |
| ENSG00000259047 | | |
| ENSG00000259145 | NA | NA |
| ENSG00000259411 | HNRNPA1P45 | heterogeneous nuclear ribonucleoprotein A1 pseudogene 45 [Source:HGNC Symbol;Acc:HGNC:48775] |
| ENSG00000259418 | | |
| ENSG00000259479 | SORD2P | sorbitol dehydrogenase 2, pseudogene [Source:HGNC Symbol;Acc:HGNC:49919] |
| ENSG00000259588 | | |
| ENSG00000259604 | | |
| ENSG00000259761 | | |
| ENSG00000259802 | | |
| ENSG00000260198 | | |
| ENSG00000260229 | | |
| ENSG00000260282 | EIF4EBP2P2 | eukaryotic translation initiation factor 4E binding protein 2 pseudogene 2 [Source:HGNC Symbol;Acc:HGNC:49317] |
| ENSG00000261340 | | |
| ENSG00000261665 | TUBA8P2 | tubulin, alpha 8 pseudogene 2 [Source:HGNC Symbol;Acc:HGNC:44569] |
| ENSG00000263253 | | |
| ENSG00000263435 | | |
| ENSG00000263493 | NA | NA |
| ENSG00000263542 | | |
| ENSG00000263740 | RN7SL4P | RNA, 7SL, cytoplasmic 4, pseudogene [Source:HGNC Symbol;Acc:HGNC:10039] |
| ENSG00000263774 | | |
| ENSG00000263929 | NA | NA |
| ENSG00000264235 | | |
| ENSG00000264296 | | |
| ENSG00000264386 | MIR4513 | microRNA 4513 [Source:HGNC Symbol;Acc:HGNC:41855] |
| ENSG00000264439 | | |
| ENSG00000264469 | | |
| ENSG00000264910 | RN7SL525P | RNA, 7SL, cytoplasmic 525, pseudogene [Source:HGNC Symbol;Acc:HGNC:46541] |
| ENSG00000265334 | | |
| ENSG00000265408 | | |
| ENSG00000265565 | MIR3143 | microRNA 3143 [Source:HGNC Symbol;Acc:HGNC:38284] |
| ENSG00000265946 | | |
| ENSG00000266187 | RN7SL480P | RNA, 7SL, cytoplasmic 480, pseudogene [Source:HGNC Symbol;Acc:HGNC:46496] |
| ENSG00000266399 | | |
| ENSG00000266596 | NA | NA |
| ENSG00000266603 | NA | NA |
| ENSG00000266667 | | |
| ENSG00000266941 | | |
| ENSG00000267513 | | |
| ENSG00000267650 | | |
| ENSG00000267670 | | |
| ENSG00000268230 | | |
| ENSG00000268357 | VN1R81P | vomeronasal 1 receptor 81 pseudogene [Source:HGNC Symbol;Acc:HGNC:37401] |
| ENSG00000268995 | VN1R82P | vomeronasal 1 receptor 82 pseudogene [Source:HGNC Symbol;Acc:HGNC:37402] |
| ENSG00000269028 | MTRNR2L12 | MT-RNR2-like 12 [Source:HGNC Symbol;Acc:HGNC:37169] |
| ENSG00000269069 | | |
| ENSG00000270371 | | |
| ENSG00000270377 | | |
| ENSG00000270457 | | |
| ENSG00000270496 | BNIP3P7 | BCL2/adenovirus E1B 19 kDa interacting protein 3 pseudogene 7 [Source:HGNC Symbol;Acc:HGNC:49101] |
| ENSG00000270680 | | |
| ENSG00000270683 | FAM71BP1 | family with sequence similarity 71, member B pseudogene 1 [Source:HGNC Symbol;Acc:HGNC:49805] |
| ENSG00000270798 | | |
| ENSG00000271361 | HTATSF1P2 | HIV-1 Tat specific factor 1 pseudogene 2 [Source:HGNC Symbol;Acc:HGNC:38586] |
| ENSG00000271415 | | |
| ENSG00000272468 | | |
| ENSG00000272626 | | |
| ENSG00000273154 | | |

TABLE 2

All biological sample sources collected in year 1: blood, urine, and saliva

| Ensembl_ID | HGNC_symbol | Description |
| --- | --- | --- |
| ENSG00000178172 | SPINK6 | serine peptidase inhibitor, Kazal type 6 [Source:HGNC Symbol;Acc:HGNC:29486] |
| ENSG00000204566 | C10orf115 | chromosome 10 open reading frame 115 [Source:HGNC Symbol;Acc:HGNC:31449] |
| ENSG00000223881 | | |
| ENSG00000237027 | | |
| ENSG00000243075 | RN7SL519P | RNA, 7SL, cytoplasmic 519, pseudogene [Source:HGNC Symbol;Acc:HGNC:46535] |
| ENSG00000256721 | CACNA1C-IT3 | CACNA1C intronic transcript 3 (non-protein coding) [Source:HGNC Symbol;Acc:HGNC:41314] |
| ENSG00000268280 | NA | NA |
| ENSG00000273185 | | |
| ENSG00000260265 | | |
| ENSG00000256915 | | |
| ENSG00000236559 | | |
| ENSG00000258406 | | |
| ENSG00000212297 | RNU6-821P | RNA, U6 small nuclear 821, pseudogene [Source:HGNC Symbol;Acc:HGNC:47784] |
| ENSG00000230140 | | |
| ENSG00000068366 | ACSL4 | acyl-CoA synthetase long-chain family member 4 [Source:HGNC Symbol;Acc:HGNC:3571] |
| ENSG00000175879 | HOXD8 | homeobox D8 [Source:HGNC Symbol;Acc:HGNC:5139] |
| ENSG00000210194 | MT-TE | mitochondrially encoded tRNA glutamic acid [Source:HGNC Symbol;Acc:HGNC:7479] |
| ENSG00000206652 | RNU1-1 | RNA, U1 small nuclear 1 [Source:HGNC Symbol;Acc:HGNC:10120] |
| ENSG00000219074 | SOD1P1 | superoxide dismutase 1, soluble pseudogene 1 [Source:HGNC Symbol;Acc:HGNC:45134] |
| ENSG00000232833 | NA | NA |
| ENSG00000270878 | | |
| ENSG00000234629 | WDR82P1 | WD repeat domain 82 pseudogene 1 [Source:HGNC Symbol;Acc:HGNC:32447] |
| ENSG00000236641 | | |
| ENSG00000206172 | HBA1 | hemoglobin, alpha 1 [Source:HGNC Symbol;Acc:HGNC:4823] |
| ENSG00000228857 | | |
| ENSG00000257718 | | |
| ENSG00000253759 | IGHV3-57 | immunoglobulin heavy variable 3-57 (pseudogene) [Source:HGNC Symbol;Acc:HGNC:5612] |
| ENSG00000259770 | | |
| ENSG00000264280 | NA | NA |
| ENSG00000200087 | SNORA73B | small nucleolar RNA, H/ACA box 73B [Source:HGNC Symbol;Acc:HGNC:10116] |
| ENSG00000206634 | SNORA22 | small nucleolar RNA, H/ACA box 22 [Source:HGNC Symbol;Acc:HGNC:32612] |
| ENSG00000239002 | SCARNA10 | small Cajal body-specific RNA 10 [Source:HGNC Symbol;Acc:HGNC:32567] |
| ENSG00000185640 | KRT79 | keratin 79 [Source:HGNC Symbol;Acc:HGNC:28930] |
| ENSG00000184261 | KCNK12 | potassium channel, subfamily K, member 12 [Source:HGNC Symbol;Acc:HGNC:6274] |
| ENSG00000237181 | | |
| ENSG00000222040 | NA | NA |
| ENSG00000168993 | CPLX1 | complexin 1 [Source:HGNC Symbol;Acc:HGNC:2309] |
| ENSG00000169683 | LRRC45 | leucine rich repeat containing 45 [Source:HGNC Symbol;Acc:HGNC:28302] |
| ENSG00000258991 | DUX4L19 | double homeobox 4 like 19 [Source:HGNC Symbol;Acc:HGNC:37718] |
| ENSG00000196911 | KPNA5 | karyopherin alpha 5 (importin alpha 6) [Source:HGNC Symbol;Acc:HGNC:6398] |
| ENSG00000171612 | SLC25A33 | solute carrier family 25 (pyrimidine nucleotide carrier), member 33 [Source:HGNC Symbol;Acc:HGNC:29681] |
| ENSG00000265933 | LINC00668 | long intergenic non-protein coding RNA 668 [Source:HGNC Symbol;Acc:HGNC:44328] |
| ENSG00000154822 | PLCL2 | phospholipase C-like 2 [Source:HGNC Symbol;Acc:HGNC:9064] |
| ENSG00000109536 | FRG1 | FSHD region gene 1 [Source:HGNC Symbol;Acc:HGNC:3954] |
| ENSG00000047662 | FAM184B | family with sequence similarity 184, member B [Source:HGNC Symbol;Acc:HGNC:29235] |
| ENSG00000062524 | LTK | leukocyte receptor tyrosine kinase [Source:HGNC Symbol;Acc:HGNC:6721] |
| ENSG00000109680 | TBC1D19 | TBC1 domain family, member 19 [Source:HGNC Symbol;Acc:HGNC:25624] |
| ENSG00000112992 | NNT | nicotinamide nucleotide transhydrogenase [Source:HGNC Symbol;Acc:HGNC:7863] |
| ENSG00000119523 | ALG2 | ALG2, alpha-1,3/1,6-mannosyltransferase [Source:HGNC Symbol;Acc:HGNC:23159] |
| ENSG00000127990 | SGCE | sarcoglycan, epsilon [Source:HGNC Symbol;Acc:HGNC:10808] |

TABLE 2-continued

All biological sample sources collected in year 1: blood, urine, and saliva

| Ensembl_ID | HGNC_symbol | Description |
| --- | --- | --- |
| ENSG00000132825 | PPP1R3D | protein phosphatase 1, regulatory subunit 3D [Source:HGNC Symbol;Acc:HGNC:9294] |
| ENSG00000135637 | CCDC142 | coiled-coil domain containing 142 [Source:HGNC Symbol;Acc:HGNC:25889] |
| ENSG00000152465 | NMT2 | N-myristoyltransferase 2 [Source:HGNC Symbol;Acc:HGNC:7858] |
| ENSG00000160993 | ALKBH4 | alkB, alkylation repair homolog 4 (*E. coli*) [Source:HGNC Symbol;Acc:HGNC:21900] |
| ENSG00000164078 | MST1R | macrophage stimulating 1 receptor (c-met-related tyrosine kinase) [Source:HGNC Symbol;Acc:HGNC:7381] |
| ENSG00000167524 | | uncharacterized serine/threonine-protein kinase SgK494 [Source:EntrezGene;Acc:124923] |
| ENSG00000171243 | SOSTDC1 | sclerostin domain containing 1 [Source:HGNC Symbol;Acc:HGNC:21748] |
| ENSG00000173212 | MAB21L3 | mab-21-like 3 (*C. elegans*) [Source:HGNC Symbol;Acc:HGNC:26787] |
| ENSG00000177947 | ODF3 | outer dense fiber of sperm tails 3 [Source:HGNC Symbol;Acc:HGNC:19905] |
| ENSG00000196123 | KIAA0895L | KIAA0895-like [Source:HGNC Symbol;Acc:HGNC:34408] |
| ENSG00000223358 | EHHADH-AS1 | EHHADH antisense RNA 1 [Source:HGNC Symbol;Acc:HGNC:44133] |
| ENSG00000226742 | HSBP1L1 | heat shock factor binding protein 1-like 1 [Source:HGNC Symbol;Acc:HGNC:37243] |
| ENSG00000233393 | | |
| ENSG00000237037 | NDUFA6-AS1 | NDUFA6 antisense RNA 1 (head to head) [Source:HGNC Symbol;Acc:HGNC:45273] |
| ENSG00000255537 | | |
| ENSG00000258705 | | |
| ENSG00000157593 | SLC35B2 | solute carrier family 35 (adenosine 3'-phospho 5'-phosphosulfate transporter), member B2 [Source:HGNC Symbol;Acc:HGNC:16872] |
| ENSG00000160588 | MPZL3 | myelin protein zero-like 3 [Source:HGNC Symbol;Acc:HGNC:27279] |
| ENSG00000170044 | ZPLD1 | zona pellucida-like domain containing 1 [Source:HGNC Symbol;Acc:HGNC:27022] |
| ENSG00000198382 | UVRAG | UV radiation resistance associated [Source:HGNC Symbol;Acc:HGNC:12640] |
| ENSG00000131732 | ZCCHC9 | zinc finger, CCHC domain containing 9 [Source:HGNC Symbol;Acc:HGNC:25424] |
| ENSG00000141582 | CBX4 | chromobox homolog 4 [Source:HGNC Symbol;Acc:HGNC:1554] |
| ENSG00000162591 | MEGF6 | multiple EGF-like-domains 6 [Source:HGNC Symbol;Acc:HGNC:3232] |
| ENSG00000206149 | HERC2P9 | hect domain and RLD 2 pseudogene 9 [Source:HGNC Symbol;Acc:HGNC:30495] |
| ENSG00000070950 | RAD18 | RAD18 E3 ubiquitin protein ligase [Source:HGNC Symbol;Acc:HGNC:18278] |
| ENSG00000100299 | ARSA | arylsulfatase A [Source:HGNC Symbol;Acc:HGNC:713] |
| ENSG00000259959 | | |
| ENSG00000075336 | TIMM21 | translocase of inner mitochondrial membrane 21 homolog (yeast) [Source:HGNC Symbol;Acc:HGNC:25010] |
| ENSG00000088833 | NSFL1C | NSFL1 (p97) cofactor (p47) [Source:HGNC Symbol;Acc:HGNC:15912] |
| ENSG00000104756 | KCTD9 | potassium channel tetramerization domain containing 9 [Source:HGNC Symbol;Acc:HGNC:22401] |
| ENSG00000152763 | WDR78 | WD repeat domain 78 [Source:HGNC Symbol;Acc:HGNC:26252] |
| ENSG00000138346 | DNA2 | DNA replication helicase/nuclease 2 [Source:HGNC Symbol;Acc:HGNC:2939] |
| ENSG00000144909 | OSBPL11 | oxysterol binding protein-like 11 [Source:HGNC Symbol;Acc:HGNC:16397] |
| ENSG00000199237 | RNU6-834P | RNA, U6 small nuclear 834, pseudogene [Source:HGNC Symbol;Acc:HGNC:47797] |
| ENSG00000254014 | | |
| ENSG00000172201 | ID4 | inhibitor of DNA binding 4, dominant negative helix-loop-helix protein [Source:HGNC Symbol;Acc:HGNC:5363] |
| ENSG00000214772 | | |
| ENSG00000253469 | | |
| ENSG00000235858 | | |
| ENSG00000244060 | RPS2P41 | ribosomal protein S2 pseudogene 41 [Source:HGNC Symbol;Acc:HGNC:36357] |
| ENSG00000250535 | STK19B | serine/threonine kinase 19B, pseudogene [Source:HGNC Symbol;Acc:HGNC:21668] |
| ENSG00000120699 | EXOSC8 | exosome component 8 [Source:HGNC Symbol;Acc:HGNC:17035] |
| ENSG00000163577 | EIF5A2 | eukaryotic translation initiation factor 5A2 [Source:HGNC Symbol;Acc:HGNC:3301] |

TABLE 2-continued

All biological sample sources collected in year 1: blood, urine, and saliva

| Ensembl_ID | HGNC_symbol | Description |
|---|---|---|
| ENSG00000164114 | MAP9 | microtubule-associated protein 9 [Source:HGNC Symbol;Acc:HGNC:26118] |
| ENSG00000180708 | OR10K2 | olfactory receptor, family 10, subfamily K, member 2 [Source:HGNC Symbol;Acc:HGNC:14826] |
| ENSG00000221571 | RNU6ATAC35P | RNA, U6atac small nuclear 35, pseudogene [Source:HGNC Symbol;Acc:HGNC:46934] |
| ENSG00000226471 | | |
| ENSG00000228445 | UGT1A2P | UDP glucuronosyltransferase 1 family, polypeptide A2 pseudogene [Source:HGNC Symbol;Acc:HGNC:12534] |
| ENSG00000228695 | CES1P1 | carboxylesterase 1 pseudogene 1 [Source:HGNC Symbol;Acc:HGNC:18546] |
| ENSG00000229571 | PRAMEF26 | PRAME family member 26 [Source:HGNC Symbol;Acc:HGNC:49178] |
| ENSG00000230205 | | |
| ENSG00000251634 | | |
| ENSG00000255040 | | |
| ENSG00000256660 | CLEC12B | C-type lectin domain family 12, member B [Source:HGNC Symbol;Acc:HGNC:31966] |
| ENSG00000270423 | | |
| ENSG00000272729 | | |
| ENSG00000223963 | PRKRIRP8 | protein-kinase, interferon-inducible double stranded RNA dependent inhibitor, repressor of (P58 repressor) pseudogene 8 [Source:HGNC Symbol;Acc:HGNC:39572] |
| ENSG00000259431 | THTPA | thiamine triphosphatase [Source:HGNC Symbol;Acc:HGNC:18987] |
| ENSG00000224682 | SOCS5P2 | suppressor of cytokine signaling 5 pseudogene 2 [Source:HGNC Symbol;Acc:HGNC:44598] |
| ENSG00000250437 | | |
| ENSG00000258590 | NBEAP1 | neurobeachin pseudogene 1 [Source:HGNC Symbol;Acc:HGNC:1007] |
| ENSG00000060762 | MPC1 | mitochondrial pyruvate carrier 1 [Source:HGNC Symbol;Acc:HGNC:21606] |
| ENSG00000120306 | CYSTM1 | cysteine-rich transmembrane module containing 1 [Source:HGNC Symbol;Acc:HGNC:30239] |
| ENSG00000164825 | DEFB1 | defensin, beta 1 [Source:HGNC Symbol;Acc:HGNC:2766] |
| ENSG00000165685 | TMEM52B | transmembrane protein 52B [Source:HGNC Symbol;Acc:HGNC:26438] |
| ENSG00000169344 | UMOD | uromodulin [Source:HGNC Symbol;Acc:HGNC:12559] |
| ENSG00000184908 | CLCNKB | chloride channel, voltage-sensitive Kb [Source:HGNC Symbol;Acc:HGNC:2027] |
| ENSG00000185275 | CD24P4 | CD24 molecule pseudogene 4 [Source:HGNC Symbol;Acc:HGNC:1649] |
| ENSG00000197061 | HIST1H4C | histone cluster 1, H4c [Source:HGNC Symbol;Acc:HGNC:4787] |
| ENSG00000205795 | CYS1 | cystin 1 [Source:HGNC Symbol;Acc:HGNC:18525] |
| ENSG00000210127 | MT-TA | mitochondrially encoded tRNA alanine [Source:HGNC Symbol;Acc:HGNC:7475] |
| ENSG00000269900 | RMRP | RNA component of mitochondrial RNA processing endoribonuclease [Source:HGNC Symbol;Acc:HGNC:10031] |
| ENSG00000270103 | RNU11 | RNA, U11 small nuclear [Source:HGNC Symbol;Acc:HGNC:10108] |
| ENSG00000104327 | CALB1 | calbindin 1, 28 kDa [Source:HGNC Symbol;Acc:HGNC:1434] |
| ENSG00000113889 | KNG1 | kininogen 1 [Source:HGNC Symbol;Acc:HGNC:6383] |
| ENSG00000107485 | GATA3 | GATA binding protein 3 [Source:HGNC Symbol;Acc:HGNC:4172] |
| ENSG00000008438 | PGLYRP1 | peptidoglycan recognition protein 1 [Source:HGNC Symbol;Acc:HGNC:8904] |
| ENSG00000105647 | PIK3R2 | phosphoinositide-3-kinase, regulatory subunit 2 (beta) [Source:HGNC Symbol;Acc:HGNC:8980] |
| ENSG00000116032 | GRIN3B | glutamate receptor, ionotropic, N-methyl-D-aspartate 3B [Source:HGNC Symbol;Acc:HGNC:16768] |
| ENSG00000122862 | SRGN | serglycin [Source:HGNC Symbol;Acc:HGNC:9361] |
| ENSG00000128645 | HOXD1 | homeobox D1 [Source:HGNC Symbol;Acc:HGNC:5132] |
| ENSG00000134809 | TIMM10 | translocase of inner mitochondrial membrane 10 homolog (yeast) [Source:HGNC Symbol;Acc:HGNC:11814] |
| ENSG00000138207 | RBP4 | retinol binding protein 4, plasma [Source:HGNC Symbol;Acc:HGNC:9922] |
| ENSG00000143546 | S100A8 | S100 calcium binding protein A8 [Source:HGNC Symbol;Acc:HGNC:10498] |
| ENSG00000160181 | TFF2 | trefoil factor 2 [Source:HGNC Symbol;Acc:HGNC:11756] |
| ENSG00000161992 | PRR35 | proline rich 35 [Source:HGNC Symbol;Acc:HGNC:14139] |
| ENSG00000163209 | SPRR3 | small proline-rich protein 3 [Source:HGNC Symbol;Acc:HGNC:11268] |
| ENSG00000164729 | SLC35G3 | solute carrier family 35, member G3 [Source:HGNC Symbol;Acc:HGNC:26848] |
| ENSG00000165799 | RNASE7 | ribonuclease, RNase A family, 7 [Source:HGNC Symbol;Acc:HGNC:19278] |

TABLE 2-continued

All biological sample sources collected in year 1: blood, urine, and saliva

| Ensembl_ID | HGNC_symbol | Description |
| --- | --- | --- |
| ENSG00000168746 | C20orf62 | chromosome 20 open reading frame 62 [Source:HGNC Symbol;Acc:HGNC:16195] |
| ENSG00000173915 | USMG5 | up-regulated during skeletal muscle growth 5 homolog (mouse) [Source:HGNC Symbol;Acc:HGNC:30889] |
| ENSG00000175197 | DDIT3 | DNA-damage-inducible transcript 3 [Source:HGNC Symbol;Acc:HGNC:2726] |
| ENSG00000175283 | DOLK | dolichol kinase [Source:HGNC Symbol;Acc:HGNC:23406] |
| ENSG00000176125 | UFSP1 | UFM1-specific peptidase 1 (non-functional) [Source:HGNC Symbol;Acc:HGNC:33821] |
| ENSG00000179751 | SYCN | syncollin [Source:HGNC Symbol;Acc:HGNC:18442] |
| ENSG00000181499 | OR6T1 | olfactory receptor, family 6, subfamily T, member 1 [Source:HGNC Symbol;Acc:HGNC:14848] |
| ENSG00000187186 | | HCG2040265, isoform CRA_a; Uncharacterized protein; cDNA FLJ50015 [Source:UniProtKB/TrEMBL;Acc:B7Z3J9] |
| ENSG00000187808 | SOWAHD | sosondowah ankyrin repeat domain family member D [Source:HGNC Symbol;Acc:HGNC:32960] |
| ENSG00000194297 | RNU1-75P | RNA, U1 small nuclear 75, pseudogene [Source:HGNC Symbol;Acc:HGNC:48417] |
| ENSG00000197674 | OR51C1P | olfactory receptor, family 51, subfamily C, member 1 pseudogene [Source:HGNC Symbol;Acc:HGNC:15191] |
| ENSG00000198518 | NA | NA |
| ENSG00000199212 | RNU105C | RNA, U105C small nucleolar [Source:HGNC Symbol;Acc:HGNC:10104] |
| ENSG00000199378 | | Y RNA [Source:RFAM;Acc:RF00019] |
| ENSG00000199536 | RNU6-315P | RNA, U6 small nuclear 315, pseudogene [Source:HGNC Symbol;Acc:HGNC:47278] |
| ENSG00000200131 | RN7SKP77 | RNA, 7SK small nuclear pseudogene 77 [Source:HGNC Symbol;Acc:HGNC:45801] |
| ENSG00000200408 | RNA5SP74 | RNA, 5S ribosomal pseudogene 74 [Source:HGNC Symbol;Acc:HGNC:42851] |
| ENSG00000201098 | RNY1 | RNA, Ro-associated Y1 [Source:HGNC Symbol;Acc:HGNC:10242] |
| ENSG00000201640 | RN7SKP28 | RNA, 7SK small nuclear pseudogene 28 [Source:HGNC Symbol;Acc:HGNC:45752] |
| ENSG00000201984 | | Y RNA [Source:RFAM;Acc:RF00019] |
| ENSG00000203616 | RHOT1P2 | ras homolog family member T1 pseudogene 2 [Source:HGNC Symbol;Acc:HGNC:37838] |
| ENSG00000204444 | APOM | apolipoprotein M [Source:HGNC Symbol;Acc:HGNC:13916] |
| ENSG00000204544 | MUC21 | mucin 21, cell surface associated [Source:HGNC Symbol;Acc:HGNC:21661 ] |
| ENSG00000205559 | CHKB-AS1 | CHKB antisense RNA 1 (head to head) [Source:HGNC Symbol;Acc:HGNC:40146] |
| ENSG00000207010 | RNU6-1295P | RNA, U6 small nuclear 1295, pseudogene [Source:HGNC Symbol;Acc:HGNC:48258] |
| ENSG00000212497 | RNA5SP465 | RNA, 5S ribosomal pseudogene 465 [Source:HGNC Symbol;Acc:HGNC:43365] |
| ENSG00000213343 | RPL21P18 | ribosomal protein L21 pseudogene 18 [Source:HGNC Symbol;Acc:HGNC:28362] |
| ENSG00000213871 | TAF9BP1 | TAF9B RNA polymerase II, TATA box binding protein (TBP)-associated factor, 31 kDa pseudogene 1 [Source:HGNC Symbol;Acc:HGNC:30687] |
| ENSG00000213896 | | |
| ENSG00000214070 | | |
| ENSG00000214381 | LINC00488 | long intergenic non-protein coding RNA 488 [Source:HGNC Symbol;Acc:HGNC:32675] |
| ENSG00000214759 | | |
| ENSG00000215043 | GLULP6 | glutamate-ammonia ligase (glutamine synthetase) pseudogene 6 [Source:HGNC Symbol;Acc:HGNC:37990] |
| ENSG00000215481 | BCRP3 | breakpoint cluster region pseudogene 3 [Source:HGNC Symbol;Acc:HGNC:1016] |
| ENSG00000216966 | | |
| ENSG00000218180 | SLC25A5P7 | solute carrier family 25 (mitochondrial carrier; adenine nucleotide translocator), member 5 pseudogene 7 [Source:HGNC Symbol;Acc:HGNC:513] |
| ENSG00000218803 | GSTM2P1 | glutathione S-transferase mu 2 (muscle) pseudogene 1 [Source:HGNC Symbol;Acc:HGNC:38009] |
| ENSG00000222281 | RN7SKP111 | RNA, 7SK small nuclear pseudogene 111 [Source:HGNC Symbol;Acc:HGNC:45835] |
| ENSG00000222460 | RN7SKP271 | RNA, 7SK small nuclear pseudogene 271 [Source:HGNC Symbol;Acc:HGNC:45995] |
| ENSG00000222678 | RN7SKP213 | RNA, 7SK small nuclear pseudogene 213 [Source:HGNC Symbol;Acc:HGNC:45937] |
| ENSG00000222985 | RNU2-14P | RNA, U2 small nuclear 14, pseudogene [Source:HGNC Symbol;Acc:HGNC:48507] |
| ENSG00000223581 | | |
| ENSG00000223916 | | |

TABLE 2-continued

All biological sample sources collected in year 1: blood, urine, and saliva

| Ensembl_ID | HGNC_symbol | Description |
|---|---|---|
| ENSG00000225770 | | |
| ENSG00000226403 | | |
| ENSG00000226868 | | |
| ENSG00000227401 | RPL37P1 | ribosomal protein L37 pseudogene 1 [Source:HGNC Symbol;Acc:HGNC:16337] |
| ENSG00000227415 | | |
| ENSG00000227646 | STEAP2-AS1 | STEAP2 antisense RNA 1 [Source:HGNC Symbol;Acc:HGNC:40820] |
| ENSG00000227704 | | |
| ENSG00000227818 | | |
| ENSG00000227864 | ARL5AP1 | ADP-ribosylation factor-like 5A pseudogene 1 [Source:HGNC Symbol;Acc:HGNC:43933] |
| ENSG00000228366 | | |
| ENSG00000228436 | | |
| ENSG00000229242 | | |
| ENSG00000229313 | | |
| ENSG00000229376 | CICP3 | capicua transcriptional repressor pseudogene 3 [Source:HGNC Symbol;Acc:HGNC:37742] |
| ENSG00000229925 | | |
| ENSG00000229932 | YWHAZP3 | tyrosine 3-monooxygenase/tryptophan 5-monooxygenase activation protein, zeta pseudogene 3 [Source:HGNC Symbol;Acc:HGNC:31101] |
| ENSG00000230696 | | |
| ENSG00000230706 | | |
| ENSG00000230710 | LINC00332 | long intergenic non-protein coding RNA 332 [Source:HGNC Symbol;Acc:HGNC:42049] |
| ENSG00000231937 | | |
| ENSG00000232015 | HSPE1P25 | heat shock 10 kDa protein 1 pseudogene 25 [Source:HGNC Symbol;Acc:HGNC:49344] |
| ENSG00000232464 | | |
| ENSG00000232524 | | |
| ENSG00000232658 | | |
| ENSG00000233558 | | |
| ENSG00000235573 | | |
| ENSG00000235578 | | |
| ENSG00000235942 | LCE6A | late cornified envelope 6A [Source:HGNC Symbol;Acc:HGNC:31824] |
| ENSG00000236209 | | |
| ENSG00000236751 | LINC01186 | long intergenic non-protein coding RNA 1186 [Source:HGNC Symbol;Acc:HGNC:49573] |
| ENSG00000236824 | BCYRN1 | brain cytoplasmic RNA 1 [Source:HGNC Symbol;Acc:HGNC:1022] |
| ENSG00000237213 | RPL23AP22 | ribosomal protein L23a pseudogene 22 [Source:HGNC Symbol;Acc:HGNC:35505] |
| ENSG00000237979 | | |
| ENSG00000237991 | RPL35P1 | ribosomal protein L35 pseudogene 1 [Source:HGNC Symbol;Acc:HGNC:36695] |
| ENSG00000238073 | RBMY2HP | RNA binding motif protein, Y-linked, family 2, member H pseudogene [Source:HGNC Symbol;Acc:HGNC:23893] |
| ENSG00000238337 | NA | NA |
| ENSG00000238609 | RNU7-94P | RNA, U7 small nuclear 94 pseudogene [Source:HGNC Symbol;Acc:HGNC:45628] |
| ENSG00000239126 | NA | NA |
| ENSG00000239183 | SNORA84 | small nucleolar RNA, H/ACA box 84 [Source:HGNC Symbol;Acc:HGNC:33615] |
| ENSG00000239196 | NA | NA |
| ENSG00000239272 | RPL21P10 | ribosomal protein L21 pseudogene 10 [Source:HGNC Symbol;Acc:HGNC:19795] |
| ENSG00000239542 | RN7SL399P | RNA, 7SL, cytoplasmic 399, pseudogene [Source:HGNC Symbol;Acc:HGNC:46415] |
| ENSG00000239857 | GET4 | golgi to ER traffic protein 4 homolog (*S. cerevisiae*) [Source:HGNC Symbol;Acc:HGNC:21690] |
| ENSG00000240803 | RN7SL231P | RNA, 7SL, cytoplasmic 231, pseudogene [Source:HGNC Symbol;Acc:HGNC:46247] |
| ENSG00000242229 | RPS3AP14 | ribosomal protein S3a pseudogene 14 [Source:HGNC Symbol;Acc:HGNC:35715] |
| ENSG00000243004 | | |
| ENSG00000243974 | VTI1BP1 | vesicle transport through interaction with t-SNAREs 1B pseudogene 1 [Source:HGNC Symbol;Acc:HGNC:43727] |
| ENSG00000244063 | | |
| ENSG00000244260 | | |
| ENSG00000244582 | RPL21P120 | ribosomal protein L21 pseudogene 120 [Source:HGNC Symbol;Acc:HGNC:35743] |
| ENSG00000248240 | | |
| ENSG00000248370 | | |

TABLE 2-continued

All biological sample sources collected in year 1: blood, urine, and saliva

| Ensembl_ID | HGNC_symbol | Description |
|---|---|---|
| ENSG00000248834 | MARK2P5 | MAP/microtubule affinity-regulating kinase 2 pseudogene 5 [Source:HGNC Symbol;Acc:HGNC:39796] |
| ENSG00000248890 | HHIP-AS1 | HHIP antisense RNA 1 [Source:HGNC Symbol;Acc:HGNC:44182] |
| ENSG00000249014 | HMGN2P4 | high mobility group nucleosomal binding domain 2 pseudogene 4 [Source:HGNC Symbol;Acc:HGNC:33567] |
| ENSG00000249256 | ATP5LP3 | ATP synthase, H+ transporting, mitochondrial Fo complex, subunit g, pseudogene 3 [Source:HGNC Symbol;Acc:HGNC:13216] |
| ENSG00000249942 | | |
| ENSG00000250120 | PCDHA10 | protocadherin alpha 10 [Source:HGNC Symbol;Acc:HGNC:8664] |
| ENSG00000250234 | | |
| ENSG00000250411 | | |
| ENSG00000251445 | | |
| ENSG00000251583 | | |
| ENSG00000252350 | RPPH1-3P | ribonuclease P RNA component HI, 3 pseudogene [Source:HGNC Symbol;Acc:HGNC:47030] |
| ENSG00000252376 | RNA5SP395 | RNA, 5S ribosomal pseudogene 395 [Source:HGNC Symbol;Acc:HGNC:43295] |
| ENSG00000252396 | RN7SKP195 | RNA, 7SK small nuclear pseudogene 195 [Source:HGNC Symbol;Acc:HGNC:45919] |
| ENSG00000252731 | | |
| ENSG00000253112 | | |
| ENSG00000253292 | MIOXP1 | myo-inositol oxygenase pseudogene 1 [Source:HGNC Symbol;Acc:HGNC:50748] |
| ENSG00000253560 | | |
| ENSG00000253597 | NA | NA |
| ENSG00000253882 | | |
| ENSG00000253892 | | |
| ENSG00000253920 | IGLV3-31 | immunoglobulin lambda variable 3-31 (pseudogene) [Source:HGNC Symbol;Acc:HGNC:5913] |
| ENSG00000254057 | | |
| ENSG00000254082 | | |
| ENSG00000254086 | | |
| ENSG00000254260 | | |
| ENSG00000254389 | RHPN1-AS1 | RHPN1 antisense RNA 1 (head to head) [Source:HGNC Symbol;Acc:HGNC:28457] |
| ENSG00000254509 | | |
| ENSG00000254832 | OR4A40P | olfactory receptor, family 4, subfamily A, member 40 pseudogene [Source:HGNC Symbol;Acc:HGNC:31259] |
| ENSG00000255038 | | |
| ENSG00000255142 | | |
| ENSG00000256037 | MRPL40P1 | mitochondrial ribosomal protein L40 pseudogene 1 [Source:HGNC Symbol;Acc:HGNC:44532] |
| ENSG00000257022 | | |
| ENSG00000257241 | | |
| ENSG00000257292 | | |
| ENSG00000257476 | | |
| ENSG00000257640 | | |
| ENSG00000257803 | | |
| ENSG00000258225 | | |
| ENSG00000258379 | | |
| ENSG00000258486 | RN7SL1 | RNA, 7SL, cytoplasmic 1 [Source:HGNC Symbol;Acc:HGNC:10038] |
| ENSG00000259035 | | |
| ENSG00000259211 | | |
| ENSG00000259564 | | |
| ENSG00000260077 | | |
| ENSG00000260571 | BNIP3P5 | BCL2/adenovirus E1B 19 kDa interacting protein 3 pseudogene 5 [Source:HGNC Symbol;Acc:HGNC:39658] |
| ENSG00000260601 | | |
| ENSG00000261916 | | |
| ENSG00000261996 | | |
| ENSG00000262001 | DLGAP1-AS2 | DLGAP1 antisense RNA 2 [Source:HGNC Symbol;Acc:HGNC:28146] |
| ENSG00000262313 | | |
| ENSG00000265713 | | |
| ENSG00000266021 | NA | NA |
| ENSG00000267142 | | |
| ENSG00000267363 | | |
| ENSG00000267493 | CIRBP-AS1 | CIRBP antisense RNA 1 [Source:HGNC Symbol;Acc:HGNC:28588] |
| ENSG00000267706 | | |
| ENSG00000268582 | | |
| ENSG00000268798 | | |

TABLE 2-continued

All biological sample sources collected in year 1: blood, urine, and saliva

| Ensembl_ID | HGNC_symbol | Description |
|---|---|---|
| ENSG00000269364 | LINC01233 | long intergenic non-protein coding RNA 1233 [Source:HGNC Symbol;Acc:HGNC:49756] |
| ENSG00000269815 | | |
| ENSG00000270010 | | |
| ENSG00000270188 | MTRNR2L11 | MT-RNR2-like 11 (pseudogene) [Source:HGNC Symbol;Acc:HGNC:37168] |
| ENSG00000270708 | | |
| ENSG00000271225 | | |
| ENSG00000271365 | | |
| ENSG00000271581 | | |
| ENSG00000271767 | NA | NA |
| ENSG00000272870 | | |
| ENSG00000273106 | | |
| ENSG00000273327 | OR6L2P | olfactory receptor, family 6, subfamily L, member 2 pseudogene [Source:HGNC Symbol;Acc:HGNC:15125] |
| ENSG00000125652 | ALKBH7 | alkB, alkylation repair homolog 7 (*E. coli*) [Source:HGNC Symbol;Acc:HGNC:21306] |
| ENSG00000127528 | KLF2 | Kruppel-like factor 2 [Source:HGNC Symbol;Acc:HGNC:6347] |
| ENSG00000170891 | CYTL1 | cytokine-like 1 [Source:HGNC Symbol;Acc:HGNC:24435] |
| ENSG00000185130 | HIST1H2BL | histone cluster 1, H2b1[Source:HGNC Symbol;Acc:HGNC:4748] |
| ENSG00000224172 | | |
| ENSG00000227125 | | |
| ENSG00000233115 | FAM90A11P | family with sequence similarity 90, member A11, pseudogene [Source:HGNC Symbol;Acc:HGNC:32259] |
| ENSG00000255079 | | |
| ENSG00000267762 | | |
| ENSG00000271029 | | |
| ENSG00000150201 | FXYD4 | FXYD domain containing ion transport regulator 4 [Source:HGNC Symbol;Acc:HGNC:4028] |
| ENSG00000211698 | TRGV4 | T cell receptor gamma variable 4 [Source:HGNC Symbol;Acc:HGNC:12289] |
| ENSG00000217643 | PTGES3P2 | prostaglandin E synthase 3 (cytosolic) pseudogene 2 [Source:HGNC Symbol;Acc:HGNC:43822] |
| ENSG00000244734 | HBB | hemoglobin, beta [Source:HGNC Symbol;Acc:HGNC:4827] |
| ENSG00000254325 | | |
| ENSG00000163739 | CXCL1 | chemokine (C-X-C motif) ligand 1 (melanoma growth stimulating activity, alpha) [Source:HGNC Symbol;Acc:HGNC:4602] |
| ENSG00000215004 | MESTP4 | mesoderm specific transcript pseudogene 4 [Source:HGNC Symbol;Acc:HGNC:38554] |
| ENSG00000230312 | | |
| ENSG00000230799 | | |
| ENSG00000242770 | | |
| ENSG00000254638 | | |
| ENSG00000258676 | | |
| ENSG00000234519 | | |
| ENSG00000236495 | | |
| ENSG00000216629 | OR2W4P | olfactory receptor, family 2, subfamily W, member 4 pseudogene [Source:HGNC Symbol;Acc:HGNC:15071] |
| ENSG00000259108 | | |
| ENSG00000198868 | MIR4461 | microRNA 4461 [Source:HGNC Symbol;Acc:HGNC:41656] |
| ENSG00000086666 | ZFAND6 | zinc finger, AN1-type domain 6 [Source:HGNC Symbol;Acc:HGNC:30164] |
| ENSG00000129562 | DAD1 | defender against cell death 1 [Source:HGNC Symbol;Acc:HGNC:2664] |
| ENSG00000165480 | SKA3 | spindle and kinetochore associated complex subunit 3 [Source:HGNC Symbol;Acc:HGNC:20262] |
| ENSG00000210196 | MT-TP | mitochondrially encoded tRNA proline [Source:HGNC Symbol;Acc:HGNC:7494] |
| ENSG00000214114 | MYCBP | MYC binding protein [Source:HGNC Symbol;Acc:HGNC:7554] |
| ENSG00000259834 | | potassium voltage-gated channel, shaker-related subfamily, member 3 [Source:EntrezGene;Acc:3738] |
| ENSG00000007306 | CEACAM7 | carcinoembryonic antigen-related cell adhesion molecule 7 [Source:HGNC Symbol;Acc:HGNC:1819] |
| ENSG00000043462 | LCP2 | lymphocyte cytosolic protein 2 (SH2 domain containing leukocyte protein of 76 kDa) [Source:HGNC Symbol;Acc:HGNC:6529] |
| ENSG00000057657 | PRDM1 | PR domain containing 1, with ZNF domain [Source:HGNC Symbol;Acc:HGNC:9346] |
| ENSG00000059728 | MXD1 | MAX dimerization protein 1 [Source:HGNC Symbol;Acc:HGNC:6761] |
| ENSG00000101336 | HCK | HCK proto-oncogene, Src family tyrosine kinase [Source:HGNC Symbol;Acc:HGNC:4840] |
| ENSG00000103569 | AQP9 | aquaporin 9 [Source:HGNC Symbol;Acc:HGNC:643] |
| ENSG00000120738 | EGR1 | early growth response 1 [Source:HGNC Symbol;Acc:HGNC:3238] |

TABLE 2-continued

All biological sample sources collected in year 1: blood, urine, and saliva

| Ensembl_ID | HGNC_symbol | Description |
|---|---|---|
| ENSG00000122861 | PLAU | plasminogen activator, urokinase [Source:HGNC Symbol;Acc:HGNC:9052] |
| ENSG00000123395 | ATG101 | autophagy related 101 [Source:HGNC Symbol;Acc:HGNC:25679] |
| ENSG00000140279 | DUOX2 | dual oxidase 2 [Source:HGNC Symbol;Acc:HGNC:13273] |
| ENSG00000140678 | ITGAX | integrin, alpha X (complement component 3 receptor 4 subunit) [Source:HGNC Symbol;Acc:HGNC:6152] |
| ENSG00000140749 | IGSF6 | immunoglobulin superfamily, member 6 [Source:HGNC Symbol;Acc:HGNC:5953] |
| ENSG00000145113 | MUC4 | mucin 4, cell surface associated [Source:HGNC Symbol;Acc:HGNC:7514] |
| ENSG00000147180 | ZNF711 | zinc finger protein 711 [Source:HGNC Symbol;Acc:HGNC:13128] |
| ENSG00000169429 | CXCL8 | chemokine (C-X-C motif) ligand 8 [Source:HGNC Symbol;Acc:HGNC:6025] |
| ENSG00000171223 | JUNB | jun B proto-oncogene [Source:HGNC Symbol;Acc:HGNC:6205] |
| ENSG00000188215 | DCUN1D3 | DCN1, defective in cullin neddylation 1, domain containing 3 [Source:HGNC Symbol;Acc:HGNC:28734] |
| ENSG00000196352 | CD55 | CD55 molecule, decay accelerating factor for complement (Cromer blood group) [Source:HGNC Symbol;Acc:HGNC:2665] |
| ENSG00000212443 | SNORA53 | small nucleolar RNA, H/ACA box 53 [Source:HGNC Symbol;Acc:HGNC:32646] |
| ENSG00000223880 | LINC01078 | long intergenic non-protein coding RNA 1078 [Source:HGNC Symbol;Acc:HGNC:49121] |
| ENSG00000227056 | RPL6P2 | ribosomal protein L6 pseudogene 2 [Source:HGNC Symbol;Acc:HGNC:35964] |
| ENSG00000231259 | | |
| ENSG00000232990 | MTATP6P7 | mitochondrially encoded ATP synthase 6 pseudogene 7 [Source:HGNC Symbol;Acc:HGNC:44581] |
| ENSG00000241983 | RN7SL566P | RNA, 7SL, cytoplasmic 566, pseudogene [Source:HGNC Symbol;Acc:HGNC:46582] |
| ENSG00000249588 | | |
| ENSG00000254124 | EEF1A1P37 | eukaryotic translation elongation factor 1 alpha 1 pseudogene 37 [Source:HGNC Symbol;Acc:HGNC:37915] |
| ENSG00000264462 | MIR3648-1 | microRNA 3648-1 [Source:HGNC Symbol;Acc:HGNC:38941] |
| ENSG00000268543 | | |

TABLE 3

Some biomarkers differentially expressed in blood samples

| Ensembl_ID | HGNC_symbol | Description |
|---|---|---|
| ENSG00000086666 | ZFAND6 | zinc finger, AN1-type domain 6 [Source:HGNC Symbol;Acc:HGNC:30164] |
| ENSG00000129562 | DAD1 | defender against cell death 1 [Source:HGNC Symbol;Acc:HGNC:2664] |
| ENSG00000165480 | SKA3 | spindle and kinetochore associated complex subunit 3 [Source:HGNC Symbol;Acc:HGNC:20262] |
| ENSG00000168993 | CPLX1 | complexin 1 [Source:HGNC Symbol;Acc:HGNC:2309] |
| ENSG00000169683 | LRRC45 | leucine rich repeat containing 45 [Source:HGNC Symbol;Acc:HGNC:28302] |
| ENSG00000172201 | ID4 | inhibitor of DNA binding 4, dominant negative helix-loop-helix protein [Source:HGNC Symbol;Acc:HGNC:5363] |
| ENSG00000178172 | SPINK6 | serine peptidase inhibitor, Kazal type 6 [Source:HGNC Symbol;Acc:HGNC:29486] |
| ENSG00000184261 | KCNK12 | potassium channel, subfamily K, member 12 [Source:HGNC Symbol;Acc:HGNC:6274] |
| ENSG00000185640 | KRT79 | keratin 79 [Source:HGNC Symbol;Acc:HGNC:28930] |
| ENSG00000204566 | C10orf115 | chromosome 10 open reading frame 115 [Source:HGNC Symbol;Acc:HGNC:31449] |
| ENSG00000210196 | MT-TP | mitochondrially encoded tRNA proline [Source:HGNC Symbol;Acc:HGNC:7494] |
| ENSG00000212297 | RNU6-821P | RNA, U6 small nuclear 821, pseudogene [Source:HGNC Symbol;Acc:HGNC:47784] |
| ENSG00000214114 | MYCBP | MYC binding protein [Source:HGNC Symbol;Acc:HGNC:7554] |
| ENSG00000214772 | | |
| ENSG00000222040 | NA | NA |
| ENSG00000223881 | | |
| ENSG00000230140 | | |

TABLE 3-continued

Some biomarkers differentially expressed in blood samples

| Ensembl_ID | HGNC_symbol | Description |
|---|---|---|
| ENSG00000235858 | | |
| ENSG00000236559 | | |
| ENSG00000237027 | | |
| ENSG00000237181 | | |
| ENSG00000243075 | RN7SL519P | RNA, 7SL, cytoplasmic 519, pseudogene [Source:HGNC Symbol;Acc:HGNC:46535] |
| ENSG00000244060 | RPS2P41 | ribosomal protein S2 pseudogene 41 [Source:HGNC Symbol;Acc:HGNC:36357] |
| ENSG00000250535 | STK19B | serine/threonine kinase 19B, pseudogene [Source:HGNC Symbol;Acc:HGNC:21668] |
| ENSG00000253469 | | |
| ENSG00000256721 | CACNA1C-IT3 | CACNA1C intronic transcript 3 (non-protein coding) [Source:HGNC Symbol;Acc:HGNC:41314] |
| ENSG00000256915 | | |
| ENSG00000258406 | | |
| ENSG00000258991 | DUX4L19 | double homeobox 4 like 19 [Source:HGNC Symbol;Acc:HGNC:37718] |
| ENSG00000259834 | | potassium voltage-gated channel, shaker-related subfamily, member 3 [Source:EntrezGene;Acc:3738] |
| ENSG00000260265 | | |
| ENSG00000268280 | NA | NA |
| ENSG00000273185 | | |

TABLE 4

Some biomarkers differentially expressed in saliva samples

| Ensembl_ID | HGNC_symbol | Description |
|---|---|---|
| ENSG00000120699 | EXOSC8 | exosome component 8 [Source:HGNC Symbol;Acc:HGNC:17035] |
| ENSG00000163577 | EIF5A2 | eukaryotic translation initiation factor 5A2 [Source:HGNC Symbol;Acc:HGNC:3301] |
| ENSG00000164114 | MAP9 | microtubule-associated protein 9 [Source:HGNC Symbol;Acc:HGNC:26118] |
| ENSG00000180708 | OR10K2 | olfactory receptor, family 10, subfamily K, member 2 [Source:HGNC Symbol;Acc:HGNC:14826] |
| ENSG00000221571 | RNU6ATAC35P | RNA, U6atac small nuclear 35, pseudogene [Source:HGNC Symbol;Acc:HGNC:46934] |
| ENSG00000223963 | PRKRIRP8 | protein-kinase, interferon-inducible double stranded RNA dependent inhibitor, repressor of (P58 repressor) pseudogene 8 [Source:HGNC Symbol;Acc:HGNC:39572] |
| ENSG00000224682 | SOCS5P2 | suppressor of cytokine signaling 5 pseudogene 2 [Source:HGNC Symbol;Acc:HGNC:44598] |
| ENSG00000226471 | | |
| ENSG00000228445 | UGT1A2P | UDP glucuronosyltransferase 1 family, polypeptide A2 pseudogene [Source:HGNC Symbol;Acc:HGNC:12534] |
| ENSG00000228695 | CES1P1 | carboxylesterase 1 pseudogene 1 [Source:HGNC Symbol;Acc:HGNC:18546] |
| ENSG00000229571 | PRAMEF26 | PRAME family member 26 [Source:HGNC Symbol;Acc:HGNC:49178] |
| ENSG00000230205 | | |
| ENSG00000250437 | | |
| ENSG00000251634 | | |
| ENSG00000255040 | | |
| ENSG00000256660 | CLEC12B | C-type lectin domain family 12, member B [Source:HGNC Symbol;Acc:HGNC:31966] |
| ENSG00000258590 | NBEAP1 | neurobeachin pseudogene 1 [Source:HGNC Symbol;Acc:HGNC:1007] |
| ENSG00000259431 | THTPA | thiamine triphosphatase [Source:HGNC Symbol;Acc:HGNC:18987] |
| ENSG00000270423 | | |
| ENSG00000272729 | | |

TABLE 5

Some biomarkers differentially expressed in urine samples

| Ensembl_ID | HGNC_symbol | Description |
|---|---|---|
| ENSG00000068366 | ACSL4 | acyl-CoA synthetase long-chain family member 4 [Source:HGNC Symbol;Acc:HGNC:3571] |
| ENSG00000175879 | HOXD8 | homeobox D8 [Source:HGNC Symbol;Acc:HGNC:5139] |
| ENSG00000210194 | MT-TE | mitochondrially encoded tRNA glutamic acid [Source:HGNC Symbol;Acc:HGNC:7479] |
| ENSG00000206652 | RNU1-1 | RNA, U1 small nuclear 1 [Source:HGNC Symbol;Acc:HGNC:10120] |
| ENSG00000219074 | SOD1P1 | superoxide dismutase 1, soluble pseudogene 1 [Source:HGNC Symbol;Acc:HGNC:45134] |
| ENSG00000232833 | NA | NA |
| ENSG00000270878 | | |
| ENSG00000234629 | WDR82P1 | WD repeat domain 82 pseudogene 1 [Source:HGNC Symbol;Acc:HGNC:32447] |
| ENSG00000236641 | | |
| ENSG00000206172 | HBA1 | hemoglobin, alpha 1 [Source:HGNC Symbol;Acc:HGNC:4823] |
| ENSG00000228857 | | |
| ENSG00000257718 | | |
| ENSG00000253759 | IGHV3-57 | immunoglobulin heavy variable 3-57 (pseudogene) [Source:HGNC Symbol;Acc:HGNC:5612] |
| ENSG00000259770 | | |
| ENSG00000264280 | NA | NA |
| ENSG00000200087 | SNORA73B | small nucleolar RNA, H/ACA box 73B [Source:HGNC Symbol;Acc:HGNC:10116] |
| ENSG00000206634 | SNORA22 | small nucleolar RNA, H/ACA box 22 [Source:HGNC Symbol;Acc:HGNC:32612] |
| ENSG00000239002 | SCARNA10 | small Cajal body-specific RNA 10 [Source:HGNC Symbol;Acc:HGNC:32567] |
| ENSG00000196911 | KPNA5 | karyopherin alpha 5 (importin alpha 6) [Source:HGNC Symbol;Acc:HGNC:6398] |
| ENSG00000171612 | SLC25A33 | solute carrier family 25 (pyrimidine nucleotide carrier), member 33 [Source:HGNC Symbol;Acc:HGNC:29681] |
| ENSG00000265933 | LINC00668 | long intergenic non-protein coding RNA 668 [Source:HGNC Symbol;Acc:HGNC:44328] |
| ENSG00000154822 | PLCL2 | phospholipase C-like 2 [Source:HGNC Symbol;Acc:HGNC:9064] |
| ENSG00000109536 | FRG1 | FSHD region gene 1 [Source:HGNC Symbol;Acc:HGNC:3954] |
| ENSG00000047662 | FAM184B | family with sequence similarity 184, member B [Source:HGNC Symbol;Acc:HGNC:29235] |
| ENSG00000062524 | LTK | leukocyte receptor tyrosine kinase [Source:HGNC Symbol;Acc:HGNC:6721] |
| ENSG00000109680 | TBC1D19 | TBC1 domain family, member 19 [Source:HGNC Symbol;Acc:HGNC:25624] |
| ENSG00000112992 | NNT | nicotinamide nucleotide transhydrogenase [Source:HGNC Symbol;Acc:HGNC:7863] |
| ENSG00000119523 | ALG2 | ALG2, alpha-1,3/1,6-mannosyltransferase [Source:HGNC Symbol;Acc:HGNC:23159] |
| ENSG00000127990 | SGCE | sarcoglycan, epsilon [Source:HGNC Symbol;Acc:HGNC:10808] |
| ENSG00000132825 | PPP1R3D | protein phosphatase 1, regulatory subunit 3D [Source:HGNC Symbol;Acc:HGNC:9294] |
| ENSG00000135637 | CCDC142 | coiled-coil domain containing 142 [Source:HGNC Symbol;Acc:HGNC:25889] |
| ENSG00000152465 | NMT2 | N-myristoyltransferase 2 [Source:HGNC Symbol;Acc:HGNC:7858] |
| ENSG00000160993 | ALKBH4 | alkB, alkylation repair homolog 4 (*E. coli*) [Source:HGNC Symbol;Acc:HGNC:21900] |
| ENSG00000164078 | MST1R | macrophage stimulating 1 receptor (c-met-related tyrosine kinase) [Source:HGNC Symbol;Acc:HGNC:7381] |
| ENSG00000167524 | | uncharacterized serine/threonine-protein kinase SgK494 [Source:EntrezGene;Acc:124923] |
| ENSG00000171243 | SOSTDC1 | sclerostin domain containing 1 [Source:HGNC Symbol;Acc:HGNC:21748] |
| ENSG00000173212 | MAB21L3 | mab-21-like 3 (*C. elegans*) [Source:HGNC Symbol;Acc:HGNC:26787] |
| ENSG00000177947 | ODF3 | outer dense fiber of sperm tails 3 [Source:HGNC Symbol;Acc:HGNC:19905] |
| ENSG00000196123 | KIAA0895L | KIAA0895-like [Source:HGNC Symbol;Acc:HGNC:34408] |
| ENSG00000223358 | EHHADH-AS1 | EHHADH antisense RNA 1 [Source:HGNC Symbol;Acc:HGNC:44133] |
| ENSG00000226742 | HSBP1L1 | heat shock factor binding protein 1-like 1 [Source:HGNC Symbol;Acc:HGNC:37243] |
| ENSG00000233393 | | |
| ENSG00000237037 | NDUFA6-AS1 | NDUFA6 antisense RNA 1 (head to head) [Source:HGNC Symbol;Acc:HGNC:45273] |
| ENSG00000255537 | | |
| ENSG00000157593 | SLC35B2 | ENSG00000258705 solute carrier family 35 (adenosine 3'-phospho 5'-phosphosulfate transporter), member B2 [Source:HGNC Symbol;Acc:HGNC:16872] |

TABLE 5-continued

Some biomarkers differentially expressed in urine samples

| Ensembl_ID | HGNC_symbol | Description |
| --- | --- | --- |
| ENSG00000160588 | MPZL3 | myelin protein zero-like 3 [Source:HGNC Symbol;Acc:HGNC:27279] |
| ENSG00000170044 | ZPLD1 | zona pellucida-like domain containing 1 [Source:HGNC Symbol;Acc:HGNC:27022] |
| ENSG00000198382 | UVRAG | UV radiation resistance associated [Source:HGNC Symbol;Acc:HGNC:12640] |
| ENSG00000131732 | ZCCHC9 | zinc finger, CCHC domain containing 9 [Source:HGNC Symbol;Acc:HGNC:25424] |
| ENSG00000141582 | CBX4 | chromobox homolog 4 [Source:HGNC Symbol;Acc:HGNC:1554] |
| ENSG00000162591 | MEGF6 | multiple EGF-like-domains 6 [Source:HGNC Symbol;Acc:HGNC:3232] |
| ENSG00000206149 | HERC2P9 | hect domain and RLD 2 pseudogene 9 [Source:HGNC Symbol;Acc:HGNC:30495] |
| ENSG00000070950 | RAD18 | RAD18 E3 ubiquitin protein ligase [Source:HGNC Symbol;Acc:HGNC:18278] |
| ENSG00000100299 | ARSA | arylsulfatase A [Source:HGNC Symbol;Acc:HGNC:713] |
| ENSG00000259959 | | |
| ENSG00000075336 | TIMM21 | translocase of inner mitochondrial membrane 21 homolog (yeast) [Source:HGNC Symbol;Acc:HGNC:25010] |
| ENSG00000088833 | NSFL1C | NSFL1 (p97) cofactor (p47) [Source:HGNC Symbol;Acc:HGNC:15912] |
| ENSG00000104756 | KCTD9 | potassium channel tetramerization domain containing 9 [Source:HGNC Symbol;Acc:HGNC:22401] |
| ENSG00000152763 | WDR78 | WD repeat domain 78 [Source:HGNC Symbol;Acc:HGNC:26252] |
| ENSG00000138346 | DNA2 | DNA replication helicase/nuclease 2 [Source:HGNC Symbol;Acc:HGNC:2939] |
| ENSG00000144909 | OSBPL11 | oxysterol binding protein-like 11 [Source:HGNC Symbol;Acc:HGNC:16397] |
| ENSG00000199237 | RNU6-834P | RNA, U6 small nuclear 834, pseudogene [Source:HGNC Symbol;Acc:HGNC:47797] |
| ENSG00000254014 | | |
| ENSG00000060762 | MPC1 | mitochondrial pyruvate carrier 1 [Source:HGNC Symbol;Acc:HGNC:21606] |
| ENSG00000120306 | CYSTM1 | cysteine-rich transmembrane module containing 1 [Source:HGNC Symbol;Acc:HGNC:30239] |
| ENSG00000164825 | DEFB1 | defensin, beta 1 [Source:HGNC Symbol;Acc:HGNC:2766] |
| ENSG00000165685 | TMEM52B | transmembrane protein 52B [Source:HGNC Symbol;Acc:HGNC:26438] |
| ENSG00000169344 | UMOD | uromodulin [Source:HGNC Symbol;Acc:HGNC:12559] |
| ENSG00000184908 | CLCNKB | chloride channel, voltage-sensitive Kb [Source:HGNC Symbol;Acc:HGNC:2027] |
| ENSG00000185275 | CD24P4 | CD24 molecule pseudogene 4 [Source:HGNC Symbol;Acc:HGNC:1649] |
| ENSG00000197061 | HIST1H4C | histone cluster 1, H4c [Source:HGNC Symbol;Acc:HGNC:4787] |
| ENSG00000205795 | CYS1 | cystin 1 [Source:HGNC Symbol;Acc:HGNC:18525] |
| ENSG00000210127 | MT-TA | mitochondrially encoded tRNA alanine [Source:HGNC Symbol;Acc:HGNC:7475] |
| ENSG00000269900 | RMRP | RNA component of mitochondrial RNA processing endoribonuclease [Source:HGNC Symbol;Acc:HGNC:10031] |
| ENSG00000270103 | RNU11 | RNA, U11 small nuclear [Source:HGNC Symbol;Acc:HGNC:10108] |
| ENSG00000104327 | CALB1 | calbindin 1, 28 kDa [Source:HGNC Symbol;Acc:HGNC:1434] |
| ENSG00000113889 | KNG1 | kininogen 1 [Source:HGNC Symbol;Acc:HGNC:6383] |
| ENSG00000107485 | GATA3 | GATA binding protein 3 [Source:HGNC Symbol;Acc:HGNC:4172] |
| ENSG00000008438 | PGLYRP1 | peptidoglycan recognition protein 1 [Source:HGNC Symbol;Acc:HGNC:8904] |
| ENSG00000105647 | PIK3R2 | phosphoinositide-3-kinase, regulatory subunit 2 (beta) [Source:HGNC Symbol;Acc:HGNC:8980] |
| ENSG00000116032 | GRIN3B | glutamate receptor, ionotropic, N-methyl-D-aspartate 3B [Source:HGNC Symbol;Acc:HGNC:16768] |
| ENSG00000122862 | SRGN | serglycin [Source:HGNC Symbol;Acc:HGNC:9361] |
| ENSG00000128645 | HOXD1 | homeobox D1 [Source:HGNC Symbol;Acc:HGNC:5132] |
| ENSG00000134809 | TIMM10 | translocase of inner mitochondrial membrane 10 homolog (yeast) [Source:HGNC Symbol;Acc:HGNC:11814] |
| ENSG00000138207 | RBP4 | retinol binding protein 4, plasma [Source:HGNC Symbol;Acc:HGNC:9922] |
| ENSG00000143546 | S100A8 | S100 calcium binding protein A8 [Source:HGNC Symbol;Acc:HGNC:10498] |
| ENSG00000160181 | TFF2 | trefoil factor 2 [Source:HGNC Symbol;Acc:HGNC:11756] |
| ENSG00000161992 | PRR35 | proline rich 35 [Source:HGNC Symbol;Acc:HGNC:14139] |
| ENSG00000163209 | SPRR3 | small proline-rich protein 3 [Source:HGNC Symbol;Acc:HGNC:11268] |
| ENSG00000164729 | SLC35G3 | solute carrier family 35, member G3 [Source:HGNC Symbol;Acc:HGNC:26848] |

TABLE 5-continued

Some biomarkers differentially expressed in urine samples

| Ensembl_ID | HGNC_symbol | Description |
| --- | --- | --- |
| ENSG00000165799 | RNASE7 | ribonuclease, RNase A family, 7 [Source:HGNC Symbol;Acc:HGNC:19278] |
| ENSG00000168746 | C20orf62 | chromosome 20 open reading frame 62 [Source:HGNC Symbol;Acc:HGNC:16195] |
| ENSG00000173915 | USMG5 | up-regulated during skeletal muscle growth 5 homolog (mouse) [Source:HGNC Symbol;Acc:HGNC:30889] |
| ENSG00000175197 | DDIT3 | DNA-damage-inducible transcript 3 [Source:HGNC Symbol;Acc:HGNC:2726] |
| ENSG00000175283 | DOLK | dolichol kinase [Source:HGNC Symbol;Acc:HGNC:23406] |
| ENSG00000176125 | UFSP1 | UFM1-specific peptidase 1 (non-functional) [Source:HGNC Symbol;Acc:HGNC:33821] |
| ENSG00000179751 | SYCN | syncollin [Source:HGNC Symbol;Acc:HGNC:18442] |
| ENSG00000181499 | OR6T1 | olfactory receptor, family 6, subfamily T, member 1 [Source:HGNC Symbol;Acc:HGNC:14848] |
| ENSG00000187186 | | HCG2040265, isoform CRA_a; Uncharacterized protein; cDNA FLJ50015 [Source:UniProtKB/TrEMBL;Acc:B7Z3J9] |
| ENSG00000187808 | SOWAHD | sosondowah ankyrin repeat domain family member D [Source:HGNC Symbol;Acc:HGNC:32960] |
| ENSG00000194297 | RNU1-75P | RNA, U1 small nuclear 75, pseudogene [Source:HGNC Symbol;Acc:HGNC:48417] |
| ENSG00000197674 | OR51C1P | olfactory receptor, family 51, subfamily C, member 1 pseudogene [Source:HGNC Symbol;Acc:HGNC:15191] |
| ENSG00000198518 | NA | NA |
| ENSG00000199212 | RNU105C | RNA, U105C small nucleolar [Source:HGNC Symbol;Acc:HGNC:10104] |
| ENSG00000199378 | | Y RNA [Source:RFAM;Acc:RF00019] |
| ENSG00000199536 | RNU6-315P | RNA, U6 small nuclear 315, pseudogene [Source:HGNC Symbol;Acc:HGNC:47278] |
| ENSG00000200131 | RN7SKP77 | RNA, 7SK small nuclear pseudogene 77 [Source:HGNC Symbol;Acc:HGNC:45801] |
| ENSG00000200408 | RNA5SP74 | RNA, 5S ribosomal pseudogene 74 [Source:HGNC Symbol;Acc:HGNC:42851] |
| ENSG00000201098 | RNY1 | RNA, Ro-associated Y1 [Source:HGNC Symbol;Acc:HGNC:10242] |
| ENSG00000201640 | RN7SKP28 | RNA, 7SK small nuclear pseudogene 28 [Source:HGNC Symbol;Acc:HGNC:45752] |
| ENSG00000201984 | | Y RNA [Source:RFAM;Acc:RF00019] |
| ENSG00000203616 | RHOT1P2 | ras homolog family member T1 pseudogene 2 [Source:HGNC Symbol;Acc:HGNC:37838] |
| ENSG00000204444 | APOM | apolipoprotein M [Source:HGNC Symbol;Acc:HGNC:13916] |
| ENSG00000204544 | MUC21 | mucin 21, cell surface associated [Source:HGNC Symbol;Acc:HGNC:21661] |
| ENSG00000205559 | CHKB-AS1 | CHKB antisense RNA 1 (head to head) [Source:HGNC Symbol;Acc:HGNC:40146] |
| ENSG00000207010 | RNU6-1295P | RNA, U6 small nuclear 1295, pseudogene [Source:HGNC Symbol;Acc:HGNC:48258] |
| ENSG00000212497 | RNA5SP465 | RNA, 5S ribosomal pseudogene 465 [Source:HGNC Symbol;Acc:HGNC:43365] |
| ENSG00000213343 | RPL21P18 | ribosomal protein L21 pseudogene 18 [Source:HGNC Symbol;Acc:HGNC:28362] |
| ENSG00000213871 | TAF9BP1 | TAF9B RNA polymerase II, TATA box binding protein (TBP)-associated factor, 31 kDa pseudogene 1 [Source:HGNC Symbol;Acc:HGNC:30687] |
| ENSG00000213896 | | |
| ENSG00000214070 | | |
| ENSG00000214381 | LINC00488 | long intergenic non-protein coding RNA 488 [Source:HGNC Symbol;Acc:HGNC:32675] |
| ENSG00000214759 | | |
| ENSG00000215043 | GLULP6 | glutamate-ammonia ligase (glutamine synthetase) pseudogene 6 [Source:HGNC Symbol;Acc:HGNC:37990] |
| ENSG00000215481 | BCRP3 | breakpoint cluster region pseudogene 3 [Source:HGNC Symbol;Acc:HGNC:1016] |
| ENSG00000216966 | | |
| ENSG00000218180 | SLC25A5P7 | solute carrier family 25 (mitochondrial carrier; adenine nucleotide translocator), member 5 pseudogene 7 [Source:HGNC Symbol;Acc:HGNC:513] |
| ENSG00000218803 | GSTM2P1 | glutathione S-transferase mu 2 (muscle) pseudogene 1 [Source:HGNC Symbol;Acc:HGNC:38009] |
| ENSG00000222281 | RN7SKP111 | RNA, 7SK small nuclear pseudogene 111 [Source:HGNC Symbol;Acc:HGNC:45835] |
| ENSG00000222460 | RN7SKP271 | RNA, 7SK small nuclear pseudogene 271 [Source:HGNC Symbol;Acc:HGNC:45995] |
| ENSG00000222678 | RN7SKP213 | RNA, 7SK small nuclear pseudogene 213 [Source:HGNC Symbol;Acc:HGNC:45937] |
| ENSG00000222985 | RNU2-14P | RNA, U2 small nuclear 14, pseudogene [Source:HGNC Symbol;Acc:HGNC:48507] |

TABLE 5-continued

Some biomarkers differentially expressed in urine samples

| Ensembl_ID | HGNC_symbol | Description |
|---|---|---|
| ENSG00000223581 | | |
| ENSG00000223916 | | |
| ENSG00000225770 | | |
| ENSG00000226403 | | |
| ENSG00000226868 | | |
| ENSG00000227401 | RPL37P1 | ribosomal protein L37 pseudogene 1 [Source:HGNC Symbol;Acc:HGNC:16337] |
| ENSG00000227415 | | |
| ENSG00000227646 | STEAP2-AS1 | STEAP2 antisense RNA 1 [Source:HGNC Symbol;Acc:HGNC:40820] |
| ENSG00000227704 | | |
| ENSG00000227818 | | |
| ENSG00000227864 | ARL5AP1 | ADP-ribosylation factor-like 5A pseudogene 1 [Source:HGNC Symbol;Acc:HGNC:43933] |
| ENSG00000228366 | | |
| ENSG00000228436 | | |
| ENSG00000229242 | | |
| ENSG00000229313 | | |
| ENSG00000229376 | CICP3 | capicua transcriptional repressor pseudogene 3 [Source:HGNC Symbol;Acc:HGNC:37742] |
| ENSG00000229925 | | |
| ENSG00000229932 | YWHAZP3 | tyrosine 3-monooxygenase/tryptophan 5-monooxygenase activation protein, zeta pseudogene 3 [Source:HGNC Symbol;Acc:HGNC:31101] |
| ENSG00000230696 | | |
| ENSG00000230706 | | |
| ENSG00000230710 | LINC00332 | long intergenic non-protein coding RNA 332 [Source:HGNC Symbol;Acc:HGNC:42049] |
| ENSG00000231937 | | |
| ENSG00000232015 | HSPE1P25 | heat shock 10 kDa protein 1 pseudogene 25 [Source:HGNC Symbol;Acc:HGNC:49344] |
| ENSG00000232464 | | |
| ENSG00000232524 | | |
| ENSG00000232658 | | |
| ENSG00000233558 | | |
| ENSG00000235573 | | |
| ENSG00000235578 | | |
| ENSG00000235942 | LCE6A | late cornified envelope 6A [Source:HGNC Symbol;Acc:HGNC:31824] |
| ENSG00000236209 | | |
| ENSG00000236751 | LINC01186 | long intergenic non-protein coding RNA 1186 [Source:HGNC Symbol;Acc:HGNC:49573] |
| ENSG00000236824 | BCYRN1 | brain cytoplasmic RNA 1 [Source:HGNC Symbol;Acc:HGNC:1022] |
| ENSG00000237213 | RPL23AP22 | ribosomal protein L23a pseudogene 22 [Source:HGNC Symbol;Acc:HGNC:35505] |
| ENSG00000237979 | | |
| ENSG00000237991 | RPL35PI | ribosomal protein L35 pseudogene 1 [Source:HGNC Symbol;Acc:HGNC:36695] |
| ENSG00000238073 | RBMY2HP | RNA binding motif protein, Y-linked, family 2, member H pseudogene [Source:HGNC Symbol;Acc:HGNC:23893] |
| ENSG00000238337 | NA | NA |
| ENSG00000238609 | RNU7-94P | RNA, U7 small nuclear 94 pseudogene [Source:HGNC Symbol;Acc:HGNC:45628] |
| ENSG00000239126 | NA | NA |
| ENSG00000239183 | SNORA84 | small nucleolar RNA, H/ACA box 84 [Source:HGNC Symbol;Acc:HGNC:33615] |
| ENSG00000239196 | NA | NA |
| ENSG00000239272 | RPL21P10 | ribosomal protein L21 pseudogene 10 [Source:HGNC Symbol;Acc:HGNC:19795] |
| ENSG00000239542 | RN7SL399P | RNA, 7SL, cytoplasmic 399, pseudogene [Source:HGNC Symbol;Acc:HGNC:46415] |
| ENSG00000239857 | GET4 | golgi to ER traffic protein 4 homolog (*S. cerevisiae*) [Source:HGNC Symbol;Acc:HGNC:21690] |
| ENSG00000240803 | RN7SL231P | RNA, 7SL, cytoplasmic 231, pseudogene [Source:HGNC Symbol;Acc:HGNC:46247] |
| ENSG00000242229 | RPS3AP14 | ribosomal protein S3a pseudogene 14 [Source:HGNC Symbol;Acc:HGNC:35715] |
| ENSG00000243004 | | |
| ENSG00000243974 | VTI1BP1 | vesicle transport through interaction with t-SNAREs 1B pseudogene 1 [Source:HGNC Symbol;Acc:HGNC:43727] |
| ENSG00000244063 | | |
| ENSG00000244260 | | |
| ENSG00000244582 | RPL21P120 | ribosomal protein L21 pseudogene 120 [Source:HGNC Symbol;Acc:HGNC:35743] |

TABLE 5-continued

Some biomarkers differentially expressed in urine samples

| Ensembl_ID | HGNC_symbol | Description |
|---|---|---|
| ENSG00000248240 | | |
| ENSG00000248370 | | |
| ENSG00000248834 | MARK2P5 | MAP/microtubule affinity-regulating kinase 2 pseudogene 5 [Source:HGNC Symbol;Acc:HGNC:39796] |
| ENSG00000248890 | HHIP-AS1 | HHIP antisense RNA 1 [Source:HGNC Symbol;Acc:HGNC:44182] |
| ENSG00000249014 | HMGN2P4 | high mobility group nucleosomal binding domain 2 pseudogene 4 [Source:HGNC Symbol;Acc:HGNC:33567] |
| ENSG00000249256 | ATP5LP3 | ATP synthase, H+ transporting, mitochondrial Fo complex, subunit g, pseudogene 3 [Source:HGNC Symbol;Acc:HGNC:13216] |
| ENSG00000249942 | | |
| ENSG00000250120 | PCDHA10 | protocadherin alpha 10 [Source:HGNC Symbol;Acc:HGNC:8664] |
| ENSG00000250234 | | |
| ENSG00000250411 | | |
| ENSG00000251445 | | |
| ENSG00000251583 | | |
| ENSG00000252350 | RPPH1-3P | ribonuclease P RNA component HI, 3 pseudogene [Source:HGNC Symbol;Acc:HGNC:47030] |
| ENSG00000252376 | RNA5SP395 | RNA, 5S ribosomal pseudogene 395 [Source:HGNC Symbol;Acc:HGNC:43295] |
| ENSG00000252396 | RN7SKP195 | RNA, 7SK small nuclear pseudogene 195 [Source:HGNC Symbol;Acc:HGNC:45919] |
| ENSG00000252731 | | |
| ENSG00000253112 | | |
| ENSG00000253292 | MIOXP1 | myo-inositol oxygenase pseudogene 1 [Source:HGNC Symbol;Acc:HGNC:50748] |
| ENSG00000253560 | | |
| ENSG00000253597 | NA | NA |
| ENSG00000253882 | | |
| ENSG00000253892 | | |
| ENSG00000253920 | IGLV3-31 | immunoglobulin lambda variable 3-31 (pseudogene) [Source:HGNC Symbol;Acc:HGNC:5913] |
| ENSG00000254057 | | |
| ENSG00000254082 | | |
| ENSG00000254086 | | |
| ENSG00000254260 | | |
| ENSG00000254389 | RHPN1-AS1 | RHPN1 antisense RNA 1 (head to head) [Source:HGNC Symbol;Acc:HGNC:28457] |
| ENSG00000254509 | | |
| ENSG00000254832 | OR4A40P | olfactory receptor, family 4, subfamily A, member 40 pseudogene [Source:HGNC Symbol;Acc:HGNC:31259] |
| ENSG00000255038 | | |
| ENSG00000255142 | | |
| ENSG00000256037 | MRPL40P1 | mitochondrial ribosomal protein L40 pseudogene 1 [Source:HGNC Symbol;Acc:HGNC:44532] |
| ENSG00000257022 | | |
| ENSG00000257241 | | |
| ENSG00000257292 | | |
| ENSG00000257476 | | |
| ENSG00000257640 | | |
| ENSG00000257803 | | |
| ENSG00000258225 | | |
| ENSG00000258379 | | |
| ENSG00000258486 | RN7SL1 | RNA, 7SL, cytoplasmic 1 [Source:HGNC Symbol;Acc:HGNC:10038] |
| ENSG00000259035 | | |
| ENSG00000259211 | | |
| ENSG00000259564 | | |
| ENSG00000260077 | | |
| ENSG00000260571 | BNIP3P5 | BCL2/adenovirus E1B 19 kDa interacting protein 3 pseudogene 5 [Source:HGNC Symbol;Acc:HGNC:39658] |
| ENSG00000260601 | | |
| ENSG00000261916 | | |
| ENSG00000261996 | | |
| ENSG00000262001 | DLGAP1-AS2 | DLGAP1 antisense RNA 2 [Source:HGNC Symbol;Acc:HGNC:28146] |
| ENSG00000262313 | | |
| ENSG00000265713 | | |
| ENSG00000266021 | NA | NA |
| ENSG00000267142 | | |
| ENSG00000267363 | | |
| ENSG00000267493 | CIRBP-AS1 | CIRBP antisense RNA 1 [Source:HGNC Symbol;Acc:HGNC:28588] |

TABLE 5-continued

Some biomarkers differentially expressed in urine samples

| Ensembl_ID | HGNC_symbol | Description |
|---|---|---|
| ENSG00000267706 | | |
| ENSG00000268582 | | |
| ENSG00000268798 | | |
| ENSG00000269364 | LINC01233 | long intergenic non-protein coding RNA 1233 [Source:HGNC Symbol;Acc:HGNC:49756] |
| ENSG00000269815 | | |
| ENSG00000270010 | | |
| ENSG00000270188 | MTRNR2L11 | MT-RNR2-like 11 (pseudogene) [Source:HGNC Symbol;Acc:HGNC:37168] |
| ENSG00000270708 | | |
| ENSG00000271225 | | |
| ENSG00000271365 | | |
| ENSG00000271581 | | |
| ENSG00000271767 | NA | NA |
| ENSG00000272870 | | |
| ENSG00000273106 | | |
| ENSG00000273327 | OR6L2P | olfactory receptor, family 6, subfamily L, member 2 pseudogene [Source:HGNC Symbol;Acc:HGNC:15125] |
| ENSG00000125652 | ALKBH7 | alkB, alkylation repair homolog 7 (*E. coli*) [Source:HGNC Symbol;Acc:HGNC:21306] |
| ENSG00000127528 | KLF2 | Kruppel-like factor 2 [Source:HGNC Symbol;Acc:HGNC:6347] |
| ENSG00000170891 | CYTL1 | cytokine-like 1 [Source:HGNC Symbol;Acc:HGNC:24435] |
| ENSG00000185130 | HIST1H2BL | histone cluster 1, H2bl[Source:HGNC Symbol;Acc:HGNC:4748] |
| ENSG00000224172 | | |
| ENSG00000227125 | | |
| ENSG00000233115 | FAM90A11P | family with sequence similarity 90, member A11, pseudogene [Source:HGNC Symbol;Acc:HGNC:32259] |
| ENSG00000255079 | | |
| ENSG00000267762 | | |
| ENSG00000271029 | | |
| ENSG00000150201 | FXYD4 | FXYD domain containing ion transport regulator 4 [Source:HGNC Symbol;Acc:HGNC:4028] |
| ENSG00000211698 | TRGV4 | T cell receptor gamma variable 4 [Source:HGNC Symbol;Acc:HGNC:12289] |
| ENSG00000217643 | PTGES3P2 | prostaglandin E synthase 3 (cytosolic) pseudogene 2 [Source:HGNC Symbol;Acc:HGNC:43822] |
| ENSG00000244734 | HBB | hemoglobin, beta [Source:HGNC Symbol;Acc:HGNC:4827] |
| ENSG00000254325 | | |
| ENSG00000163739 | CXCL1 | chemokine (C-X-C motif) ligand 1 (melanoma growth stimulating activity, alpha) [Source:HGNC Symbol;Acc:HGNC:4602] |
| ENSG00000215004 | MESTP4 | mesoderm specific transcript pseudogene 4 [Source:HGNC Symbol;Acc:HGNC:38554] |
| ENSG00000230312 | | |
| ENSG00000230799 | | |
| ENSG00000242770 | | |
| ENSG00000254638 | | |
| ENSG00000258676 | | |
| ENSG00000234519 | | |
| ENSG00000236495 | | |
| ENSG00000216629 | OR2W4P | olfactory receptor, family 2, subfamily W, member 4 pseudogene [Source:HGNC Symbol;Acc:HGNC:15071] |
| ENSG00000259108 | | |
| ENSG00000198868 | MIR4461 | microRNA 4461 [Source:HGNC Symbol;Acc:HGNC:41656] |
| ENSG00000007306 | CEACAM7 | carcinoembryonic antigen-related cell adhesion molecule 7 [Source:HGNC Symbol;Acc:HGNC:1819] |
| ENSG00000043462 | LCP2 | lymphocyte cytosolic protein 2 (SH2 domain containing leukocyte protein of 76 kDa) [Source:HGNC Symbol;Acc:HGNC:6529] |
| ENSG00000057657 | PRDM1 | PR domain containing 1, with ZNF domain [Source:HGNC Symbol;Acc:HGNC:9346] |
| ENSG00000059728 | MXD1 | MAX dimerization protein 1 [Source:HGNC Symbol;Acc:HGNC:6761] |
| ENSG00000101336 | HCK | HCK proto-oncogene, Src family tyrosine kinase [Source:HGNC Symbol;Acc:HGNC:4840] |
| ENSG00000103569 | AQP9 | aquaporin 9 [Source:HGNC Symbol;Acc:HGNC:643] |
| ENSG00000120738 | EGR1 | early growth response 1 [Source:HGNC Symbol;Acc:HGNC:3238] |
| ENSG00000122861 | PLAU | plasminogen activator, urokinase [Source:HGNC Symbol;Acc:HGNC:9052] |
| ENSG00000123395 | ATG101 | autophagy related 101 [Source:HGNC Symbol;Acc:HGNC:25679] |
| ENSG00000140279 | DUOX2 | dual oxidase 2 [Source:HGNC Symbol;Acc:HGNC:13273] |
| ENSG00000140678 | ITGAX | integrin, alpha X (complement component 3 receptor 4 subunit) [Source:HGNC Symbol;Acc:HGNC:6152] |
| ENSG00000140749 | IGSF6 | immunoglobulin superfamily, member 6 [Source:HGNC Symbol;Acc:HGNC:5953] |

TABLE 5-continued

Some biomarkers differentially expressed in urine samples

| Ensembl_ID | HGNC_symbol | Description |
|---|---|---|
| ENSG00000145113 | MUC4 | mucin 4, cell surface associated [Source:HGNC Symbol;Acc:HGNC:7514] |
| ENSG00000147180 | ZNF711 | zinc finger protein 711 [Source:HGNC Symbol;Acc:HGNC:13128] |
| ENSG00000169429 | CXCL8 | chemokine (C-X-C motif) ligand 8 [Source:HGNC Symbol;Acc:HGNC:6025] |
| ENSG00000171223 | JUNB | jun B proto-oncogene [Source:HGNC Symbol;Acc:HGNC:6205] |
| ENSG00000188215 | DCUN1D3 | DCN1, defective in cullin neddylation 1, domain containing 3 [Source:HGNC Symbol;Acc:HGNC:28734] |
| ENSG00000196352 | CD55 | CD55 molecule, decay accelerating factor for complement (Cromer blood group) [Source:HGNC Symbol;Acc:HGNC:2665] |
| ENSG00000212443 | SNORA53 | small nucleolar RNA, H/ACA box 53 [Source:HGNC Symbol;Acc:HGNC:32646] |
| ENSG00000223880 | LINC01078 | long intergenic non-protein coding RNA 1078 [Source:HGNC Symbol;Acc:HGNC:49121] |
| ENSG00000227056 | RPL6P2 | ribosomal protein L6 pseudogene 2 [Source:HGNC Symbol;Acc:HGNC:35964] |
| ENSG00000231259 | | |
| ENSG00000232990 | MTATP6P7 | mitochondrially encoded ATP synthase 6 pseudogene 7 [Source:HGNC Symbol;Acc:HGNC:44581] |
| ENSG00000241983 | RN7SL566P | RNA, 7SL, cytoplasmic 566, pseudogene [Source:HGNC Symbol;Acc:HGNC:46582] |
| ENSG00000249588 | | |
| ENSG00000254124 | EEF1A1P37 | eukaryotic translation elongation factor 1 alpha 1 pseudogene 37 [Source:HGNC Symbol;Acc:HGNC:37915] |
| ENSG00000264462 | MIR3648-1 | microRNA 3648-1 [Source:HGNC Symbol;Acc:HGNC:38941] |
| ENSG00000268543 | | |

TABLE 6

The sum of all impact sustained by the player, as measured by HITsp, regressed on RNA expression in plasma samples

| Ensembl_ID | hgnc_symbol | description | X0.5slope_0.1pvalue_0.1_Cum_HITsp_plasma | X0.8slope_0.1pvalue_0.1_Cum_HITsp_plasma |
|---|---|---|---|---|
| ENSG00000100181 | TPTEP1 | transmembrane phosphatase with tensin homology pseudogene 1 [Source:HGNC Symbol;Acc:HGNC:43648] | 0.20378777 | 0.20378777 |
| ENSG00000109272 | PF4V1 | platelet factor 4 variant 1 [Source:HGNC Symbol;Acc:HGNC:8862] | 0.597728749 | 0.597728749 |
| ENSG00000113658 | SMAD5 | SMAD family member 5 [Source:HGNC Symbol;Acc:HGNC:6771] | 0.114186069 | 0.114186069 |
| ENSG00000130600 | H19 | H19, imprinted maternally expressed transcript (non-protein coding) [Source:HGNC Symbol;Acc:HGNC:4713] | 0.122017886 | 0.122017886 |
| ENSG00000188536 | HBA2 | hemoglobin, alpha 2 [Source:HGNC Symbol;Acc:HGNC:4824] | 0.233448354 | 0.233448354 |
| ENSG00000210195 | MT-TT | mitochondrially encoded tRNA threonine [Source:HGNC Symbol;Acc:HGNC:7499] | 0.362408703 | 0.362408703 |
| ENSG00000244734 | HBB | hemoglobin, beta [Source:HGNC Symbol;Acc:HGNC:4827] | 5.585155911 | 5.585155911 |

TABLE 7

The sum of all impact sustained by the player, as measured by linear acceleration regressed on RNA expression in plasma samples

| Ensembl_ID | hgnc_symbol | description | X0.5slope_0.1pvalue_0.1_Cum_lin_acc_plasma | X0.8slope_0.1pvalue_0.1_Cum_lin_acc_plasma |
|---|---|---|---|---|
| ENSG00000100181 | TPTEP1 | transmembrane phosphatase with tensin homology pseudogene 1 [Source:HGNC Symbol;Acc:HGNC:43648] | 0.106289272 | 0.106289272 |
| ENSG00000109272 | PF4V1 | platelet factor 4 variant 1 [Source:HGNC Symbol;Acc:HGNC:8862] | 0.309869359 | 0.309869359 |
| ENSG00000188536 | HBA2 | hemoglobin, alpha 2 [Source:HGNC Symbol;Acc:HGNC:4824] | 0.117006674 | 0.117006674 |
| ENSG00000210196 | MT-TP | mitochondrially encoded tRNA proline [Source:HGNC Symbol;Acc:HGNC:7494] | 0.309422507 | 0.309422507 |
| EN5G00000244734 | HBB | hemoglobin, beta [Source:HGNC Symbol;Acc:HGNC:4827] | 2.913777061 | 2.913777061 |

TABLE 8

The highest impact sustained by the player in the game as measured by HITsp regressed on RNA expression in plasma samples

| Ensembl_ID | hgnc_symbol | description | X0.5slope_0.1pvalue_0.1_Max_HITsp_plasma | X0.8slope_0.1pvalue_0.1_Max_HITsp_plasma |
|---|---|---|---|---|
| ENSG00000007908 | SELE | selectin E [Source:HGNC Symbol;Acc:HGNC:10718] | 0.121635052 | NA |
| ENSG00000010318 | PHF7 | PHD finger protein 7 [Source:HGNC Symbol;Acc:HGNC:18458] | 0.175646559 | 0.175646559 |
| ENSG00000021852 | C8B | complement component 8, beta polypeptide [Source:HGNC Symbol;Acc:HGNC:1353] | 0.152730512 | NA |
| ENSG00000022556 | NLRP2 | NLR family, pyrin domain containing 2 [Source:HGNC Symbol;Acc:HGNC:22948] | −0.163995063 | -0.163995063 |
| ENSG00000029725 | RABEP1 | rabaptin, RAB GTPase binding effector protein 1 [Source:HGNC Symbol;Acc:HGNC:17677] | 0.216512318 | 0.216512318 |
| ENSG00000048392 | RRM2B | ribonucleotide reductase M2 B (TP53 inducible) [Source:HGNC Symbol;Acc:HGNC:17296] | 0.165078204 | 0.165078204 |
| ENSG00000055147 | FAM114A2 | family with sequence similarity 114, member A2 [Source:HGNC Symbol;Acc:HGNC:1333] | 0.161956419 | 0.161956419 |
| ENSG00000074266 | EED | embryonic ectoderm development [Source:HGNC Symbol;Acc:HGNC:3188] | 0.149505509 | 0.149505509 |
| ENSG00000074755 | ZZEF1 | zinc finger, ZZ-type with EF-hand domain 1 [Source:HGNC Symbol;Acc:HGNC:29027] | 0.381470401 | 0.381470401 |
| ENSG00000075142 | SRI | sorcin [Source:HGNC Symbol;Acc:HGNC:11292] | 0.111723067 | 0.111723067 |
| ENSG00000075292 | ZNF638 | zinc finger protein 638 [Source:HGNC Symbol;Acc:HGNC:17894] | 0.305304639 | 0.305304639 |
| ENSG00000079393 | DUSP13 | dual specificity phosphatase 13 [Source:HGNC Symbol;Acc:HGNC:19681] | 0.130119143 | NA |
| ENSG00000079459 | FDFT1 | farnesyl-diphosphate farnesyltransferase 1 [Source:HGNC Symbol;Acc:HGNC:3629] | 0.134608276 | 0.134608276 |
| ENSG00000081087 | OSTM1 | osteopetrosis associated transmembrane protein 1 [Source:HGNC Symbol;Acc:HGNC:21652] | 0.121396476 | 0.121396476 |
| ENSG00000091490 | SEL1L3 | sel-1 suppressor of lin-12-like 3 (C. elegans) [Source:HGNC Symbol;Acc:HGNC:29108] | 0.302907764 | 0.302907764 |

TABLE 8-continued

The highest impact sustained by the player in the game as measured by HITsp regressed on RNA expression in plasma samples

| Ensembl_ID | hgnc_symbol | description | X0.5slope_0.1pvalue_0.1_Max_HITsp_plasma | X0.8slope_0.1pvalue_0.1_Max_HITsp_plasma |
|---|---|---|---|---|
| ENSG00000092931 | MFSD11 | major facilitator superfamily domain containing 11 [Source:HGNC Symbol;Acc:HGNC:25458] | 0.123995301 | 0.123995301 |
| ENSG00000099246 | RAB18 | RAB18, member RAS oncogene family [Source:HGNC Symbol;Acc:HGNC:14244] | 0.165635406 | −0.165635406 |
| ENSG00000100023 | PPIL2 | peptidylprolyl isomerase (cyclophilin)-like 2 [Source:HGNC Symbol;Acc:HGNC:9261] | −0.161972775 | −0.161972775 |
| ENSG00000100888 | CHD8 | chromodomain helicase DNA binding protein 8 [Source:HGNC Symbol;Acc:HGNC:20153] | 0.229676288 | 0.229676288 |
| ENSG00000101447 | FAM83D | family with sequence similarity 83, member D [Source:HGNC Symbol;Acc:HGNC:16122] | 0.1332232 | 0.1332232 |
| ENSG00000102401 | ARMCX3 | armadillo repeat containing, X-linked 3 [Source:HGNC Symbol;Acc:HGNC:24065] | 0.59294635 | 0.59294635 |
| ENSG00000104325 | DECR1 | 2,4-dienoyl CoA reductase 1, mitochondrial [Source:HGNC Symbol;Acc:HGNC:2753] | −0.189408898 | −0.189408898 |
| ENSG00000105609 | LILRB5 | leukocyte immunoglobulin-like receptor, subfamily B (with TM and ITIM domains), member 5 [Source:HGNC Symbol;Acc:HGNC:6609] | −0.140206736 | −0.140206736 |
| ENSG00000107105 | ELAVL2 | ELAV like neuron-specific RNA binding protein 2 [Source:HGNC Symbol;Acc:HGNC:3313] | 0.127378776 | NA |
| ENSG00000109184 | DCUN1D4 | DCN1, defective in cullin neddylation 1, domain containing 4 [Source:HGNC Symbol;Acc:HGNC:28998] | 0.134859198 | 0.134859198 |
| ENSG00000109320 | NFKB1 | nuclear factor of kappa light polypeptide gene enhancer in B-cells 1 [Source:HGNC Symbol;Acc:HGNC:7794] | 0.143532697 | 0.143532697 |
| ENSG00000110002 | VWA5A | von Willebrand factor A domain containing 5A [Source:HGNC Symbol;Acc:HGNC:6658] | −0.163688271 | −0.163688271 |
| ENSG00000111215 | PRR4 | proline rich 4 (lacrimal) [Source:HGNC Symbol;Acc:HGNC:18020] | 0.111251825 | 0.111251825 |
| ENSG00000111237 | VPS29 | vacuolar protein sorting 29 homolog (S. cerevisiae) [Source:HGNC Symbol;Acc:HGNC:14340] | −0.111163487 | −0.111163487 |
| ENSG00000115641 | FHL2 | four and a half LIM domains 2 [Source:HGNC Symbol;Acc:HGNC:3703] | −0.259669317 | −0.259669317 |
| ENSG00000116984 | MTR | 5-methyltetrahydrofolate-homocysteine methyltransferase [Source:HGNC Symbol;Acc:HGNC:7468] | 0.242310216 | 0.242310216 |
| ENSG00000117707 | PROX1 | prospero homeobox 1 [Source:HGNC Symbol;Acc:HGNC:9459] | 0.15802085 | 0.15802085 |
| ENSG00000118496 | FBXO30 | F-box protein 30 [Source:HGNC Symbol;Acc:HGNC:15600] | 0.122038094 | 0.122038094 |
| ENSG00000118503 | TNFAIP3 | tumor necrosis factor, alpha-induced protein 3 [Source:HGNC Symbol;Acc:HGNC:11896] | −0.129476115 | −0.129476115 |
| ENSG00000119537 | KDSR | 3-ketodihydrosphingosine reductase [Source:HGNC Symbol;Acc:HGNC:4021] | 0.184864693 | 0.184864693 |
| ENSG00000119760 | SUPT7L | suppressor of Ty 7 (S. cerevisiae)-like [Source:HGNC Symbol;Acc:HGNC:30632] | 0.112076344 | 0.112076344 |
| ENSG00000120158 | RCL1 | RNA terminal phosphate cyclase-like 1 [Source:HGNC Symbol;Acc:HGNC:17687] | 0.11221667 | 0.11221667 |
| ENSG00000120903 | CHRNA2 | cholinergic receptor, nicotinic, alpha 2 (neuronal) [Source:HGNC Symbol;Acc:HGNC:1956] | 0.160279926 | 0.160279926 |

TABLE 8-continued

The highest impact sustained by the player in the game as measured by HITsp regressed on RNA expression in plasma samples

| Ensembl_ID | hgnc_symbol | description | X0.5slope_0.1pvalue_0.1_Max_HITsp_plasma | X0.8slope_0.1pvalue_0.1_Max_HITsp_plasma |
|---|---|---|---|---|
| ENSG00000124256 | ZBP1 | Z-DNA binding protein 1 [Source:HGNC Symbol;Acc:HGNC:16176] | −0.177678732 | −0.177678732 |
| ENSG00000127952 | STYXL1 | serine/threonine/tyrosine interacting-like 1 [Source:HGNC Symbol;Acc:HGNC:18165] | −0.143855782 | −0.143855782 |
| ENSG00000128872 | TMOD2 | tropomodulin 2 (neuronal) [Source:HGNC Symbol;Acc:HGNC:11872] | 0.196045551 | 0.196045551 |
| ENSG00000129315 | CCNT1 | cyclin Ti [Source:HGNC Symbol;Acc:HGNC:1599] | 0.174120367 | 0.174120367 |
| ENSG00000131669 | NINJ1 | ninjurin 1 [Source:HGNC Symbol;Acc:HGNC:7824] | −0.117831337 | −0.117831337 |
| ENSG00000135677 | GNS | glucosamine (N-acetyl)-6-sulfatase [Source:HGNC Symbol;Acc:HGNC:4422] | −0.166432372 | −0.166432372 |
| ENSG00000135720 | DYNC1LI2 | dynein, cytoplasmic 1, light intermediate chain 2 [Source:HGNC Symbol;Acc:HGNC:2966] | 0.146577706 | 0.146577706 |
| ENSG00000135828 | RNASEL | ribonuclease L (2',5'-oligoisoadenylate synthetase-dependent) [Source:HGNC Symbol;Acc:HGNC:10050] | 0.154329308 | 0.154329308 |
| ENSG00000136193 | SCRN1 | secernin 1 [Source:HGNC Symbol;Acc:HGNC:22192] | 0.151707537 | 0.151707537 |
| ENSG00000136770 | DNAJC1 | DnaJ (Hsp40) homolog, subfamily C, member 1 [Source:HGNC Symbol;Acc:HGNC:20090] | 0.113451701 | NA |
| ENSG00000138160 | KIF11 | kinesin family member 11 [Source:HGNC Symbol;Acc:HGNC:6388] | 0.115877374 | 0.115877374 |
| ENSG00000141076 | CIRH1A | cirrhosis, autosomal recessive 1A (cirhin) [Source:HGNC Symbol;Acc:HGNC:1983] | −0.166159403 | −0.166159403 |
| ENSG00000141161 | UNC45B | unc-45 homolog B (*C. elegans*) [Source:HGNC Symbol;Acc:HGNC:14304] | −0.28423258 | −0.28423258 |
| ENSG00000142188 | TMEM50B | transmembrane protein 50B [Source:HGNC Symbol;Acc:HGNC:1280] | 0.12486265 | 0.12486265 |
| ENSG00000143520 | FLG2 | filaggrin family member 2 [Source:HGNC Symbol;Acc:HGNC:33276] | −0.303312359 | −0.303312359 |
| ENSG00000143552 | NUP210L | nucleoporin 210 kDa-like [Source:HGNC Symbol;Acc:HGNC:29915] | 0.281078121 | 0.281078121 |
| ENSG00000144741 | SLC25A26 | solute carrier family 25 (S-adenosylmethionine carrier), member 26 [Source:HGNC Symbol;Acc:HGNC:20661] | −0.128569249 | -0.128569249 |
| ENSG00000146166 | LGSN | lengsin, lens protein with glutamine synthetase domain [Source:HGNC Symbol;Acc:HGNC:21016] | −0.12918315 | NA |
| ENSG00000146373 | RNF217 | ring finger protein 217 [Source:HGNC Symbol;Acc:HGNC:21487] | −0.150117811 | −0.150117811 |
| ENSG00000147164 | SNX12 | sorting nexin 12 [Source:HGNC Symbol;Acc:HGNC:14976] | 0.108423858 | 0.108423858 |
| ENSG00000147419 | CCDC25 | coiled-coil domain containing 25 [Source:HGNC Symbol;Acc:HGNC:25591] | 0.11439188 | 0.11439188 |
| ENSG00000148123 | | Lipid phosphate phosphatase-related protein type 1 [Source:UniProtKB/Swiss-Prot;Acc:Q8TBJ4] | 0.106165133 | NA |
| ENSG00000152404 | CWF19L2 | CWF19-like 2, cell cycle control (*S. pombe*) [Source:HGNC Symbol;Acc:HGNC:26508] | 0.106554189 | 0.106554189 |
| ENSG00000152457 | DCLRE1C | DNA cross-link repair 1C [Source:HGNC Symbol;Acc:HGNC:17642] | 0.191026562 | 0.191026562 |

TABLE 8-continued

The highest impact sustained by the player in the game as measured by HITsp regressed on RNA expression in plasma samples

| Ensembl_ID | hgnc_symbol | description | X0.5slope_0.1pvalue_0.1_Max_HITsp_plasma | X0.8slope_0.1pvalue_0.1_Max_HITsp_plasma |
|---|---|---|---|---|
| ENSG00000155966 | AFF2 | AF4/FMR2 family, member 2 [Source:HGNC Symbol;Acc:HGNC:3776] | 0.270635465 | 0.270635465 |
| ENSG00000156097 | GPR61 | G protein-coupled receptor 61 [Source:HGNC Symbol;Acc:HGNC:13300] | −0.148236127 | NA |
| ENSG00000159128 | IFNGR2 | interferon gamma receptor 2 (interferon gamma transducer 1) [Source:HGNC Symbol;Acc:HGNC:5440] | −0.129554016 | −0.129554016 |
| ENSG00000160094 | ZNF362 | zinc finger protein 362 [Source:HGNC Symbol;Acc:HGNC:18079] | −0.14269107 | −0.14269107 |
| ENSG00000162236 | STX5 | syntaxin 5 [Source:HGNC Symbol;Acc:HGNC:11440] | −0.114569378 | −0.114569378 |
| ENSG00000163029 | SMC6 | structural maintenance of chromosomes 6 [Source:HGNC Symbol;Acc:HGNC:20466] | 0.276954714 | 0.276954714 |
| ENSG00000164056 | SPRY1 | sprouty homolog 1, antagonist of FGF signaling (Drosophila) [Source:HGNC Symbol;Acc:HGNC:11269] | 0.147011146 | 0.147011146 |
| ENSG00000164167 | LSM6 | LSM6 homolog, U6 small nuclear RNA associated (*S. cerevisiae*) [Source:HGNC Symbol;Acc:HGNC:17017] | 0.123620894 | 0.123620894 |
| ENSG00000164241 | C5orf63 | chromosome 5 open reading frame 63 [Source:HGNC Symbol;Acc:HGNC:40051] | 0.185998415 | 0.185998415 |
| ENSG00000164342 | TLR3 | toll-like receptor 3 [Source:HGNC Symbol;Acc:HGNC:11849] | 0.118798462 | NA |
| ENSG00000164691 | TAGAP | T-cell activation RhoGTPase activating protein [Source:HGNC Symbol;Acc:HGNC:15669] | −0.125513291 | −0.125513291 |
| ENSG00000165819 | METTL3 | methyltransferase like 3 [Source:HGNC Symbol;Acc:HGNC:17563] | 0.131405581 | 0.131405581 |
| ENSG00000167216 | KATNAL2 | katanin p60 subunit A-like 2 [Source:HGNC Symbol;Acc:HGNC:25387] | 0.219516484 | NA |
| ENSG00000167528 | ZNF641 | zinc finger protein 641 [Source:HGNC Symbol;Acc:HGNC:31834] | −0.123686678 | −0.123686678 |
| ENSG00000167693 | NXN | nucleoredoxin [Source:HGNC Symbol;Acc:HGNC:18008] | −0.209096283 | -0.209096283 |
| ENSG00000167740 | CYB5D2 | cytochrome b5 domain containing 2 [Source:HGNC Symbol;Acc:HGNC:28471] | −0.12047966 | -0.12047966 |
| ENSG00000168234 | TTC39C | tetratricopeptide repeat domain 39C [Source:HGNC Symbol;Acc:HGNC:26595] | 0.100411688 | 0.100411688 |
| ENSG00000168394 | TAP1 | transporter 1, ATP-binding cassette, sub-family B (MDR/TAP) [Source:HGNC Symbol;Acc:HGNC:43] | −0.164176847 | -0.164176847 |
| ENSG00000169330 | KIAA1024 | KIAA1024 [Source:HGNC Symbol;Acc:HGNC:29172] | 0.140505947 | NA |
| ENSG00000169413 | RNASE6 | ribonuclease, RNase A family, k6 [Source:HGNC Symbol;Acc:HGNC:10048] | −0.132557953 | −0.132557953 |
| ENSG00000169427 | KCNK9 | potassium channel, subfamily K, member 9 [Source:HGNC Symbol;Acc:HGNC:6283] | −0.121379856 | NA |
| ENSG00000170049 | KCNAB3 | potassium voltage-gated channel, shaker-related subfamily, beta member 3 [Source:HGNC Symbol;Acc:HGNC:6230] | −0.185365138 | −0.185365138 |
| ENSG00000170423 | KRT78 | keratin 78 [Source:HGNC Symbol;Acc:HGNC:28926] | 0.187955509 | 0.187955509 |
| ENSG00000170606 | HSPA4 | heat shock 70 kDa protein 4 [Source:HGNC Symbol;Acc:HGNC:5237] | 0.20388256 | 0.20388256 |
| ENSG00000170832 | U5P32 | ubiquitin specific peptidase 32 [Source:HGNC Symbol;Acc:HGNC:19143] | 0.188947651 | 0.188947651 |

TABLE 8-continued

The highest impact sustained by the player in the game as measured by HITsp regressed on RNA expression in plasma samples

| Ensembl_ID | hgnc_symbol | description | X0.5slope_0.1pvalue_0.1_Max_HITsp_plasma | X0.8slope_0.1pvalue_0.1_Max_HITsp_plasma |
|---|---|---|---|---|
| ENSG00000171401 | KRT13 | keratin 13 [Source:HGNC Symbol;Acc:HGNC:6415] | 0.25057251 | NA |
| ENSG00000174437 | ATP2A2 | ATPase, Ca++ transporting, cardiac muscle, slow twitch 2 [Source:HGNC Symbol;Acc:HGNC:812] | 0.400805765 | 0.400805765 |
| ENSG00000174628 | IQCK | IQ motif containing K [Source:HGNC Symbol;Acc:HGNC:28556] | 0.136023094 | NA |
| ENSG00000175224 | ATG13 | autophagy related 13 [Source:HGNC Symbol;Acc:HGNC:29091] | −0.139076734 | −0.139076734 |
| ENSG00000176177 | ENTHD1 | ENTH domain containing 1 [Source:HGNC Symbol;Acc:HGNC:26352] | 0.129447716 | NA |
| ENSG00000176274 | NA | NA | 0.106120051 | −0.106120051 |
| ENSG00000176624 | MEX3C | mex-3 RNA binding family member C [Source:HGNC Symbol;Acc:HGNC:28040] | 0.180591536 | 0.180591536 |
| ENSG00000177628 | GBA | glucosidase, beta, acid [Source:HGNC Symbol;Acc:HGNC:4177] | −0.106595166 | −0.106595166 |
| ENSG00000179603 | GRM8 | glutamate receptor, metabotropic 8 [Source:HGNC Symbol;Acc:HGNC:4600] | 0.157319697 | NA |
| ENSG00000179750 | APOBEC3B | apolipoprotein B mRNA editing enzyme, catalytic polypeptide-like 3B [Source:HGNC Symbol;Acc:HGNC:17352] | 0.100224101 | NA |
| ENSG00000184083 | FAM120C | family with sequence similarity 120C [Source:HGNC Symbol;Acc:HGNC:16949] | 0.110074364 | 0.110074364 |
| ENSG00000186529 | CYP4F3 | cytochrome P450, family 4, subfamily F, polypeptide 3 [Source:HGNC Symbol;Acc:HGNC:2646] | −0.163081719 | −0.163081719 |
| ENSG00000186615 | KTN1-AS1 | KTN1 antisense RNA 1 [Source:HGNC Symbol;Acc:HGNC:19842] | 0.142901608 | NA |
| ENSG00000187600 | TMEM247 | transmembrane protein 247 [Source:HGNC Symbol;Acc:HGNC:42967] | 0.108107182 | NA |
| ENSG00000187726 | DNAJB13 | DnaJ (Hsp40) homolog, subfamily B, member 13 [Source:HGNC Symbol;Acc:HGNC:30718] | 0.103453497 | NA |
| ENSG00000188467 | SLC24A5 | solute carrier family 24 (sodium/potassium/calcium exchanger), member 5 [Source:HGNC Symbol;Acc:HGNC:20611] | 0.103370533 | NA |
| ENSG00000189292 | FAM150B | family with sequence similarity 150, member B [Source:HGNC Symbol;Acc:HGNC:27683] | 0.106279244 | NA |
| ENSG00000197170 | PSMD12 | proteasome (prosome, macropain) 26S subunit, non-ATPase, 12 [Source:HGNC Symbol;Acc:HGNC:9557] | −0.182977534 | −0.182977534 |
| ENSG00000198682 | PAPSS2 | 3'-phosphoadenosine 5'-phosphosulfate synthase 2 [Source:HGNC Symbol;Acc:HGNC:8604] | 0.31037423 | 0.31037423 |
| ENSG00000198818 | SFT2D1 | SFT2 domain containing 1 [Source:HGNC Symbol;Acc:HGNC:21102] | −0.154463245 | −0.154463245 |
| ENSG00000204217 | BMPR2 | bone morphogenetic protein receptor, type II (serine/threonine kinase) [Source:HGNC Symbol;Acc:HGNC:1078] | 0.187926619 | 0.187926619 |
| ENSG00000204956 | PCDHGA1 | protocadherin gamma subfamily A, 1 [Source:HGNC Symbol;Acc:HGNC:8696] | 0.121529553 | NA |
| ENSG00000206053 | HN1L | hematological and neurological expressed 1-like [Source:HGNC Symbol;Acc:HGNC:14137] | −0.116539758 | −0.116539758 |
| ENSG00000213023 | SYT3 | synaptotagmin III [Source:HGNC Symbol;Acc:HGNC:11511] | −0.142039238 | −0.142039238 |

TABLE 8-continued

The highest impact sustained by the player in the game as measured by HITsp regressed on RNA expression in plasma samples

| Ensembl_ID | hgnc_symbol | description | X0.5slope_0.1pvalue_0.1_Max_HITsp_plasma | X0.8slope_0.1pvalue_0.1_Max_HITsp_plasma |
|---|---|---|---|---|
| ENSG00000214324 | C3orf56 | chromosome 3 open reading frame 56 [Source:HGNC Symbol;Acc:HGNC:32481] | 0.101213919 | NA |
| ENSG00000223561 | | | 0.12794031 | NA |
| ENSG00000225492 | GBP1P1 | guanylate binding protein 1, interferon-inducible pseudogene 1 [Source:HGNC Symbol;Acc:HGNC:39561] | 0.121917628 | NA |
| ENSG00000232712 | KIZ-AS1 | KIZ antisense RNA 1 [Source:HGNC Symbol;Acc:HGNC:51231 ] | 0.203847703 | NA |
| ENSG00000233137 | NA | NA | 0.145628143 | 0.145628143 |
| ENSG00000234456 | MAGI2-AS3 | MAGI2 antisense RNA 3 [Source:HGNC Symbol;Acc:HGNC:40862] | 1.165895131 | 1.165895131 |
| ENSG00000234722 | LINC01287 | long intergenic non-protein coding RNA 1287 [Source:HGNC Symbol;Acc:HGNC:50351] | 0.120258318 | 0.120258318 |
| ENSG00000238083 | LRRC37A2 | leucine rich repeat containing 37, member A2 [Source:HGNC Symbol;Acc:HGNC:32404] | −0.122587313 | −0.122587313 |
| ENSG00000240057 | | | 0.134220987 | NA |
| ENSG00000241468 | ATP5J2 | ATP synthase, H+ transporting, mitochondrial Fo complex, subunit F2 [Source:HGNC Symbol;Acc:HGNC:848] | −0.148342124 | −0.148342124 |
| ENSG00000248360 | LINC00504 | long intergenic non-protein coding RNA 504 [Source:HGNC Symbol;Acc:HGNC:43555] | −0.127175488 | −0.127175488 |
| ENSG00000249948 | GBA3 | glucosidase, beta, acid 3 (gene/pseudogene) [Source:HGNC Symbol;Acc:HGNC:19069] | −0.114794098 | NA |
| ENSG00000250519 | | | −0.105296624 | NA |
| ENSG00000250722 | SEPP1 | selenoprotein P, plasma, 1 [Source:HGNC Symbol;Acc:HGNC:10751] | 0.102671916 | NA |
| ENSG00000255189 | GLYATL1P1 | glycine-N-acyltransferase-like 1 pseudogene 1 [Source:HGNC Symbol;Acc:HGNC:37866] | 0.151317511 | 0.151317511 |
| ENSG00000260231 | JHDM1D-AS1 | JHDM1D antisense RNA 1 (head to head) [Source:HGNC Symbol;Acc:HGNC:48959] | 0.136907921 | 0.136907921 |
| ENSG00000265489 | | | 0.15073608 | NA |

TABLE 9

The highest impact sustained by the player in the game as measured by linear acceleration regressed on RNA expression in plasma samples

| Ensembl_ID | hgnc_symbol | description | X0.5slope_0.1pvalue_0.1_Max_lin_acc_plasma | X0.8slope_0.1pvalue_0.1_Max_lin_acc_plasma |
|---|---|---|---|---|
| ENSG00000010318 | PHF7 | PHD finger protein 7 [Source:HGNC Symbol;Acc:HGNC:18458] | 0.170229865 | 0.170229865 |
| ENSG00000025770 | NCAPH2 | non-SMC condensin II complex, subunit H2 [Source:HGNC Symbol;Acc:HGNC:25071] | −0.112730034 | −0.112730034 |
| ENSG00000029725 | RABEP1 | rabaptin, RAB GTPase binding effector protein 1 [Source:HGNC Symbol;Acc:HGNC:17677] | 0.228780531 | 0.228780531 |
| ENSG00000040531 | CTNS | cystinosin, lysosomal cystine transporter [Source:HGNC Symbol;Acc:HGNC:2518] | −0.10929833 | −0.10929833 |
| ENSG00000047346 | FAM214A | family with sequence similarity 214, member A [Source:HGNC Symbol;Acc:HGNC:25609] | −0.109435184 | −0.109435184 |

TABLE 9-continued

The highest impact sustained by the player in the game as measured by linear acceleration regressed on RNA expression in plasma samples

| Ensembl_ID | hgnc_symbol | description | X0.5slope_0.1pvalue_0.1_Max_lin_acc_plasma | X0.8slope_0.1pvalue_0.1_Max_lin_acc_plasma |
|---|---|---|---|---|
| ENSG00000049167 | ERCC8 | excision repair cross-complementation group 8 [Source:HGNC Symbol;Acc:HGNC:3439] | 0.109452269 | NA |
| ENSG00000064012 | CASP8 | caspase 8, apoptosis-related cysteine peptidase [Source:HGNC Symbol;Acc:HGNC:1509] | −0.187553974 | −0.187553974 |
| ENSG00000071909 | MYO3B | myosin IIIB [Source:HGNC Symbol;Acc:HGNC:15576] | 0.251537467 | 0.251537467 |
| ENSG00000074755 | ZZEF1 | zinc finger, ZZ-type with EF-hand domain 1 [Source:HGNC Symbol;Acc:HGNC:29027] | 0.318566019 | 0.318566019 |
| ENSG00000079459 | FDFT1 | farnesyl-diphosphate farnesyltransferase 1 [Source:HGNC Symbol;Acc:HGNC:3629] | 0.141827495 | 0.141827495 |
| ENSG00000081087 | OSTM1 | osteopetrosis associated transmembrane protein 1 [Source:HGNC Symbol;Acc:HGNC:28969] | 0.121617273 | 0.121617273 |
| ENSG00000081791 | KIAA0141 | KIAA0141 [Source:HGNC Symbol;Acc:HGNC:21652] | −0.127139336 | −0.127139336 |
| ENSG00000084112 | SSH1 | slingshot protein phosphatase 1 [Source:HGNC Symbol;Acc:HGNC:30579] | 0.303239347 | 0.303239347 |
| ENSG00000089597 | GANAB | glucosidase, alpha; neutral AB [Source:HGNC Symbol;Acc:HGNC:4138] | −0.225207094 | −0.225207094 |
| ENSG00000100023 | PPIL2 | peptidylprolyl isomerase (cyclophilin)-like 2 [Source:HGNC Symbol;Acc:HGNC:9261] | −0.162688083 | −0.162688083 |
| ENSG00000100412 | ACO2 | aconitase 2, mitochondrial [Source:HGNC Symbol;Acc:HGNC:118] | 0.131888628 | 0.131888628 |
| ENSG00000101464 | PIGU | phosphatidylinositol glycan anchor biosynthesis, class U [Source:HGNC Symbol;Acc:HGNC:15791] | −0.135513742 | −0.135513742 |
| ENSG00000104859 | CLASRP | CLK4-associating serine/arginine rich protein [Source:HGNC Symbol;Acc:HGNC:17731] | −0.20844473 | −0.20844473 |
| ENSG00000105197 | TIMM50 | translocase of inner mitochondrial membrane 50 homolog (S. cerevisiae) [Source:HGNC Symbol;Acc:HGNC:23656] | −0.113849069 | −0.113849069 |
| ENSG00000105707 | HPN | hepsin [Source:HGNC Symbol;Acc:HGNC:5155] | −0.107147642 | NA |
| ENSG00000107105 | ELAVL2 | ELAV like neuron-specific RNA binding protein 2 [Source:HGNC Symbol;Acc:HGNC:3313] | 0.111552451 | NA |
| ENSG00000107951 | MTPAP | mitochondrial poly(A) polymerase [Source:HGNC Symbol;Acc:HGNC:25532] | −0.117424914 | −0.117424914 |
| ENSG00000108406 | DHX40 | DEAH (Asp-Glu-Ala-His) box polypeptide 40 [Source:HGNC Symbol;Acc:HGNC:18018] | 0.107679358 | 0.107679358 |
| ENSG00000109320 | NFKB1 | nuclear factor of kappa light polypeptide gene enhancer in B-cells 1 [Source:HGNC Symbol;Acc:HGNC:7794] | 0.136994942 | 0.136994942 |
| ENSG00000109790 | KLHL5 | kelch-like family member 5 [Source:HGNC Symbol;Acc:HGNC:6356] | 0.507065945 | 0.507065945 |
| ENSG00000110002 | VWA5A | von Willebrand factor A domain containing 5A [Source:HGNC Symbol;Acc:HGNC:6658] | −0.151667695 | −0.151667695 |
| ENSG00000111215 | PRR4 | proline rich 4 (lacrimal) [Source:HGNC Symbol;Acc:HGNC:18020] | 0.122484607 | 0.122484607 |
| ENSG00000111237 | VPS29 | vacuolar protein sorting 29 homolog (S. cerevisiae) [Source:HGNC Symbol;Acc:HGNC:14340] | −0.133121148 | −0.133121148 |
| ENSG00000111897 | SERINC1 | serine incorporator 1 [Source:HGNC Symbol;Acc:HGNC:13464] | −0.284161954 | −0.284161954 |

TABLE 9-continued

The highest impact sustained by the player in the game as measured by linear acceleration regressed on RNA expression in plasma samples

| Ensembl_ID | hgnc_symbol | description | X0.5slope_0.1pvalue_0.1_Max_lin_acc_plasma | X0.8slope_0.1pvalue_0.1_Max_lin_acc_plasma |
|---|---|---|---|---|
| ENSG00000112561 | TFEB | transcription factor EB [Source:HGNC Symbol;Acc:HGNC:11753] | 0.129049727 | 0.129049727 |
| ENSG00000114013 | CD86 | CD86 molecule [Source:HGNC Symbol;Acc:HGNC:1705] | −0.102716542 | −0.102716542 |
| ENSG00000114054 | PCCB | propionyl CoA carboxylase, beta polypeptide [Source:HGNC Symbol;Acc:HGNC:8654] | −0.155835905 | −0.155835905 |
| ENSG00000115241 | PPM1G | protein phosphatase, Mg2+/Mn2+ dependent, 1G [Source:HGNC Symbol;Acc:HGNC:9278] | 0.150004827 | 0.150004827 |
| ENSG00000115641 | FHL2 | four and a half LIM domains 2 [Source:HGNC Symbol;Acc:HGNC:3703] | −0.233055563 | −0.233055563 |
| ENSG00000116984 | MTR | 5-methyltetrahydrofolate-homocysteine methyltransferase [Source:HGNC Symbol;Acc:HGNC:7468] | 0.247644585 | 0.247644585 |
| ENSG00000118307 | CASC1 | cancer susceptibility candidate 1 [Source:HGNC Symbol;Acc:HGNC:29599] | 0.101482267 | NA |
| ENSG00000119471 | HSDL2 | hydroxysteroid dehydrogenase like 2 [Source:HGNC Symbol;Acc:HGNC:18572] | 0.134747511 | 0.134747511 |
| ENSG00000120685 | PROSER1 | proline and serine rich 1 [Source:HGNC Symbol;Acc:HGNC:20291] | −0.29165743 | −0.29165743 |
| ENSG00000120889 | TNFRSF10B | tumor necrosis factor receptor superfamily, member 10b [Source:HGNC Symbol;Acc:HGNC:11905] | −0.102924238 | −0.102924238 |
| ENSG00000122497 | NA | NA | −0.164022762 | NA |
| ENSG00000124191 | TOX2 | TOX high mobility group box family member 2 [Source:HGNC Symbol;Acc:HGNC:16095] | −0.140050174 | −0.140050174 |
| ENSG00000127952 | STYXL1 | serine/threonine/tyrosine interacting-like 1 [Source:HGNC Symbol;Acc:HGNC:18165] | −0.193382641 | −0.193382641 |
| ENSG00000128383 | APOBEC3A | apolipoprotein B mRNA editing enzyme, catalytic polypeptide-like 3A [Source:HGNC Symbol;Acc:HGNC:17343] | −0.108821233 | −0.108821233 |
| ENSG00000129315 | CCNT1 | cyclin T1 [Source:HGNC Symbol;Acc:HGNC:1599] | 0.177435166 | 0.177435166 |
| ENSG00000130176 | CNN1 | calponin 1, basic, smooth muscle [Source:HGNC Symbol;Acc:HGNC:2155] | −0.133567285 | −0.133567285 |
| ENSG00000130717 | UCK1 | uridine-cytidine kinase 1 [Source:HGNC Symbol;Acc:HGNC:14859] | 0.115335421 | NA |
| ENSG00000131351 | HAUS8 | HAUS augmin-like complex, subunit 8 [Source:HGNC Symbol;Acc:HGNC:30532] | −0.155439628 | -0.155439628 |
| ENSG00000132530 | XAF1 | XIAP associated factor 1 [Source:HGNC Symbol;Acc:HGNC:30932] | −0.165628437 | −0.165628437 |
| ENSG00000134825 | TMEM258 | transmembrane protein 258 [Source:HGNC Symbol;Acc:HGNC:1164] | −0.249985405 | -0.249985405 |
| ENSG00000135677 | GNS | glucosamine (N-acetyl)-6-sulfatase [Source:HGNC Symbol;Acc:HGNC:4422] | −0.166966877 | −0.166966877 |
| ENSG00000135838 | NPL | N-acetylneuraminate pyruvate lyase (dihydrodipicolinate synthase) [Source:HGNC Symbol;Acc:HGNC:16781] | −0.162836999 | −0.162836999 |
| ENSG00000136193 | SCRN1 | secernin 1 [Source:HGNC Symbol;Acc:HGNC:22192] | 0.12810643 | 0.12810643 |
| ENSG00000136861 | CDK5RAP2 | CDK5 regulatory subunit associated protein 2 [Source:HGNC Symbol;Acc:HGNC:18672] | 0.314399885 | 0.314399885 |

TABLE 9-continued

The highest impact sustained by the player in the game as measured by linear acceleration regressed on RNA expression in plasma samples

| Ensembl_ID | hgnc_symbol | description | X0.5slope_0.1pvalue_0.1_Max_lin_acc_plasma | X0.8slope_0.1pvalue_0.1_Max_lin_acc_plasma |
|---|---|---|---|---|
| ENSG00000138035 | PNPT1 | polyribonucleotide nucleotidyltransferase 1 [Source:HGNC Symbol;Acc:HGNC:23166] | 0.100640869 | 0.100640869 |
| ENSG00000139192 | TAPBPL | TAP binding protein-like [Source:HGNC Symbol;Acc:HGNC:30683] | −0.111668814 | −0.111668814 |
| ENSG00000139372 | TDG | thymine-DNA glycosylase [Source:HGNC Symbol;Acc:HGNC:11700] | −0.104151038 | −0.104151038 |
| ENSG00000140497 | SCAMP2 | secretory carrier membrane protein 2 [Source:HGNC Symbol;Acc:HGNC:10564] | −0.170271333 | −0.170271333 |
| ENSG00000140718 | FTO | fat mass and obesity associated [Source:HGNC Symbol;Acc:HGNC:24678] | 0.408281748 | 0.408281748 |
| ENSG00000140740 | UQCRC2 | ubiquinol-cytochrome c reductase core protein 11 [Source:HGNC Symbol;Acc:HGNC:12586] | 0.143643681 | 0.143643681 |
| ENSG00000140968 | IRF8 | interferon regulatory factor 8 [Source:HGNC Symbol;Acc:HGNC:5358] | 0.166151883 | 0.166151883 |
| ENSG00000141076 | CIRH1A | cirrhosis, autosomal recessive 1A (cirhin) [Source:HGNC Symbol;Acc:HGNC:1983] | −0.19393658 | −0.19393658 |
| ENSG00000141179 | PCTP | phosphatidylcholine transfer protein [Source:HGNC Symbol;Acc:HGNC:8752] | 0.769728362 | 0.769728362 |
| ENSG00000141720 | NA | NA | 0.181018618 | 0.181018618 |
| ENSG00000143149 | ALDH9A1 | aldehyde dehydrogenase 9 family, member A1 [Source:HGNC Symbol;Acc:HGNC:412] | 0.160034228 | 0.160034228 |
| ENSG00000143595 | AQP10 | aquaporin 10 [Source:HGNC Symbol;Acc:HGNC:16029] | −0.19468292 | −0.19468292 |
| ENSG00000143891 | GALM | galactose mutarotase (aldose 1-epimerase) [Source:HGNC Symbol;Acc:HGNC:24063] | 0.108215249 | 0.108215249 |
| ENSG00000145348 | TBCK | TBC1 domain containing kinase [Source:HGNC Symbol;Acc:HGNC:28261] | −0.189315008 | −0.189315008 |
| ENSG00000145819 | ARHGAP26 | Rho GTPase activating protein 26 [Source:HGNC Symbol;Acc:HGNC:17073] | −0.346909798 | −0.346909798 |
| ENSG00000146192 | FGD2 | FYVE, RhoGEF and PH domain containing 2 [Source:HGNC Symbol;Acc:HGNC:3664] | −0.294768171 | −0.294768171 |
| ENSG00000146574 | CCZ1B | CCZ1 vacuolar protein trafficking and biogenesis associated homolog B (S. cerevisiae) [Source:HGNC Symbol;Acc:HGNC:21717] | −0.115351222 | −0.115351222 |
| ENSG00000152022 | NA | NA | 0.107661715 | 0.107661715 |
| ENSG00000156097 | GPR61 | G protein-coupled receptor 61 [Source:HGNC Symbol;Acc:HGNC:13300] | −0.163461044 | NA |
| ENSG00000160094 | ZNF362 | zinc finger protein 362 [Source:HGNC Symbol;Acc:HGNC:18079] | −0.154109596 | −0.154109596 |
| ENSG00000160172 | FAM86C2P | family with sequence similarity 86, member C2, pseudogene [Source:HGNC Symbol;Acc:HGNC:42392] | −0.110118467 | NA |
| ENSG00000160584 | SIK3 | SIK family kinase 3 [Source:HGNC Symbol;Acc:HGNC:29165] | −0.221008005 | −0.221008005 |
| ENSG00000162236 | STX5 | syntaxin 5 [Source:HGNC Symbol;Acc:HGNC:11440] | −0.122245068 | −0.122245068 |
| ENSG00000163162 | RNF149 | ring finger protein 149 [Source:HGNC Symbol;Acc:HGNC:23137] | −0.125223232 | −0.125223232 |
| ENSG00000163431 | LMOD1 | leiomodin 1 (smooth muscle) [Source:HGNC Symbol;Acc:HGNC:6647] | −0.113030654 | NA |
| ENSG00000164691 | TAGAP | T-cell activation RhoGTPase activating protein [Source:HGNC Symbol;Acc:HGNC:15669] | −0.138824035 | −0.138824035 |

TABLE 9-continued

The highest impact sustained by the player in the game as measured by linear acceleration regressed on RNA expression in plasma samples

| Ensembl_ID | hgnc_symbol | description | X0.5slope_0.1pvalue_0.1_Max_lin_acc_plasma | X0.8slope_0.1pvalue_0.1_Max_lin_acc_plasma |
|---|---|---|---|---|
| ENSG00000164896 | FASTK | Fas-activated serine/threonine kinase [Source:HGNC Symbol;Acc:HGNC:24676] | −0.122541379 | −0.122541379 |
| ENSG00000165424 | ZCCHC24 | zinc finger, CCHC domain containing 24 [Source:HGNC Symbol;Acc:HGNC:26911] | −0.110472325 | −0.110472325 |
| ENSG00000165487 | MICU2 | mitochondrial calcium uptake 2 [Source:HGNC Symbol;Acc:HGNC:31830] | 0.118609041 | 0.118609041 |
| ENSG00000165819 | METTL3 | methyltransferase like 3 [Source:HGNC Symbol;Acc:HGNC:17563] | 0.128671739 | 0.128671739 |
| ENSG00000166446 | CDYL2 | chromodomain protein, Y-like 2 [Source:HGNC Symbol;Acc:HGNC:23030] | 0.202817183 | 0.202817183 |
| ENSG00000166579 | NDEL1 | nudE neurodevelopment protein 1-like 1 [Source:HGNC Symbol;Acc:HGNC:17620] | −0.24862421 | −0.24862421 |
| ENSG00000166963 | MAP1A | microtubule-associated protein 1A [Source:HGNC Symbol;Acc:HGNC:6835] | 2.01678209 | 2.01678209 |
| ENSG00000167216 | KATNAL2 | katanin p60 subunit A-like 2 [Source:HGNC Symbol;Acc:HGNC:25387] | 0.148293565 | NA |
| ENSG00000167491 | GATAD2A | GATA zinc finger domain containing 2A [Source:HGNC Symbol;Acc:HGNC:29989] | 0.713949079 | 0.713949079 |
| ENSG00000167693 | NXN | nucleoredoxin [Source:HGNC Symbol;Acc:HGNC:18008] | −0.215655184 | −0.215655184 |
| ENSG00000167740 | CYB5D2 | cytochrome b5 domain containing 2 [Source:HGNC Symbol;Acc:HGNC:28471] | −0.154529266 | −0.154529266 |
| ENSG00000168394 | TAP1 | transporter 1, ATP-binding cassette, sub-family B (MDR/TAP) [Source:HGNC Symbol;Acc:HGNC:43] | −0.190104087 | −0.190104087 |
| ENSG00000169018 | FEM1B | fern-1 homolog b (*C. elegans*) [Source:HGNC Symbol;Acc:HGNC:3649] | 0.143878826 | 0.143878826 |
| ENSG00000169403 | PTAFR | platelet-activating factor receptor [Source:HGNC Symbol;Acc:HGNC:9582] | −0.197625182 | −0.197625182 |
| ENSG00000170049 | KCNAB3 | potassium voltage-gated channel, shaker-related subfamily, beta member 3 [Source:HGNC Symbol;Acc:HGNC:6230] | −0.169352002 | −0.169352002 |
| ENSG00000170365 | SMAD1 | SMAD family member 1 [Source:HGNC Symbol;Acc:HGNC:6767] | −0.274366666 | −0.274366666 |
| ENSG00000170458 | CD14 | CD14 molecule [Source:HGNC Symbol;Acc:HGNC:1628] | 0.121428527 | NA |
| ENSG00000170606 | HSPA4 | heat shock 70 kDa protein 4 [Source:HGNC Symbol;Acc:HGNC:5237] | 0.162021198 | 0.162021198 |
| ENSG00000170876 | TMEM43 | transmembrane protein 43 [Source:HGNC Symbol;Acc:HGNC:28472] | −0.129208162 | −0.129208162 |
| ENSG00000171466 | ZNF562 | zinc finger protein 562 [Source:HGNC Symbol;Acc:HGNC:25950] | 0.156962027 | 0.156962027 |
| ENSG00000171853 | TRAPPC12 | trafficking protein particle complex 12 [Source:HGNC Symbol;Acc:HGNC:24284] | −0.191519409 | −0.191519409 |
| ENSG00000176177 | ENTHD1 | ENTH domain containing 1 [Source:HGNC Symbol;Acc:HGNC:26352] | 0.151712936 | NA |
| ENSG00000177628 | GBA | glucosidase, beta, acid [Source:HGNC Symbol;Acc:HGNC:4177] | −0.110647138 | −0.110647138 |
| ENSG00000178449 | COX14 | cytochrome c oxidase assembly homolog 14 (*S. cerevisiae*) [Source:HGNC Symbol;Acc:HGNC:28216] | −0.347340835 | −0.347340835 |

TABLE 9-continued

The highest impact sustained by the player in the game as measured by linear acceleration regressed on RNA expression in plasma samples

| Ensembl_ID | hgnc_symbol | description | X0.5slope_0.1pvalue_0.1_Max_lin_acc_plasma | X0.8slope_0.1pvalue_0.1_Max_lin_acc_plasma |
|---|---|---|---|---|
| ENSG00000181837 | OR5D17P | olfactory receptor, family 5, subfamily D, member 17 pseudogene [Source:HGNC Symbol;Acc:HGNC:15284] | 0.120218825 | NA |
| ENSG00000181929 | PRKAG1 | protein kinase, AMP-activated, gamma 1 non-catalytic subunit [Source:HGNC Symbol;Acc:HGNC:9385] | −0.128936457 | −0.128936457 |
| ENSG00000182022 | CHST15 | carbohydrate (N-acetylgalactosamine 4-sulfate 6-0) sulfotransferase 15 [Source:HGNC Symbol;Acc:HGNC:18137] | −0.132490353 | −0.132490353 |
| ENSG00000185052 | SLC24A3 | solute carrier family 24 (sodium/potassium/calcium exchanger), member 3 [Source:HGNC Symbol;Acc:HGNC:10977] | 0.500342517 | 0.500342517 |
| ENSG00000188636 | LDOC1L | leucine zipper, down-regulated in cancer 1-like [Source:HGNC Symbol;Acc:HGNC:13343] | 0.172136223 | 0.172136223 |
| ENSG00000189339 | SLC35E2B | solute carrier family 35, member E2B [Source:HGNC Symbol;Acc:HGNC:33941] | 0.128946098 | 0.128946098 |
| ENSG00000197006 | METTL9 | methyltransferase like 9 [Source:HGNC Symbol;Acc:HGNC:24586] | 0.237131756 | 0.237131756 |
| ENSG00000197024 | ZNF398 | zinc finger protein 398 [Source:HGNC Symbol;Acc:HGNC:18373] | 0.152839795 | 0.152839795 |
| ENSG00000197170 | PSMD12 | proteasome (prosome, macropain) 26S subunit, non-ATPase, 12 [Source:HGNC Symbol;Acc:HGNC:9557] | −0.18262561 | −0.18262561 |
| ENSG00000197249 | SERPINA1 | serpin peptidase inhibitor, clade A (alpha-1 antiproteinase, antitrypsin), member 1 [Source:HGNC Symbol;Acc:HGNC:8941] | −0.262362563 | −0.262362563 |
| ENSG00000197989 | SNHG12 | small nucleolar RNA host gene 12 (non-protein coding) [Source:HGNC Symbol;Acc:HGNC:30062] | −0.281270998 | −0.281270998 |
| ENSG00000198053 | SIRPA | signal-regulatory protein alpha [Source:HGNC Symbol;Acc:HGNC:9662] | −0.116808258 | −0.116808258 |
| ENSG00000198682 | PAPSS2 | 3'-phosphoadenosine 5'-phosphosulfate synthase 2 [Source:HGNC Symbol;Acc:HGNC:8604] | 0.277734156 | 0.277734156 |
| ENSG00000198818 | SFT2D1 | SFT2 domain containing 1 [Source:HGNC Symbol;Acc:HGNC:21102] | −0.146314776 | −0.146314776 |
| ENSG00000204427 | ABHD16A | abhydrolase domain containing 16A [Source:HGNC Symbol;Acc:HGNC:13921 ] | −0.123372105 | −0.123372105 |
| ENSG00000206053 | HN1L | hematological and neurological expressed 1-like [Source:HGNC Symbol;Acc:HGNC:14137] | −0.134975971 | −0.134975971 |
| ENSG00000206077 | ZDHHC11B | zinc finger, DHHC-type containing 11B [Source:HGNC Symbol;Acc:HGNC:32962] | 0.13138876 | NA |
| ENSG00000213023 | SYT3 | synaptotagmin III [Source:HGNC Symbol;Acc:HGNC:11511] | −0.135433001 | −0.135433001 |
| ENSG00000213889 | PPM1N | protein phosphatase, Mg2+/Mn2+ dependent, 1N (putative) [Source:HGNC Symbol;Acc:HGNC:26845] | −0.111596208 | −0.111596208 |
| ENSG00000215853 | RPTN | repetin [Source:HGNC Symbol;Acc:HGNC:26809] | −0.290132783 | NA |
| ENSG00000230590 | FTX | FTX transcript, XIST regulator (non-protein coding) [Source:HGNC Symbol;Acc:HGNC:37190] | −0.105300895 | −0.105300895 |
| ENSG00000232177 | MTND4P24 | MT-ND4 pseudogene 24 [Source:HGNC Symbol;Acc:HGNC:42220] | 0.159020151 | NA |

TABLE 9-continued

The highest impact sustained by the player in the game as measured by linear acceleration regressed on RNA expression in plasma samples

| Ensembl_ID | hgnc_symbol | description | X0.5slope_0.1pvalue_0.1_Max_lin_acc_plasma | X0.8slope_0.1pvalue_0.1_Max_lin_acc_plasma |
|---|---|---|---|---|
| ENSG00000233614 | DDX11L10 | DEAD/H (Asp-Glu-Ala-Asp/His) box helicase 11 like 10 [Source:HGNC Symbol;Acc:HGNC:14125] | −1.173682324 | NA |
| ENSG00000234456 | MAGI2-AS3 | MAGI2 antisense RNA 3 [Source:HGNC Symbol;Acc:HGNC:40862] | 0.90738652 | 0.90738652 |
| ENSG00000235568 | NFAM1 | NFAT activating protein with ITAM motif 1 [Source:HGNC Symbol;Acc:HGNC:29872] | −0.188277675 | −0.188277675 |
| ENSG00000237973 | MIR6723 | microRNA 6723 [Source:HGNC Symbol;Acc:HGNC:50152] | 14.86928693 | 14.86928693 |
| ENSG00000238083 | LRRC37A2 | leucine rich repeat containing 37, member A2 [Source:HGNC Symbol;Acc:HGNC:32404] | −0.161517096 | −0.161517096 |
| ENSG00000239437 | RN7SL752P | RNA, 7SL, cytoplasmic 752, pseudogene [Source:HGNC Symbol;Acc:HGNC:46768] | 0.20389067 | NA |
| ENSG00000241468 | ATP5J2 | ATP synthase, H+ transporting, mitochondrial Fo complex, subunit F2 [Source:HGNC Symbol;Acc:HGNC:848] | −0.159288511 | −0.159288511 |
| ENSG00000242588 | | | 0.162348015 | 0.162348015 |
| ENSG00000245248 | USP2-AS1 | USP2 antisense RNA 1 (head to head) [Source:HGNC Symbol;Acc:HGNC:48673] | −0.161323318 | −0.161323318 |
| ENSG00000245526 | LINC00461 | long intergenic non-protein coding RNA 461 [Source:HGNC Symbol;Acc:HGNC:42810] | −0.1372132 | −0.1372132 |
| ENSG00000248360 | LINC00504 | long intergenic non-protein coding RNA 504 [Source:HGNC Symbol;Acc:HGNC:43555] | −0.127378703 | −0.127378703 |
| ENSG00000248538 | | | −0.182292708 | NA |
| ENSG00000250519 | | | −0.124538483 | NA |
| ENSG00000251441 | RTEL1P1 | regulator of telomere elongation helicase 1 pseudogene 1 [Source:HGNC Symbol;Acc:HGNC:44213] | −0.111558201 | NA |
| ENSG00000256050 | | | 0.201644537 | NA |
| ENSG00000262497 | FAM187B2P | family with sequence similarity 187, member B2, pseudogene [Source:HGNC Symbol;Acc:HGNC:49213] | −0.112441006 | NA |

TABLE 10

The highest impact sustained by the player in the game as measured by rotational acceleration regressed on RNA expression in plasma samples

| Ensembl_ID | hgnc_symbol | description | X0.5slope_0.1pvalue_0.1_Max_rot_acc_plasma | X0.8slope_0.1pvalue_0.1_Max_rot_acc_plasma |
|---|---|---|---|---|
| ENSG00000198899 | MT-ATP6 | mitochondrially encoded ATP synthase 6 [Source:HGNC Symbol;Acc:HGNC:7414] | −1.710072511 | −1.710072511 |

TABLE 11

The highest impact sustained by the player in the game as measured by the number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000002919 | SNX11 | sorting nexin 11 [Source:HGNC Symbol;Acc:HGNC:14975] | −0.18130183 | −0.18130183 |
| ENSG00000006607 | FARP2 | FERM, RhoGEF and pleckstrin domain protein 2 [Source:HGNC Symbol;Acc:HGNC:16460] | −0.413103168 | −0.413103168 |
| ENSG00000010219 | DYRK4 | dual-specificity tyrosine-(Y)-phosphorylation regulated kinase 4 [Source:HGNC Symbol;Acc:HGNC:3095] | −0.268530317 | −0.268530317 |
| ENSG00000011021 | CLCN6 | chloride channel, voltage-sensitive 6 [Source:HGNC Symbol;Acc:HGNC:2024] | −0.300156067 | −0.300156067 |
| ENSG00000011132 | APBA3 | amyloid beta (A4) precursor protein-binding, family A, member 3 [Source:HGNC Symbol;Acc:HGNC:580] | 0.16775879 | 0.16775879 |
| ENSG00000011638 | TMEM159 | transmembrane protein 159 [Source:HGNC Symbol;Acc:HGNC:30136] | −0.228627306 | −0.228627306 |
| ENSG00000012061 | ERCC1 | excision repair cross-complementation group 1 [Source:HGNC Symbol;Acc:HGNC:3433] | −0.190496391 | −0.190496391 |
| ENSG00000013306 | SLC25A39 | solute carrier family 25, member 39 [Source:HGNC Symbol;Acc:HGNC:24279] | 0.71738695 | 0.71738695 |
| ENSG00000029559 | IBSP | integrin-binding sialoprotein [Source:HGNC Symbol;Acc:HGNC:5341] | −0.273970392 | NA |
| ENSG00000036530 | CYP46A1 | cytochrome P450, family 46, subfamily A, polypeptide 1 [Source:HGNC Symbol;Acc:HGNC:2641] | −0.341725844 | −0.341725844 |
| ENSG00000047230 | CTPS2 | CTP synthase 2 [Source:HGNC Symbol;Acc:HGNC:2520] | 0.152436371 | 0.152436371 |
| ENSG00000047932 | GOPC | golgi-associated PDZ and coiled-coil motif containing [Source:HGNC Symbol;Acc:HGNC:17643] | 0.41112031 | 0.41112031 |
| ENSG00000050327 | ARHGEF5 | Rho guanine nucleotide exchange factor (GEF) 5 [Source:HGNC Symbol;Acc:HGNC:13209] | −0.172498356 | −0.172498356 |
| ENSG00000052841 | TTC17 | tetratricopeptide repeat domain 17 [Source:HGNC Symbol;Acc:HGNC:25596] | −0.333510806 | −0.333510806 |
| ENSG00000053372 | MRT04 | mRNA turnover 4 homolog (*S. cerevisiae*) [Source:HGNC Symbol;Acc:HGNC:18477] | −0.282938139 | −0.282938139 |
| ENSG00000056277 | ZNF280C | zinc finger protein 280C [Source:HGNC Symbol;Acc:HGNC:25955] | −0.119273171 | NA |
| ENSG00000060558 | GNA15 | guanine nucleotide binding protein (G protein), alpha 15 (Gq class) [Source:HGNC Symbol;Acc:HGNC:4383] | 0.383424973 | 0.383424973 |
| ENSG00000061936 | SFSWAP | splicing factor, suppressor of white-apricot family [Source:HGNC Symbol;Acc:HGNC:10790] | −0.328160243 | −0.328160243 |
| ENSG00000061987 | MON2 | MON2 homolog (*S. cerevisiae*) [Source:HGNC Symbol;Acc:HGNC:29177] | −0.247236391 | −0.247236391 |
| ENSG00000063244 | U2AF2 | U2 small nuclear RNA auxiliary factor 2 [Source:HGNC Symbol;Acc:HGNC:23156] | 0.384874145 | 0.384874145 |
| ENSG00000064012 | CASP8 | caspase 8, apoptosis-related cysteine peptidase [Source:HGNC Symbol;Acc:HGNC:1509] | −0.301014707 | −0.301014707 |
| ENSG00000065054 | SLC9A3R2 | solute carrier family 9, subfamily A (NHE3, cation proton antiporter 3), member 3 regulator 2 [Source:HGNC Symbol;Acc:HGNC:11076] | 0.475185163 | 0.475185163 |

TABLE 11-continued

The highest impact sustained by the player in the game as measured by the number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000065268 | WDR18 | WD repeat domain 18 [Source:HGNC Symbol;Acc:HGNC:17956] | 0.140777372 | NA |
| ENSG00000065883 | CDK13 | cyclin-dependent kinase 13 [Source:HGNC Symbol;Acc:HGNC:1733] | 0.491099008 | 0.491099008 |
| ENSG00000066557 | LRRC40 | leucine rich repeat containing 40 [Source:HGNC Symbol;Acc:HGNC:26004] | 0.154029534 | NA |
| ENSG00000067369 | TP53BP1 | tumor protein p53 binding protein 1 [Source:HGNC Symbol;Acc:HGNC:11999] | −0.45179204 | −0.45179204 |
| ENSG00000068745 | IP6K2 | inositol hexakisphosphate kinase 2 [Source:HGNC Symbol;Acc:HGNC:17313] | −0.340595998 | −0.340595998 |
| ENSG00000072364 | AFF4 | AF4/FMR2 family, member 4 [Source:HGNC Symbol;Acc:HGNC:17869] | −0.377940237 | −0.377940237 |
| ENSG00000074755 | ZZEF1 | zinc finger, ZZ-type with EF-hand domain 1 [Source:HGNC Symbol;Acc:HGNC:29027] | −0.547759839 | −0.547759839 |
| ENSG00000075856 | SART3 | squamous cell carcinoma antigen recognized by T cells 3 [Source:HGNC Symbol;Acc:HGNC:16860] | −0.290538331 | −0.290538331 |
| ENSG00000076382 | SPAG5 | sperm associated antigen 5 [Source:HGNC Symbol;Acc:HGNC:13452] | −0.294534162 | −0.294534162 |
| ENSG00000077380 | DYNC1I2 | dynein, cytoplasmic 1, intermediate chain 2 [Source:HGNC Symbol;Acc:HGNC:2964] | 0.316867603 | 0.316867603 |
| ENSG00000077984 | CST7 | cystatin F (leukocystatin) [Source:HGNC Symbol;Acc:HGNC:2479] | 0.878464548 | 0.878464548 |
| ENSG00000078808 | SDF4 | stromal cell derived factor 4 [Source:HGNC Symbol;Acc:HGNC:24188] | 0.767915274 | 0.767915274 |
| ENSG00000079313 | REXO1 | REX1, RNA exonuclease 1 homolog (S. cerevisiae) [Source:HGNC Symbol;Acc:HGNC:24616] | 0.251033654 | 0.251033654 |
| ENSG00000079332 | SAR1A | secretion associated, Ras related GTPase 1A [Source:HGNC Symbol;Acc:HGNC:10534] | 0.385716192 | 0.385716192 |
| ENSG00000081791 | KIAA0141 | KIAA0141 [Source:HGNC Symbol;Acc:HGNC:28969] | −0.22694511 | −0.22694511 |
| ENSG00000083099 | LYRM2 | LYR motif containing 2 [Source:HGNC Symbol;Acc:HGNC:25229] | −0.154230851 | −0.154230851 |
| ENSG00000083635 | NUFIP1 | nuclear fragile X mental retardation protein interacting protein 1 [Source:HGNC Symbol;Acc:HGNC:8057] | −0.193120866 | −0.193120866 |
| ENSG00000084234 | APLP2 | amyloid beta (A4) precursor-like protein 2 [Source:HGNC Symbol;Acc:HGNC:598] | −0.445100705 | −0.445100705 |
| ENSG00000085719 | CPNE3 | copine III [Source:HGNC Symbol;Acc:HGNC:2316] | 0.337011459 | 0.337011459 |
| ENSG00000085978 | ATG16L1 | autophagy related 16-like 1 (S. cerevisiae) [Source:HGNC Symbol;Acc:HGNC:21498] | −0.224370196 | −0.224370196 |
| ENSG00000086730 | LAT2 | linker for activation of T cells family, member 2 [Source:HGNC Symbol;Acc:HGNC:12749] | −0.15860923 | −0.15860923 |
| ENSG00000087111 | PIGS | phosphatidylinositol glycan anchor biosynthesis, class S [Source:HGNC Symbol;Acc:HGNC:14937] | −0.218275213 | −0.218275213 |
| ENSG00000087191 | PSMC5 | proteasome (prosome, macropain) 26S subunit, ATPase, 5 [Source:HGNC Symbol;Acc:HGNC:9552] | −0.316917034 | −0.316917034 |

TABLE 11-continued

The highest impact sustained by the player in the game as measured by the number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000087589 | CASS4 | Cas scaffolding protein family member 4 [Source:HGNC Symbol;Acc:HGNC:15878] | −0.164417008 | −0.164417008 |
| ENSG00000087884 | AAMDC | adipogenesis associated, Mth938 domain containing [Source:HGNC Symbol;Acc:HGNC:30205] | −0.146359987 | NA |
| ENSG00000089177 | K1F16B | kinesin family member 16B [Source:HGNC Symbol;Acc:HGNC:15869] | −0.270083492 | −0.270083492 |
| ENSG00000091164 | TXNL1 | thioredoxin-like 1 [Source:HGNC Symbol;Acc:HGNC:12436] | −0.271836525 | −0.271836525 |
| ENSG00000092098 | RNF31 | ring finger protein 31 [Source:HGNC Symbol;Acc:HGNC:16031] | −0.234769781 | −0.234769781 |
| ENSG00000099810 | MTAP | methylthioadenosine phosphorylase [Source: HGNC Symbol;Acc:HGNC:7413] | −0.177894282 | −0.177894282 |
| ENSG00000100181 | TPTEP1 | transmembrane phosphatase with tensin homology pseudogene 1 [Source:HGNC Symbol;Acc:HGNC:43648] | 4.020177071 | 4.020177071 |
| ENSG00000100359 | SGSM3 | small G protein signaling modulator 3 [Source:HGNC Symbol;Acc:HGNC:25228] | 0.279110078 | 0.279110078 |
| ENSG00000100811 | YY1 | YY1 transcription factor [Source:HGNC Symbol;Acc:HGNC:12856] | 0.639748136 | 0.639748136 |
| ENSG00000100836 | PABPN1 | poly(A) binding protein, nuclear 1 [Source:HGNC Symbol;Acc:HGNC:8565] | 0.135052692 | 0.135052692 |
| ENSG00000100938 | GMPR2 | guanosine monophosphate reductase 2 [Source:HGNC Symbol;Acc:HGNC:4377] | −0.367031082 | −0.367031082 |
| ENSG00000101266 | CSNK2A1 | casein kinase 2, alpha 1 polypeptide [Source:HGNC Symbol;Acc:HGNC:2457] | 0.215976365 | 0.215976365 |
| ENSG00000101337 | TM9SF4 | transmembrane 9 superfamily protein member 4 [Source:HGNC Symbol;Acc:HGNC:30797] | −0.327607154 | −0.327607154 |
| ENSG00000101452 | DHX35 | DEAH (Asp-Glu-Ala-His) box polypeptide 35 [Source:HGNC Symbol;Acc:HGNC:15861] | −0.271561028 | −0.271561028 |
| ENSG00000102003 | SYP | synaptophysin [Source:HGNC Symbol;Acc:HGNC:11506] | −0.232683457 | NA |
| ENSG00000102024 | PLS3 | plastin 3 [Source:HGNC Symbol;Acc:HGNC:9091] | 0.134990538 | NA |
| ENSG00000102053 | ZC3H12B | zinc finger CCCH-type containing 12B [Source:HGNC Symbol;Acc:HGNC:17407] | −0.202615192 | −0.202615192 |
| ENSG00000102174 | PHEX | phosphate regulating endopeptidase homolog, X-linked [Source:HGNC Symbol;Acc:HGNC:8918] | −0.122550026 | NA |
| ENSG00000102743 | SLC25A15 | solute carrier family 25 (mitochondrial carrier; ornithine transporter) member 15 [Source:HGNC Symbol;Acc:HGNC:10985] | −0.144896419 | −0.144896419 |
| ENSG00000102978 | POLR2C | polymerase (RNA) II (DNA directed) polypeptide C, 33 kDa [Source:HGNC Symbol;Acc:HGNC:9189] | −0.200616615 | −0.200616615 |
| ENSG00000103260 | METRN | meteorin, glial cell differentiation regulator [Source:HGNC Symbol;Acc:HGNC:14151] | 0.119367309 | NA |
| ENSG00000103569 | AQP9 | aquaporin 9 [Source:HGNC Symbol;Acc:HGNC:643] | −0.127208941 | −0.127208941 |
| ENSG00000104518 | GSDMD | gasdermin D [Source:HGNC Symbol;Acc:HGNC:25697] | 0.319544945 | 0.319544945 |
| ENSG00000104722 | NEFM | neurofilament, medium polypeptide [Source:HGNC Symbol;Acc:HGNC:7734] | −0.1251566 | NA |

TABLE 11-continued

The highest impact sustained by the player in the game as measured by the
number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000104964 | AES | amino-terminal enhancer of split [Source:HGNC Symbol;Acc:HGNC:307] | 0.932109933 | 0.932109933 |
| ENSG00000105383 | CD33 | CD33 molecule [Source:HGNC Symbol;Acc:HGNC:1659] | −0.334137071 | −0.334137071 |
| ENSG00000105619 | TFPT | TCF3 (E2A) fusion partner (in childhood Leukemia) [Source:HGNC Symbol;Acc:HGNC:13630] | 0.229743673 | NA |
| ENSG00000105792 | CFAP69 | cilia and flagella associated protein 69 [Source:HGNC Symbol;Acc:HGNC:26107] | −0.279866829 | NA |
| ENSG00000105821 | DNAJC2 | DnaJ (Hsp40) homolog, subfamily C, member 2 [Source:HGNC Symbol;Acc:HGNC:13192] | 0.279798004 | 0.279798004 |
| ENSG00000105879 | CBLL1 | Cbl proto-oncogene-like 1, E3 ubiquitin protein ligase [Source:HGNC Symbol;Acc:HGNC:21225] | −0.297249955 | −0.297249955 |
| ENSG00000105971 | CAV2 | caveolin 2 [Source:HGNC Symbol;Acc:HGNC:1528] | −0.389555214 | −0.389555214 |
| ENSG00000106628 | POLD2 | polymerase (DNA directed), delta 2, accessory subunit [Source:HGNC Symbol;Acc:HGNC:9176] | 0.196918487 | 0.196918487 |
| ENSG00000106772 | PRUNE2 | prune homolog 2 (Drosophila) [Source:HGNC Symbol;Acc:HGNC:25209] | −0.769920327 | −0.769920327 |
| ENSG00000106803 | SEC61B | 5ec61 beta subunit [Source:HGNC Symbol;Acc:HGNC:16993] | −0.115862109 | −0.115862109 |
| ENSG00000107829 | FBXW4 | F-box and WD repeat domain containing 4 [Source:HGNC Symbol;Acc:HGNC:10847] | −0.38916892 | −0.38916892 |
| ENSG00000108219 | TSPAN14 | tetraspanin 14 [Source:HGNC Symbol;Acc:HGNC:23303] | −0.593916068 | −0.593916068 |
| ENSG00000108344 | PSMD3 | proteasome (prosome, macropain) 26S subunit, non-ATPase, 3 [Source:HGNC Symbol;Acc:HGNC:9560] | −0.253290858 | −0.253290858 |
| ENSG00000108439 | PNPO | pyridoxamine 5′-phosphate oxidase [Source:HGNC Symbol;Acc:HGNC:30260] | −0.105362262 | −0.105362262 |
| ENSG00000108465 | CDK5RAP3 | CDK5 regulatory subunit associated protein 3 [Source:HGNC Symbol;Acc:HGNC:18673] | −0.338333206 | −0.338333206 |
| ENSG00000109272 | PF4V1 | platelet factor 4 variant 1 [Source:HGNC Symbol;Acc:HGNC:8862] | 11.0501801 | 11.0501801 |
| ENSG00000109758 | HGFAC | HGF activator [Source:HGNC Symbol;Acc:HGNC:4894] | 0.264047523 | NA |
| ENSG00000110079 | M54A4A | membrane-spanning 4-domains, subfamily A, member 4A [Source:HGNC Symbol;Acc:HGNC:13371] | −0.24370514 | NA |
| ENSG00000110107 | PRPF19 | pre-mRNA processing factor 19 [Source:HGNC Symbol;Acc:HGNC:17896] | 0.780895954 | 0.780895954 |
| ENSG00000110108 | TMEM109 | transmembrane protein 109 [Source:HGNC Symbol;Acc:HGNC:28771] | −0.168302183 | −0.168302183 |
| ENSG00000110169 | HPX | hemopexin [Source:HGNC Symbol;Acc:HGNC:5171 ] | −0.257263857 | NA |
| ENSG00000111237 | VPS29 | vacuolar protein sorting 29 homolog (S. cerevisiae) [Source:HGNC Symbol;Acc:HGNC:14340] | −0.228985346 | −0.228985346 |
| ENSG00000111729 | CLEC4A | C-type lectin domain family 4, member A [Source:HGNC Symbol;Acc:HGNC:13257] | −0.122305695 | NA |
| ENSG00000111860 | CEP85L | centrosomal protein 85 kDa-like [Source:HGNC Symbol;Acc:HGNC:21638] | −0.18194886 | −0.18194886 |

TABLE 11-continued

The highest impact sustained by the player in the game as measured by the number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000111880 | RNGTT | RNA guanylyltransferase and 5-phosphatase [Source:HGNC Symbol;Acc:HGNC:10073] | −0.162725004 | −0.162725004 |
| ENSG00000112561 | TFEB | transcription factor EB [Source:HGNC Symbol;Acc:HGNC:11753] | 0.187014223 | 0.187014223 |
| ENSG00000112812 | PRSS16 | protease, serine, 16 (thymus) [Source:HGNC Symbol;Acc:HGNC:9480] | −0.513500979 | −0.513500979 |
| ENSG00000113658 | SMAD5 | SMAD family member 5 [Source:HGNC Symbol;Acc:HGNC:6771] | 2.438979927 | 2.438979927 |
| ENSG00000114021 | NIT2 | nitrilase family, member 2 [Source:HGNC Symbol;Acc:HGNC:29878] | −0.149608143 | NA |
| ENSG00000115267 | IFIH1 | interferon induced with helicase C domain 1 [Source:HGNC Symbol;Acc:HGNC:18873] | −0.103073933 | −0.103073933 |
| ENSG00000115484 | CCT4 | chaperon in containing TCP1, subunit 4 (delta) [Source:HGNC Symbol;Acc:HGNC:1617] | 0.282495067 | 0.282495067 |
| ENSG00000115486 | GGCX | gamma-glutamyl carboxylase [Source:HGNC Symbol;Acc:HGNC:4247] | −0.282843188 | −0.282843188 |
| ENSG00000115504 | EHBP1 | EH domain binding protein 1 [Source:HGNC Symbol;Acc:HGNC:29144] | 0.342346276 | 0.342346276 |
| ENSG00000115896 | PLCL1 | phospholipase C-like 1 [Source:HGNC Symbol;Acc:HGNC:9063] | −0.238214243 | −0.238214243 |
| ENSG00000116117 | PARD3B | par-3 family cell polarity regulator beta [Source:HGNC Symbol;Acc:HGNC:14446] | 0.776502959 | 0.776502959 |
| ENSG00000117226 | GBP3 | guanylate binding protein 3 [Source:HGNC Symbol;Acc:HGNC:4184] | −0.224991748 | −0.224991748 |
| ENSG00000117448 | AKR1A1 | aldo-keto reductase family 1, member A1 (aldehyde reductase) [Source:HGNC Symbol;Acc:HGNC:380] | −0.165680072 | −0.165680072 |
| ENSG00000117481 | NSUN4 | NOP2/Sun domain family, member 4 [Source:HGNC Symbol;Acc:HGNC:31802] | −0.470387718 | −0.470387718 |
| ENSG00000117616 | RSRP1 | arginine/serine-rich protein 1 [Source:HGNC Symbol;Acc:HGNC:25234] | −0.379259917 | −0.379259917 |
| ENSG00000117834 | SLC5A9 | solute carrier family 5 (sodium/sugar cotransporter), member 9 [Source:HGNC Symbol;Acc:HGNC:22146] | −0.324404916 | −0.324404916 |
| ENSG00000119321 | FKBP15 | FK506 binding protein 15, 133 kDa [Source:HGNC Symbol;Acc:HGNC:23397] | −0.30904328 | −0.30904328 |
| ENSG00000119725 | ZNF410 | zinc finger protein 410 [Source:HGNC Symbol;Acc:HGNC:20144] | −0.156064848 | −0.156064848 |
| ENSG00000119943 | PYROXD2 | pyridine nucleotide-disulphide oxidoreductase domain 2 [Source:HGNC Symbol;Acc:HGNC:23517] | −0.283809537 | −0.283809537 |
| ENSG00000120662 | MTRF1 | mitochondrial translational release factor 1 [Source:HGNC Symbol;Acc:HGNC:7469] | 0.167354665 | 0.167354665 |
| ENSG00000120708 | TGFBI | transforming growth factor, beta-induced, 68 kDa [Source:HGNC Symbol;Acc:HGNC:11771] | −0.401291447 | −0.401291447 |
| ENSG00000120889 | TNFRSF10B | tumor necrosis factor receptor superfamily, member 10b [Source:HGNC Symbol;Acc:HGNC:11905] | −0.159792098 | −0.159792098 |
| ENSG00000121481 | RNF2 | ring finger protein 2 [Source:HGNC Symbol;Acc:HGNC:10061] | −0.172574383 | −0.172574383 |

TABLE 11-continued

The highest impact sustained by the player in the game as measured by the number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000122484 | RPAP2 | RNA polymerase 11 associated protein 2 [Source:HGNC Symbol;Acc:HGNC:25791] | −0.477597758 | −0.477597758 |
| ENSG00000124459 | ZNF45 | zinc finger protein 45 [Source:HGNC Symbol;Acc:HGNC:13111] | −0.157277664 | −0.157277664 |
| ENSG00000124541 | RRP36 | ribosomal RNA processing 36 homolog (S. cerevisiae) [Source:HGNC Symbol;Acc:HGNC:21374] | 0.165299754 | 0.165299754 |
| ENSG00000124588 | NQO2 | NAD(P)H dehydrogenase, quinone 2 [Source:HGNC Symbol;Acc:HGNC:7856] | −0.213251218 | −0.213251218 |
| ENSG00000124602 | UNC5CL | unc-5 homolog C (C. elegans)-like [Source:HGNC Symbol;Acc:HGNC:21203] | −0.181414722 | NA |
| ENSG00000125166 | GOT2 | glutamic-oxaloacetic transaminase 2, mitochondrial [Source:HGNC Symbol;Acc:HGNC:4433] | 0.164458841 | 0.164458841 |
| ENSG00000125445 | MRPS7 | mitochondrial ribosomal protein S7 [Source:HGNC Symbol;Acc:HGNC:14499] | −0.185603919 | −0.185603919 |
| ENSG00000125630 | POLR1B | polymerase (RNA) I polypeptide B, 128 kDa [Source:HGNC Symbol;Acc:HGNC:20454] | −0.265939431 | −0.265939431 |
| ENSG00000125633 | CCDC93 | coiled-coil domain containing 93 [Source:HGNC Symbol;Acc:HGNC:25611] | −0.316544829 | −0.316544829 |
| ENSG00000125779 | PANK2 | pantothenate kinase 2 [Source:HGNC Symbol;Acc:HGNC:15894] | −0.21463338 | −0.21463338 |
| ENSG00000125846 | ZNF133 | zinc finger protein 133 [Source:HGNC Symbol;Acc:HGNC:12917] | −0.303985979 | −0.303985979 |
| ENSG00000125997 | BPIFB9P | BPI fold containing family B, member 9, pseudogene [Source:HGNC Symbol;Acc:HGNC:16109] | −0.115137701 | NA |
| ENSG00000126012 | KDM5C | lysine (K)-specific demethylase 5C [Source:HGNC Symbol;Acc:HGNC:11114] | −0.327948032 | −0.327948032 |
| ENSG00000126216 | TUBGCP3 | tubulin, gamma complex associated protein 3 [Source:HGNC Symbol;Acc:HGNC:18598] | −0.276604625 | −0.276604625 |
| ENSG00000126461 | SCAF1 | SR-related CTD-associated factor 1 [Source:HGNC Symbol;Acc:HGNC:30403] | 0.228635347 | 0.228635347 |
| ENSG00000126653 | NSRP1 | nuclear speckle splicing regulatory protein 1 [Source:HGNC Symbol;Acc:HGNC:25305] | −0.308333688 | −0.308333688 |
| ENSG00000128383 | APOBEC3A | apolipoprotein B mRNA editing enzyme, catalytic polypeptide-like 3A [Source:HGNC Symbol;Acc:HGNC:17343] | −0.167275864 | −0.167275864 |
| ENSG00000128881 | TTBK2 | tau tubulin kinase 2 [Source:HGNC Symbol;Acc:HGNC:19141] | −0.288481704 | −0.288481704 |
| ENSG00000130589 | HELZ2 | helicase with zinc finger 2, transcriptional coactivator [Source:HGNC Symbol;Acc:HGNC:30021] | 0.458283236 | 0.458283236 |
| ENSG00000130600 | H19 | H19, imprinted maternally expressed transcript (non-protein coding) [Source:HGNC Symbol;Acc:HGNC:4713] | 2.354612983 | 2.354612983 |
| ENSG00000130703 | OSBPL2 | oxysterol binding protein-like 2 [Source:HGNC Symbol;Acc:HGNC:15761] | 0.364186697 | 0.364186697 |
| ENSG00000130935 | NOL11 | nucleolar protein 11 [Source:HGNC Symbol;Acc:HGNC:24557] | −0.143170588 | −0.143170588 |
| ENSG00000131016 | AKAP12 | A kinase (PRKA) anchor protein 12 [Source:HGNC Symbol;Acc:HGNC:370] | −0.284729614 | −0.284729614 |

TABLE 11-continued

The highest impact sustained by the player in the game as measured by the number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000131068 | DEFB118 | defensin, beta 118 [Source:HGNC Symbol;Acc:HGNC:16196] | −0.103207397 | NA |
| ENSG00000131469 | RPL27 | ribosomal protein L27 [Source:HGNC Symbol;Acc:HGNC:10328] | 1.593865307 | 1.593865307 |
| ENSG00000131508 | UBE2D2 | ubiquitin-conjugating enzyme E2D 2 [Source:HGNC Symbol;Acc:HGNC:12475] | 0.917517388 | 0.917517388 |
| ENSG00000132530 | XAF1 | XIAP associated factor 1 [Source:HGNC Symbol;Acc:HGNC:30932] | −0.317553234 | −0.317553234 |
| ENSG00000133106 | EPSTI1 | epithelial stromal interaction 1 (breast) [Source:HGNC Symbol;Acc:HGNC:16465] | 0.368204938 | 0.368204938 |
| ENSG00000133460 | SLC2A11 | solute carrier family 2 (facilitated glucose transporter), member 11 [Source:HGNC Symbol;Acc:HGNC:14239] | −0.796053407 | −0.796053407 |
| ENSG00000133704 | IPO8 | importin 8 [Source:HGNC Symbol;Acc:HGNC:9853] | −0.196186167 | −0.196186167 |
| ENSG00000133835 | HSD17B4 | hydroxysteroid (17-beta) dehydrogenase 4 [Source:HGNC Symbol;Acc:HGNC:5213] | −0.264490829 | −0.264490829 |
| ENSG00000134184 | GSTM1 | glutathione S-transferase mu 1 [Source:HGNC Symbol;Acc:HGNC:4632] | 0.190616913 | NA |
| ENSG00000134330 | IAH1 | isoamyl acetate-hydrolyzing esterase 1 homolog (S. cerevisiae) [Source:HGNC Symbol;Acc:HGNC:27696] | −0.186984626 | −0.186984626 |
| ENSG00000134853 | PDGFRA | platelet-derived growth factor receptor, alpha polypeptide [Source:HGNC Symbol;Acc:HGNC:8803] | −0.258883375 | −0.258883375 |
| ENSG00000134899 | ERCC5 | excision repair cross-complementation group 5 [Source:HGNC Symbol;Acc:HGNC:3437] | 0.188493076 | 0.188493076 |
| ENSG00000134954 | ETS1 | v-ets avian erythroblastosis virus E26 oncogene homolog 1 [Source:HGNC Symbol;Acc:HGNC:3488] | 1.367586635 | 1.367586635 |
| ENSG00000135074 | ADAM19 | ADAM metallopeptidase domain 19 [Source:HGNC Symbol;Acc:HGNC:197] | −0.285510493 | −0.285510493 |
| ENSG00000135249 | RINT1 | RAD50 interactor 1 [Source:HGNC Symbol;Acc:HGNC:21876] | −0.172799072 | −0.172799072 |
| ENSG00000135776 | ABCB10 | ATP-binding cassette, sub-family B (MDR/TAP), member 10 [Source:HGNC Symbol;Acc:HGNC:41] | 0.138199013 | 0.138199013 |
| ENSG00000135828 | RNASEL | ribonuclease L (2′,5′-oligoisoadenylate synthetase-dependent) [Source:HGNC Symbol;Acc:HGNC:10050] | −0.233082 | −0.233082 |
| ENSG00000135925 | WNT10A | wingless-type MMTV integration site family, member 10A [Source:HGNC Symbol;Acc:HGNC:13829] | 0.132456504 | NA |
| ENSG00000136048 | DRAM1 | DNA-damage regulated autophagy modulator 1 [Source:HGNC Symbol;Acc:HGNC:25645] | −0.158362576 | −0.158362576 |
| ENSG00000136869 | TLR4 | toll-like receptor 4 [Source:HGNC Symbol;Acc:HGNC:11850] | −0.187905349 | −0.187905349 |
| ENSG00000136881 | BAAT | bile acid CoA:amino acid N-acyltransferase [Source:HGNC Symbol;Acc:HGNC:932] | −0.179763218 | NA |
| ENSG00000137101 | CD72 | CD72 molecule [Source:HGNC Symbol;Acc:HGNC:1696] | −0.250696821 | −0.250696821 |
| ENSG00000137337 | MDC1 | mediator of DNA-damage checkpoint 1 [Source:HGNC Symbol;Acc:HGNC:21163] | −0.435575453 | −0.435575453 |

TABLE 11-continued

The highest impact sustained by the player in the game as measured by the
number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000137513 | NARS2 | asparaginyl-tRNA synthetase 2, mitochondrial (putative) [Source:HGNC Symbol;Acc:HGNC:26274] | −0.157310972 | −0.157310972 |
| ENSG00000137713 | PPP2R1B | protein phosphatase 2, regulatory subunit A, beta [Source:HGNC Symbol;Acc:HGNC:9303] | −0.393093416 | −0.393093416 |
| ENSG00000137819 | PAQR5 | progestin and adipoQ receptor family member V [Source:HGNC Symbol;Acc:HGNC:29645] | −0.269509334 | NA |
| ENSG00000137955 | RABGGTB | Rab geranylgeranyltransferase, beta subunit [Source:HGNC Symbol;Acc:HGNC:9796] | −0.154111805 | −0.154111805 |
| ENSG00000137965 | IFI44 | interferon-induced protein 44 [Source:HGNC Symbol;Acc:HGNC:16938] | −0.122874288 | −0.122874288 |
| ENSG00000138152 | BTBD16 | BTB (POZ) domain containing 16 [Source:HGNC Symbol;Acc:HGNC:26340] | 0.34233563 | NA |
| ENSG00000138297 | NA | NA | −0.142481452 | NA |
| ENSG00000138459 | SLC35A5 | solute carrier family 35, member A5 [Source:HGNC Symbol;Acc:HGNC:20792] | −0.155735853 | −0.155735853 |
| ENSG00000138796 | HADH | hydroxyacyl-CoA dehydrogenase [Source:HGNC Symbol;Acc:HGNC:4799] | 0.197773445 | 0.197773445 |
| ENSG00000139192 | TAPBPL | TAP binding protein-like [Source:HGNC Symbol;Acc:HGNC:30683] | −0.154699461 | −0.154699461 |
| ENSG00000139436 | GIT2 | G protein-coupled receptor kinase interacting ArfGAP 2 [Source:HGNC Symbol;Acc:HGNC:4273] | −0.356554053 | −0.356554053 |
| ENSG00000139515 | PDX1 | pancreatic and duodenal homeobox 1 [Source:HGNC Symbol;Acc:HGNC:6107] | −0.163009091 | NA |
| ENSG00000139874 | SSTR1 | somatostatin receptor 1 [Source:HGNC Symbol;Acc:HGNC:11330] | −0.173526356 | NA |
| ENSG00000140015 | KCNH5 | potassium voltage-gated channel, subfamily H (eag-related), member 5 [Source:HGNC Symbol;Acc:HGNC:6254] | −0.291948339 | NA |
| ENSG00000140379 | BCL2A1 | BCL2-related protein A1 [Source:HGNC Symbol;Acc:HGNC:991] | −0.189089134 | NA |
| ENSG00000140740 | UQCRC2 | ubiquinol-cytochrome c reductase core protein 11 [Source:HGNC Symbol;Acc:HGNC:12586] | 0.202041894 | 0.202041894 |
| ENSG00000141101 | NOB1 | NIN1/RPN12 binding protein 1 homolog (S. cerevisiae) [Source:HGNC Symbol;Acc:HGNC:29540] | −0.14120592 | −0.14120592 |
| ENSG00000141179 | PCTP | phosphatidylcholine transfer protein [Source:HGNC Symbol;Acc:HGNC:8752] | 0.946862159 | 0.946862159 |
| ENSG00000141391 | SLMO1 | slowmo homolog 1 (Drosophila) [Source:HGNC Symbol;Acc:HGNC:24639] | −0.121053874 | NA |
| ENSG00000141582 | CBX4 | chromobox homolog 4 [Source:HGNC Symbol;Acc:HGNC:1554] | 0.126638185 | NA |
| ENSG00000141665 | FBX015 | F-box protein 15 [Source:HGNC Symbol;Acc:HGNC:13617] | −0.351552536 | −0.351552536 |
| ENSG00000141858 | SAMD1 | sterile alpha motif domain containing 1 [Source:HGNC Symbol;Acc:HGNC:17958] | 0.103377803 | NA |
| ENSG00000141946 | ZIM3 | zinc finger, imprinted 3 [Source:HGNC Symbol;Acc:HGNC:16366] | −0.129758699 | NA |

TABLE 11-continued

The highest impact sustained by the player in the game as measured by the
number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000142856 | ITGB3BP | integrin beta 3 binding protein (beta3-endonexin) [Source:HGNC Symbol;Acc:HGNC:6157] | 0.352560138 | 0.352560138 |
| ENSG00000143226 | FCGR2A | Fc fragment of IgG, low affinity IIa, receptor (CD32) [Source:HGNC Symbol;Acc:HGNC:3616] | −0.339026469 | −0.339026469 |
| ENSG00000143314 | MRPL24 | mitochondrial ribosomal protein L24 [Source:HGNC Symbol;Acc:HGNC:14037] | 0.167078328 | 0.167078328 |
| ENSG00000143390 | RFX5 | regulatory factor X, 5 (influences HLA class 11 expression) [Source:HGNC Symbol;Acc:HGNC:9986] | −0.273652914 | −0.273652914 |
| ENSG00000143536 | CRNN | cornulin [Source:HGNC Symbol;Acc:HGNC:1230] | −0.504517688 | −0.504517688 |
| ENSG00000143633 | C1orf131 | chromosome 1 open reading frame 131 [Source:HGNC Symbol;Acc:HGNC:25332] | −0.296642104 | −0.296642104 |
| ENSG00000143774 | GUK1 | guanylate kinase 1 [Source:HGNC Symbol;Acc:HGNC:4693] | 0.375454312 | 0.375454312 |
| ENSG00000144026 | ZNF514 | zinc finger protein 514 [Source:HGNC Symbol;Acc:HGNC:25894] | −0.159206514 | −0.159206514 |
| ENSG00000144559 | TAMM41 | TAM41, mitochondrial translocator assembly and maintenance protein, homolog (S. cerevisiae) [Source:HGNC Symbol;Acc:HGNC:25187] | −0.202585771 | −0.202585771 |
| ENSG00000144802 | NFKBIZ | nuclear factor of kappa light polypeptide gene enhancer in B-cells inhibitor, zeta [Source:HGNC Symbol;Acc:HGNC:29805] | −0.30522935 | −0.30522935 |
| ENSG00000145214 | DGKQ | diacylglycerol kinase, theta 110 kDa [Source:HGNC Symbol;Acc:HGNC:2856] | 0.338305913 | 0.338305913 |
| ENSG00000145439 | CBR4 | carbonyl reductase 4 [Source:HGNC Symbol;Acc:HGNC:25891] | 0.268785989 | 0.268785989 |
| ENSG00000145476 | CYP4V2 | cytochrome P450, family 4, subfamily V, polypeptide 2 [Source:HGNC Symbol;Acc:HGNC:23198] | −0.304900483 | −0.304900483 |
| ENSG00000145863 | GABRA6 | gamma-aminobutyric acid (GABA) A receptor, alpha 6 [Source:HGNC Symbol;Acc:HGNC:4080] | −0.122296325 | NA |
| ENSG00000146192 | FGD2 | FYVE, RhoGEF and PH domain containing 2 [Source:HGNC Symbol;Acc:HGNC:3664] | −0.433566775 | −0.433566775 |
| ENSG00000146535 | GNA12 | guanine nucleotide binding protein (G protein) alpha 12 [Source:HGNC Symbol;Acc:HGNC:4380] | 0.559219799 | 0.559219799 |
| ENSG00000147124 | ZNF41 | zinc finger protein 41 [Source:HGNC Symbol;Acc:HGNC:13107] | −0.16831668 | −0.16831668 |
| ENSG00000147402 | NA | NA | −0.17974862 | NA |
| ENSG00000147454 | SLC25A37 | solute carrier family 25 (mitochondrial iron transporter), member 37 [Source:HGNC Symbol;Acc:HGNC:29786] | 2.024656588 | 2.024656588 |
| ENSG00000147471 | PROSC | proline synthetase co-transcribed homolog (bacterial) [Source:HGNC Symbol;Acc:HGNC:9457] | 0.34892489 | 0.34892489 |
| ENSG00000148219 | ASTN2 | astrotactin 2 [Source:HGNC Symbol;Acc:HGNC:17021] | −0.42723069 | −0.42723069 |
| ENSG00000149090 | PAMR1 | peptidase domain containing associated with muscle regeneration 1 [Source:HGNC Symbol;Acc:HGNC:24554] | −0.19414373 | −0.19414373 |
| ENSG00000149474 | CSRP2BP | CSRP2 binding protein [Source:HGNC Symbol;Acc:HGNC:15904] | −0.17555367 | −0.17555367 |

TABLE 11-continued

The highest impact sustained by the player in the game as measured by the
number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000149499 | EML3 | echinoderm microtubule associated protein like 3 [Source:HGNC Symbol;Acc:HGNC:26666] | −0.276933033 | −0.276933033 |
| ENSG00000150457 | LATS2 | large tumor suppressor kinase 2 [Source:HGNC Symbol;Acc:HGNC:6515] | −0.152222375 | −0.152222375 |
| ENSG00000151239 | TWF1 | twinfilin actin-binding protein 1 [Source:HGNC Symbol;Acc:HGNC:9620] | −0.132016998 | NA |
| ENSG00000151572 | ANO4 | anoctamin 4 [Source:HGNC Symbol;Acc:HGNC:23837] | −0.332189885 | −0.332189885 |
| ENSG00000151577 | DRD3 | dopamine receptor D3 [Source:HGNC Symbol;Acc:HGNC:3024] | −0.152498795 | NA |
| ENSG00000151726 | ACSL1 | acyl-CoA synthetase long-chain family member 1 [Source:HGNC Symbol;Acc:HGNC:3569] | −0.305164415 | −0.305164415 |
| ENSG00000152049 | KCNE4 | potassium voltage-gated channel, Isk-related family, member 4 [Source:HGNC Symbol;Acc:HGNC:6244] | −0.164073615 | NA |
| ENSG00000152219 | ARL14EP | ADP-ribosylation factor-like 14 effector protein [Source:HGNC Symbol;Acc:HGNC:26798] | −0.165131265 | −0.165131265 |
| ENSG00000152348 | ATG10 | autophagy related 10 [Source:HGNC Symbol;Acc:HGNC:20315] | −0.189974522 | −0.189974522 |
| ENSG00000152457 | DCLRE1C | DNA cross-link repair 1C [Source:HGNC Symbol;Acc:HGNC:17642] | −0.309025285 | −0.309025285 |
| ENSG00000152591 | DSPP | dentin sialophosphoprotein [Source:HGNC Symbol;Acc:HGNC:3054] | −1.107310915 | −1.107310915 |
| ENSG00000153560 | UBP1 | upstream binding protein 1 (LBP-1a) [Source:HGNC Symbol;Acc:HGNC:12507] | 0.487512878 | 0.487512878 |
| ENSG00000154065 | ANKRD29 | ankyrin repeat domain 29 [Source:HGNC Symbol;Acc:HGNC:27110] | −0.270364727 | NA |
| ENSG00000154217 | PITPNC1 | phosphatidylinositol transfer protein, cytoplasmic 1 [Source:HGNC Symbol;Acc:HGNC:21045] | 0.184098148 | 0.184098148 |
| ENSG00000154920 | EME1 | essential meiotic structure-specific endonuclease 1 [Source:HGNC Symbol;Acc:HGNC:24965] | −0.175166827 | NA |
| ENSG00000155307 | SAMSN1 | SAM domain, SH3 domain and nuclear localization signals 1 [Source:HGNC Symbol;Acc:HGNC:10528] | −0.334492222 | −0.334492222 |
| ENSG00000155330 | C16orf87 | chromosome 16 open reading frame 87 [Source:HGNC Symbol;Acc:HGNC:33754] | −0.196420793 | −0.196420793 |
| ENSG00000155749 | ALS2CR12 | amyotrophic lateral sclerosis 2 (juvenile) chromosome region, candidate 12 [Source:HGNC Symbol;Acc:HGNC:14439] | 0.17679216 | 0.17679216 |
| ENSG00000155827 | RNF20 | ring finger protein 20, E3 ubiquitin protein ligase [Source:HGNC Symbol;Acc:HGNC:10062] | −0.35020149 | −0.35020149 |
| ENSG00000156398 | SFXN2 | sideroflexin 2 [Source:HGNC Symbol;Acc:HGNC:16086] | −0.279110846 | −0.279110846 |
| ENSG00000156650 | KAT6B | K(lysine) acetyltransferase 6B [Source:HGNC Symbol;Acc:HGNC:17582] | −0.343476766 | −0.343476766 |
| ENSG00000157036 | EXOG | endo/exonuclease (5'-3'), endonuclease G-like [Source:HGNC Symbol;Acc:HGNC:3347] | −0.195141631 | −0.195141631 |
| ENSG00000157542 | KCNJ6 | potassium inwardly-rectifying channel, subfamily J, member 6 [Source:HGNC Symbol;Acc:HGNC:6267] | −0.52400914 | −0.52400914 |

TABLE 11-continued

The highest impact sustained by the player in the game as measured by the
number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000157827 | FMNL2 | formin-like 2 [Source:HGNC Symbol;Acc:HGNC:18267] | −0.296967858 | −0.296967858 |
| ENSG00000158106 | RHPN1 | rhophilin, Rho GTPase binding protein 1 [Source:HGNC Symbol;Acc:HGNC:19973] | 0.226466468 | NA |
| ENSG00000158352 | SHROOM4 | shroom family member 4 [Source:HGNC Symbol;Acc:HGNC:29215] | −0.297192674 | −0.297192674 |
| ENSG00000158578 | ALAS2 | aminolevulinate, delta-, synthase 2 [Source:HGNC Symbol;Acc:HGNC:397] | 0.431841882 | 0.431841882 |
| ENSG00000158987 | RAPGEF6 | Rap guanine nucleotide exchange factor (GEF) 6 [Source:HGNC Symbol;Acc:HGNC:20655] | −0.166980492 | −0.166980492 |
| ENSG00000159339 | PAD 14 | peptidyl arginine deiminase, type IV [Source:HGNC Symbol;Acc:HGNC:18368] | −0.507543043 | −0.507543043 |
| ENSG00000159398 | CES5A | carboxylesterase 5A [Source:HGNC Symbol;Acc:HGNC:26459] | −0.327309834 | −0.327309834 |
| ENSG00000159674 | SPON2 | spondin 2, extracellular matrix protein [Source:HGNC Symbol;Acc:HGNC:11253] | 0.335120133 | 0.335120133 |
| ENSG00000160172 | FAM86C2P | family with sequence similarity 86, member C2, pseudogene [Source:HGNC Symbol;Acc:HGNC:42392] | −0.159269559 | NA |
| ENSG00000160233 | LRRC3 | leucine rich repeat containing 3 [Source:HGNC Symbol;Acc:HGNC:14965] | 0.170594569 | NA |
| ENSG00000160336 | ZNF761 | zinc finger protein 761 [Source:HGNC Symbol;Acc:HGNC:23179] | −0.162895236 | −0.162895236 |
| ENSG00000160584 | SIK3 | SIK family kinase 3 [Source:HGNC Symbol;Acc:HGNC:29165] | −0.421688526 | −0.421688526 |
| ENSG00000160818 | GPATCH4 | G patch domain containing 4 [Source:HGNC Symbol;Acc:HGNC:25982] | −0.245177172 | −0.245177172 |
| ENSG00000161551 | ZNF577 | zinc finger protein 577 [Source:HGNC Symbol;Acc:HGNC:28673] | −0.18526194 | −0.18526194 |
| ENSG00000162006 | MSLNL | mesothelin-like [Source:HGNC Symbol;Acc:HGNC:14170] | 0.184037758 | NA |
| ENSG00000162086 | ZNF75A | zinc finger protein 75a [Source:HGNC Symbol;Acc:HGNC:13146] | −0.169535209 | NA |
| ENSG00000162174 | ASRGL1 | asparaginase like 1 [Source:HGNC Symbol;Acc:HGNC:16448] | −0.239517911 | −0.239517911 |
| ENSG00000162645 | GBP2 | guanylate binding protein 2, interferon-inducible [Source:HGNC Symbol;Acc:HGNC:4183] | −0.538214742 | −0.538214742 |
| ENSG00000162695 | SLC30A7 | solute carrier family 30 (zinc transporter), member 7 [Source:HGNC Symbol;Acc:HGNC:19306] | −0.165053222 | −0.165053222 |
| ENSG00000162733 | DDR2 | discoidin domain receptor tyrosine kinase 2 [Source:HGNC Symbol;Acc:HGNC:2731] | −0.37037397 | −0.37037397 |
| ENSG00000162736 | NCSTN | nicastrin [Source:HGNC Symbol;Acc:HGNC:17091] | −0.299631159 | −0.299631159 |
| ENSG00000163380 | LMOD3 | leiomodin 3 (fetal) [Source:HGNC Symbol;Acc:HGNC:6649] | −0.212595649 | NA |
| ENSG00000163431 | LMOD1 | leiomodin 1 (smooth muscle) [Source:HGNC Symbol;Acc:HGNC:6647] | −0.170738272 | NA |
| ENSG00000163463 | KRTCAP2 | keratinocyte associated protein 2 [Source:HGNC Symbol;Acc:HGNC:28942] | −0.156575708 | −0.156575708 |
| ENSG00000163611 | SPICE1 | spindle and centriole associated protein 1 [Source:HGNC Symbol;Acc:HGNC:25083] | −0.254944321 | −0.254944321 |

TABLE 11-continued

The highest impact sustained by the player in the game as measured by the number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000163823 | CCR1 | chemokine (C-C motif) receptor 1 [Source:HGNC Symbol;Acc:HGNC:1602] | −0.146844607 | −0.146844607 |
| ENSG00000164022 | AIMP1 | aminoacyl tRNA synthetase complex-interacting multifunctional protein 1 [Source:HGNC Symbol;Acc:HGNC:10648] | −0.135480176 | NA |
| ENSG00000164056 | SPRY1 | sprouty homolog 1, antagonist of FGF signaling (Drosophila) [Source:HGNC Symbol;Acc:HGNC:11269] | −0.223768011 | −0.223768011 |
| ENSG00000164134 | NAA15 | N(alpha)-acetyltransferase 15, NatA auxiliary subunit [Source:HGNC Symbol;Acc:HGNC:30782] | −0.283214671 | −0.283214671 |
| ENSG00000164451 | FAM26D | family with sequence similarity 26, member D [Source:HGNC Symbol;Acc:HGNC:21094] | −0.134450736 | NA |
| ENSG00000164902 | PHAX | phosphorylated adaptor for RNA export [Source:HGNC Symbol;Acc:HGNC:10241] | −0.195139648 | −0.195139648 |
| ENSG00000165028 | NIPSNAP3B | nipsnap homolog 3B (*C. elegans*) [Source:HGNC Symbol;Acc:HGNC:23641] | 0.146588799 | NA |
| ENSG00000165091 | TMC1 | transmembrane channel-like 1 [Source:HGNC Symbol;Acc:HGNC:16513] | −0.232626923 | NA |
| ENSG00000165120 | SSMEM1 | serine-rich single-pass membrane protein 1 [Source:HGNC Symbol;Acc:HGNC:29580] | −0.126816678 | NA |
| ENSG00000166164 | BRD7 | bromodomain containing 7 [Source:HGNC Symbol;Acc:HGNC:14310] | 0.403386129 | 0.403386129 |
| ENSG00000166428 | PLD4 | phospholipase D family, member 4 [Source:HGNC Symbol;Acc:HGNC:23792] | 0.217585702 | 0.217585702 |
| ENSG00000166432 | ZMAT1 | zinc finger, matrin-type 1 [Source:HGNC Symbol;Acc:HGNC:29377] | −0.114299765 | NA |
| ENSG00000166579 | NDEL1 | nudE neurodevelopment protein 1-like 1 [Source:HGNC Symbol;Acc:HGNC:17620] | −0.576552434 | −0.576552434 |
| ENSG00000166743 | ACSM1 | acyl-CoA synthetase medium-chain family member 1 [Source:HGNC Symbol;Acc:HGNC:18049] | −0.215717692 | −0.215717692 |
| ENSG00000166825 | ANPEP | alanyl (membrane) aminopeptidase [Source:HGNC Symbol;Acc:HGNC:500] | −0.503749533 | −0.503749533 |
| ENSG00000166928 | MS4A14 | membrane-spanning 4-domains, subfamily A, member 14 [Source:HGNC Symbol;Acc:HGNC:30706] | −0.204502412 | −0.204502412 |
| ENSG00000167264 | DUS2 | dihydrouridine synthase 2 [Source:HGNC Symbol;Acc:HGNC:26014] | −0.218993775 | −0.218993775 |
| ENSG00000167562 | ZNF701 | zinc finger protein 701 [Source:HGNC Symbol;Acc:HGNC:25597] | −0.206263045 | −0.206263045 |
| ENSG00000167671 | UBXN6 | UBX domain protein 6 [Source:HGNC Symbol;Acc:HGNC:14928] | 0.455725512 | 0.455725512 |
| ENSG00000167986 | DDB1 | damage-specific DNA binding protein 1, 127 kDa [Source:HGNC Symbol;Acc:HGNC:2717] | −0.269982898 | −0.269982898 |
| ENSG00000168237 | GLYCTK | glycerate kinase [Source:HGNC Symbol;Acc:HGNC:24247] | −0.228938069 | −0.228938069 |
| ENSG00000168405 | CMAHP | cytidine monophospho-N-acetylneuraminic acid hydroxylase, pseudogene [Source:HGNC Symbol;Acc:HGNC:2098] | 0.417242996 | 0.417242996 |
| ENSG00000168496 | FEN1 | flap structure-specific endonuclease 1 [Source:HGNC Symbol;Acc:HGNC:3650] | −0.153126534 | −0.153126534 |

TABLE 11-continued

The highest impact sustained by the player in the game as measured by the number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000168899 | VAMP5 | vesicle-associated membrane protein 5 [Source:HGNC Symbol;Acc:HGNC:12646] | 0.11902243 | NA |
| ENSG00000169410 | PTPN9 | protein tyrosine phosphatase, non-receptor type 9 [Source:HGNC Symbol;Acc:HGNC:9661] | −0.162806486 | −0.162806486 |
| ENSG00000169583 | CLIC3 | chloride intracellular channel 3 [Source:HGNC Symbol;Acc:HGNC:2064] | 0.420172779 | NA |
| ENSG00000169814 | BTD | biotinidase [Source:HGNC Symbol;Acc:HGNC:1122] | −0.153315448 | NA |
| ENSG00000170807 | LMOD2 | leiomodin 2 (cardiac) [Source:HGNC Symbol;Acc:HGNC:6648] | −0.12798119 | NA |
| ENSG00000170954 | ZNF415 | zinc finger protein 415 [Source:HGNC Symbol;Acc:HGNC:20636] | −0.16348594 | NA |
| ENSG00000171227 | TMEM37 | transmembrane protein 37 [Source:HGNC Symbol;Acc:HGNC:18216] | −0.137482976 | NA |
| ENSG00000171604 | CXXC5 | CXXC finger protein 5 [Source:HGNC Symbol;Acc:HGNC:26943] | 0.297490763 | 0.297490763 |
| ENSG00000171649 | ZIK1 | zinc finger protein interacting with K protein 1 [Source:HGNC Symbol;Acc:HGNC:33104] | −0.141838729 | −0.141838729 |
| ENSG00000171804 | WDR87 | WD repeat domain 87 [Source:HGNC Symbol;Acc:HGNC:29934] | −0.518560175 | −0.518560175 |
| ENSG00000171860 | C3AR1 | complement component 3a receptor 1 [Source:HGNC Symbol;Acc:HGNC:1319] | −0.193301684 | NA |
| ENSG00000172059 | KLF11 | Kruppel-like factor 11 [Source:HGNC Symbol;Acc:HGNC:11811] | 0.341315009 | 0.341315009 |
| ENSG00000172367 | PDZD3 | PDZ domain containing 3 [Source:HGNC Symbol;Acc:HGNC:19891] | −0.177350325 | NA |
| ENSG00000172653 | NA | NA | −0.172022851 | NA |
| ENSG00000173334 | TRIB1 | tribbles pseudokinase 1 [Source:HGNC Symbol;Acc:HGNC:16891] | −0.196550302 | −0.196550302 |
| ENSG00000173369 | C1QB | complement component 1, q subcomponent, B chain [Source:HGNC Symbol;Acc:HGNC:1242] | −0.124839375 | NA |
| ENSG00000173391 | OLR1 | oxidized low density lipoprotein (lectin-like) receptor 1 [Source:HGNC Symbol;Acc:HGNC:8133] | −0.159206313 | NA |
| ENSG00000173597 | SULT1B1 | sulfotransferase family, cytosolic, 1B, member 1 [Source:HGNC Symbol;Acc:HGNC:17845] | −0.235586513 | −0.235586513 |
| ENSG00000173933 | RBM4 | RNA binding motif protein 4 [Source:HGNC Symbol;Acc:HGNC:9901] | −0.135920039 | −0.135920039 |
| ENSG00000174417 | TRHR | thyrotropin-releasing hormone receptor [Source:HGNC Symbol;Acc:HGNC:12299] | −0.1942987 | NA |
| ENSG00000175029 | CTBP2 | C-terminal binding protein 2 [Source:HGNC Symbol;Acc:HGNC:2495] | 0.368157478 | 0.368157478 |
| ENSG00000175040 | CHST2 | carbohydrate (N-acetylglucosamine-6-O) sulfotransferase 2 [Source:HGNC Symbol;Acc:HGNC:1970] | 0.163933576 | NA |
| ENSG00000175155 | YPEL2 | yippee-like 2 (Drosophila) [Source:HGNC Symbol;Acc:HGNC:18326] | 0.912413876 | 0.912413876 |
| ENSG00000175224 | ATG13 | autophagy related 13 [Source:HGNC Symbol;Acc:HGNC:29091] | −0.296603347 | −0.296603347 |

TABLE 11-continued

The highest impact sustained by the player in the game as measured by the number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000175691 | ZNF77 | zinc finger protein 77 [Source:HGNC Symbol;Acc:HGNC:13150] | −0.116937542 | NA |
| ENSG00000176485 | PLA2G16 | phospholipase A2, group XVI [Source:HGNC Symbol;Acc:HGNC:17825] | −0.154817362 | −0.154817362 |
| ENSG00000176845 | METRNL | meteorin, glial cell differentiation regulator-like [Source:HGNC Symbol;Acc:HGNC:27584] | 0.187720515 | 0.187720515 |
| ENSG00000177000 | MTHFR | methylenetetrahydrofolate reductase (NAD(P)H) [Source:HGNC Symbol;Acc:HGNC:7436] | −0.287460753 | −0.287460753 |
| ENSG00000177337 | DLGAP1-AS1 | DLGAP1 antisense RNA 1 [Source:HGNC Symbol;Acc:HGNC:31676] | −0.124554317 | −0.124554317 |
| ENSG00000177359 | | | −0.475105891 | −0.475105891 |
| ENSG00000177370 | T1MM22 | translocase of inner mitochondrial membrane 22 homolog (yeast) [Source:HGNC Symbol;Acc:HGNC:17317] | −0.119372538 | −0.119372538 |
| ENSG00000177479 | ARIH2 | ariadne RBR E3 ubiquitin protein ligase 2 [Source:HGNC Symbol;Acc:HGNC:690] | −0.372741031 | −0.372741031 |
| ENSG00000177575 | CD163 | CD163 molecule [Source:HGNC Symbol;Acc:HGNC:1631] | −0.315699194 | −0.315699194 |
| ENSG00000177646 | ACAD9 | acyl-CoA dehydrogenase family, member 9 [Source:HGNC Symbol;Acc:HGNC:21497] | −0.202601143 | −0.202601143 |
| ENSG00000177674 | AGTRAP | angiotensin 11 receptor-associated protein [Source:HGNC Symbol;Acc:HGNC:13539] | −0.132216496 | −0.132216496 |
| ENSG00000177683 | THAP5 | THAP domain containing 5 [Source:HGNC Symbol;Acc:HGNC:23188] | −0.129846416 | −0.129846416 |
| ENSG00000177868 | CCDC23 | coiled-coil domain containing 23 [Source:HGNC Symbol;Acc:HGNC:29204] | −0.108167815 | −0.108167815 |
| ENSG00000178386 | ZNF223 | zinc finger protein 223 [Source:HGNC Symbol;Acc:HGNC:13016] | −0.146368231 | NA |
| ENSG00000178462 | TUBAL3 | tubulin, alpha-like 3 [Source:HGNC Symbol;Acc:HGNC:23534] | −0.161937894 | NA |
| ENSG00000178567 | EPM2A1P1 | EPM2A (laforin) interacting protein 1 [Source:HGNC Symbol;Acc:HGNC:19735] | −0.15061393 | −0.15061393 |
| ENSG00000178623 | GPR35 | G protein-coupled receptor 35 [Source:HGNC Symbol;Acc:HGNC:4492] | 0.129576478 | NA |
| ENSG00000178917 | ZNF852 | zinc finger protein 852 [Source:HGNC Symbol;Acc:HGNC:27713] | −0.19624491 | −0.19624491 |
| ENSG00000178965 | ERICH3 | glutamate-rich 3 [Source:HGNC Symbol;Acc:HGNC:25346] | −0.334601985 | −0.334601985 |
| ENSG00000178974 | FBX034 | F-box protein 34 [Source:HGNC Symbol;Acc:HGNC:20201] | −0.189250392 | −0.189250392 |
| ENSG00000178997 | EXD1 | exonuclease 3'-5 domain containing 1 [Source:HGNC Symbol;Acc:HGNC:28507] | −0.170508154 | NA |
| ENSG00000180008 | 50054 | suppressor of cytokine signaling 4 [Source:HGNC Symbol;Acc:HGNC:19392] | −0.149357471 | −0.149357471 |
| ENSG00000180667 | YOD1 | YOD1 deubiquitinase [Source:HGNC Symbol;Acc:HGNC:25035] | 1.460095794 | 1.460095794 |
| ENSG00000180771 | NA | NA | −0.111139539 | NA |
| ENSG00000181458 | TMEM45A | transmembrane protein 45A [Source:HGNC Symbol;Acc:HGNC:25480] | −0.20960528 | −0.20960528 |

TABLE 11-continued

The highest impact sustained by the player in the game as measured by the number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000182054 | IDH2 | isocitrate dehydrogenase 2 (NADP+), mitochondrial [Source:HGNC Symbol;Acc:HGNC:5383] | 0.442800518 | 0.442800518 |
| ENSG00000182885 | GPR97 | G protein-coupled receptor 97 [Source:HGNC Symbol;Acc:HGNC:13728] | −0.210363075 | −0.210363075 |
| ENSG00000182898 | TCHHL1 | trichohyalin-like 1 [Source:HGNC Symbol;Acc:HGNC:31796] | −0.229019793 | NA |
| ENSG00000183145 | RIPPLY3 | ripply transcriptional repressor 3 [Source:HGNC Symbol;Acc:HGNC:3047] | −0.126308067 | NA |
| ENSG00000183722 | LHFP | lipoma HMGIC fusion partner [Source:HGNC Symbol;Acc:HGNC:6586] | −0.111798531 | −0.111798531 |
| ENSG00000183921 | SDR42E2 | short chain dehydrogenase/reductase family 42E, member 2 [Source:HGNC Symbol;Acc:HGNC:35414] | −0.165479768 | NA |
| ENSG00000184319 | RPL23AP82 | ribosomal protein L23a pseudogene 82 [Source:HGNC Symbol;Acc:HGNC:33730] | 0.392529136 | NA |
| ENSG00000184601 | C14orf180 | chromosome 14 open reading frame 180 [Source:HGNC Symbol;Acc:HGNC:33795] | 0.101784654 | NA |
| ENSG00000185164 | NOMO2 | NODAL modulator 2 [Source:HGNC Symbol;Acc:HGNC:22652] | −0.102084963 | NA |
| ENSG00000185187 | SIGIRR | single immunoglobulin and toll-interleukin 1 receptor (TIR) domain [Source:HGNC Symbol;Acc:HGNC:30575] | 0.140935062 | NA |
| ENSG00000185298 | CCDC137 | coiled-coil domain containing 137 [Source:HGNC Symbol;Acc:HGNC:33451] | 0.26108327 | NA |
| ENSG00000185860 | C1orf110 | chromosome 1 open reading frame 110 [Source:HGNC Symbol;Acc:HGNC:28736] | −0.230196066 | NA |
| ENSG00000186163 | | trypsinogen-like pseudogene [Source:EntrezGene;Acc:207147] | −0.177096942 | NA |
| ENSG00000186335 | SLC36A2 | solute carrier family 36 (proton/amino acid symporter), member 2 [Source:HGNC Symbol;Acc:HGNC:18762] | −0.246423368 | NA |
| ENSG00000186407 | CD300E | CD300e molecule [Source:HGNC Symbol;Acc:HGNC:28874] | −0.401181378 | −0.401181378 |
| ENSG00000187116 | LILRA5 | leukocyte immunoglobulin-like receptor, subfamily A (with TM domain), member 5 [Source:HGNC Symbol;Acc:HGNC:16309] | −0.135587282 | −0.135587282 |
| ENSG00000187979 | | | −0.197353089 | NA |
| ENSG00000187990 | NA | NA | 1.230076089 | 1.230076089 |
| ENSG00000188322 | SBK1 | SH3 domain binding kinase 1 [Source:HGNC Symbol;Acc:HGNC:17699] | 0.283124513 | 0.283124513 |
| ENSG00000188536 | HBA2 | hemoglobin, alpha 2 [Source:HGNC Symbol;Acc:HGNC:4824] | 4.258424612 | 4.258424612 |
| ENSG00000188761 | BCL2L15 | BCL2-like 15 [Source:HGNC Symbol;Acc:HGNC:33624] | −0.135276205 | NA |
| ENSG00000188785 | ZNF548 | zinc finger protein 548 [Source:HGNC Symbol;Acc:HGNC:26561] | −0.180896338 | −0.180896338 |
| ENSG00000188933 | USP32P1 | ubiquitin specific peptidase 32 pseudogene 1 [Source:HGNC Symbol;Acc:HGNC:43570] | −0.170492461 | NA |
| ENSG00000189046 | ALKBH2 | alkB, alkylation repair homolog 2 (*E. coli*) [Source:HGNC Symbol;Acc:HGNC:32487] | −0.127674621 | NA |
| ENSG00000189339 | SLC35E2B | solute carrier family 35, member E2B [Source:HGNC Symbol;Acc:HGNC:33941] | 0.235773815 | 0.235773815 |

TABLE 11-continued

The highest impact sustained by the player in the game as measured by the number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000189343 | RPS2P46 | ribosomal protein S2 pseudogene 46 [Source:HGNC Symbol;Acc:HGNC:35839] | 0.529956999 | 0.529956999 |
| ENSG00000196189 | SEMA4A | sema domain, immunoglobulin domain (Ig), transmembrane domain (TM) and short cytoplasmic domain, (semaphorin) 4A [Source:HGNC Symbol;Acc:HGNC:10729] | −0.295647233 | −0.295647233 |
| ENSG00000196453 | ZNF777 | zinc finger protein 777 [Source:HGNC Symbol;Acc:HGNC:22213] | 0.199366514 | 0.199366514 |
| ENSG00000196502 | SULT1A1 | sulfotransferase family, cytosolic, 1A, phenol-preferring, member 1 [Source:HGNC Symbol;Acc:HGNC:11453] | −0.243654476 | −0.243654476 |
| ENSG00000196652 | ZKSCAN5 | zinc finger with KRAB and SCAN domains 5 [Source:HGNC Symbol;Acc:HGNC:12867] | −0.187422891 | −0.187422891 |
| ENSG00000196693 | ZNF33B | zinc finger protein 33B [Source:HGNC Symbol;Acc:HGNC:13097] | −0.157550964 | −0.157550964 |
| ENSG00000196735 | HLA-DQA1 | major histocompatibility complex, class II, DQ alpha 1 [Source:HGNC Symbol;Acc:HGNC:4942] | 0.375325641 | 0.375325641 |
| ENSG00000196743 | GM2A | GM2 ganglioside activator [Source:HGNC Symbol;Acc:HGNC:4367] | −0.184789361 | −0.184789361 |
| ENSG00000196981 | WDR5B | WD repeat domain 5B [Source:HGNC Symbol;Acc:HGNC:17826] | −0.233300195 | NA |
| ENSG00000197013 | ZNF429 | zinc finger protein 429 [Source:HGNC Symbol;Acc:HGNC:20817] | −0.228412404 | −0.228412404 |
| ENSG00000197083 | ZNF300P1 | zinc finger protein 300 pseudogene 1 (functional) [Source:HGNC Symbol;Acc:HGNC:27032] | −0.146514604 | NA |
| ENSG00000197302 | ZNF720 | zinc finger protein 720 [Source:HGNC Symbol;Acc:HGNC:26987] | −0.18798112 | −0.18798112 |
| ENSG00000197343 | ZNF655 | zinc finger protein 655 [Source:HGNC Symbol;Acc:HGNC:30899] | −0.212949896 | −0.212949896 |
| ENSG00000197414 | NA | NA | −0.141068539 | NA |
| ENSG00000197548 | ATG7 | autophagy related 7 [Source:HGNC Symbol;Acc:HGNC:16935] | −0.379355148 | −0.379355148 |
| ENSG00000197599 | CCDC154 | coiled-coil domain containing 154 [Source:HGNC Symbol;Acc:HGNC:34454] | 0.184705043 | NA |
| ENSG00000197646 | PDCD1LG2 | programmed cell death 1 ligand 2 [Source:HGNC Symbol;Acc:HGNC:18731] | −0.110184048 | NA |
| ENSG00000197779 | ZNF81 | zinc finger protein 81 [Source:HGNC Symbol;Acc:HGNC:13156] | −0.142247292 | −0.142247292 |
| ENSG00000197857 | ZNF44 | zinc finger protein 44 [Source:HGNC Symbol;Acc:HGNC:13110] | −0.286352369 | −0.286352369 |
| ENSG00000198131 | ZNF544 | zinc finger protein 544 [Source:HGNC Symbol;Acc:HGNC:16759] | −0.206585267 | −0.206585267 |
| ENSG00000198223 | CSF2RA | colony stimulating factor 2 receptor, alpha, low-affinity (granulocyte-macrophage) [Source:HGNC Symbol;Acc:HGNC:2435] | −0.234620375 | −0.234620375 |
| ENSG00000198563 | DDX39B | DEAD (Asp-Glu-Ala-Asp) box polypeptide 39B [Source:HGNC Symbol;Acc:HGNC:13917] | −0.220385678 | −0.220385678 |
| ENSG00000198657 | OR8B4 | olfactory receptor, family 8, subfamily B, member 4 [Source:HGNC Symbol;Acc:HGNC:8473] | −0.161081721 | NA |

TABLE 11-continued

The highest impact sustained by the player in the game as measured by the
number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000198723 | C19orf45 | chromosome 19 open reading frame 45 [Source:HGNC Symbol;Acc:HGNC:24745] | −0.198512226 | −0.198512226 |
| ENSG00000198740 | ZNF652 | zinc finger protein 652 [Source:HGNC Symbol;Acc:HGNC:29147] | 0.709702366 | 0.709702366 |
| ENSG00000198755 | RPL10A | ribosomal protein L10a [Source:HGNC Symbol;Acc:HGNC:10299] | 0.406926049 | 0.406926049 |
| ENSG00000198912 | C1orf174 | chromosome 1 open reading frame 174 [Source:HGNC Symbol;Acc:HGNC:27915] | −0.181616083 | −0.181616083 |
| ENSG00000203805 | PPAPDC1A | phosphatidic acid phosphatase type 2 domain containing 1A [Source:HGNC Symbol;Acc:HGNC:23531] | −0.201347805 | NA |
| ENSG00000203825 | | | −0.193698104 | NA |
| ENSG00000203849 | NA | NA | −0.376035075 | −0.376035075 |
| ENSG00000204103 | MAFB | v-maf avian musculoaponeurotic fibrosarcoma oncogene homolog B [Source:HGNC Symbol;Acc:HGNC:6408] | 0.124948255 | 0.124948255 |
| ENSG00000204362 | | | −0.314891592 | −0.314891592 |
| ENSG00000204463 | BAG6 | BCL2-associated athanogene 6 [Source:HGNC Symbol;Acc:HGNC:13919] | 0.943103177 | 0.943103177 |
| ENSG00000204713 | TRIM27 | tripartite motif containing 27 [Source:HGNC Symbol;Acc:HGNC:9975] | −0.257524614 | −0.257524614 |
| ENSG00000205628 | LINC01446 | long intergenic non-protein coding RNA 1446 [Source:HGNC Symbol;Acc:HGNC:50773] | −0.120082591 | NA |
| ENSG00000205976 | | | −0.262326119 | −0.262326119 |
| ENSG00000206172 | HBA1 | hemoglobin, alpha 1 [Source:HGNC Symbol;Acc:HGNC:4823] | 0.902138597 | 0.902138597 |
| ENSG00000210195 | MT-TT | mitochondrially encoded tRNA threonine [Source:HGNC Symbol;Acc:HGNC:7499] | 6.848136516 | 6.848136516 |
| ENSG00000211445 | GPX3 | glutathione peroxidase 3 (plasma) [Source:HGNC Symbol;Acc:HGNC:4555] | −0.178654533 | −0.178654533 |
| ENSG00000211940 | NA | NA | −0.143844223 | NA |
| ENSG00000213020 | ZNF611 | zinc finger protein 611 [Source:HGNC Symbol;Acc:HGNC:28766] | −0.259329982 | −0.259329982 |
| ENSG00000213088 | ACKR1 | atypical chemokine receptor 1 (Duffy blood group) [Source:HGNC Symbol;Acc:HGNC:4035] | −0.128327477 | NA |
| ENSG00000213533 | TMEM110 | transmembrane protein 110 [Source:HGNC Symbol;Acc:HGNC:30526] | −0.107013536 | NA |
| ENSG00000213626 | LBH | limb bud and heart development [Source:HGNC Symbol;Acc:HGNC:29532] | 0.623364127 | 0.623364127 |
| ENSG00000214212 | C19orf38 | chromosome 19 open reading frame 38 [Source:HGNC Symbol;Acc:HGNC:34073] | −0.135417642 | −0.135417642 |
| ENSG00000214782 | M54A18 | membrane-spanning 4-domains, subfamily A, member 18 [Source:HGNC Symbol;Acc:HGNC:37636] | −0.156586447 | NA |
| ENSG00000215256 | DHRS4-AS1 | DHRS4 antisense RNA 1 [Source:HGNC Symbol;Acc:HGNC:23175] | −0.186141459 | −0.186141459 |
| ENSG00000215386 | MIR99AHG | mir-99a-let-7c cluster host gene (non-protein coding) [Source:HGNC Symbol;Acc:HGNC:1274] | −0.250013734 | NA |
| ENSG00000215764 | NA | NA | 0.262621436 | NA |
| ENSG00000215853 | RPTN | repetin [Source:HGNC Symbol;Acc:HGNC:26809] | −0.464578408 | NA |

TABLE 11-continued

The highest impact sustained by the player in the game as measured by the number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000215864 | NBPF7 | neuroblastoma breakpoint family, member 7 [Source:HGNC Symbol;Acc:HGNC:31989] | −0.143526164 | NA |
| ENSG00000215887 | ZNF859P | zinc finger protein 859, pseudogene [Source:HGNC Symbol;Acc:HGNC:34507] | −0.273183578 | NA |
| ENSG00000219448 | | | −0.236180736 | NA |
| ENSG00000223528 | | | −0.258929764 | NA |
| ENSG00000223843 | EFCAB6-AS1 | EFCAB6 antisense RNA 1 [Source:HGNC Symbol;Acc:HGNC:39999] | −0.124469557 | NA |
| ENSG00000224051 | CPTP | ceramide-1-phosphate transfer protein [Source:HGNC Symbol;Acc:HGNC:28116] | 0.209225527 | NA |
| ENSG00000224082 | UBTFL8 | upstream binding transcription factor, RNA polymerase I-like 8 (pseudogene) [Source:HGNC Symbol;Acc:HGNC:44476] | −0.220169926 | NA |
| ENSG00000224442 | | | −0.189075329 | NA |
| ENSG00000224896 | SIGLEC30P | sialic acid binding Ig-like lectin 30, pseudogene [Source:HGNC Symbol;Acc:HGNC:15623] | −0.114996185 | NA |
| ENSG00000225901 | MTND2P9 | MT-ND2 pseudogene 9 [Source:HGNC Symbol;Acc:HGNC:42110] | −0.127889211 | NA |
| ENSG00000225972 | MTND1P23 | MT-ND1 pseudogene 23 [Source:HGNC Symbol;Acc:HGNC:42092] | 42.13892989 | 42.13892989 |
| ENSG00000226686 | | | −0.113280249 | NA |
| ENSG00000226995 | LINC00658 | long intergenic non-protein coding RNA 658 [Source:HGNC Symbol;Acc:HGNC:44315] | −0.161639525 | NA |
| ENSG00000227339 | THRAP3P1 | thyroid hormone receptor associated protein 3 pseudogene 1 [Source:HGNC Symbol;Acc:HGNC:32386] | −0.245411465 | NA |
| ENSG00000227372 | TP73-AS1 | TP73 antisense RNA 1 [Source:HGNC Symbol;Acc:HGNC:29052] | 0.31982772 | 0.31982772 |
| ENSG00000227500 | SCAMP4 | secretory carrier membrane protein 4 [Source:HGNC Symbol;Acc:HGNC:30385] | 0.229215804 | 0.229215804 |
| ENSG00000227972 | PRKRIRP3 | protein-kinase, interferon-inducible double stranded RNA dependent inhibitor, repressor of (P58 repressor) pseudogene 3 [Source:HGNC Symbol;Acc:HGNC:39567] | −0.113340677 | NA |
| ENSG00000228215 | | | −0.126130156 | NA |
| ENSG00000228753 | EIF4BP2 | eukaryotic translation initiation factor 4B pseudogene 2 [Source:HGNC Symbol;Acc:HGNC:37935] | −0.199072583 | NA |
| ENSG00000228828 | | | −0.141012861 | NA |
| ENSG00000229344 | | | 1.731408495 | 1.731408495 |
| ENSG00000229696 | KARSP1 | lysyl-tRNA synthetase pseudogene 1 [Source:HGNC Symbol;Acc:HGNC:39207] | −0.125478733 | NA |
| ENSG00000230448 | LINC00276 | long intergenic non-protein coding RNA 276 [Source:HGNC Symbol;Acc:HGNC:38663] | −0.171384523 | NA |
| ENSG00000230880 | NA | NA | −0.260494382 | −0.260494382 |
| ENSG00000231043 | | | −0.168594923 | NA |
| ENSG00000231276 | E2F4P1 | E2F transcription factor 4, p107/p130-binding pseudogene 1 [Source:HGNC Symbol;Acc:HGNC:38684] | −0.132551729 | NA |
| ENSG00000231721 | LINC-PINT | long intergenic non-protein coding RNA, p53 induced transcript [Source:HGNC Symbol;Acc:HGNC:26885] | −0.171442837 | −0.171442837 |

TABLE 11-continued

The highest impact sustained by the player in the game as measured by the
number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000232327 | | | 0.13135561 | NA |
| ENSG00000232722 | MR0H4P | maestro heat-like repeat family member 4, pseudogene [Source:HGNC Symbol;Acc:HGNC:44902] | 0.104588946 | NA |
| ENSG00000233755 | | | −0.140940391 | NA |
| ENSG00000233922 | | | −0.130672957 | NA |
| ENSG00000234420 | ZNF37BP | zinc finger protein 37B, pseudogene [Source:HGNC Symbol;Acc:HGNC:13103] | −0.347517612 | −0.347517612 |
| ENSG00000234444 | ZNF736 | zinc finger protein 736 [Source:HGNC Symbol;Acc:HGNC:32467] | −0.382466167 | −0.382466167 |
| ENSG00000234709 | UPF3AP3 | UPF3A pseudogene 3 [Source:HGNC Symbol;Acc:HGNC:38395] | −0.13929854 | NA |
| ENSG00000235106 | LINC00094 | long intergenic non-protein coding RNA 94 [Source:HGNC Symbol;Acc:HGNC:24742] | 0.165641267 | 0.165641267 |
| ENSG00000236990 | | | −0.116330885 | NA |
| ENSG00000237290 | LINC01343 | long intergenic non-protein coding RNA 1343 [Source:HGNC Symbol;Acc:HGNC:50553] | −0.179447695 | NA |
| ENSG00000238083 | LRRC37A2 | leucine rich repeat containing 37, member A2 [Source:HGNC Symbol;Acc:HGNC:32404] | −0.158451543 | −0.158451543 |
| ENSG00000238208 | | | −0.217256857 | NA |
| ENSG00000238243 | OR2W3 | olfactory receptor, family 2, subfamily W, member 3 [Source:HGNC Symbol;Acc:HGNC:15021] | −0.185364224 | −0.185364224 |
| ENSG00000238278 | ALG1L6P | asparagine-linked glycosylation 1-like 6, pseudogene [Source:HGNC Symbol;Acc:HGNC:44375] | 0.107200388 | NA |
| ENSG00000239789 | MRPS17 | mitochondrial ribosomal protein S17 [Source:HGNC Symbol;Acc:HGNC:14047] | −0.104360759 | NA |
| ENSG00000240954 | RPL4P1 | ribosomal protein L4 pseudogene 1 [Source:HGNC Symbol;Acc:HGNC:23551] | −0.171298291 | NA |
| ENSG00000242732 | RGAG4 | retrotransposon gag domain containing 4 [Source:HGNC Symbol;Acc:HGNC:29430] | −0.1237928 | NA |
| ENSG00000242759 | LINC00882 | long intergenic non-protein coding RNA 882 [Source:HGNC Symbol;Acc:HGNC:48568] | −0.173358615 | NA |
| ENSG00000244306 | LINC01296 | long intergenic non-protein coding RNA 1296 [Source:HGNC Symbol;Acc:HGNC:48904] | −0.168835608 | NA |
| ENSG00000244480 | | | −0.100412433 | NA |
| ENSG00000244625 | MIATNB | MIAT neighbor (non-protein coding) [Source:HGNC Symbol;Acc:HGNC:50731] | −0.318979642 | −0.318979642 |
| ENSG00000244734 | HBB | hemoglobin, beta [Source:HGNC Symbol;Acc:HGNC:4827] | 109.5087838 | 109.5087838 |
| ENSG00000245281 | | | −0.113045576 | NA |
| ENSG00000246250 | | | −0.212714334 | NA |
| ENSG00000246339 | EXTL3-AS1 | EXTL3 antisense RNA 1 [Source:HGNC Symbol;Acc:HGNC:27985] | −0.113036851 | NA |
| ENSG00000248724 | NPHP3-AS1 | NPHP3 antisense RNA 1 [Source:HGNC Symbol;Acc:HGNC:24129] | −0.182694059 | NA |
| ENSG00000250067 | YJEFN3 | YjeF N-terminal domain containing 3 [Source:HGNC Symbol;Acc:HGNC:24785] | −0.482058637 | −0.482058637 |
| ENSG00000250303 | | | −0.213124179 | −0.213124179 |
| ENSG00000250565 | ATP6V1E2 | ATPase, H+ transporting, lysosomal 31 kDa, V1 subunit E2 [Source:HGNC Symbol;Acc:HGNC:18125] | −0.248463482 | −0.248463482 |

TABLE 11-continued

The highest impact sustained by the player in the game as measured by the number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000253665 | | | −0.106655671 | NA |
| ENSG00000254290 | | | −0.124740686 | NA |
| ENSG00000254718 | | | −0.15305955 | NA |
| ENSG00000255507 | | | −0.124782855 | NA |
| ENSG00000255836 | | | −0.125463823 | NA |
| ENSG00000256596 | | | −0.129305477 | NA |
| ENSG00000256612 | CYP2B7P | cytochrome P450, family 2, subfamily B, polypeptide 7, pseudogene [Source:HGNC Symbol;Acc:HGNC:2616] | −0.27215482 | −0.27215482 |
| ENSG00000257335 | MGAM | maltase-glucoamylase (alpha-glucosidase) [Source:HGNC Symbol;Acc:HGNC:7043] | −0.604937865 | −0.604937865 |
| ENSG00000258616 | | | −0.264079574 | NA |
| ENSG00000258634 | | | −0.135548354 | NA |
| ENSG00000258783 | KRT18P6 | keratin 18 pseudogene 6 [Source:HGNC Symbol;Acc:HGNC:20280] | −0.116670007 | NA |
| ENSG00000259029 | DUX4L18 | double homeobox 4 like 18 [Source:HGNC Symbol;Acc:HGNC:37716] | 0.155741858 | NA |
| ENSG00000259345 | | | −0.225236375 | −0.225236375 |
| ENSG00000259417 | LINC01314 | long intergenic non-protein coding RNA 1314 [Source:HGNC Symbol;Acc:HGNC:50507] | −0.232468575 | NA |
| ENSG00000259703 | LINC00593 | long intergenic non-protein coding RNA 593 [Source:HGNC Symbol;Acc:HGNC:32382] | −0.139199501 | NA |
| ENSG00000259845 | HERC2P10 | hect domain and RLD 2 pseudogene 10 [Source:HGNC Symbol;Acc:HGNC:39056] | −0.183062825 | NA |
| ENSG00000260303 | | | −0.214352381 | NA |
| ENSG00000260392 | | | −0.164078762 | NA |
| ENSG00000260776 | | | −0.222848391 | −0.222848391 |
| ENSG00000260840 | | | −0.171448953 | NA |
| ENSG00000261226 | | | 0.213547775 | NA |
| ENSG00000261360 | | | −0.144182385 | NA |
| ENSG00000261649 | GOLGA6L7P | golgin A6 family-like 7, pseudogene [Source:HGNC Symbol;Acc:HGNC:37442] | −0.184249007 | NA |
| ENSG00000261824 | LINC00662 | long intergenic non-protein coding RNA 662 [Source:HGNC Symbol;Acc:HGNC:27122] | −0.288689728 | −0.288689728 |
| ENSG00000261934 | PCDHGA9 | protocadherin gamma subfamily A, 9 [Source:HGNC Symbol;Acc:HGNC:8707] | −0.133685949 | NA |
| ENSG00000262561 | | | −0.115702096 | NA |
| ENSG00000263914 | | | −0.213490416 | NA |
| ENSG00000266173 | STRADA | STE20-related kinase adaptor alpha [Source:HGNC Symbol;Acc:HGNC:30172] | −0.166186341 | −0.166186341 |
| ENSG00000266537 | | | −0.128245629 | NA |
| ENSG00000266904 | LINC00663 | long intergenic non-protein coding RNA 663 [Source:HGNC Symbol;Acc:HGNC:28609] | −0.232081247 | −0.232081247 |
| ENSG00000266913 | | | −0.141142048 | NA |
| ENSG00000266947 | | | −0.109348188 | NA |
| ENSG00000267106 | ZNF561-AS1 | ZNF561 antisense RNA 1 (head to head) [Source:HGNC Symbol;Acc:HGNC:27613] | −0.187392298 | −0.187392298 |
| ENSG00000267372 | | | −0.213066741 | NA |
| ENSG00000267575 | | | −0.228500466 | −0.228500466 |
| ENSG00000267650 | | | −0.208510187 | NA |
| ENSG00000269837 | IPO5P1 | importin 5 pseudogene 1 [Source:HGNC Symbol;Acc:HGNC:49687] | −0.139039195 | NA |
| ENSG00000270442 | | | −0.167429075 | NA |
| ENSG00000271220 | | | 0.136971852 | NA |
| ENSG00000272005 | NA | NA | −0.156552099 | NA |
| ENSG00000272054 | | | −0.146334126 | NA |

TABLE 11-continued

The highest impact sustained by the player in the game as measured by the number of hits regressed on RNA expression in plasma samples

| Ensembl_ID | hgnc_symbol | description | X0.5slope_0.1pvalue_0.1_Number_of_hits_plasma | X0.8slope_0.1pvalue_0.1_Number_of_hits_plasma |
|---|---|---|---|---|
| ENSG00000272374 | | | −0.23487933 | NA |
| ENSG00000273374 | | | −0.131128191 | NA |

TABLE 12

The sum of all impact sustained by the player, as measured by HITsp, regressed on RNA expression in urine samples

| Ensembl_ID | hgnc_symbol | description | X0.5slope_0.1pvalue_0.1_Cum_HITsp_urine | X0.8slope_0.1pvalue_0.1_Cum_HITsp_urine |
|---|---|---|---|---|
| ENSG00000209082 | MT-TL1 | mitochondrially encoded tRNA leucine 1 (UUA/G) [Source: HGNC Symbol; Acc: HGNC: 7490] | 0.184735959 | 0.184735959 |
| ENSG00000210156 | MT-TK | mitochondrially encoded tRNA lysine [Source: HGNC Symbol; Acc: HGNC: 7489] | 0.123469871 | 0.123469871 |
| ENSG00000210196 | MT-TP | mitochondrially encoded tRNA proline [Source: HGNC Symbol; Acc: HGNC: 7494] | 0.102709777 | 0.102709777 |

TABLE 13

The sum of all impact sustained by the player, as measured by linear rotation, regressed on RNA expression in urine samples

| Ensembl_ID | hgnc_symbol | description | X0.5slope_0.1pvalue_0.1_Cum_lin_acc_urine | X0.8slope_0.1pvalue_0.1_Cum_lin_acc_urine |
|---|---|---|---|---|
| ENSG00000198712 | MT-CO2 | mitochondrially encoded cytochrome c oxidase II [Source: HGNC Symbol; Acc: HGNC: 7421] | 1.060970772 | 1.060970772 |
| ENSG00000198840 | MT-ND3 | mitochondrially encoded NADH dehydrogenase 3 [Source: HGNC Symbol; Acc: HGNC: 7458] | 0.423175824 | 0.423175824 |
| ENSG00000198938 | MT-CO3 | mitochondrially encoded cytochrome c oxidase III [Source: HGNC Symbol; Acc: HGNC: 7422] | 1.826905522 | 1.826905522 |
| ENSG00000209082 | MT-TL1 | mitochondrially encoded tRNA leucine 1 (UUA/G) [Source: HGNC Symbol; Acc: HGNC: 7490] | 0.106648801 | 0.106648801 |
| ENSG00000228253 | MT-ATP8 | mitochondrially encoded ATP synthase 8 [Source: HGNC Symbol; Acc: HGNC: 7415] | 0.324958434 | 0.324958434 |

TABLE 14

The highest impact sustained by the player in the game as measured by HITsp regressed on RNA expression in urine samples

| Ensembl_ID | hgnc_symbol | description | X0.5slope_0.1pvalue_Max_HITsp_urine | X0.8slope_0.1pvalue_Max_HITsp_urine |
|---|---|---|---|---|
| ENSG00000002586 | CD99 | CD99 molecule [Source: HGNC Symbol; Acc: HGNC: 7082] | 0.126839875 | 0.126839875 |
| ENSG00000003987 | MTMR7 | myotubularin related protein 7 [Source: HGNC Symbol; Acc: HGNC: 7454] | −0.104493328 | −0.104493328 |

TABLE 14-continued

The highest impact sustained by the player in the game as measured by HITsp regressed on RNA expression in urine samples

| Ensembl_ID | hgnc_symbol | description | X0.5slope_0.1pvalue_Max_HITsp_urine | X0.8slope_0.1pvalue_Max_HITsp_urine |
|---|---|---|---|---|
| ENSG00000004864 | SLC25A13 | solute carrier family 25 (aspartate/glutamate carrier), member 13 [Source: HGNC Symbol; Acc: HGNC: 10983] | −0.122839256 | −0.122839256 |
| ENSG00000005175 | RPAP3 | RNA polymerase 11 associated protein 3 [Source: HGNC Symbol; Acc: HGNC: 26151] | 0.165078296 | 0.165078296 |
| ENSG00000005249 | PRKAR2B | protein kinase, cAMP-dependent, regulatory, type II, beta [Source: HGNC Symbol; Acc: HGNC: 9392] | 0.581721586 | 0.581721586 |
| ENSG00000005801 | ZNF195 | zinc finger protein 195 [Source: HGNC Symbol; Acc: HGNC: 12986] | 0.112661978 | 0.112661978 |
| ENSG00000005810 | MYCBP2 | MYC binding protein 2, E3 ubiquitin protein ligase [Source: HGNC Symbol; Acc: HGNC: 23386] | 0.334133677 | 0.334133677 |
| ENSG00000005961 | ITGA2B | integrin, alpha 2b (platelet glycoprotein IIb of IIb/IIIa complex, antigen CD41) [Source: HGNC Symbol; Acc: HGNC: 6138] | 0.257722578 | 0.257722578 |
| ENSG00000006432 | MAP3K9 | mitogen-activated protein kinase kinase kinase 9 [Source: HGNC Symbol; Acc: HGNC: 6861] | 0.207240949 | 0.207240949 |
| ENSG00000006715 | VPS41 | vacuolar protein sorting 41 homolog (*S. cerevisiae*) [Source: HGNC Symbol; Acc: HGNC: 12713] | 0.32418401 | 0.32418401 |
| ENSG00000007047 | MARK4 | MAP/microtubule affinity-regulating kinase 4 [Source: HGNC Symbol; Acc: HGNC: 13538] | 0.149286836 | 0.149286836 |
| ENSG00000008323 | PLEKHG6 | pleckstrin homology domain containing, family G (with RhoGef domain) member 6 [Source: HGNC Symbol; Acc: HGNC: 25562] | 0.188514525 | 0.188514525 |
| ENSG00000011275 | RNF216 | ring finger protein 216 [Source: HGNC Symbol; Acc: HGNC: 21698] | 0.200742457 | 0.200742457 |
| ENSG00000011376 | LARS2 | leucyl-tRNA synthetase 2, mitochondrial [Source: HGNC Symbol; Acc: HGNC: 17095] | 0.158614373 | 0.158614373 |
| ENSG00000011638 | TMEM159 | transmembrane protein 159 [Source: HGNC Symbol; Acc: HGNC: 30136] | 0.18025885 | 0.18025885 |
| ENSG00000012779 | ALOX5 | arachidonate 5-lipoxygenase [Source: HGNC Symbol; Acc: HGNC: 435] | 0.365154546 | 0.365154546 |
| ENSG00000013016 | EHD3 | EH-domain containing 3 [Source: HGNC Symbol; Acc: HGNC: 3244] | 0.105112549 | 0.105112549 |
| ENSG00000021574 | SPAST | spastin [Source: HGNC Symbol; Acc: HGNC: 11233] | 0.101822754 | 0.101822754 |
| ENSG00000025293 | PHF20 | PHD finger protein 20 [Source: HGNC Symbol; Acc: HGNC: 16098] | 0.308279226 | 0.308279226 |
| ENSG00000031003 | FAM13B | family with sequence similarity 13, member B [Source: HGNC Symbol; Acc: HGNC: 1335] | 0.280432554 | 0.280432554 |
| ENSG00000033170 | FUT8 | fucosyltransferase 8 (alpha (1,6) fucosyltransferase) [Source: HGNC Symbol; Acc: HGNC: 4019] | 0.140437657 | 0.140437657 |
| ENSG00000034677 | RNF19A | ring finger protein 19A, RBR E3 ubiquitin protein ligase [Source: HGNC Symbol; Acc: HGNC: 13432] | 0.380697512 | 0.380697512 |
| ENSG00000035403 | VCL | vinculin [Source: HGNC Symbol; Acc: HGNC: 12665] | 0.800493703 | 0.800493703 |
| ENSG00000041353 | RAB27B | RAB27B, member RAS oncogene family [Source: HGNC Symbol; Acc: HGNC: 9767] | 1.154708123 | 1.154708123 |
| ENSG00000044090 | CUL7 | cullin 7 [Source: HGNC Symbol; Acc: HGNC: 21024] | 0.138205514 | 0.138205514 |
| ENSG00000048405 | ZNF800 | zinc finger protein 800 [Source: HGNC Symbol; Acc: HGNC: 27267] | 0.131989059 | 0.131989059 |

TABLE 14-continued

The highest impact sustained by the player in the game as measured by HITsp regressed on RNA expression in urine samples

| Ensembl_ID | hgnc_symbol | description | X0.5slope_0.1pvalue_Max_HITsp_urine | X0.8slope_0.1pvalue_Max_HITsp_urine |
|---|---|---|---|---|
| ENSG00000048740 | CELF2 | CUGBP, Elav-like family member 2 [Source: HGNC Symbol; Acc: HGNC: 2550] | 0.179995745 | 0.179995745 |
| ENSG00000048991 | R3HDM1 | R3H domain containing 1 [Source: HGNC Symbol; Acc: HGNC: 9757] | 0.156568778 | 0.156568778 |
| ENSG00000049323 | LTBP1 | latent transforming growth factor beta binding protein 1 [Source: HGNC Symbol; Acc: HGNC: 6714] | 0.407651458 | 0.407651458 |
| ENSG00000049656 | CLPTM1L | CLPTM1-like [Source: HGNC Symbol; Acc: HGNC: 24308] | −0.117394386 | −0.117394386 |
| ENSG00000058063 | ATP11B | ATPase, class VI, type 11B [Source: HGNC Symbol; Acc: HGNC: 13553] | 0.329116611 | 0.329116611 |
| ENSG00000061918 | GUCY1B3 | guanylate cyclase 1, soluble, beta 3 [Source: HGNC Symbol; Acc: HGNC: 4687] | 0.143191421 | 0.143191421 |
| ENSG00000062598 | ELMO2 | engulfment and cell motility 2 [Source: HGNC Symbol; Acc: HGNC: 17233] | 0.328452394 | 0.328452394 |
| ENSG00000064102 | ASUN | asunder spermatogenesis regulator [Source: HGNC Symbol; Acc: HGNC: 20174] | 0.160003638 | 0.160003638 |
| ENSG00000064313 | TAF2 | TAF2 RNA polymerase II, TATA box binding protein (TBP)-associated factor, 150 kDa [Source: HGNC Symbol; Acc: HGNC: 11536] | 0.18412105 | 0.18412105 |
| ENSG00000064545 | TMEM161A | transmembrane protein 161A [Source: HGNC Symbol; Acc: HGNC: 26020] | −0.101928753 | −0.101928753 |
| ENSG00000066322 | ELOVL1 | ELOVL fatty acid elongase 1 [Source: HGNC Symbol; Acc: HGNC: 14418] | 0.37012654 | 0.37012654 |
| ENSG00000066629 | EML1 | echinoderm microtubule associated protein like 1 [Source: HGNC Symbol; Acc: HGNC: 3330] | 0.168702634 | 0.168702634 |
| ENSG00000067167 | TRAM1 | translocation associated membrane protein 1 [Source: HGNC Symbol; Acc: HGNC: 20568] | 0.176334589 | 0.176334589 |
| ENSG00000067369 | TP53BP1 | tumor protein p53 binding protein 1 [Source: HGNC Symbol; Acc: HGNC: 11999] | 0.316851129 | 0.316851129 |
| ENSG00000068796 | KIF2A | kinesin heavy chain member 2A [Source: HGNC Symbol; Acc: HGNC: 6318] | 0.443154366 | 0.443154366 |
| ENSG00000069869 | NEDD4 | neural precursor cell expressed, developmentally down-regulated 4, E3 ubiquitin protein ligase [Source: HGNC Symbol; Acc: HGNC: 7727] | 0.13353304 | 0.13353304 |
| ENSG00000070190 | DAPP1 | dual adaptor of phosphotyrosine and 3-phosphoinositides [Source: HGNC Symbol; Acc: HGNC: 16500] | 0.334739101 | 0.334739101 |
| ENSG00000072135 | PTPN18 | protein tyrosine phosphatase, non-receptor type 18 (brain-derived) [Source: HGNC Symbol; Acc: HGNC: 9649] | 0.6446986 | 0.6446986 |
| ENSG00000072657 | TRHDE | thyrotropin-releasing hormone degrading enzyme [Source: HGNC Symbol; Acc: HGNC: 30748] | −0.121750066 | −0.121750066 |
| ENSG00000075151 | EIF4G3 | eukaryotic translation initiation factor 4 gamma, 3 [Source: HGNC Symbol; Acc: HGNC: 3298] | 0.79102486 | 0.79102486 |
| ENSG00000075624 | ACTB | actin, beta [Source: HGNC Symbol; Acc: HGNC: 132] | 13.16966173 | 13.16966173 |
| ENSG00000078124 | ACER3 | alkaline ceramidase 3 [Source: HGNC Symbol; Acc: HGNC: 16066] | −0.116568958 | −0.116568958 |
| ENSG00000078142 | PIK3C3 | phosphatidylinositol 3-kinase, catalytic subunit type 3 [Source: HGNC Symbol; Acc: HGNC: 8974] | 0.210110272 | 0.210110272 |
| ENSG00000080608 | KIAA0020 | KIAA0020 [Source: HGNC Symbol; Acc: HGNC: 29676] | 0.266493195 | 0.266493195 |

TABLE 14-continued

The highest impact sustained by the player in the game as measured by HITsp regressed on RNA expression in urine samples

| Ensembl_ID | hgnc_symbol | description | X0.5slope_0.1pvalue_Max_HITsp_urine | X0.8slope_0.1pvalue_Max_HITsp_urine |
|---|---|---|---|---|
| ENSG00000081320 | STK17B | serine/threonine kinase 17b [Source: HGNC Symbol; Acc: HGNC: 11396] | 0.168493738 | 0.168493738 |
| ENSG00000082397 | EPB41L3 | erythrocyte membrane protein band 4.1-like 3 [Source: HGNC Symbol; Acc: HGNC: 3380] | 0.267548883 | 0.267548883 |
| ENSG00000083544 | TDRD3 | tudor domain containing 3 [Source: HGNC Symbol; Acc: HGNC: 20612] | 0.120739157 | 0.120739157 |
| ENSG00000086189 | DIMT1 | DIM1 dimethyladenosine transferase 1 homolog (S. cerevisiae) [Source: HGNC Symbol; Acc: HGNC: 30217] | 0.106525588 | 0.106525588 |
| ENSG00000086232 | EIF2AK1 | eukaryotic translation initiation factor 2-alpha kinase 1 [Source: HGNC Symbol; Acc: HGNC: 24921] | 0.602897763 | 0.602897763 |
| ENSG00000086619 | ERO1LB | ERO1-like beta (S. cerevisiae) [Source: HGNC Symbol; Acc: HGNC: 14355] | −0.126810199 | −0.126810199 |
| ENSG00000087095 | NLK | nemo-like kinase [Source: HGNC Symbol; Acc: HGNC: 29858] | 0.223717032 | 0.223717032 |
| ENSG00000088053 | GP6 | glycoprotein VI (platelet) [Source: HGNC Symbol; Acc: HGNC: 14388] | 0.112208462 | 0.112208462 |
| ENSG00000089327 | FXYD5 | FXYD domain containing ion transport regulator 5 [Source: HGNC Symbol; Acc: HGNC: 4029] | 0.200859973 | 0.200859973 |
| ENSG00000095303 | PTGS1 | prostaglandin-endoperoxide synthase 1 (prostaglandin G/H synthase and cyclooxygenase) [Source: HGNC Symbol; Acc: HGNC: 9604] | 0.733879376 | 0.733879376 |
| ENSG00000099834 | CDHR5 | cadherin-related family member 5 [Source: HGNC Symbol; Acc: HGNC: 7521] | −0.179748368 | −0.179748368 |
| ENSG00000100077 | ADRBK2 | adrenergic, beta, receptor kinase 2 [Source: HGNC Symbol; Acc: HGNC: 290] | 0.579989071 | 0.579989071 |
| ENSG00000100351 | GRAP2 | GRB2-related adaptor protein 2 [Source: HGNC Symbol; Acc: HGNC: 4563] | 0.372875678 | 0.372875678 |
| ENSG00000100422 | CERK | ceramide kinase [Source: HGNC Symbol; Acc: HGNC: 19256] | −0.117307396 | −0.117307396 |
| ENSG00000100580 | TMED8 | transmembrane emp24 protein transport domain containing 8 [Source: HGNC Symbol; Acc: HGNC: 18633] | 0.203951184 | 0.203951184 |
| ENSG00000100592 | DAAM1 | dishevelled associated activator of morphogenesis 1 [Source: HGNC Symbol; Acc: HGNC: 18142] | 0.296800198 | 0.296800198 |
| ENSG00000101162 | TUBB1 | tubulin, beta 1 class VI [Source: HGNC Symbol; Acc: HGNC: 16257] | 0.93464511 | 0.93464511 |
| ENSG00000101210 | EEF1A2 | eukaryotic translation elongation factor 1 alpha 2 [Source: HGNC Symbol; Acc: HGNC: 3192] | 0.269827941 | 0.269827941 |
| ENSG00000101544 | ADNP2 | ADNP homeobox 2 [Source: HGNC Symbol; Acc: HGNC: 23803] | 0.108650713 | 0.108650713 |
| ENSG00000101608 | MYL12A | myosin, light chain 12A, regulatory, non-sarcomeric [Source: HGNC Symbol; Acc: HGNC: 16701] | 0.726900736 | 0.726900736 |
| ENSG00000101782 | RIOK3 | RIO kinase 3 [Source: HGNC Symbol; Acc: HGNC: 11451] | 0.23805903 | 0.23805903 |
| ENSG00000101856 | PGRMC1 | progesterone receptor membrane component 1 [Source: HGNC Symbol; Acc: HGNC: 16090] | 0.361020607 | NA |
| ENSG00000101871 | MID1 | midline 1 [Source: HGNC Symbol; Acc: HGNC: 7095] | 0.102338145 | 0.102338145 |
| ENSG00000102243 | VGLL1 | vestigial-like family member 1 [Source: HGNC Symbol; Acc: HGNC: 20985] | 0.513257603 | 0.513257603 |
| ENSG00000102572 | STK24 | serine/threonine kinase 24 [Source: HGNC Symbol; Acc: HGNC: 11403] | 0.291512329 | 0.291512329 |

TABLE 14-continued

The highest impact sustained by the player in the game as measured by HITsp regressed on RNA expression in urine samples

| Ensembl_ID | hgnc_symbol | description | X0.5slope_0.1pvalue_Max_HITsp_urine | X0.8slope_0.1pvalue_Max_HITsp_urine |
|---|---|---|---|---|
| ENSG00000102804 | TSC22D1 | TSC22 domain family, member 1 [Source: HGNC Symbol; Acc: HGNC: 16826] | 0.62464408 | 0.62464408 |
| ENSG00000103194 | USP10 | ubiquitin specific peptidase 10 [Source: HGNC Symbol; Acc: HGNC: 12608] | 0.260120846 | 0.260120846 |
| ENSG00000103876 | FAH | fumarylacetoacetate hydrolase (fumarylacetoacetase) [Source: HGNC Symbol; Acc: HGNC: 3579] | 0.143367228 | 0.143367228 |
| ENSG00000104447 | TRPS1 | trichorhinophalangeal syndrome I [Source: HGNC Symbol; Acc: HGNC: 12340] | 0.201685685 | 0.201685685 |
| ENSG00000104763 | ASAH1 | N-acylsphingosine amidohydrolase (acid ceramidase) 1 [Source: HGNC Symbol; Acc: HGNC: 735] | 0.229623019 | 0.229623019 |
| ENSG00000105186 | ANKRD27 | ankyrin repeat domain 27 (VPS9 domain) [Source: HGNC Symbol; Acc: HGNC: 25310] | 0.155274119 | 0.155274119 |
| ENSG00000105329 | TGFB1 | transforming growth factor, beta 1 [Source: HGNC Symbol; Acc: HGNC: 11766] | 0.174204583 | 0.174204583 |
| ENSG00000105778 | AVL9 | AVL9 homolog (S. cerevisiase) [Source: HGNC Symbol; Acc: HGNC: 28994] | 0.280409696 | 0.280409696 |
| ENSG00000105887 | MTPN | myotrophin [Source: HGNC Symbol; Acc: HGNC: 15667] | 0.370822464 | 0.370822464 |
| ENSG00000106615 | RHEB | Ras homolog enriched in brain [Source: HGNC Symbol; Acc: HGNC: 10011] | 0.149766607 | 0.149766607 |
| ENSG00000107077 | KDM4C | lysine (K)-specific demethylase 4C [Source: HGNC Symbol; Acc: HGNC: 17071] | 0.109162843 | 0.109162843 |
| ENSG00000107099 | DOCK8 | dedicator of cytokinesis 8 [Source: HGNC Symbol; Acc: HGNC: 19191] | 0.347940675 | 0.347940675 |
| ENSG00000107438 | PDLIM1 | PDZ and LIM domain 1 [Source: HGNC Symbol; Acc: HGNC: 2067] | 0.330990056 | 0.330990056 |
| ENSG00000107669 | ATE1 | arginyltransferase 1 [Source: HGNC Symbol; Acc: HGNC: 782] | 0.372522035 | 0.372522035 |
| ENSG00000107863 | ARHGAP21 | Rho GTPase activating protein 21 [Source: HGNC Symbol; Acc: HGNC: 23725] | 0.303455407 | 0.303455407 |
| ENSG00000108094 | CUL2 | cullin 2 [Source: HGNC Symbol; Acc: HGNC: 2552] | 0.186832148 | 0.186832148 |
| ENSG00000108389 | MTMR4 | myotubularin related protein 4 [Source: HGNC Symbol; Acc: HGNC: 7452] | 0.379527121 | 0.379527121 |
| ENSG00000108883 | EFTUD2 | elongation factor Tu GTP binding domain containing 2 [Source: HGNC Symbol; Acc: HGNC: 30858] | 0.3006319 | 0.3006319 |
| ENSG00000108960 | MMD | monocyte to macrophage differentiation-associated [Source: HGNC Symbol; Acc: HGNC: 7153] | 0.165657861 | 0.165657861 |
| ENSG00000109084 | TMEM97 | transmembrane protein 97 [Source: HGNC Symbol; Acc: HGNC: 28106] | 0.79542134 | 0.79542134 |
| ENSG00000110060 | PUS3 | pseudouridylate synthase 3 [Source: HGNC Symbol; Acc: HGNC: 25461] | 0.154578345 | 0.154578345 |
| ENSG00000110514 | MADD | MAP-kinase activating death domain [Source: HGNC Symbol; Acc: HGNC: 6766] | 0.503549474 | 0.503549474 |
| ENSG00000110906 | KCTD10 | potassium channel tetramerization domain containing 10 [Source: HGNC Symbol; Acc: HGNC: 23236] | 0.161059712 | 0.161059712 |
| ENSG00000110934 | BIN2 | bridging integrator 2 [Source: HGNC Symbol; Acc: HGNC: 1053] | 0.248982133 | 0.248982133 |
| ENSG00000111348 | ARHGDIB | Rho GDP dissociation inhibitor (GDI) beta [Source: HGNC Symbol; Acc: HGNC: 679] | 1.141723559 | 1.141723559 |

TABLE 14-continued

The highest impact sustained by the player in the game as measured by HITsp regressed on RNA expression in urine samples

| Ensembl_ID | hgnc_symbol | description | X0.5slope_0.1pvalue_Max_HITsp_urine | X0.8slope_0.1pvalue_Max_HITsp_urine |
|---|---|---|---|---|
| ENSG00000112118 | MCM3 | minichromosome maintenance complex component 3 [Source: HGNC Symbol; Acc: HGNC: 6945] | 0.227295728 | 0.227295728 |
| ENSG00000112499 | SLC22A2 | solute carrier family 22 (organic cation transporter), member 2 [Source: HGNC Symbol; Acc: HGNC: 10966] | −0.133185802 | −0.133185802 |
| ENSG00000112541 | PDE10A | phosphodiesterase 10A [Source: HGNC Symbol; Acc: HGNC: 8772] | 0.828007185 | 0.828007185 |
| ENSG00000112796 | ENPP5 | ectonucleotide pyrophosphatase/phosphodiesterase 5 (putative) [Source: HGNC Symbol; Acc: HGNC: 13717] | 0.10593299 | 0.10593299 |
| ENSG00000112893 | MAN2A1 | mannosidase, alpha, class 2A, member 1 [Source: HGNC Symbol; Acc: HGNC: 6824] | 0.217921951 | 0.217921951 |
| ENSG00000113140 | SPARC | secreted protein, acidic, cysteine-rich (osteonectin) [Source: HGNC Symbol; Acc: HGNC: 11219] | 0.511013974 | 0.511013974 |
| ENSG00000113494 | PRLR | prolactin receptor [Source: HGNC Symbol; Acc: HGNC: 9446] | −0.201971842 | −0.201971842 |
| ENSG00000113580 | NR3C1 | nuclear receptor subfamily 3, group C, member 1 (glucocorticoid receptor) [Source: HGNC Symbol; Acc: HGNC: 7978] | −0.140459284 | −0.140459284 |
| ENSG00000113649 | TCERG1 | transcription elongation regulator 1 [Source: HGNC Symbol; Acc: HGNC: 15630] | 0.401292787 | 0.401292787 |
| ENSG00000114098 | ARMC8 | armadillo repeat containing 8 [Source: HGNC Symbol; Acc: HGNC: 24999] | 0.430175492 | 0.430175492 |
| ENSG00000114166 | KAT2B | K(lysine) acetyltransferase 2B [Source: HGNC Symbol; Acc: HGNC: 8638] | 0.133553074 | 0.133553074 |
| ENSG00000114541 | FRMD4B | FERM domain containing 4B [Source: HGNC Symbol; Acc: HGNC: 24886] | 0.183283074 | 0.183283074 |
| ENSG00000114638 | UPK1B | uroplakin 1B [Source: HGNC Symbol; Acc: HGNC: 12578] | 0.303753692 | 0.303753692 |
| ENSG00000114805 | PLCH1 | phospholipase C, eta 1 [Source: HGNC Symbol; Acc: HGNC: 29185] | 0.158661406 | 0.158661406 |
| ENSG00000115159 | GPD2 | glycerol-3-phosphate dehydrogenase 2 (mitochondrial) [Source: HGNC Symbol; Acc: HGNC: 4456] | 0.171842902 | 0.171842902 |
| ENSG00000115464 | USP34 | ubiquitin specific peptidase 34 [Source: HGNC Symbol; Acc: HGNC: 20066] | 0.481266265 | 0.481266265 |
| ENSG00000115525 | ST3GAL5 | ST3 beta-galactoside alpha-2,3-sialyltransferase 5 [Source: HGNC Symbol; Acc: HGNC: 10872] | 0.16022356 | 0.16022356 |
| ENSG00000115641 | FHL2 | four and a half LIM domains 2 [Source: HGNC Symbol; Acc: HGNC: 3703] | 0.146032055 | 0.146032055 |
| ENSG00000115935 | WIPF1 | WAS/WASL interacting protein family, member 1 [Source: HGNC Symbol; Acc: HGNC: 12736] | 0.286397025 | 0.286397025 |
| ENSG00000116191 | RALGPS2 | Ral GEF with PH domain and SH3 binding motif 2 [Source: HGNC Symbol; Acc: HGNC: 30279] | 0.135643961 | 0.135643961 |
| ENSG00000116237 | ICMT | isoprenylcysteine carboxyl methyltransferase [Source: HGNC Symbol; Acc: HGNC: 5350] | −0.110133125 | −0.110133125 |
| ENSG00000116580 | GON4L | gon-4-like (C. elegans) [Source: HGNC Symbol; Acc: HGNC: 25973] | 0.335638953 | 0.335638953 |
| ENSG00000117139 | KDM5B | lysine (K)-specific demethylase 5B [Source: HGNC Symbol; Acc: HGNC: 18039] | 0.481213482 | 0.481213482 |
| ENSG00000117335 | CD46 | CD46 molecule, complement regulatory protein [Source: HGNC Symbol; Acc: HGNC: 6953] | 0.208538675 | 0.208538675 |

TABLE 14-continued

The highest impact sustained by the player in the game as measured by HITsp regressed on RNA expression in urine samples

| Ensembl_ID | hgnc_symbol | description | X0.5slope_0.1pvalue_Max_HITsp_urine | X0.8slope_0.1pvalue_Max_HITsp_urine |
|---|---|---|---|---|
| ENSG00000117400 | MPL | MPL proto-oncogene, thrombopoietin receptor [Source: HGNC Symbol; Acc: HGNC: 7217] | 0.189039952 | 0.189039952 |
| ENSG00000117461 | PIK3R3 | phosphoinositide-3-kinase, regulatory subunit 3 (gamma) [Source: HGNC Symbol; Acc: HGNC: 8981] | 0.390225521 | 0.390225521 |
| ENSG00000118855 | MFSD1 | major facilitator superfamily domain containing 1 [Source: HGNC Symbol; Acc: HGNC: 25874] | 0.161327765 | 0.161327765 |
| ENSG00000119242 | CCDC92 | coiled-coil domain containing 92 [Source: HGNC Symbol; Acc: HGNC: 29563] | 0.174015024 | 0.174015024 |
| ENSG00000119684 | MLH3 | mutL homolog 3 [Source: HGNC Symbol; Acc: HGNC: 7128] | 0.339439682 | 0.339439682 |
| ENSG00000119938 | PPP1R3C | protein phosphatase 1, regulatory subunit 3C [Source: HGNC Symbol; Acc: HGNC: 9293] | 0.195538023 | 0.195538023 |
| ENSG00000120162 | MOB3B | MOB kinase activator 3B [Source: HGNC Symbol; Acc: HGNC: 23825] | −0.128479144 | −0.128479144 |
| ENSG00000120690 | ELF1 | E74-like factor 1 (ets domain transcription factor) [Source: HGNC Symbol; Acc: HGNC: 3316] | 0.405314708 | 0.405314708 |
| ENSG00000120885 | CLU | clusterin [Source: HGNC Symbol; Acc: HGNC: 2095] | 0.46226576 | 0.46226576 |
| ENSG00000121989 | ACVR2A | activin A receptor, type IIA [Source: HGNC Symbol; Acc: HGNC: 173] | 0.148006169 | 0.148006169 |
| ENSG00000122176 | FMOD | fibromodulin [Source: HGNC Symbol; Acc: HGNC: 3774] | 0.118763672 | 0.118763672 |
| ENSG00000122545 | 7-Sep | septin 7 [Source: HGNC Symbol; Acc: HGNC: 1717] | 0.232295239 | 0.232295239 |
| ENSG00000122550 | KLHL7 | kelch-like family member 7 [Source: HGNC Symbol; Acc: HGNC: 15646] | 0.101786764 | 0.101786764 |
| ENSG00000122557 | HERPUD2 | HERPUD family member 2 [Source: HGNC Symbol; Acc: HGNC: 21915] | 0.183005889 | 0.183005889 |
| ENSG00000122779 | TRIM24 | tripartite motif containing 24 [Source: HGNC Symbol; Acc: HGNC: 11812] | 0.488522926 | 0.488522926 |
| ENSG00000123091 | RNF11 | ring finger protein 11 [Source: HGNC Symbol; Acc: HGNC: 10056] | 0.880092531 | 0.880092531 |
| ENSG00000123095 | BHLHE41 | basic helix-loop-helix family, member e41 [Source: HGNC Symbol; Acc: HGNC: 16617] | 0.290146569 | 0.290146569 |
| ENSG00000124228 | DDX27 | DEAD (Asp-Glu-Ala-Asp) box polypeptide 27 [Source: HGNC Symbol; Acc: HGNC: 15837] | 0.155817465 | 0.155817465 |
| ENSG00000124333 | VAMP7 | vesicle-associated membrane protein 7 [Source: HGNC Symbol; Acc: HGNC: 11486] | 0.12828441 | 0.12828441 |
| ENSG00000124491 | F13A1 | coagulation factor XIII, A1 polypeptide [Source: HGNC Symbol; Acc: HGNC: 3531] | 0.546443396 | 0.546443396 |
| ENSG00000124635 | HIST1H2BJ | histone cluster 1, H2bj [Source: HGNC Symbol; Acc: HGNC: 4761] | 0.156372055 | 0.156372055 |
| ENSG00000124813 | RUNX2 | runt-related transcription factor 2 [Source: HGNC Symbol; Acc: HGNC: 10472] | 0.120780718 | 0.120780718 |
| ENSG00000125246 | CLYBL | citrate lyase beta like [Source: HGNC Symbol; Acc: HGNC: 18355] | −0.107136431 | −0.107136431 |
| ENSG00000125676 | THOC2 | THO complex 2 [Source: HGNC Symbol; Acc: HGNC: 19073] | 0.616135842 | 0.616135842 |
| ENSG00000125734 | GPR108 | G protein-coupled receptor 108 [Source: HGNC Symbol; Acc: HGNC: 17829] | −0.105816696 | −0.105816696 |
| ENSG00000125945 | ZNF436 | zinc finger protein 436 [Source: HGNC Symbol; Acc: HGNC: 20814] | 0.165003054 | 0.165003054 |

TABLE 14-continued

The highest impact sustained by the player in the game as measured by HITsp regressed on RNA expression in urine samples

| Ensembl_ID | hgnc_symbol | description | X0.5slope_0.1pvalue_Max_HITsp_urine | X0.8slope_0.1pvalue_Max_HITsp_urine |
|---|---|---|---|---|
| ENSG00000125952 | MAX | MYC associated factor X [Source: HGNC Symbol; Acc: HGNC: 6913] | 0.415943432 | 0.415943432 |
| ENSG00000126351 | THRA | thyroid hormone receptor, alpha [Source: HGNC Symbol; Acc: HGNC: 11796] | −0.123070122 | −0.123070122 |
| ENSG00000127314 | RAP1B | RAP1B, member of RAS oncogene family [Source: HGNC Symbol; Acc: HGNC: 9857] | 0.515735425 | 0.515735425 |
| ENSG00000127920 | GNG11 | guanine nucleotide binding protein (G protein), gamma 11 [Source: HGNC Symbol; Acc: HGNC: 4403] | 0.150922583 | 0.150922583 |
| ENSG00000127947 | PTPN12 | protein tyrosine phosphatase, non-receptor type 12 [Source: HGNC Symbol; Acc: HGNC: 9645] | 0.324687197 | 0.324687197 |
| ENSG00000127980 | PEX1 | peroxisomal biogenesis factor 1 [Source: HGNC Symbol; Acc: HGNC: 8850] | −0.113166927 | −0.113166927 |
| ENSG00000128045 | RASL11B | RAS-like, family 11, member B [Source: HGNC Symbol; Acc: HGNC: 23804] | 0.101121756 | 0.101121756 |
| ENSG00000128245 | YWHAH | tyrosine 3-monooxygenase/tryptophan 5-monooxygenase activation protein, eta [Source: HGNC Symbol; Acc: HGNC: 12853] | 0.154477464 | 0.154477464 |
| ENSG00000128266 | GNAZ | guanine nucleotide binding protein (G protein), alpha z polypeptide [Source: HGNC Symbol; Acc: HGNC: 4395] | 0.117449745 | 0.117449745 |
| ENSG00000129353 | SLC44A2 | solute carrier family 44 (choline transporter), member 2 [Source: HGNC Symbol; Acc: HGNC: 17292] | 0.718830106 | 0.718830106 |
| ENSG00000129422 | MTUS1 | microtubule associated tumor suppressor 1 [Source: HGNC Symbol; Acc: HGNC: 29789] | 0.693637092 | 0.693637092 |
| ENSG00000130830 | MPP1 | membrane protein, palmitoylated 1, 55 kDa [Source: HGNC Symbol; Acc: HGNC: 7219] | 0.226645535 | 0.226645535 |
| ENSG00000131171 | SH3BGRL | SH3 domain binding glutamate-rich protein like [Source: HGNC Symbol; Acc: HGNC: 10823] | 0.719515363 | 0.719515363 |
| ENSG00000131725 | WDR44 | WD repeat domain 44 [Source: HGNC Symbol; Acc: HGNC: 30512] | 0.434981931 | 0.434981931 |
| ENSG00000131781 | FMO5 | flavin containing monooxygenase 5 [Source: HGNC Symbol; Acc: HGNC: 3773] | −0.128089256 | −0.128089256 |
| ENSG00000132170 | PPARG | peroxisome proliferator-activated receptor gamma [Source: HGNC Symbol; Acc: HGNC: 9236] | 1.953750607 | 1.953750607 |
| ENSG00000132357 | CARD6 | caspase recruitment domain family, member 6 [Source: HGNC Symbol; Acc: HGNC: 16394] | 0.137262799 | 0.137262799 |
| ENSG00000132824 | SERINC3 | serine incorporator 3 [Source: HGNC Symbol; Acc: HGNC: 11699] | 0.107902612 | 0.107902612 |
| ENSG00000133606 | MKRN1 | makorin ring finger protein 1 [Source: HGNC Symbol; Acc: HGNC: 7112] | 0.490172081 | 0.490172081 |
| ENSG00000134240 | HMGCS2 | 3-hydroxy-3-methylglutaryl-CoA synthase 2 (mitochondrial) [Source: HGNC Symbol; Acc: HGNC: 5008] | 1.398835274 | 1.398835274 |
| ENSG00000134265 | NAPG | N-ethylmaleimide-sensitive factor attachment protein, gamma [Source: HGNC Symbol; Acc: HGNC: 7642] | 0.210671394 | 0.210671394 |
| ENSG00000135365 | PHF21A | PHD finger protein 21A [Source: HGNC Symbol; Acc: HGNC: 24156] | 0.298980862 | 0.298980862 |
| ENSG00000135521 | LTV1 | LTV1 ribosome biogenesis factor [Source: HGNC Symbol; Acc: HGNC: 21173] | 0.158856248 | 0.158856248 |

TABLE 14-continued

The highest impact sustained by the player in the game as measured by HITsp regressed on RNA expression in urine samples

| Ensembl_ID | hgnc_symbol | description | X0.5slope_0.1pvalue_Max_HITsp_urine | X0.8slope_0.1pvalue_Max_HITsp_urine |
|---|---|---|---|---|
| ENSG00000135540 | NHSL1 | NHS-like 1 [Source: HGNC Symbol; Acc: HGNC: 21021] | 0.46724515 | 0.46724515 |
| ENSG00000135597 | REPS1 | RALBP1 associated Eps domain containing 1 [Source: HGNC Symbol; Acc: HGNC: 15578] | 0.114862103 | 0.114862103 |
| ENSG00000135966 | TGFBRAP1 | transforming growth factor, beta receptor associated protein 1 [Source: HGNC Symbol; Acc: HGNC: 16836] | 0.124184608 | 0.124184608 |
| ENSG00000135976 | ANKRD36 | ankyrin repeat domain 36 [Source: HGNC Symbol; Acc: HGNC: 24079] | −0.109182456 | −0.109182456 |
| ENSG00000136231 | IGF2BP3 | insulin-like growth factor 2 mRNA binding protein 3 [Source: HGNC Symbol; Acc: HGNC: 28868] | 0.276307789 | 0.276307789 |
| ENSG00000136689 | IL1RN | interleukin 1 receptor antagonist [Source: HGNC Symbol; Acc: HGNC: 6000] | 2.077635851 | 2.077635851 |
| ENSG00000136715 | SAP130 | Sin3A-associated protein, 130 kDa [Source: HGNC Symbol; Acc: HGNC: 29813] | 0.439952614 | 0.439952614 |
| ENSG00000136717 | BIN1 | bridging integrator 1 [Source: HGNC Symbol; Acc: HGNC: 1052] | −0.143377353 | −0.143377353 |
| ENSG00000136738 | STAM | signal transducing adaptor molecule (SH3 domain and ITAM motif) 1 [Source: HGNC Symbol; Acc: HGNC: 11357] | 0.353135957 | 0.353135957 |
| ENSG00000136868 | SLC31A1 | solute carrier family 31 (copper transporter), member 1 [Source: HGNC Symbol; Acc: HGNC: 11016] | 0.110813662 | 0.110813662 |
| ENSG00000136925 | TSTD2 | thiosulfate sulfurtransferase (rhodanese)-like domain containing 2 [Source: HGNC Symbol; Acc: HGNC: 30087] | 0.128876718 | 0.128876718 |
| ENSG00000137073 | UBAP2 | ubiquitin associated protein 2 [Source: HGNC Symbol; Acc: HGNC: 14185] | 0.418369571 | 0.418369571 |
| ENSG00000137076 | TLN1 | talin 1 [Source: HGNC Symbol; Acc: HGNC: 11845] | 1.597978957 | 1.597978957 |
| ENSG00000138293 | NA | NA | 2.156656327 | 2.156656327 |
| ENSG00000138735 | PDE5A | phosphodiesterase 5A, cGMP-specific [Source: HGNC Symbol; Acc: HGNC: 8784] | 0.282062238 | 0.282062238 |
| ENSG00000139055 | ERP27 | endoplasmic reticulum protein 27 [Source: HGNC Symbol; Acc: HGNC: 26495] | 0.357585235 | 0.357585235 |
| ENSG00000139323 | POC1B | POC1 centriolar protein B [Source: HGNC Symbol; Acc: HGNC: 30836] | 0.17988861 | 0.17988861 |
| ENSG00000139998 | RAB15 | RAB15, member RAS oncogene family [Source: HGNC Symbol; Acc: HGNC: 20150] | 0.138583198 | 0.138583198 |
| ENSG00000140022 | STON2 | stonin 2 [Source: HGNC Symbol; Acc: HGNC: 30652] | 0.324331784 | 0.324331784 |
| ENSG00000140299 | BNIP2 | BCL2/adenovirus E1B 19 kDa interacting protein 2 [Source: HGNC Symbol; Acc: HGNC: 1083] | 0.206087205 | 0.206087205 |
| ENSG00000140374 | ETFA | electron-transfer-flavoprotein, alpha polypeptide [Source: HGNC Symbol; Acc: HGNC: 3481] | 0.778717155 | 0.778717155 |
| ENSG00000140750 | ARHGAP17 | Rho GTPase activating protein 17 [Source: HGNC Symbol; Acc: HGNC: 18239] | 0.151421455 | 0.151421455 |
| ENSG00000141298 | SSH2 | slingshot protein phosphatase 2 [Source: HGNC Symbol; Acc: HGNC: 30580] | 0.414272422 | 0.414272422 |
| ENSG00000141556 | TBCD | tubulin folding cofactor D [Source: HGNC Symbol; Acc: HGNC: 11581] | 0.171961864 | 0.171961864 |
| ENSG00000141664 | ZCCHC2 | zinc finger, CCHC domain containing 2 [Source: HGNC Symbol; Acc: HGNC: 22916] | 0.376619618 | 0.376619618 |

TABLE 14-continued

The highest impact sustained by the player in the game as measured by HITsp regressed on RNA expression in urine samples

| Ensembl_ID | hgnc_symbol | description | X0.5slope_0.1pvalue_Max_HITsp_urine | X0.8slope_0.1pvalue_Max_HITsp_urine |
|---|---|---|---|---|
| ENSG00000142669 | SH3BGRL3 | SH3 domain binding glutamate-rich protein like 3 [Source: HGNC Symbol; Acc: HGNC: 15568] | 1.622707315 | 1.622707315 |
| ENSG00000143179 | UCK2 | uridine-cytidine kinase 2 [Source: HGNC Symbol; Acc: HGNC: 12562] | 0.117654114 | 0.117654114 |
| ENSG00000143207 | RFWD2 | ring finger and WD repeat domain 2, E3 ubiquitin protein ligase [Source: HGNC Symbol; Acc: HGNC: 17440] | 0.100026363 | 0.100026363 |
| ENSG00000143379 | SETDB1 | SET domain, bifurcated 1 [Source: HGNC Symbol; Acc: HGNC: 10761] | 0.141059768 | 0.141059768 |
| ENSG00000143409 | FAM63A | family with sequence similarity 63, member A [Source: HGNC Symbol; Acc: HGNC: 25648] | 0.254846943 | 0.254846943 |
| ENSG00000143494 | VASH2 | vasohibin 2 [Source: HGNC Symbol; Acc: HGNC: 25723] | −0.100842302 | −0.100842302 |
| ENSG00000143624 | INTS3 | integrator complex subunit 3 [Source: HGNC Symbol; Acc: HGNC: 26153] | 0.145035158 | 0.145035158 |
| ENSG00000144120 | TMEM177 | transmembrane protein 177 [Source: HGNC Symbol; Acc: HGNC: 28143] | 0.103732969 | 0.103732969 |
| ENSG00000144468 | RHBDD1 | rhomboid domain containing 1 [Source: HGNC Symbol; Acc: HGNC: 23081] | 0.568537348 | 0.568537348 |
| ENSG00000146006 | LRRTM2 | leucine rich repeat transmembrane neuronal 2 [Source: HGNC Symbol; Acc: HGNC: 19409] | −0.1015115 | −0.1015115 |
| ENSG00000146859 | TMEM140 | transmembrane protein 140 [Source: HGNC Symbol; Acc: HGNC: 21870] | 0.1056982 | 0.1056982 |
| ENSG00000146904 | EPHA1 | EPH receptor A1 [Source: HGNC Symbol; Acc: HGNC: 3385] | 0.113076631 | 0.113076631 |
| ENSG00000147394 | ZNF185 | zinc finger protein 185 (LIM domain) [Source: HGNC Symbol; Acc: HGNC: 12976] | 0.305348237 | 0.305348237 |
| ENSG00000147606 | SLC26A7 | solute carrier family 26 (anion exchanger), member 7 [Source: HGNC Symbol; Acc: HGNC: 14467] | −0.135780362 | −0.135780362 |
| ENSG00000147649 | MTDH | metadherin [Source: HGNC Symbol; Acc: HGNC: 29608] | 0.152534374 | 0.152534374 |
| ENSG00000148175 | STOM | stomatin [Source: HGNC Symbol; Acc: HGNC: 3383] | 0.102889947 | 0.102889947 |
| ENSG00000148396 | SEC16A | SEC16 homolog A (*S. cerevisiae*) [Source: HGNC Symbol; Acc: HGNC: 29006] | 0.45980412 | 0.45980412 |
| ENSG00000148484 | RSU1 | Ras suppressor protein 1 [Source: HGNC Symbol; Acc: HGNC: 10464] | 0.315640995 | 0.315640995 |
| ENSG00000148498 | PARD3 | par-3 family cell polarity regulator [Source: HGNC Symbol; Acc: HGNC: 16051] | 0.165264157 | 0.165264157 |
| ENSG00000148660 | CAMK2G | calcium/calmodulin-dependent protein kinase 11 gamma [Source: HGNC Symbol; Acc: HGNC: 1463] | 0.206367559 | 0.206367559 |
| ENSG00000148840 | PPRC1 | peroxisome proliferator-activated receptor gamma, coactivator-related 1 [Source: HGNC Symbol; Acc: HGNC: 30025] | 0.538595703 | 0.538595703 |
| ENSG00000148843 | PDCD11 | programmed cell death 11 [Source: HGNC Symbol; Acc: HGNC: 13408] | 0.174944261 | 0.174944261 |
| ENSG00000148908 | RGS10 | regulator of G-protein signaling 10 [Source: HGNC Symbol; Acc: HGNC: 9992] | 0.292282672 | 0.292282672 |
| ENSG00000149177 | PTPRJ | protein tyrosine phosphatase, receptor type, J [Source: HGNC Symbol; Acc: HGNC: 9673] | 0.200352211 | 0.200352211 |

TABLE 14-continued

The highest impact sustained by the player in the game as measured by HITsp regressed on RNA expression in urine samples

| Ensembl_ID | hgnc_symbol | description | X0.5slope_0.1pvalue_Max_HITsp_urine | X0.8slope_0.1pvalue_Max_HITsp_urine |
| --- | --- | --- | --- | --- |
| ENSG00000150054 | MPP7 | membrane protein, palmitoylated 7 (MAGUK p55 subfamily member 7) [Source: HGNC Symbol; Acc: HGNC: 26542] | 0.455594167 | 0.455594167 |
| ENSG00000150093 | ITGB1 | integrin, beta 1 (fibronectin receptor, beta polypeptide, antigen CD29 includes MDF2, MSK12) [Source: HGNC Symbol; Acc: HGNC: 6153] | 0.42848484 | 0.42848484 |
| ENSG00000150637 | CD226 | CD226 molecule [Source: HGNC Symbol; Acc: HGNC: 16961] | 0.145668728 | 0.145668728 |
| ENSG00000150867 | PIP4K2A | phosphatidylinositol-5-phosphate 4-kinase, type II, alpha [Source: HGNC Symbol; Acc: HGNC: 8997] | 0.159042165 | 0.159042165 |
| ENSG00000151414 | NEK7 | NIMA-related kinase 7 [Source: HGNC Symbol; Acc: HGNC: 13386] | 0.161350347 | 0.161350347 |
| ENSG00000151576 | QTRTD1 | queuine tRNA-ribosyltransferase domain containing 1 [Source: HGNC Symbol; Acc: HGNC: 25771] | 0.144212504 | 0.144212504 |
| ENSG00000151702 | FLI1 | Fli-1 proto-oncogene, ETS transcription factor [Source: HGNC Symbol; Acc: HGNC: 3749] | 0.180062833 | 0.180062833 |
| ENSG00000152061 | RABGAP1L | RAB GTPase activating protein 1-like [Source: HGNC Symbol; Acc: HGNC: 24663] | 1.171136762 | 1.171136762 |
| ENSG00000152127 | MGAT5 | mannosyl (alpha-1,6-)-glycoprotein beta-1,6-N-acetyl-glucosaminyltransferase [Source: HGNC Symbol; Acc: HGNC: 7049] | 0.148717437 | 0.148717437 |
| ENSG00000152601 | MBNL1 | muscleblind-like splicing regulator 1 [Source: HGNC Symbol; Acc: HGNC: 6923] | 2.124148939 | 2.124148939 |
| ENSG00000152926 | ZNF117 | zinc finger protein 117 [Source: HGNC Symbol; Acc: HGNC: 12897] | 0.288912125 | 0.288912125 |
| ENSG00000153071 | DAB2 | Dab, mitogen-responsive phosphoprotein, homolog 2 (Drosophila) [Source: HGNC Symbol; Acc: HGNC: 2662] | 1.970334898 | 1.970334898 |
| ENSG00000153310 | FAM49B | family with sequence similarity 49, member B [Source: HGNC Symbol; Acc: HGNC: 25216] | 0.225356306 | 0.225356306 |
| ENSG00000153317 | ASAP1 | ArfGAP with SH3 domain, ankyrin repeat and PH domain 1 [Source: HGNC Symbol; Acc: HGNC: 2720] | 0.261303062 | 0.261303062 |
| ENSG00000154229 | PRKCA | protein kinase C, alpha [Source: HGNC Symbol; Acc: HGNC: 9393] | 0.171395515 | 0.171395515 |
| ENSG00000155530 | LRGUK | leucine-rich repeats and guanylate kinase domain containing [Source: HGNC Symbol; Acc: HGNC: 21964] | −0.117734369 | −0.117734369 |
| ENSG00000155903 | RASA2 | RAS p21 protein activator 2 [Source: HGNC Symbol; Acc: HGNC: 9872] | 0.153128973 | 0.153128973 |
| ENSG00000156026 | MCU | mitochondrial calcium uniporter [Source: HGNC Symbol; Acc: HGNC: 23526] | 0.137850826 | 0.137850826 |
| ENSG00000156265 | MAP3K7CL | MAP3K7 C-terminal like [Source: HGNC Symbol; Acc: HGNC: 16457] | 0.478343633 | 0.478343633 |
| ENSG00000156642 | NPTN | neuroplastin [Source: HGNC Symbol; Acc: HGNC: 17867] | 0.116218446 | 0.116218446 |
| ENSG00000156958 | GALK2 | galactokinase 2 [Source: HGNC Symbol; Acc: HGNC: 4119] | 0.165082885 | 0.165082885 |
| ENSG00000157191 | NECAP2 | NECAP endocytosis associated 2 [Source: HGNC Symbol; Acc: HGNC: 25528] | 0.13810038 | 0.13810038 |
| ENSG00000157895 | C12orf43 | chromosome 12 open reading frame 43 [Source: HGNC Symbol; Acc: HGNC: 25719] | −0.112628987 | −0.112628987 |

TABLE 14-continued

The highest impact sustained by the player in the game as measured by HITsp regressed on RNA expression in urine samples

| Ensembl_ID | hgnc_symbol | description | X0.5slope_0.1pvalue_Max_HITsp_urine | X0.8slope_0.1pvalue_Max_HITsp_urine |
|---|---|---|---|---|
| ENSG00000158710 | TAGLN2 | transgelin 2 [Source: HGNC Symbol; Acc: HGNC: 11554] | 0.614972326 | 0.614972326 |
| ENSG00000159023 | EPB41 | erythrocyte membrane protein band 4.1 [Source: HGNC Symbol; Acc: HGNC: 3377] | 0.539881931 | 0.539881931 |
| ENSG00000159256 | MORC3 | MORC family CW-type zinc finger 3 [Source: HGNC Symbol; Acc: HGNC: 23572] | 0.758914986 | 0.758914986 |
| ENSG00000159267 | HLCS | holocarboxylase synthetase (biotin-(proprionyl-CoA-carboxylase (ATP-hydrolysing)) ligase) [Source: HGNC Symbol; Acc: HGNC: 4976] | 0.174980594 | 0.174980594 |
| ENSG00000159346 | ADIPOR1 | adiponectin receptor 1 [Source: HGNC Symbol; Acc: HGNC: 24040] | 0.727523194 | 0.727523194 |
| ENSG00000159840 | ZYX | zyxin [Source: HGNC Symbol; Acc: HGNC: 13200] | 0.144777358 | 0.144777358 |
| ENSG00000161533 | ACOX1 | acyl-CoA oxidase 1, palmitoyl [Source: HGNC Symbol; Acc: HGNC: 119] | 0.809566065 | 0.809566065 |
| ENSG00000161570 | NA | NA | 1.032379771 | 1.032379771 |
| ENSG00000161911 | TREML1 | triggering receptor expressed on myeloid cells-like 1 [Source: HGNC Symbol; Acc: HGNC: 20434] | 0.123634521 | NA |
| ENSG00000162105 | SHANK2 | SH3 and multiple ankyrin repeat domains 2 [Source: HGNC Symbol; Acc: HGNC: 14295] | 0.246685655 | 0.246685655 |
| ENSG00000162434 | JAK1 | Janus kinase 1 [Source: HGNC Symbol; Acc: HGNC: 6190] | 0.482198988 | 0.482198988 |
| ENSG00000162722 | TRIM58 | tripartite motif containing 58 [Source: HGNC Symbol; Acc: HGNC: 24150] | 0.101513502 | 0.101513502 |
| ENSG00000162852 | CNST | consortin, connexin sorting protein [Source: HGNC Symbol; Acc: HGNC: 26486] | 0.138455689 | 0.138455689 |
| ENSG00000163346 | PBXIP1 | pre-B-cell leukemia homeobox interacting protein 1 [Source: HGNC Symbol; Acc: HGNC: 21199] | 0.106013633 | 0.106013633 |
| ENSG00000163590 | PPM1L | protein phosphatase, Mg2+/Mn2+ dependent, 1L [Source: HGNC Symbol; Acc: HGNC: 16381] | 0.146308014 | 0.146308014 |
| ENSG00000163602 | RYBP | RING1 and YY1 binding protein [Source: HGNC Symbol; Acc: HGNC: 10480] | 0.207794377 | 0.207794377 |
| ENSG00000163735 | CXCL5 | chemokine (C-X-C motif) ligand 5 [Source: HGNC Symbol; Acc: HGNC: 10642] | 0.436775595 | NA |
| ENSG00000164134 | NAA15 | N(alpha)-acetyltransferase 15, NatA auxiliary subunit [Source: HGNC Symbol; Acc: HGNC: 30782] | 0.166966709 | 0.166966709 |
| ENSG00000164181 | ELOVL7 | ELOVL fatty acid elongase 7 [Source: HGNC Symbol; Acc: HGNC: 26292] | 0.343620943 | 0.343620943 |
| ENSG00000164266 | SPINK1 | serine peptidase inhibitor, Kazal type 1 [Source: HGNC Symbol; Acc: HGNC: 11244] | 0.229695948 | 0.229695948 |
| ENSG00000164305 | CASP3 | caspase 3, apoptosis-related cysteine peptidase [Source: HGNC Symbol; Acc: HGNC: 1504] | 0.161082798 | 0.161082798 |
| ENSG00000164402 | 8-Sep | septin 8 [Source: HGNC Symbol; Acc: HGNC: 16511] | 0.438118618 | 0.438118618 |
| ENSG00000164808 | SPIDR | scaffolding protein involved in DNA repair [Source: HGNC Symbol; Acc: HGNC: 28971] | 0.216089141 | 0.216089141 |
| ENSG00000164924 | YWHAZ | tyrosine 3-monooxygenase/tryptophan 5-monooxygenase activation protein, zeta [Source: HGNC Symbol; Acc: HGNC: 12855] | 2.8151181 | 2.8151181 |
| ENSG00000165097 | KDM1B | lysine (K)-specific demethylase 1B [Source: HGNC Symbol; Acc: HGNC: 21577] | 0.129948737 | 0.129948737 |

TABLE 14-continued

The highest impact sustained by the player in the game as measured by HITsp regressed on RNA expression in urine samples

| Ensembl_ID | hgnc_symbol | description | X0.5slope_0.1pvalue_Max_HITsp_urine | X0.8slope_0.1pvalue_Max_HITsp_urine |
|---|---|---|---|---|
| ENSG00000165702 | GFI1B | growth factor independent 1B transcription repressor [Source: HGNC Symbol; Acc: HGNC: 4238] | 0.183122257 | 0.183122257 |
| ENSG00000165929 | TC2N | tandem C2 domains, nuclear [Source: HGNC Symbol; Acc: HGNC: 19859] | 0.659066708 | 0.659066708 |
| ENSG00000166004 | KIAA1731 | KIAA1731 [Source: HGNC Symbol; Acc: HGNC: 29366] | 0.225572018 | 0.225572018 |
| ENSG00000166086 | JAM3 | junctional adhesion molecule 3 [Source: HGNC Symbol; Acc: HGNC: 15532] | 0.289140461 | 0.289140461 |
| ENSG00000166224 | SGPL1 | sphingosine-1-phosphate lyase 1 [Source: HGNC Symbol; Acc: HGNC: 10817] | 0.137913948 | 0.137913948 |
| ENSG00000166387 | PPFIBP2 | PTPRF interacting protein, binding protein 2 (liprin beta 2) [Source: HGNC Symbol; Acc: HGNC: 9250] | 1.655069459 | 1.655069459 |
| ENSG00000166478 | ZNF143 | zinc finger protein 143 [Source: HGNC Symbol; Acc: HGNC: 12928] | 0.179673424 | 0.179673424 |
| ENSG00000166501 | PRKCB | protein kinase C, beta [Source: HGNC Symbol; Acc: HGNC: 9395] | 0.295744677 | 0.295744677 |
| ENSG00000166710 | B2M | beta-2-microglobulin [Source: HGNC Symbol; Acc: HGNC: 914] | 4.496484843 | 4.496484843 |
| ENSG00000166750 | SLFN5 | schlafen family member 5 [Source: HGNC Symbol; Acc: HGNC: 28286] | 0.325737786 | 0.325737786 |
| ENSG00000166938 | DIS3L | DIS3 like exosome 3'-5' exoribonuclease [Source: HGNC Symbol; Acc: HGNC: 28698] | 0.119131994 | 0.119131994 |
| ENSG00000167257 | RNF214 | ring finger protein 214 [Source: HGNC Symbol; Acc: HGNC: 25335] | 0.127744953 | 0.127744953 |
| ENSG00000167258 | CDK12 | cyclin-dependent kinase 12 [Source: HGNC Symbol; Acc: HGNC: 24224] | 0.153129356 | 0.153129356 |
| ENSG00000168300 | PCMTD1 | protein-L-isoaspartate (D-aspartate) O-methyltransferase domain containing 1 [Source: HGNC Symbol; Acc: HGNC: 30483] | 1.065572832 | 1.065572832 |
| ENSG00000168310 | IRF2 | interferon regulatory factor 2 [Source: HGNC Symbol; Acc: HGNC: 6117] | 0.185064835 | 0.185064835 |
| ENSG00000168497 | SDPR | serum deprivation response [Source: HGNC Symbol; Acc: HGNC: 10690] | 0.46748538 | 0.46748538 |
| ENSG00000168769 | TET2 | tet methylcytosine dioxygenase 2 [Source: HGNC Symbol; Acc: HGNC: 25941] | 0.29323869 | 0.29323869 |
| ENSG00000169247 | SH3TC2 | SH3 domain and tetratricopeptide repeats 2 [Source: HGNC Symbol; Acc: HGNC: 29427] | 0.247290195 | 0.247290195 |
| ENSG00000169313 | P2RY12 | purinergic receptor P2Y, G-protein coupled, 12 [Source: HGNC Symbol; Acc: HGNC: 18124] | 0.135294865 | NA |
| ENSG00000169474 | SPRR1A | small proline-rich protein 1A [Source: HGNC Symbol; Acc: HGNC: 11259] | 0.168877928 | NA |
| ENSG00000169621 | APLF | aprataxin and PNKP like factor [Source: HGNC Symbol; Acc: HGNC: 28724] | 0.125437738 | 0.125437738 |
| ENSG00000169756 | LIMS1 | LIM and senescent cell antigen-like domains 1 [Source: HGNC Symbol; Acc: HGNC: 6616] | 0.258104105 | 0.258104105 |
| ENSG00000170043 | TRAPPC1 | trafficking protein particle complex 1 [Source: HGNC Symbol; Acc: HGNC: 19894] | 0.341070426 | 0.341070426 |
| ENSG00000170325 | PRDM10 | PR domain containing 10 [Source: HGNC Symbol; Acc: HGNC: 13995] | 0.142571737 | 0.142571737 |

TABLE 14-continued

The highest impact sustained by the player in the game as measured by HITsp regressed on RNA expression in urine samples

| Ensembl_ID | hgnc_symbol | description | X0.5slope_0.1pvalue_Max_HITsp_urine | X0.8slope_0.1pvalue_Max_HITsp_urine |
| --- | --- | --- | --- | --- |
| ENSG00000170485 | NPAS2 | neuronal PAS domain protein 2 [Source: HGNC Symbol; Acc: HGNC: 7895] | 0.266419951 | 0.266419951 |
| ENSG00000170500 | LONRF2 | LON peptidase N-terminal domain and ring finger 2 [Source: HGNC Symbol; Acc: HGNC: 24788] | −0.140749468 | −0.140749468 |
| ENSG00000170802 | FOXN2 | forkhead box N2 [Source: HGNC Symbol; Acc: HGNC: 5281] | 0.215981377 | 0.215981377 |
| ENSG00000171311 | EXOSC1 | exosome component 1 [Source: HGNC Symbol; Acc: HGNC: 17286] | 0.144462988 | 0.144462988 |
| ENSG00000171467 | ZNF318 | zinc finger protein 318 [Source: HGNC Symbol; Acc: HGNC: 13578] | 0.133403376 | 0.133403376 |
| ENSG00000172183 | ISG20 | interferon stimulated exonuclease gene 20 kDa [Source: HGNC Symbol; Acc: HGNC: 6130] | −0.132523483 | −0.132523483 |
| ENSG00000173210 | ABLIM3 | actin binding LIM protein family, member 3 [Source: HGNC Symbol; Acc: HGNC: 29132] | 0.946294206 | 0.946294206 |
| ENSG00000174233 | ADCY6 | adenylate cyclase 6 [Source: HGNC Symbol; Acc: HGNC: 237] | 0.172218544 | 0.172218544 |
| ENSG00000175567 | UCP2 | uncoupling protein 2 (mitochondrial, proton carrier) [Source: HGNC Symbol; Acc: HGNC: 12518] | 0.637523997 | 0.637523997 |
| ENSG00000176928 | GCNT4 | glucosaminyl (N-acetyl) transferase 4, core 2 [Source: HGNC Symbol; Acc: HGNC: 17973] | 0.164625593 | 0.164625593 |
| ENSG00000177119 | ANO6 | anoctamin 6 [Source: HGNC Symbol; Acc: HGNC: 25240] | 0.421488814 | 0.421488814 |
| ENSG00000177125 | ZBTB34 | zinc finger and BTB domain containing 34 [Source: HGNC Symbol; Acc: HGNC: 31446] | 0.186014362 | 0.186014362 |
| ENSG00000177200 | CHD9 | chromodomain helicase DNA binding protein 9 [Source: HGNC Symbol; Acc: HGNC: 25701] | 0.84980392 | 0.84980392 |
| ENSG00000177324 | BEND2 | BEN domain containing 2 [Source: HGNC Symbol; Acc: HGNC: 28509] | 0.214957462 | 0.214957462 |
| ENSG00000177853 | ZNF518A | zinc finger protein 518A [Source: HGNC Symbol; Acc: HGNC: 29009] | 0.210018134 | 0.210018134 |
| ENSG00000178222 | RNF212 | ring finger protein 212 [Source: HGNC Symbol; Acc: HGNC: 27729] | −0.110184033 | −0.110184033 |
| ENSG00000180182 | MED14 | mediator complex subunit 14 [Source: HGNC Symbol; Acc: HGNC: 2370] | 0.179758964 | 0.179758964 |
| ENSG00000180488 | FAM73A | family with sequence similarity 73, member A [Source: HGNC Symbol; Acc: HGNC: 24741] | 0.161075392 | 0.161075392 |
| ENSG00000180573 | HIST1H2AC | histone cluster 1, H2ac [Source: HGNC Symbol; Acc: HGNC: 4733] | 0.673344658 | 0.673344658 |
| ENSG00000180694 | TMEM64 | transmembrane protein 64 [Source: HGNC Symbol; Acc: HGNC: 25441] | 0.166737406 | 0.166737406 |
| ENSG00000181104 | F2R | coagulation factor II (thrombin) receptor [Source: HGNC Symbol; Acc: HGNC: 3537] | 0.121614855 | 0.121614855 |
| ENSG00000182446 | NPLOC4 | nuclear protein localization 4 homolog (*S. cerevisiae*) [Source: HGNC Symbol; Acc: HGNC: 18261] | 0.170807299 | 0.170807299 |
| ENSG00000182481 | KPNA2 | karyopherin alpha 2 (RAG cohort 1, importin alpha 1) [Source: HGNC Symbol; Acc: HGNC: 6395] | 0.151727599 | 0.151727599 |
| ENSG00000182606 | TRAK1 | trafficking protein, kinesin binding 1 [Source: HGNC Symbol; Acc: HGNC: 29947] | 0.700261402 | 0.700261402 |
| ENSG00000183726 | TMEM50A | transmembrane protein 50A [Source: HGNC Symbol; Acc: HGNC: 30590] | 0.121322558 | 0.121322558 |

TABLE 14-continued

The highest impact sustained by the player in the game as measured by HITsp regressed on RNA expression in urine samples

| Ensembl_ID | hgnc_symbol | description | X0.5slope_0.1pvalue_Max_HITsp_urine | X0.8slope_0.1pvalue_Max_HITsp_urine |
|---|---|---|---|---|
| ENSG00000184178 | SCFD2 | sec1 family domain containing 2 [Source: HGNC Symbol; Acc: HGNC: 30676] | 0.112150892 | 0.112150892 |
| ENSG00000184602 | SNN | stannin [Source: HGNC Symbol; Acc: HGNC: 11149] | 0.123344813 | 0.123344813 |
| ENSG00000185008 | ROBO2 | roundabout, axon guidance receptor, homolog 2 (Drosophila) [Source: HGNC Symbol; Acc: HGNC: 10250] | −0.176023148 | −0.176023148 |
| ENSG00000185245 | GP1BA | glycoprotein 1b (platelet), alpha polypeptide [Source: HGNC Symbol; Acc: HGNC: 4439] | 0.156428222 | 0.156428222 |
| ENSG00000186298 | PPP1CC | protein phosphatase 1, catalytic subunit, gamma isozyme [Source: HGNC Symbol; Acc: HGNC: 9283] | 0.281181523 | 0.281181523 |
| ENSG00000187109 | NAP1L1 | nucleosome assembly protein 1-like 1 [Source: HGNC Symbol; Acc: HGNC: 7637] | 0.630375971 | 0.630375971 |
| ENSG00000187554 | TLR5 | toll-like receptor 5 [Source: HGNC Symbol; Acc: HGNC: 11851] | 0.209734995 | 0.209734995 |
| ENSG00000187699 | C2orf88 | chromosome 2 open reading frame 88 [Source: HGNC Symbol; Acc: HGNC: 28191] | 0.253185892 | 0.253185892 |
| ENSG00000189308 | LIN54 | lin-54 DREAM MuvB core complex component [Source: HGNC Symbol; Acc: HGNC: 25397] | 0.137504827 | 0.137504827 |
| ENSG00000189403 | HMGB1 | high mobility group box 1 [Source: HGNC Symbol; Acc: HGNC: 4983] | 0.325629479 | 0.325629479 |
| ENSG00000196116 | TDRD7 | tudor domain containing 7 [Source: HGNC Symbol; Acc: HGNC: 30831] | 0.129014991 | 0.129014991 |
| ENSG00000196678 | ERI2 | ERI1 exoribonuclease family member 2 [Source: HGNC Symbol; Acc: HGNC: 30541] | 0.105444259 | 0.105444259 |
| ENSG00000196782 | MAML3 | mastermind-like 3 (Drosophila) [Source: HGNC Symbol; Acc: HGNC: 16272] | 0.285976894 | 0.285976894 |
| ENSG00000197147 | LRRC8B | leucine rich repeat containing 8 family, member B [Source: HGNC Symbol; Acc: HGNC: 30692] | 0.125211782 | 0.125211782 |
| ENSG00000197566 | ZNF624 | zinc finger protein 624 [Source: HGNC Symbol; Acc: HGNC: 29254] | 0.111470664 | 0.111470664 |
| ENSG00000198286 | CARD11 | caspase recruitment domain family, member 11 [Source: HGNC Symbol; Acc: HGNC: 16393] | 0.141821377 | 0.141821377 |
| ENSG00000198466 | ZNF587 | zinc finger protein 587 [Source: HGNC Symbol; Acc: HGNC: 30955] | 0.515936917 | 0.515936917 |
| ENSG00000198478 | SH3BGRL2 | SH3 domain binding glutamate-rich protein like 2 [Source: HGNC Symbol; Acc: HGNC: 15567] | 2.135999854 | 2.135999854 |
| ENSG00000198513 | ATL1 | atlastin GTPase 1 [Source: HGNC Symbol; Acc: HGNC: 11231] | 0.11638794 | 0.11638794 |
| ENSG00000198948 | MFAP3L | microfibrillar-associated protein 3-like [Source: HGNC Symbol; Acc: HGNC: 29083] | 0.297833822 | 0.297833822 |
| ENSG00000204310 | AGPAT1 | 1-acylglycerol-3-phosphate O-acyltransferase 1 [Source: HGNC Symbol; Acc: HGNC: 324] | 0.10136124 | 0.10136124 |
| ENSG00000204420 | C6orf25 | chromosome 6 open reading frame 25 [Source: HGNC Symbol; Acc: HGNC: 13937] | 0.42024942 | 0.42024942 |
| ENSG00000204842 | ATXN2 | ataxin 2 [Source: HGNC Symbol; Acc: HGNC: 10555] | 0.372568288 | 0.372568288 |
| ENSG00000205542 | TMSB4X | thymosin beta 4, X-linked [Source: HGNC Symbol; Acc: HGNC: 11881] | 6.744611196 | 6.744611196 |
| ENSG00000206560 | ANKRD28 | ankyrin repeat domain 28 [Source: HGNC Symbol; Acc: HGNC: 29024] | 0.187959185 | 0.187959185 |

TABLE 14-continued

The highest impact sustained by the player in the game as measured by HITsp regressed on RNA expression in urine samples

| Ensembl_ID | hgnc_symbol | description | X0.5slope_0.1pvalue_Max_HITsp_urine | X0.8slope_0.1pvalue_Max_HITsp_urine |
|---|---|---|---|---|
| ENSG00000209082 | MT-TL1 | mitochondrially encoded tRNA leucine 1 (UUA/G) [Source: HGNC Symbol; Acc: HGNC: 7490] | 3.117140247 | 3.117140247 |
| ENSG00000213516 | RBMXL1 | RNA binding motif protein, X-linked-like 1 [Source: HGNC Symbol; Acc: HGNC: 25073] | 0.131637518 | 0.131637518 |
| ENSG00000214049 | UCA1 | urothelial cancer associated 1 (non-protein coding) [Source: HGNC Symbol; Acc: HGNC: 37126] | 0.426710459 | 0.426710459 |
| ENSG00000215271 | HOMEZ | homeobox and leucine zipper encoding [Source: HGNC Symbol; Acc: HGNC: 20164] | 0.118937964 | 0.118937964 |
| ENSG00000215421 | ZNF407 | zinc finger protein 407 [Source: HGNC Symbol; Acc: HGNC: 19904] | 0.151443222 | 0.151443222 |
| ENSG00000215834 | FMO9P | flavin containing monooxygenase 9 pseudogene [Source: HGNC Symbol; Acc: HGNC: 32210] | 0.205901188 | 0.205901188 |
| ENSG00000221823 | PPP3R1 | protein phosphatase 3, regulatory subunit B, alpha [Source: HGNC Symbol; Acc: HGNC: 9317] | 0.216269193 | 0.216269193 |
| ENSG00000226759 | DAB1-AS1 | DAB1 antisense RNA 1 [Source: HGNC Symbol; Acc: HGNC: 49443] | −0.114905454 | −0.114905454 |
| ENSG00000227165 | WDR11-AS1 | WDR11 antisense RNA 1 [Source: HGNC Symbol; Acc: HGNC: 27437] | 0.10770574 | 0.10770574 |
| ENSG00000228474 | OST4 | oligosaccharyltransferase 4 homolog (S. cerevisiae) [Source: HGNC Symbol; Acc: HGNC: 32483] | 1.417131385 | 1.417131385 |
| ENSG00000228794 | LINC01128 | long intergenic non-protein coding RNA 1128 [Source: HGNC Symbol; Acc: HGNC: 49377] | 0.101019848 | 0.101019848 |
| ENSG00000229124 | VIM-AS1 | VIM antisense RNA 1 [Source: HGNC Symbol; Acc: HGNC: 44879] | 0.159633467 | NA |
| ENSG00000229754 | CXCR2P1 | chemokine (C-X-C motif) receptor 2 pseudogene 1 [Source: HGNC Symbol; Acc: HGNC: 6028] | 0.332552072 | 0.332552072 |
| ENSG00000241945 | PWP2 | PWP2 periodic tryptophan protein homolog (yeast) [Source: HGNC Symbol; Acc: HGNC: 9711] | 0.131951558 | 0.131951558 |
| ENSG00000244734 | HBB | hemoglobin, beta [Source: HGNC Symbol; Acc: HGNC: 4827] | 0.439040702 | 0.439040702 |
| ENSG00000249307 | LINC01088 | long intergenic non-protein coding RNA 1088 [Source: HGNC Symbol; Acc: HGNC: 49148] | 0.150687296 | 0.150687296 |
| ENSG00000250508 | | | 0.104851059 | 0.104851059 |
| ENSG00000253729 | PRKDC | protein kinase, DNA-activated, catalytic polypeptide [Source: HGNC Symbol; Acc: HGNC: 9413] | 0.37333201 | 0.37333201 |
| ENSG00000255240 | | | 0.119700484 | 0.119700484 |
| ENSG00000259207 | ITGB3 | integrin, beta 3 (platelet glycoprotein IIIa, antigen CD61) [Source: HGNC Symbol; Acc: HGNC: 6156] | 0.277129861 | NA |
| ENSG00000259673 | IQCH-AS1 | IQCH antisense RNA 1 [Source: HGNC Symbol; Acc: HGNC: 44104] | −0.123239864 | −0.123239864 |
| ENSG00000272631 | | | 0.113665967 | 0.113665967 |

TABLE 15

The highest impact sustained by the player in the game as measured by the number of hits regressed on RNA expression in urine samples

| Ensembl_ID | hgnc_symbol | description | X0.5slope_0.1pvalue_0.1_Number_of_hits_urine | X0.8slope_0.1pvalue_0.1_Number_of_hits_urine |
|---|---|---|---|---|
| ENSG00000004864 | SLC25A13 | solute carrier family 25 (aspartate/glutamate carrier), member 13 [Source:HGNC Symbol; Acc:HGNC:10983] | −0.110127348 | −0.110127348 |

TABLE 15-continued

The highest impact sustained by the player in the game as measured by the number of hits regressed on RNA expression in urine samples

| Ensembl_ID | hgnc_symbol | description | X0.5slope_0.1pvalue_0.1_Number_of_hits_urine | X0.8slope_0.1pvalue_0.1_Number_of_hits_urine |
|---|---|---|---|---|
| ENSG00000005189 | | Putative RNA exonuclease NEF-sp [Source:UniProtKB/Swiss-Prot; Acc:Q96IC2] | −0.111815797 | −0.111815797 |
| ENSG00000011451 | WIZ | widely interspaced zinc finger motifs [Source:HGNC Symbol; Acc:HGNC:30917] | 0.122786525 | 0.122786525 |
| ENSG00000016602 | CLCA4 | chloride channel accessory 4 [Source:HGNC Symbol; Acc:HGNC:2018] | 0.227126793 | 0.227126793 |
| ENSG00000057294 | PKP2 | plakophilin 2 [Source:HGNC Symbol; Acc:HGNC:9024] | 0.11972821 | 0.11972821 |
| ENSG00000059588 | TARBP1 | TAR (HIV-1) RNA binding protein 1 [Source:HGNC Symbol; Acc:HGNC:11568] | 0.163273139 | 0.163273139 |
| ENSG00000064270 | ATP2C2 | ATPase, Ca++ transporting, type 2C, member 2 [Source:HGNC Symbol; Acc:HGNC:29103] | 0.161536114 | 0.161536114 |
| ENSG00000066027 | PPP2R5A | protein phosphatase 2, regulatory subunit B', alpha [Source:HGNC Symbol; Acc:HGNC:9309] | −0.118772549 | −0.118772549 |
| ENSG00000070915 | SLC12A3 | solute carrier family 12 (sodium/chloride transporter), member 3 [Source:HGNC Symbol; Acc:HGNC:10912] | 0.191921278 | 0.191921278 |
| ENSG00000075043 | KCNQ2 | potassium voltage-gated channel, KQT-like subfamily, member 2 [Source:HGNC Symbol; Acc:HGNC:6296] | 0.208091842 | 0.208091842 |
| ENSG00000075218 | GTSE1 | G-2 and S-phase expressed 1 [Source:HGNC Symbol; Acc:HGNC:13698] | 0.147670253 | 0.147670253 |
| ENSG00000076984 | MAP2K7 | mitogen-activated protein kinase kinase 7 [Source:HGNC Symbol; Acc:HGNC:6847] | 0.114517641 | 0.114517641 |
| ENSG00000077044 | DGKD | diacylglycerol kinase, delta 130 kDa [Source:HGNC Symbol; Acc:HGNC:2851] | 0.314768539 | 0.314768539 |
| ENSG00000078124 | ACER3 | alkaline ceramidase 3 [Source:HGNC Symbol; Acc:HGNC:16066] | −0.154178092 | −0.154178092 |
| ENSG00000080189 | SLC35C2 | solute carrier family 35 (GDP-fucose transporter), member C2 [Source:HGNC Symbol; Acc:HGNC:17117] | 0.110284769 | 0.110284769 |
| ENSG00000081803 | CADPS2 | Ca++ dependent secretion activator 2 [Source:HGNC Symbol; Acc:HGNC:16018] | 0.232518544 | 0.232518544 |
| ENSG00000082929 | C4orf6 | chromosome 4 open reading frame 6 [Source:HGNC Symbol; Acc:HGNC:13716] | 0.126772668 | NA |
| ENSG00000086015 | MAST2 | microtubule associated serine/threonine kinase 2 [Source:HGNC Symbol; Acc:HGNC:19035] | 0.216637512 | 0.216637512 |
| ENSG00000086967 | MYBPC2 | myosin binding protein C, fast type [Source:HGNC Symbol; Acc:HGNC:7550] | 0.203070289 | 0.203070289 |
| ENSG00000090530 | LEPREL1 | leprecan-like 1 [Source:HGNC Symbol; Acc:HGNC:19317] | 0.12250088 | 0.12250088 |
| ENSG00000100478 | AP4S1 | adaptor-related protein complex 4, sigma 1 subunit [Source:HGNC Symbol; Acc:HGNC:575] | −0.102729491 | −0.102729491 |
| ENSG00000102606 | ARHGEF7 | Rho guanine nucleotide exchange factor (GEF) 7 [Source:HGNC Symbol; Acc:HGNC:15607] | 0.167882897 | 0.167882897 |
| ENSG00000102882 | MAPK3 | mitogen-activated protein kinase 3 [Source:HGNC Symbol; Acc:HGNC:6877] | 0.185955908 | 0.185955908 |
| ENSG00000103540 | CCP110 | centriolar coiled coil protein 110 kDa [Source:HGNC Symbol; Acc:HGNC:24342] | 0.159911215 | 0.159911215 |
| ENSG00000104081 | BMF | Bcl2 modifying factor [Source:HGNC Symbol; Acc:HGNC:24132] | 0.128283042 | 0.128283042 |

TABLE 15-continued

The highest impact sustained by the player in the game as measured by the number of hits regressed on RNA expression in urine samples

| Ensembl_ID | hgnc_symbol | description | X0.5slope_0.1pvalue_0.1_Number_of_hits_urine | X0.8slope_0.1pvalue_0.1_Number_of_hits urine |
|---|---|---|---|---|
| ENSG00000104522 | TSTA3 | tissue specific transplantation antigen P35B [Source:HGNC Symbol; Acc:HGNC:12390] | 0.115170328 | 0.115170328 |
| ENSG00000104866 | PPP1R37 | protein phosphatase 1, regulatory subunit 37 [Source:HGNC Symbol; Acc:HGNC:27607] | 0.141274881 | 0.141274881 |
| ENSG00000105778 | AVL9 | AVL9 homolog (*S. cerevisiase*) [Source:HGNC Symbol; Acc:HGNC:28994] | 0.259806443 | 0.259806443 |
| ENSG00000106078 | COBL | cordon-bleu WH2 repeat protein [Source:HGNC Symbol; Acc:HGNC:22199] | 0.268699256 | 0.268699256 |
| ENSG00000106799 | TGFBR1 | transforming growth factor, beta receptor 1 [Source:HGNC Symbol; Acc:HGNC:11772] | −0.14151085 | −0.14151085 |
| ENSG00000107164 | FUBP3 | far upstream element (FUSE) binding protein 3 [Source:HGNC Symbol; Acc:HGNC:4005] | 0.13205712 | 0.13205712 |
| ENSG00000108262 | GIT1 | G protein-coupled receptor kinase interacting ArfGAP 1 [Source:HGNC Symbol; Acc:HGNC:4272] | 0.121783678 | 0.121783678 |
| ENSG00000108509 | CAMTA2 | calmodulin binding transcription activator 2 [Source:HGNC Symbol; Acc:HGNC:18807] | 0.145777329 | 0.145777329 |
| ENSG00000109101 | FOXN1 | forkhead box N1 [Source:HGNC Symbol; Acc:HGNC:12765] | 0.102486654 | 0.102486654 |
| ENSG00000110906 | KCTD10 | potassium channel tetramerization domain containing 10 [Source:HGNC Symbol; Acc:HGNC:23236] | 0.206396894 | 0.206396894 |
| ENSG00000111581 | NUP107 | nucleoporin 107 kDa [Source:HGNC Symbol; Acc:HGNC:29914] | −0.130990824 | −0.130990824 |
| ENSG00000111752 | PHC1 | polyhomeotic homolog 1 (*Drosophila*) [Source:HGNC Symbol; Acc:HGNC:3182] | 0.12426254 | 0.12426254 |
| ENSG00000111788 | | | 0.115531105 | 0.115531105 |
| ENSG00000111846 | GCNT2 | glucosaminyl (N-acetyl) transferase 2, I-branching enzyme (I blood group) [Source:HGNC Symbol; Acc:HGNC:4204] | 0.175996115 | 0.175996115 |
| ENSG00000112679 | DUSP22 | dual specificity phosphatase 22 [Source:HGNC Symbol; Acc:HGNC:16077] | 0.366644466 | 0.366644466 |
| ENSG00000113494 | PRLR | prolactin receptor [Source:HGNC Symbol; Acc:HGNC:9446] | −0.170802527 | −0.170802527 |
| ENSG00000115159 | GPD2 | glycerol-3-phosphate dehydrogenase 2 (mitochondrial) [Source:HGNC Symbol; Acc:HGNC:4456] | 0.164714658 | 0.164714658 |
| ENSG00000115339 | GALNT3 | polypeptide N-acetylgalactosaminyltransferase 3 [Source:HGNC Symbol; Acc:HGNC:4125] | 0.15392124 | 0.15392124 |
| ENSG00000116005 | PCYOX1 | prenylcysteine oxidase 1 [Source:HGNC Symbol; Acc:HGNC:20588] | 0.130228451 | 0.130228451 |
| ENSG00000116138 | DNAJC16 | DnaJ (Hsp40) homolog, subfamily C, member 16 [Source:HGNC Symbol; Acc:HGNC:29157] | −0.163592011 | −0.163592011 |
| ENSG00000117569 | PTBP2 | polypyrimidine tract binding protein 2 [Source:HGNC Symbol; Acc:HGNC:17662] | −0.129890437 | −0.129890437 |
| ENSG00000118194 | TNNT2 | troponin T type 2 (cardiac) [Source:HGNC Symbol; Acc:HGNC:11949] | 0.219544874 | 0.219544874 |
| ENSG00000119242 | CCDC92 | coiled-coil domain containing 92 [Source:HGNC Symbol; Acc:HGNC:29563] | 0.184147564 | 0.184147564 |
| ENSG00000119943 | PYROXD2 | pyridine nucleotide-disulphide oxidoreductase domain 2 [Source:HGNC Symbol; Acc:HGNC:23517] | 0.168384424 | 0.168384424 |
| ENSG00000120088 | CRHR1 | corticotropin releasing hormone receptor 1 [Source:HGNC Symbol; Acc:HGNC:2357] | 0.116938068 | 0.116938068 |

TABLE 15-continued

The highest impact sustained by the player in the game as measured by the number of hits regressed on RNA expression in urine samples

| Ensembl_ID | hgnc_symbol | description | X0.5slope_0.1pvalue_0.1_Number_of_hits_urine | X0.8slope_0.1pvalue_0.1_Number_of_ hits urine |
|---|---|---|---|---|
| ENSG00000121957 | GPSM2 | G-protein signaling modulator 2 [Source:HGNC Symbol; Acc:HGNC:29501] | −0.109771975 | −0.109771975 |
| ENSG00000124302 | CHST8 | carbohydrate (N-acetylgalactosamine 4-0) sulfotransferase 8 [Source:HGNC Symbol; Acc:HGNC:15993] | 0.118261551 | 0.118261551 |
| ENSG00000124466 | LYPD3 | LY6/PLAUR domain containing 3 [Source:HGNC Symbol; Acc:HGNC:24880] | 0.123140736 | 0.123140736 |
| ENSG00000125746 | EML2 | echinoderm microtubule associated protein like 2 [Source:HGNC Symbol; Acc:HGNC:18035] | 0.207340861 | 0.207340861 |
| ENSG00000127124 | HIVEP3 | human immunodeficiency virus type I enhancer binding protein 3 [Source:HGNC Symbol; Acc:HGNC:13561] | 0.285164542 | 0.285164542 |
| ENSG00000128284 | APOL3 | apolipoprotein L, 3 [Source:HGNC Symbol; Acc:HGNC:14868] | 0.148601853 | 0.148601853 |
| ENSG00000128309 | MPST | mercaptopyruvate sulfurtransferase [Source: HGNC Symbol; Acc:HGNC:7223] | 0.246697583 | 0.246697583 |
| ENSG00000129946 | SHC2 | SHC (Src homology 2 domain containing) transforming protein 2 [Source:HGNC Symbol; Acc:HGNC:29869] | 0.111409901 | 0.111409901 |
| ENSG00000131398 | KCNC3 | potassium voltage-gated channel, Shaw-related subfamily, member 3 [Source:HGNC Symbol; Acc:HGNC:6235] | 0.102329443 | 0.102329443 |
| ENSG00000131771 | PPP1R1B | protein phosphatase 1, regulatory (inhibitor) subunit 1B [Source:HGNC Symbol; Acc:HGNC:9287] | 0.21384967 | 0.21384967 |
| ENSG00000132518 | GUCY2D | guanylate cyclase 2D, membrane (retina-specific) [Source:HGNC Symbol; Acc:HGNC:4689] | 0.177486345 | 0.177486345 |
| ENSG00000132570 | PCBD2 | pterin-4 alpha-carbinolamine dehydratase/dimerization cofactor of hepatocyte nuclear factor 1 alpha (TCF1) 2 [Source:HGNC Symbol; Acc:HGNC:24474] | 0.13642788 | 0.13642788 |
| ENSG00000134531 | EMP1 | epithelial membrane protein 1 [Source:HGNC Symbol; Acc:HGNC:3333] | 0.20283912 | 0.20283912 |
| ENSG00000136367 | ZFHX2 | zinc finger homeobox 2 [Source:HGNC Symbol; Acc:HGNC:20152] | 0.234495015 | 0.234495015 |
| ENSG00000136861 | CDK5RAP2 | CDK5 regulatory subunit associated protein 2 [Source:HGNC Symbol; Acc:HGNC:18672] | 0.334534954 | 0.334534954 |
| ENSG00000137504 | CREBZF | CREB/ATF bZIP transcription factor [Source:HGNC Symbol; Acc:HGNC:24905] | 0.111526524 | 0.111526524 |
| ENSG00000138101 | DTNB | dystrobrevin, beta [Source:HGNC Symbol; Acc:HGNC:3058] | −0.122242688 | −0.122242688 |
| ENSG00000140274 | DUOXA2 | dual oxidase maturation factor 2 [Source:HGNC Symbol; Acc:HGNC:32698] | 0.1254845 | NA |
| ENSG00000140750 | ARHGAP17 | Rho GTPase activating protein 17 [Source:HGNC Symbol; Acc:HGNC:18239] | 0.193254366 | 0.193254366 |
| ENSG00000143013 | LMO4 | LIM domain only 4 [Source:HGNC Symbol; Acc:HGNC:6644] | 0.106151504 | 0.106151504 |
| ENSG00000143179 | UCK2 | uridine-cytidine kinase 2 [Source:HGNC Symbol; Acc:HGNC:12562] | 0.164205324 | 0.164205324 |
| ENSG00000143322 | ABL2 | ABL proto-oncogene 2, non-receptor tyrosine kinase [Source:HGNC Symbol; Acc:HGNC:77] | −0.217758256 | −0.217758256 |
| ENSG00000144130 | NT5DC4 | 5'-nucleotidase domain containing 4 [Source:HGNC Symbol; Acc:HGNC:27678] | 0.103745073 | 0.103745073 |

TABLE 15-continued

The highest impact sustained by the player in the game as measured by the
number of hits regressed on RNA expression in urine samples

| Ensembl_ID | hgnc_symbol | description | X0.5slope_0.1pvalue_0.1_Number_of_hits_urine | X0.8slope_0.1pvalue_0.1_Number_of_hits_urine |
|---|---|---|---|---|
| ENSG00000144339 | TMEFF2 | transmembrane protein with EGF-like and two follistatin-like domains 2 [Source:HGNC Symbol; Acc:HGNC:11867] | 0.120238816 | 0.120238816 |
| ENSG00000145016 | KIAA0226 | KIAA0226 [Source:HGNC Symbol; Acc:HGNC:28991] | −0.298082516 | −0.298082516 |
| EN5G00000148204 | CRB2 | crumbs family member 2 [Source:HGNC Symbol; Acc:HGNC:18688] | 0.119128829 | 0.119128829 |
| ENSG00000150093 | ITGB1 | integrin, beta 1 (fibronectin receptor, beta polypeptide, antigen CD29 includes MDF2, MSK12) [Source:HGNC Symbol; Acc:HGNC:6153] | 0.271478366 | 0.271478366 |
| ENSG00000151176 | PLBD2 | phospholipase B domain containing 2 [Source:HGNC Symbol; Acc:HGNC:27283] | 0.11988385 | 0.11988385 |
| ENSG00000151418 | ATP6V1G3 | ATPase, H transporting, lysosomal 13k Da, V1 subunit G3 [Source:HGNC Symbol; Acc:HGNC:18265] | −0.275920997 | NA |
| ENSG00000151650 | VENTX | VENT homeobox [Source:HGNC Symbol; Acc:HGNC:13639] | 0.106920255 | 0.106920255 |
| ENSG00000154040 | CABYR | calcium binding tyrosine-(Y)-phosphorylation regulated [Source:HGNC Symbol; Acc:HGNC:15569] | −0.10106877 | −0.10106877 |
| ENSG00000157978 | LDLRAP1 | low density lipoprotein receptor adaptor protein 1 [Source:HGNC Symbol; Acc:HGNC:18640] | 0.12547496 | 0.12547496 |
| ENSG00000158747 | NBL1 | neuroblastoma 1, DAN family BMP antagonist [Source:HGNC Symbol; Acc:HGNC:7650] | 0.102166884 | 0.102166884 |
| ENSG00000159267 | HLCS | holocarboxylase synthetase (biotin-(proprionyl-CoA-carboxylase (ATP-hydrolysing)) ligase) [Source:HGNC Symbol; Acc:HGNC:4976] | 0.231199561 | 0.231199561 |
| ENSG00000160917 | CPSF4 | cleavage and polyadenylation specific factor 4, 30 kDa [Source:HGNC Symbol; Acc:HGNC:2327] | 0.110691457 | 0.110691457 |
| ENSG00000161103 | | | −0.235903358 | −0.235903358 |
| ENSG00000161649 | CD300LG | CD300 molecule-like family member g [Source:HGNC Symbol; Acc:HGNC:30455] | 0.14510522 | 0.14510522 |
| ENSG00000161654 | LSM12 | LSM12 homolog (*S. cerevisiae*) [Source:HGNC Symbol; Acc:HGNC:26407] | 0.10849167 | 0.10849167 |
| ENSG00000162458 | FBLIM1 | filamin binding LIM protein 1 [Source:HGNC Symbol; Acc:HGNC:24686] | 0.150448664 | 0.150448664 |
| ENSG00000163029 | SMC6 | structural maintenance of chromosomes 6 [Source:HGNC Symbol; Acc:HGNC:20466] | −0.217725066 | −0.217725066 |
| ENSG00000164011 | ZNF691 | zinc finger protein 691 [Source:HGNC Symbol; Acc:HGNC:28028] | 0.103609573 | 0.103609573 |
| ENSG00000164076 | CAMKV | CaM kinase-like vesicle-associated [Source:HGNC Symbol; Acc:HGNC:28788] | 0.116482874 | 0.116482874 |
| ENSG00000164078 | MST1R | macrophage stimulating 1 receptor (c-met-related tyrosine kinase) [Source:HGNC Symbol; Acc:HGNC:7381] | 0.173140081 | 0.173140081 |
| ENSG00000164080 | RAD54L2 | RAD54-like 2 (*S. cerevisiae*) [Source:HGNC Symbol; Acc:HGNC:29123] | 0.276992712 | 0.276992712 |
| ENSG00000165238 | WNK2 | WNK lysine deficient protein kinase 2 [Source:HGNC Symbol; Acc:HGNC:14542] | 0.313527705 | 0.313527705 |
| ENSG00000165406 | 8-Mar | membrane-associated ring finger (C3HC4) 8, E3 ubiquitin protein ligase [Source:HGNC Symbol; Acc:HGNC:23356] | 0.196983114 | 0.196983114 |

TABLE 15-continued

The highest impact sustained by the player in the game as measured by the number of hits regressed on RNA expression in urine samples

| Ensembl_ID | hgnc_symbol | description | X0.5slope_0.1pvalue_0.1_Number_of_hits_urine | X0.8slope_0.1pvalue_0.1_Number_of_hits_urine |
|---|---|---|---|---|
| ENSG00000166897 | ELFN2 | extracellular leucine-rich repeat and fibronectin type III domain containing 2 [Source:HGNC Symbol; Acc:HGNC:29396] | 0.149450538 | 0.149450538 |
| ENSG00000167333 | TR1M68 | tripartite motif containing 68 [Source:HGNC Symbol; Acc:HGNC:21161] | 0.191617012 | 0.191617012 |
| ENSG00000170113 | NIPA1 | non imprinted in Prader-Willi/Angelman syndrome 1 [Source:HGNC Symbol; Acc:HGNC:17043] | 0.184095954 | 0.184095954 |
| ENSG00000170382 | LRRN2 | leucine rich repeat neuronal 2 [Source:HGNC Symbol; Acc:HGNC:16914] | 0.129756093 | 0.129756093 |
| ENSG00000170485 | NPAS2 | neuronal PAS domain protein 2 [Source:HGNC Symbol; Acc:HGNC:7895] | 0.314985749 | 0.314985749 |
| ENSG00000171124 | FUT3 | fucosyltransferase 3 (galactoside 3(4)-L-fucosyltransferase, Lewis blood group) [Source:HGNC Symbol; Acc:HGNC:4014] | 0.114542381 | 0.114542381 |
| ENSG00000171282 | NA | NA | 0.204037734 | 0.204037734 |
| ENSG00000172350 | ABCG4 | ATP-binding cassette, sub-family G (WHITE), member 4 [Source:HGNC Symbol; Acc:HGNC:13884] | 0.165612528 | 0.165612528 |
| ENSG00000172732 | MUS81 | MUS81 structure-specific endonuclease subunit [Source:HGNC Symbol; Acc:HGNC:29814] | 0.107666424 | 0.107666424 |
| ENSG00000174403 | C20orf166-AS1 | C20orf166 antisense RNA 1 [Source:HGNC Symbol; Acc:HGNC:26393] | 0.101093828 | 0.101093828 |
| ENSG00000176490 | DIRAS1 | DIRAS family, GTP-binding RAS-like 1 [Source:HGNC Symbol; Acc:HGNC:19127] | 0.109381543 | 0.109381543 |
| ENSG00000176619 | LMNB2 | lamin B2 [Source:HGNC Symbol; Acc:HGNC:6638] | 0.113686714 | 0.113686714 |
| ENSG00000177409 | SAMD9L | sterile alpha motif domain containing 9-like [Source:HGNC Symbol; Acc:HGNC:1349] | −0.100124985 | −0.100124985 |
| ENSG00000177463 | NR2C2 | nuclear receptor subfamily 2, group C, member 2 [Source:HGNC Symbol; Acc:HGNC:7972] | 0.145768463 | 0.145768463 |
| ENSG00000177732 | SOX12 | SRY (sex determining region Y)-box 12 [Source:HGNC Symbol; Acc:HGNC:11198] | 0.107453892 | 0.107453892 |
| ENSG00000178222 | RNF212 | ring finger protein 212 [Source:HGNC Symbol; Acc:HGNC:27729] | −0.129043541 | −0.129043541 |
| ENSG00000178381 | ZFAND2A | zinc finger, AN1-type domain 2A [Source:HGNC Symbol; Acc:HGNC:28073] | 0.114942582 | 0.114942582 |
| ENSG00000179344 | HLA-DQB1 | major histocompatibility complex, class II, DQ beta 1 [Source:HGNC Symbol; Acc:HGNC:4944] | 0.110543773 | 0.110543773 |
| ENSG00000179364 | PACS2 | phosphofurin acidic cluster sorting protein 2 [Source:HGNC Symbol; Acc:HGNC:23794] | 0.23829197 | 0.23829197 |
| ENSG00000179954 | SSC5D | scavenger receptor cysteine rich family, 5 domains [Source:HGNC Symbol; Acc:HGNC:26641] | 0.229332392 | 0.229332392 |
| ENSG00000181830 | SLC35C1 | solute carrier family 35 (GDP-fucose transporter), member C1 [Source:HGNC Symbol; Acc:HGNC:20197] | 0.109327452 | 0.109327452 |
| ENSG00000182173 | TSEN54 | TSEN54 tRNA splicing endonuclease subunit [Source:HGNC Symbol; Acc:HGNC:27561] | 0.101454141 | 0.101454141 |
| ENSG00000182872 | RBM10 | RNA binding motif protein 10 [Source:HGNC Symbol; Acc:HGNC:9896] | 0.137603426 | 0.137603426 |

TABLE 15-continued

The highest impact sustained by the player in the game as measured by the
number of hits regressed on RNA expression in urine samples

| Ensembl_ID | hgnc_symbol | description | X0.5slope_0.1pvalue_0.1_Number_of_hits_urine | X0.8slope_0.1pvalue_0.1_Number_of_hits_urine |
|---|---|---|---|---|
| ENSG00000182979 | MTA1 | metastasis associated 1 [Source:HGNC Symbol; Acc:HGNC:7410] | 0.170722298 | 0.170722298 |
| ENSG00000184428 | TOP1MT | topoisomerase (DNA) I, mitochondria [Source:HGNC Symbol; Acc:HGNC:29787] | 0.156880641 | 0.156880641 |
| ENSG00000185681 | MORN5 | MORN repeat containing 5 [Source:HGNC Symbol; Acc:HGNC:17841] | 0.110300187 | 0.110300187 |
| ENSG00000186716 | BCR | breakpoint cluster region [Source:HGNC Symbol; Acc:HGNC:1014] | 0.22887557 | 0.22887557 |
| ENSG00000187091 | PLCD1 | phospholipase C, delta 1 [Source:HGNC Symbol; Acc:HGNC:9060] | 0.149312832 | 0.149312832 |
| EN5G00000187726 | DNAJB13 | DnaJ (Hsp40) homolog, subfamily B, member 13 [Source:HGNC Symbol; Acc:HGNC:30718] | 0.109771337 | 0.109771337 |
| ENSG00000188295 | ZNF669 | zinc finger protein 669 [Source:HGNC Symbol; Acc:HGNC:25736] | −0.114965733 | −0.114965733 |
| ENSG00000188305 | C19orf35 | chromosome 19 open reading frame 35 [Source:HGNC Symbol; Acc:HGNC:24793] | 0.109109673 | 0.109109673 |
| ENSG00000188342 | GTF2F2 | general transcription factor IIF, polypeptide 2, 30 kDa [Source:HGNC Symbol; Acc:HGNC:4653] | −0.111631344 | −0.111631344 |
| ENSG00000188522 | FAM83G | family with sequence similarity 83, member G [Source:HGNC Symbol; Acc:HGNC:32554] | 0.132724731 | 0.132724731 |
| ENSG00000196912 | ANKRD36B | ankyrin repeat domain 36B [Source:HGNC Symbol; Acc:HGNC:29333] | 0.156343623 | 0.156343623 |
| ENSG00000196979 | | | 0.119560483 | 0.119560483 |
| ENSG00000197588 | KLKP1 | kallikrein pseudogene 1 [Source:HGNC Symbol; Acc:HGNC:21260] | 0.102829337 | 0.102829337 |
| ENSG00000198712 | MT-CO2 | mitochondrially encoded cytochrome c oxidase II [Source:HGNC Symbol; Acc:HGNC:7421] | 39.44977646 | 39.44977646 |
| ENSG00000198763 | MT-ND2 | mitochondrially encoded NADH dehydrogenase 2 [Source:HGNC Symbol; Acc:HGNC:7456] | 58.26926395 | 58.26926395 |
| ENSG00000198840 | MT-ND3 | mitochondrially encoded NADH dehydrogenase 3 [Source:HGNC Symbol; Acc:HGNC:7458] | 15.75329743 | 15.75329743 |
| ENSG00000198938 | MT-CO3 | mitochondrially encoded cytochrome c oxidase III [Source:HGNC Symbol; Acc:HGNC:7422] | 69.19449684 | 69.19449684 |
| ENSG00000200786 | RNA5SP234 | RNA, 5S ribosomal pseudogene 234 [Source:HGNC Symbol; Acc:HGNC:43134] | 0.132518474 | 0.132518474 |
| ENSG00000204227 | RING1 | ring finger protein 1 [Source:HGNC Symbol; Acc:HGNC:10018] | 0.100397335 | 0.100397335 |
| ENSG00000204394 | VARS | valyl-tRNA synthetase [Source:HGNC Symbol; Acc:HGNC:12651] | 0.137036746 | 0.137036746 |
| ENSG00000204544 | MUC21 | mucin 21, cell surface associated [Source:HGNC Symbol; Acc:HGNC:21661] | 0.436615679 | 0.436615679 |
| ENSG00000205913 | SRRM2-AS1 | SRRM2 antisense RNA 1 [Source:HGNC Symbol; Acc:HGNC:44162] | 0.179522346 | 0.179522346 |
| ENSG00000206072 | SERPINB11 | serpin peptidase inhibitor, clade B (ovalbumin), member 11 (gene/pseudogene) [Source:HGNC Symbol; Acc:HGNC:14221] | 0.174187171 | 0.174187171 |
| ENSG00000209082 | MT-TL1 | mitochondrially encoded tRNA leucine 1 (UUA/G) [Source:HGNC Symbol; Acc:HGNC:7490] | 3.752960902 | 3.752960902 |
| ENSG00000210049 | MT-TF | mitochondrially encoded tRNA phenylalanine [Source:HGNC Symbol; Acc:HGNC:7481] | 1.326454211 | 1.326454211 |

TABLE 15-continued

The highest impact sustained by the player in the game as measured by the number of hits regressed on RNA expression in urine samples

| Ensembl_ID | hgnc_symbol | description | X0.5slope_0.1pvalue_0.1_Number_of_hits_urine | X0.8slope_0.1pvalue_0.1_Number_of_hits_urine |
|---|---|---|---|---|
| ENSG00000210077 | MT-TV | mitochondrially encoded tRNA valine [Source:HGNC Symbol; Acc:HGNC:7500] | 1.931189951 | 1.931189951 |
| ENSG00000210100 | MT-TI | mitochondrially encoded tRNA isoleucine [Source:HGNC Symbol; Acc:HGNC:7488] | 0.748172138 | NA |
| ENSG00000210107 | MT-TQ | mitochondrially encoded tRNA glutamine [Source:HGNC Symbol; Acc:HGNC:7495] | 0.827008658 | 0.827008658 |
| ENSG00000210117 | MT-TW | mitochondrially encoded tRNA tryptophan [Source:HGNC Symbol; Acc:HGNC:7501] | 0.954577644 | 0.954577644 |
| ENSG00000210140 | MT-TC | mitochondrially encoded tRNA cysteine [Source:HGNC Symbol; Acc:HGNC:7477] | 1.479211632 | 1.479211632 |
| ENSG00000210156 | MT-TK | mitochondrially encoded tRNA lysine [Source:HGNC Symbol; Acc:HGNC:7489] | 2.666703242 | 2.666703242 |
| ENSG00000210176 | MT-TH | mitochondrially encoded tRNA histidine [Source:HGNC Symbol; Acc:HGNC:7487] | 0.682012426 | 0.682012426 |
| ENSG00000210191 | MT-TL2 | mitochondrially encoded tRNA leucine 2 (CUN) [Source:HGNC Symbol; Acc:HGNC:7491] | 0.922588714 | 0.922588714 |
| ENSG00000210194 | MT-TE | mitochondrially encoded tRNA glutamic acid [Source:HGNC Symbol; Acc:HGNC:7479] | 1.836315218 | 1.836315218 |
| ENSG00000210195 | MT-TT | mitochondrially encoded tRNA threonine [Source:HGNC Symbol; Acc:HGNC:7499] | 1.382306537 | 1.382306537 |
| ENSG00000210196 | MT-TP | mitochondrially encoded tRNA proline [Source:HGNC Symbol; Acc:HGNC:7494] | 2.287555836 | 2.287555836 |
| ENSG00000214717 | ZBED1 | zinc finger, BED-type containing 1 [Source:HGNC Symbol; Acc:HGNC:447] | 0.117523428 | 0.117523428 |
| ENSG00000215764 | NA | NA | 0.147764961 | NA |
| ENSG00000224546 | EIF4BP3 | eukaryotic translation initiation factor 4B pseudogene 3 [Source:HGNC Symbol; Acc:HGNC:37936] | 0.106753603 | 0.106753603 |
| ENSG00000225630 | MTND2P28 | MT-ND2 pseudogene 28 [Source:HGNC Symbol; Acc:HGNC:42129] | 2.381423925 | 2.381423925 |
| ENSG00000228253 | MT-ATP8 | mitochondrially encoded ATP synthase 8 [Source:HGNC Symbol; Acc:HGNC:7415] | 11.70455103 | 11.70455103 |
| ENSG00000229344 | | | 0.876864647 | NA |
| ENSG00000232040 | ZBED9 | zinc finger, BED-type containing 9 [Source:HGNC Symbol; Acc:HGNC:13851] | 0.105378625 | 0.105378625 |
| ENSG00000232111 | | | 0.420895402 | 0.420895402 |
| ENSG00000234690 | | | 0.105457816 | 0.105457816 |
| ENSG00000236279 | CLEC2L | C-type lectin domain family 2, member L [Source:HGNC Symbol; Acc:HGNC:21969] | 0.114925734 | 0.114925734 |
| ENSG00000240707 | LINC01168 | long intergenic non-protein coding RNA 1168 [Source:HGNC Symbol; Acc:HGNC:49537] | 0.16582864 | 0.16582864 |
| ENSG00000241945 | PWP2 | PWP2 periodic tryptophan protein homolog (yeast) [Source:HGNC Symbol; Acc:HGNC:9711] | 0.15435837 | 0.15435837 |
| ENSG00000247498 | | | 0.117411337 | 0.117411337 |
| ENSG00000249307 | LINC01088 | long intergenic non-protein coding RNA 1088 [Source:HGNC Symbol; Acc:HGNC:49148] | 0.129530264 | 0.129530264 |
| ENSG00000249476 | | | 0.142630541 | 0.142630541 |
| ENSG00000249713 | | | 0.11885548 | NA |
| ENSG00000250198 | | | 0.108768085 | 0.108768085 |
| ENSG00000250508 | | | 0.113241056 | 0.113241056 |
| ENSG00000250519 | | | 0.196753321 | 0.196753321 |
| ENSG00000253641 | | | 0.108338901 | 0.108338901 |
| ENSG00000258628 | | | −0.167706429 | −0.167706429 |
| ENSG00000259176 | | | −0.14367802 | −0.14367802 |

TABLE 15-continued

The highest impact sustained by the player in the game as measured by the number of hits regressed on RNA expression in urine samples

| Ensembl_ID | hgnc_symbol | description | X0.5slope_0.1pvalue_0.1_Number_of_hits_urine | X0.8slope_0.1pvalue_0.1_Number_of_hits_urine |
|---|---|---|---|---|
| ENSG00000259479 | SORD2P | sorbitol dehydrogenase 2, pseudogene [Source:HGNC Symbol; Acc:HGNC:49919] | 0.273747163 | 0.273747163 |
| ENSG00000260139 | CSPG4P13 | chondroitin sulfate proteoglycan 4 pseudogene 13 [Source:HGNC Symbol; Acc:HGNC:49195] | 0.12083532 | 0.12083532 |
| ENSG00000269190 | FBXO17 | F-box protein 17 [Source:HGNC Symbol; Acc:HGNC:18754] | 0.106896024 | 0.106896024 |
| ENSG00000271178 | IGHV30R16-13 | immunoglobulin heavy variable 3/OR16-13 (non-functional) [Source:HGNC Symbol; Acc:HGNC:5637] | 0.103406674 | NA |

TABLE 16

Biomarkers differentially expressed in the blood samples of subjects who experienced most forceful head impact (Max_HITsp) when compared with the subjects' baseline, subjects who experienced least forceful head impact (Min_HITsp), or subjects who are not contact sports athletes (Track_field_control)

| Ensembl_ID | HGNC_symbol | Description | Max_HITsp_blood_vs_Track_field_control_blood | Max_HITsp_blood_vs_baseline_blood_previous_day | Max_HITsp_blood_vs_Min_HITsp_blood_previous_day | Max_HITsp_blood_vs_Track_field_control_blood_previous_day |
|---|---|---|---|---|---|---|
| ENSG00000015413 | DPEP1 | dipeptidase 1 (renal) [Source: HGNC Symbol; Acc: HGNC: 3002] | NA | NA | NA | −2.07 |
| ENSG00000099998 | GGT5 | gamma-glutamyltransferase 5 [Source: HGNC Symbol; Acc: HGNC: 4260] | NA | NA | NA | −2.27 |
| ENSG00000102098 | SCML2 | sex comb on midleg-like 2 (Drosophila) [Source: HGNC Symbol; Acc: HGNC: 10581] | NA | NA | 4.04 | NA |
| ENSG00000135587 | SMPD2 | sphingomyelin phosphodiesterase 2, neutral membrane (neutral sphingomyelinase) [Source: HGNC Symbol; Acc: HGNC: 11121] | NA | NA | NA | −2.51 |
| ENSG00000138433 | CIR1 | corepressor interacting with RBPJ, 1 [Source: HGNC Symbol; Acc: HGNC: 24217] | NA | −2.25 | NA | NA |
| ENSG00000163029 | SMC6 | structural maintenance of chromosomes 6 [Source: HGNC Symbol; Acc: HGNC: 20466] | NA | NA | NA | 2.01 |
| ENSG00000177045 | SIX5 | SIX homeobox 5 [Source: HGNC Symbol; Acc: HGNC: 10891] | NA | −2.69 | −3.62 | −3.80 |
| ENSG00000181885 | CLDN7 | claudin 7 [Source: HGNC Symbol; Acc: HGNC: 2049] | NA | −2.93 | NA | NA |
| ENSG00000185252 | ZNF74 | zinc finger protein 74 [Source: HGNC Symbol; Acc: HGNC: 13144] | NA | NA | NA | −2.34 |
| ENSG00000185338 | SOCS1 | suppressor of cytokine signaling 1 [Source: HGNC Symbol; Acc: HGNC: 19383] | NA | −3.19 | −4.52 | −3.90 |
| ENSG00000188365 | | | NA | −3.80 | NA | −4.57 |
| ENSG00000212857 | NA | NA | NA | NA | NA | −4.47 |
| ENSG00000213443 | | C-type lectin domain family 2, member D [Source: EntrezGene; Acc: 29121] | NA | −4.55 | NA | NA |
| ENSG00000214708 | | | NA | −3.99 | NA | NA |
| ENSG00000219926 | | | NA | −2.49 | NA | NA |
| ENSG00000227603 | | | NA | −3.43 | NA | NA |
| ENSG00000230843 | | | NA | −3.90 | NA | NA |
| ENSG00000231232 | | | NA | −3.78 | NA | NA |
| ENSG00000231435 | | | NA | −2.55 | NA | −3.26 |

TABLE 16-continued

Biomarkers differentially expressed in the blood samples of subjects who experienced most forceful head impact (Max_HITsp) when compared with the subjects' baseline, subjects who experienced least forceful head impact (Min_HITsp), or subjects who are not contact sports athletes (Track_field_control)

| Ensembl_ID | HGNC_symbol | Description | Max_HITsp_blood_vs_Track_field_control_blood | Max_HITsp_blood_vs_baseline_blood_previous_day | Max_HITsp_blood_vs_Min_HITsp_blood_previous_day | Max_HITsp_blood_vs_Track_field_control_blood_previous_day |
|---|---|---|---|---|---|---|
| ENSG00000234009 | RPL5P34 | ribosomal protein L5 pseudogene 34 [Source: HGNC Symbol; Acc: HGNC: 36463] | NA | −4.22 | NA | NA |
| ENSG00000236559 | | | 4.58 | NA | NA | 4.31 |
| ENSG00000237027 | | | NA | NA | NA | 3.75 |
| ENSG00000240752 | | | NA | NA | NA | −4.02 |
| ENSG00000241552 | RN7SL58P | RNA, 7SL, cytoplasmic 58, pseudogene [Source: HGNC Symbol; Acc: HGNC: 46074] | NA | −3.71 | NA | NA |
| ENSG00000243075 | RN7SL519P | RNA, 7SL, cytoplasmic 519, pseudogene [Source: HGNC Symbol; Acc: HGNC: 46535] | NA | NA | NA | 4.84 |
| ENSG00000248498 | ASNSP1 | asparagine synthetase pseudogene 1 [Source: HGNC Symbol; Acc: HGNC: 754] | NA | NA | NA | 5.34 |
| ENSG00000249734 | | | NA | NA | NA | 3.90 |
| ENSG00000254681 | PKD1P5 | polycystic kidney disease 1 (autosomal dominant) pseudogene 5 [Source: HGNC Symbol; Acc: HGNC: 30069] | NA | −3.37 | NA | −4.62 |
| ENSG00000256915 | | | 4.47 | NA | NA | 4.47 |
| ENSG00000258406 | | | 4.97 | NA | NA | 4.62 |
| ENSG00000259842 | IGHV3OR16-16 | immunoglobulin heavy variable 3/OR16-16 (pseudogene) [Source: HGNC Symbol; Acc: HGNC: 5640] | NA | −3.74 | NA | NA |
| ENSG00000262539 | | | NA | −3.71 | NA | NA |
| ENSG00000269316 | | | NA | −3.46 | −4.27 | −3.99 |
| ENSG00000269753 | NA | NA | NA | −3.73 | NA | NA |
| ENSG00000270170 | NCBP2-AS2 | NCBP2 antisense RNA 2 (head to head) [Source: HGNC Symbol; Acc: HGNC: 25121] | NA | −4.00 | NA | NA |
| ENSG00000271945 | | | NA | −4.75 | NA | NA |
| ENSG00000272183 | | | NA | −4.19 | NA | NA |
| ENSG00000273185 | | | NA | NA | NA | 4.15 |

TABLE 17

Biomarkers differentially expressed in the urine or saliva samples of subjects who experienced most forceful head impact (Max_HITsp) as compared to the subjects' baseline or subjects who are not contact sports athletes (Track_field_control).

| Ensembl_ID | HGNC_symbol | Descriptiom | Max_HITsp_urine_vs_baseline_urine | Max_HITsp_urine_vs_Track_field_control_urine | Max_HITsp_saliva_vs_Track_field_control_saliva_previous_day |
|---|---|---|---|---|---|
| ENSG00000104327 | CALB1 | calbindin 1, 28 kDa [Source:HGNC Symbol; Acc:HGNC:1434] | −2.36 | NA | NA |
| ENSG00000113889 | KNG1 | kininogen 1 [Source:HGNC Symbol; Acc:HGNC:6383] | −2.55 | NA | NA |
| ENSG00000125652 | ALKBH7 | alkB, alkylation repair homolog 7 (*E. coli*) [Source:HGNC Symbol; Acc:HGNC:21306] | NA | 2.38 | NA |
| ENSG00000125780 | TGM3 | transglutaminase 3 [Source:HGNC Symbol; Acc:HGNC:11779] | NA | NA | 2.43 |
| ENSG00000127528 | KLF2 | Kruppel-like factor 2 [Source:HGNC Symbol; Acc:HGNC:6347] | NA | 3.21 | NA |
| ENSG00000150201 | FXYD4 | FXYD domain containing ion transport regulator 4 [Source:HGNC Symbol; Acc:HGNC:4028] | NA | −2.48 | NA |
| ENSG00000170891 | CYTL1 | cytokine-like 1 [Source:HGNC Symbol; Acc:HGNC:24435] | NA | 4.25 | NA |
| ENSG00000185130 | HIST1H2BL | histone cluster 1, H2bl [Source:HGNC Symbol; Acc:HGNC:4748] | NA | 4.01 | NA |

TABLE 17-continued

Biomarkers differentially expressed in the urine or saliva samples of subjects who experienced most forceful head impact (Max_HITsp) as compared to the subjects' baseline or subjects who are not contact sports athletes (Track_field_control1).

| Ensembl_ID | HGNC_symbol | Descriptiom | Max_HITsp_urine_vs_baseline_urine | Max_HITsp_urine_vs_Track_field_control_urine | Max_HITsp_saliva_vs_Track_field_control_saliva_previous_day |
|---|---|---|---|---|---|
| ENSG00000206172 | HBA1 | hemoglobin, alpha 1 [Source:HGNC Symbol; Acc:HGNC:4823] | NA | 4.22 | NA |
| ENSG00000211698 | TRGV4 | T cell receptor gamma variable 4 [Source:HGNC Symbol; Acc:HGNC:12289] | NA | 3.92 | NA |
| ENSG00000217643 | PTGES3P2 | prostaglandin E synthase 3 (cytosolic) pseudogene 2 [Source:HGNC Symbol; Acc:HGNC:43822] | NA | 3.24 | NA |
| ENSG00000224172 | | | NA | 4.55 | |
| ENSG00000227125 | | | NA | 3.35 | NA |
| ENSG00000228857 | | | NA | 4.04 | NA |
| ENSG00000233115 | FAM90A11P | family with sequence similarity 90, member A11, pseudogene [Source:HGNC Symbol; Acc:HGNC:32259] | NA | 4.44 | NA |
| ENSG00000234519 | | | NA | −3.85 | NA |
| ENSG00000234629 | WDR82P1 | WD repeat domain 82 pseudogene 1 [Source:HGNC Symbol; Acc:HGNC:32447] | NA | 3.74 | NA |
| ENSG00000236495 | | | NA | −4.14 | NA |
| ENSG00000236641 | | | NA | 3.98 | NA |
| ENSG00000253759 | IGHV3-57 | immunoglobulin heavy variable 3-57 (pseudogene) [Source:HGNC Symbol; Acc:HGNC:5612] | NA | 4.17 | NA |
| ENSG00000255079 | | | NA | 3.81 | NA |
| ENSG00000257718 | | | NA | 3.90 | NA |
| ENSG00000259770 | | | NA | 3.65 | NA |
| ENSG00000264280 | NA | NA | NA | 4.35 | NA |
| ENSG00000267762 | | | NA | 3.63 | NA |
| ENSG00000271029 | | | NA | 3.98 | NA |

TABLE 18

Biomarkers differentially expressed when the blood samples of subjects who experienced most frequent head impact (Max_freq_hits) are compared to the subject's baseline or subjects who are not contact sports athletes (Track_field_control)

| Ensembl_ID | HGNC_symbol | Descriptiom | Max_freq_hits_blood_vs_baseline_blood | Max_freq_hits_blood_vs_Track_field_control_blood | Max_feq_hits_blood_vs_Track_field_control_blood_previous_day |
|---|---|---|---|---|---|
| ENSG00000172201 | ID4 | inhibitor of DNA binding 4, dominant negative helix-loop-helix protein [Source:HGNC Symbol; Acc:HGNC:5363] | −3.88 | NA | NA |
| ENSG00000210196 | MT-TP | mitochondrially encoded tRNA proline [Source:HGNC Symbol; Acc:HGNC:7494] | NA | NA | 3.89 |
| ENSG00000214772 | | | −3.94 | NA | NA |
| ENSG00000235858 | | | NA | 4.24 | NA |
| ENSG00000244060 | RPS2P41 | ribosomal protein S2 pseudogene 41 [Source:HGNC Symbol; Acc:HGNC:36357] | NA | 3.74 | NA |
| ENSG00000250535 | STK19B | serine/threonine kinase 19B, pseudogene [Source:HGNC Symbol; Acc:HGNC:21668] | NA | −4.06 | NA |
| ENSG00000253469 | | | −4.43 | NA | NA |
| ENSG00000256915 | | | NA | 4.19 | NA |
| ENSG00000260265 | | | −4.56 | NA | NA |

TABLE 19

Biomarkers differentially expressed when the urine samples of subjects who experienced most frequent head impacts (Max_freq_hits) are compared to the subjects 'baseline, subjects who experienced least forceful head impact (Min_freq_hits), or subjects who are not contact sports athletes (Track_field_control)

| Ensembl_ID | HGNC_symbol | Description | Max_freq_hits_urine_vs_baseline_urine | Ma'_freq_hits_urine_vs_Min_freq_hits_urine | Max_freq_hits_urine_vs_Track_field_control_urine | Max_freq_hits_urine_vs_baseline_urine_previous_day | Max_freq_hits_urine_vs_Track_field_control_urine_previous_day |
|---|---|---|---|---|---|---|---|
| ENSG00000008438 | PGLYRP1 | peptidoglycan recognition protein 1 [Source: HGNC Symbol; Acc: HGNC: 8904] | NA | NA | 3.29 | NA | NA |
| ENSG00000060762 | MPC1 | mitochondrial pyruvate carrier 1 [Source: HGNC Symbol; Acc: HGNC: 21606] | −2.26 | NA | NA | NA | NA |
| ENSG00000104327 | CALB1 | calbindin 1, 28 kDa [Source: HGNC Symbol; Acc: HGNC: 1434] | −2.57 | NA | NA | −2.44 | NA |
| ENSG00000105518 | TMEM205 | transmembrane protein 205 [Source: HGNC Symbol; Acc: HGNC: 29631] | NA | NA | NA | NA | −2.05 |
| ENSG00000105647 | PIK3R2 | phosphoinositide-3-kinase, regulatory subunit 2 (beta) [Source: HGNC Symbol; Acc: HGNC: 8980] | NA | NA | 2.65 | NA | NA |
| ENSG00000107485 | GATA3 | GATA binding protein 3 [Source: HGNC Symbol; Acc: HGNC: 4172] | NA | −2.33 | NA | NA | NA |
| ENSG00000113889 | KNG1 | kininogen 1 [Source: HGNC Symbol; Acc: HGNC: 6383] | −2.63 | NA | NA | −2.58 | NA |
| ENSG00000116032 | GRIN3B | glutamate receptor, ionotropic, N-methyl-D-aspartate 3B [Source: HGNC Symbol; Acc: HGNC: 16768] | NA | NA | 2.41 | NA | NA |
| ENSG00000120306 | CYSTM1 | cysteine-rich transmembrane module containing 1 [Source: HGNC Symbol; Acc: HGNC: 30239] | −2.02 | NA | NA | NA | NA |
| ENSG00000120699 | EXOSC8 | exosome component 8 [Source: HGNC Symbol; Acc: HGNC: 17035] | NA | NA | NA | NA | NA |
| ENSG00000122862 | SRGN | serglycin [Source: HGNC Symbol; Acc: HGNC: 9361] | NA | NA | 3.03 | NA | NA |
| ENSG00000125652 | ALKBH7 | alkB, alkylation repair homolog 7 (E. coli) [Source: HGNC Symbol; Acc: HGNC: 21306] | NA | NA | 2.39 | NA | 2.49 |
| ENSG00000127528 | KLF2 | Kruppel-like factor 2 [Source: HGNC Symbol; Acc: HGNC: 6347] | NA | NA | 3.28 | NA | NA |
| ENSG00000128645 | HOXD1 | homeobox D1 [Source: HGNC Symbol; Acc: HGNC: 5132] | NA | NA | 2.26 | NA | NA |
| ENSG00000134809 | TIMM10 | translocase of inner mitochondrial membrane 10 homolog (yeast) [Source: HGNC Symbol; Acc: HGNC: 11814] | NA | NA | −2.21 | NA | NA |
| ENSG00000137731 | FXYD2 | FXYD domain containing ion transport regulator 2 [Source: HGNC Symbol; Acc: HGNC: 4026] | NA | NA | NA | −2.14 | NA |
| ENSG00000138207 | RBP4 | retinol binding protein 4, plasma [Source: HGNC Symbol; Acc: HGNC: 9922] | NA | NA | −2.23 | NA | NA |
| ENSG00000143546 | S100A8 | S100 calcium binding protein A8 [Source: HGNC Symbol; Acc: HGNC: 10498] | NA | NA | 2.65 | NA | NA |
| ENSG00000150201 | FXYD4 | FXYD domain containing ion transport regulator 4 [Source: HGNC Symbol; Acc: HGNC: 4028] | NA | NA | −2.58 | NA | −2.57 |

TABLE 19-continued

Biomarkers differentially expressed when the urine samples of subjects who experienced most frequent head impacts (Max_freq_hits) are compared to the subjects 'baseline, subjects who experienced least forceful head impact (Min_freq_hits), or subjects who are not contact sports athletes (Track_field_control)

| Ensembl_ID | HGNC_symbol | Description | Max_freq_hits_urine_vs_baseline_urine | Max_freq_hits_urine_vs_Min_freq_hits_urine | Max_freq_hits_urine_vs_Track_field_control_urine | Max_freq_hits_urine_vs_baseline_urine_previous_day | Max_freq_hits_urine_vs_Track_field_control_urine_previous_day |
|---|---|---|---|---|---|---|---|
| ENSG00000160181 | TFF2 | trefoil factor 2 [Source: HGNC Symbol; Acc: HGNC: 11756] | NA | NA | 2.78 | NA | NA |
| ENSG00000161992 | PRR35 | proline rich 35 [Source: HGNC Symbol; Acc: HGNC: 14139] | NA | NA | 3.16 | NA | NA |
| ENSG00000163209 | SPRR3 | small proline-rich protein 3 [Source: HGNC Symbol; Acc: HGNC: 11268] | NA | NA | 2.86 | NA | NA |
| ENSG00000163577 | EIF5A2 | eukaryotic translation initiation factor 5A2 [Source: HGNC Symbol; Acc: HGNC: 3301] | NA | NA | NA | NA | NA |
| ENSG00000163739 | CXCL1 | chemokine (C-X-C motif) ligand 1(melanoma growth stimulating activity, alpha) [Source: HGNC Symbol; Acc: HGNC: 4602] | NA | NA | 2.66 | NA | NA |
| ENSG00000164114 | MAP9 | microtubule-associated protein 9 [Source: HGNC Symbol; Acc: HGNC: 26118] | NA | NA | NA | NA | NA |
| ENSG00000164729 | SLC35G3 | solute carrier family 35, member G3 [Source: HGNC Symbol; Acc: HGNC: 26848] | NA | NA | 2.38 | NA | NA |
| ENSG00000164825 | DEFB1 | defensin, beta 1 [Source: HGNC Symbol; Acc: HGNC: 2766] | −3.23 | NA | NA | NA | NA |
| ENSG00000165685 | TMEM52B | transmembrane protein 52B [Source: HGNC Symbol; Acc: HGNC: 26438] | −2.27 | NA | NA | −3.00 | NA |
| ENSG00000165799 | RNASE7 | ribonuclease, RNase A family, 7 [Source: HGNC Symbol; Acc: HGNC: 19278] | NA | NA | 2.63 | NA | NA |
| ENSG00000168746 | C20orf62 | chromosome 20 open reading frame 62 [Source: HGNC Symbol; Acc: HGNC: 16195] | NA | NA | 3.41 | NA | NA |
| ENSG00000169344 | UMOD | uromodulin [Source: HGNC Symbol; Acc: HGNC: 12559] | −2.08 | NA | NA | NA | NA |
| ENSG00000170891 | CYTL1 | cytokine-like 1 [Source: HGNC Symbol; Acc: HGNC: 24435] | NA | NA | 3.24 | NA | NA |
| ENSG00000173915 | USMG5 | up-regulated during skeletal muscle growth 5 homolog (mouse) [Source: HGNC Symbol; Acc: HGNC: 30889] | NA | NA | −2.09 | NA | NA |
| ENSG00000175197 | DDIT3 | DNA-damage-inducible transcript 3 [Source: HGNC Symbol; Acc: HGNC: 2726] | NA | NA | 2.25 | NA | NA |
| ENSG00000175283 | DOLK | dolichol kinase [Source: HGNC Symbol; Acc: HGNC: 23406] | NA | NA | 2.17 | NA | NA |
| ENSG00000176125 | UFSP1 | UFM1-specific peptidase 1 (non-functional) [Source: HGNC Symbol; Acc: HGNC: 33821] | NA | NA | 3.85 | NA | NA |
| ENSG00000179751 | SYCN | syncollin [Source: HGNC Symbol; Acc: HGNC: 18442] | NA | NA | 2.85 | NA | NA |
| ENSG00000181499 | OR6T1 | olfactory receptor, family 6, subfamily T, member 1 [Source: HGNC Symbol; Acc: HGNC: 14848] | NA | NA | 3.35 | NA | NA |

TABLE 19-continued

Biomarkers differentially expressed when the urine samples of subjects who experienced most frequent head impacts (Max_freq_hits) are compared to the subjects 'baseline, subjects who experienced least forceful head impact (Min_freq_hits), or subjects who are not contact sports athletes (Track_field_control)

| Ensembl_ID | HGNC_symbol | Description | Max_freq_hits_urine_vs_baseline_urine | Ma'_freq_hits_urine_vs_Min_freq_hits_urine | Max_freq_hits_urine_vs_Track_field_control_urine | Max_freq_hits_urine_vs_baseline_urine_previous_day | Max_freq_hits_urine_vs_Track_field_control_urine_previous_day |
|---|---|---|---|---|---|---|---|
| ENSG00000184908 | CLCNKB | chloride channel, voltage-sensitive Kb [Source: HGNC Symbol; Acc: HGNC: 2027] | −2.34 | NA | NA | −2.40 | NA |
| ENSG00000185130 | HIST1H2BL | histone cluster 1, H2bl [Source: HGNC Symbol; Acc: HGNC: 4748] | NA | 3.91 | NA | NA | NA |
| ENSG00000185275 | CD24P4 | CD24 molecule pseudogene 4 [Source: HGNC Symbol; Acc: HGNC: 1649] | −2.13 | NA | NA | NA | NA |
| ENSG00000187186 | | HCG2040265, isoform CRA_a; Uncharacterized protein; cDNA FLJ50015 [Source: UniProtKB/TrEMBL; Acc: B7Z3J9] | NA | NA | 2.85 | NA | NA |
| ENSG00000187808 | SOWAHD | sosondowah ankyrin repeat domain family member D [Source: HGNC Symbol; Acc: HGNC: 32960] | NA | NA | 3.42 | NA | NA |
| ENSG00000194297 | RNU1-75P | RNA, U1 small nuclear 75, pseudogene [Source: HGNC Symbol; Acc: HGNC: 48417] | NA | NA | 3.18 | NA | NA |
| ENSG00000197061 | HIST1H4C | histone cluster 1, H4c [Source: HGNC Symbol; Acc: HGNC: 4787] | −2.05 | NA | NA | NA | NA |
| ENSG00000197674 | OR51C1P | olfactory receptor, family 51, subfamily C, member 1 pseudogene [Source: HGNC Symbol; Acc: HGNC: 15191] | NA | NA | 2.60 | NA | NA |
| ENSG00000198518 | NA | NA | NA | NA | −2.01 | NA | NA |
| ENSG00000198888 | MT-ND1 | mitochondrially encoded NADH dehydrogenase 1 [Source: HGNC Symbol; Acc: HGNC: 7455] | NA | NA | NA | −2.13 | NA |
| ENSG00000199212 | RNU105C | RNA, U105C small nucleolar [Source: HGNC Symbol; Acc: HGNC: 10104] | NA | NA | 3.03 | NA | NA |
| ENSG00000199378 | | Y RNA [Source: RFAM; Acc: RF00019] | NA | NA | 3.56 | NA | NA |
| ENSG00000199536 | RNU6-315P | RNA, U6 small nuclear 315, pseudogene [Source: HGNC Symbol; Acc: HGNC: 47278] | NA | NA | 2.83 | NA | NA |
| ENSG00000200087 | SNORA73B | small nucleolar RNA, H/ACA box 73B [Source: HGNC Symbol; Acc: HGNC: 10116] | NA | NA | 3.84 | NA | 3.44 |
| ENSG00000200131 | RN7SKP77 | RNA, 7SK small nuclear pseudogene 77 [Source: HGNC Symbol; Acc: HGNC: 45801] | NA | NA | 4.78 | NA | 4.33 |
| ENSG00000200408 | RNA5SP74 | RNA, 5S ribosomal pseudogene 74 [Source: HGNC Symbol; Acc: HGNC: 42851] | NA | NA | 3.83 | NA | NA |
| ENSG00000201098 | RNY1 | RNA, Ro-associated Y1 [Source: HGNC Symbol; Acc: HGNC: 10242] | NA | NA | −2.69 | NA | −2.68 |
| ENSG00000201640 | RN7SKP28 | RNA, 7SK small nuclear pseudogene 28 [Source: HGNC Symbol; Acc: HGNC: 45752] | NA | NA | 3.29 | NA | NA |
| ENSG00000201984 | | Y RNA [Source: RFAM; Acc: RF00019] | NA | NA | 3.57 | NA | NA |

TABLE 19-continued

Biomarkers differentially expressed when the urine samples of subjects who experienced most frequent head impacts (Max_freq_hits) are compared to the subjects' baseline, subjects who experienced least forceful head impact (Min_freq_hits), or subjects who are not contact sports athletes (Track_field_control)

| Ensembl_ID | HGNC_symbol | Description | Max_freq_hits_urine_vs_baseline_urine | Ma'_freq_hits_urine_vs_Min_freq_hits_urine | Max_freq_hits_urine_vs_Track_field_control_urine | Max_freq_hits_urine_vs_baseline_urine_previous_day | Max_freq_hits_urine_vs_Track_field_control_urine_previous_day |
|---|---|---|---|---|---|---|---|
| ENSG00000203616 | RHOT1P2 | ras homolog family member Ti pseudogene 2 [Source: HGNC Symbol; Acc: HGNC: 37838] | NA | NA | 3.37 | NA | NA |
| ENSG00000204444 | APOM | apolipoprotein M [Source: HGNC Symbol; Acc: HGNC: 13916] | NA | NA | −2.73 | NA | −2.78 |
| ENSG00000204544 | MUC21 | mucin 21, cell surface associated [Source: HGNC Symbol; Acc: HGNC: 21661] | NA | NA | 2.75 | NA | NA |
| ENSG00000205559 | CHKB-AS1 | CHKB antisense RNA 1 (head to head) [Source: HGNC Symbol; Acc: HGNC: 40146] | NA | NA | 3.27 | NA | NA |
| ENSG00000205795 | CYS1 | cystin 1 [Source: HGNC Symbol; Acc: HGNC: 18525] | −2.38 | NA | NA | NA | NA |
| ENSG00000206172 | HBA1 | hemoglobin, alpha 1 [Source: HGNC Symbol; Acc: HGNC: 4823] | NA | NA | 3.27 | NA | 3.65 |
| ENSG00000206634 | SNORA22 | small nucleolar RNA, H/ACA box 22 [Source: HGNC Symbol; Acc: HGNC: 32612] | NA | NA | 3.37 | NA | NA |
| ENSG00000206652 | RNU1-1 | RNA, U1 small nuclear 1 [Source: HGNC Symbol; Acc: HGNC: 10120] | NA | NA | 2.13 | NA | NA |
| ENSG00000207010 | RNU6-1295P | RNA, U6 small nuclear 1295, pseudogene [Source: HGNC Symbol; Acc: HGNC: 48258] | NA | NA | 3.60 | NA | NA |
| ENSG00000210127 | MT-TA | mitochondrially encoded tRNA alanine [Source: HGNC Symbol; Acc: HGNC: 7475] | −2.25 | NA | NA | −2.60 | NA |
| ENSG00000210140 | MT-TC | mitochondrially encoded tRNA cysteine [Source: HGNC Symbol; Acc: HGNC: 7477] | NA | NA | NA | −2.23 | NA |
| ENSG00000210196 | MT-TP | mitochondrially encoded tRNA proline [Source: HGNC Symbol; Acc: HGNC: 7494] | NA | NA | NA | NA | NA |
| ENSG00000211698 | TRGV4 | T cell receptor gamma variable 4 [Source: HGNC Symbol; Acc: HGNC: 12289] | NA | NA | 4.35 | NA | 4.22 |
| ENSG00000212497 | RNA5SP465 | RNA, 5S ribosomal pseudogene 465 [Source: HGNC Symbol; Acc: HGNC: 43365] | NA | NA | 3.53 | NA | NA |
| ENSG00000213343 | RPL21P18 | ribosomal protein L21 pseudogene 18 [Source: HGNC Symbol; Acc: HGNC: 28362] | NA | NA | 3.50 | NA | NA |
| ENSG00000213871 | TAF9BP1 | TAF9B RNA polymerase II, TATA box binding protein (TBP)-associated factor, 31 kDa pseudogene 1 [Source: HGNC Symbol; Acc: HGNC: 30687] | NA | NA | 3.06 | NA | NA |
| ENSG00000213896 | | | NA | NA | 4.31 | NA | NA |
| ENSG00000214070 | | | NA | NA | 3.27 | NA | NA |
| ENSG00000214381 | LINC00488 | long intergenic non-protein coding RNA 488 [Source: HGNC Symbol; Acc: HGNC: 32675] | NA | NA | 2.61 | NA | NA |

TABLE 19-continued

Biomarkers differentially expressed when the urine samples of subjects who experienced most frequent head impacts (Max_freq_hits) are compared to the subjects 'baseline, subjects who experienced least forceful head impact (Min_freq_hits), or subjects who are not contact sports athletes (Track_field_control)

| Ensembl_ID | HGNC_symbol | Description | Max_freq_hits_urine_vs_baseline_urine | Ma'_freq_hits_urine_vs_Min_freq_hits_urine | Max_freq_hits_urine_vs_Track_field_control_urine | Max_freq_hits_urine_vs_baseline_urine_previous_day | Max_freq_hits_urine_vs_Track_field_control_urine_previous_day |
|---|---|---|---|---|---|---|---|
| ENSG00000214759 | | | NA | NA | 3.22 | NA | NA |
| ENSG00000215004 | MESTP4 | mesoderm specific transcript pseudogene 4 [Source: HGNC Symbol; Acc: HGNC: 38554] | NA | NA | 3.14 | NA | NA |
| ENSG00000215043 | GLULP6 | glutamate-ammonia ligase (glutamine synthetase) pseudogene 6 [Source: HGNC Symbol; Acc: HGNC: 37990] | NA | NA | 3.79 | NA | NA |
| ENSG00000215481 | BCRP3 | breakpoint cluster region pseudogene 3 [Source: HGNC Symbol; Acc: HGNC: 1016] | NA | NA | 3.07 | NA | NA |
| ENSG00000216966 | | | NA | NA | 3.41 | NA | NA |
| ENSG00000217643 | PTGES3P2 | prostaglandin E synthase 3 (cytosolic) pseudogene 2 [Source: HGNC Symbol; Acc: HGNC: 43822] | NA | NA | 3.33 | NA | 3.27 |
| ENSG00000218180 | SLC25A5P7 | solute carrier family 25 (mitochondrial carrier; adenine nucleotide translocator), member 5 pseudogene 7 [Source: HGNC Symbol; Acc: HGNC: 513] | NA | NA | 2.85 | NA | NA |
| ENSG00000218803 | GSTM2P1 | glutathione S-transferase mu 2 (muscle) pseudogene 1 [Source: HGNC Symbol; Acc: HGNC: 38009] | NA | NA | 2.75 | NA | 2.84 |
| ENSG00000219074 | SOD1P1 | superoxide dismutase 1, soluble pseudogene 1 [Source: HGNC Symbol; Acc: HGNC: 45134] | NA | NA | 3.03 | NA | NA |
| ENSG00000221571 | RNU6ATAC35P | RNA, U6atac small nuclear 35, pseudogene [Source: HGNC Symbol; Acc: HGNC: 46934] | NA | NA | | NA | NA |
| ENSG00000222281 | RN7SKP111 | RNA, 7SK small nuclear pseudogene 111 [Source: HGNC Symbol; Acc: HGNC: 45835] | NA | NA | 3.68 | NA | NA |
| ENSG00000222460 | RN7SKP271 | RNA, 7SK small nuclear pseudogene 271 [Source: HGNC Symbol; Acc: HGNC: 45995] | NA | NA | 4.25 | NA | NA |
| ENSG00000222678 | RN7SKP213 | RNA, 7SK small nuclear pseudogene 213 [Source: HGNC Symbol; Acc: HGNC: 45937] | NA | NA | 2.85 | NA | NA |
| ENSG00000222985 | RNU2-14P | RNA, U2 small nuclear 14, pseudogene [Source: HGNC Symbol; Acc: HGNC: 48507] | NA | NA | 3.72 | NA | NA |
| ENSG00000223581 | | | NA | NA | 3.84 | NA | NA |
| ENSG00000223916 | | | NA | NA | 3.64 | NA | NA |
| ENSG00000223963 | PRKRIRP8 | protein-kinase, interferon-inducible double stranded RNA dependent inhibitor, repressor of (P58 repressor) pseudogene 8 [Source: HGNC Symbol; Acc: HGNC: 39572] | NA | NA | | NA | NA |
| ENSG00000224172 | | | NA | NA | 4.79 | NA | 4.28 |
| ENSG00000224682 | SOCS5P2 | suppressor of cytokine signaling 5 pseudogene 2 [Source: HGNC Symbol; Acc: HGNC: 44598] | NA | NA | | NA | NA |
| ENSG00000225255 | | | NA | NA | | NA | NA |
| ENSG00000225770 | | | NA | NA | 3.53 | NA | 3.45 |

TABLE 19-continued

Biomarkers differentially expressed when the urine samples of subjects who experienced most frequent
head impacts (Max_freq_hits) are compared to the subjects 'baseline, subjects who experienced
least forceful head impact (Min_freq_hits), or subjects who are not contact sports athletes (Track_field_control)

| Ensembl_ID | HGNC_symbol | Description | Max_freq_hits_urine_vs_baseline_urine | Ma'_freq_hits_urine_vs_Min_freq_hits_urine | Max_freq_hits_urine_vs_Track_field_control_urine | Max_freq_hits_urine_vs_baseline_urine_previous_day | Max_freq_hits_urine_vs_Track_field_control_urine_previous_day |
|---|---|---|---|---|---|---|---|
| ENSG00000226403 | | | NA | NA | 3.50 | NA | NA |
| ENSG00000226471 | | | NA | NA | NA | NA | NA |
| ENSG00000226868 | | | NA | NA | 3.29 | NA | NA |
| ENSG00000227056 | RPL6P2 | ribosomal protein L6 pseudogene 2 [Source: HGNC Symbol; Acc: HGNC: 35964] | NA | NA | | NA | NA |
| ENSG00000227125 | | | NA | NA | 2.60 | NA | NA |
| ENSG00000227401 | RPL37P1 | ribosomal protein L37 pseudogene 1 [Source: HGNC Symbol; Acc: HGNC: 16337] | NA | NA | 3.30 | NA | NA |
| ENSG00000227415 | | | NA | NA | 3.39 | NA | NA |
| ENSG00000227603 | | | NA | NA | NA | NA | NA |
| ENSG00000227646 | STEAP2-AS1 | STEAP2 antisense RNA 1 [Source: HGNC Symbol; Acc: HGNC: 40820] | NA | NA | 3.16 | NA | NA |
| ENSG00000227675 | NA | NA | NA | NA | NA | NA | NA |
| ENSG00000227704 | | | NA | NA | 3.83 | NA | NA |
| ENSG00000227818 | | | NA | NA | 3.57 | NA | NA |
| ENSG00000227864 | ARL5AP1 | ADP-ribosylation factor-like 5A pseudogene 1 [Source: HGNC Symbol; Acc: HGNC: 43933] | NA | NA | 3.57 | NA | NA |
| ENSG00000228366 | | | NA | NA | 3.28 | NA | NA |
| ENSG00000228436 | | | NA | NA | 2.51 | NA | NA |
| ENSG00000228857 | | | NA | NA | 4.14 | NA | NA |
| ENSG00000229242 | | | NA | NA | 3.04 | NA | NA |
| ENSG00000229313 | | | NA | NA | 3.05 | NA | NA |
| ENSG00000229376 | CICP3 | capicua transcriptional repressor pseudogene 3 [Source: HGNC Symbol; Acc: HGNC: 37742] | NA | NA | 2.92 | NA | NA |
| ENSG00000229925 | | | NA | NA | 2.91 | NA | NA |
| ENSG00000229932 | YWHAZP3 | tyrosine 3-monooxygenase/tryptophan 5-monooxygenase activation protein, zeta pseudogene 3 [Source: HGNC Symbol; Acc: HGNC: 31101] | NA | NA | 3.50 | NA | NA |
| ENSG00000230185 | C9orf147 | chromosome 9 open reading frame 147 [Source: HGNC Symbol; Acc: HGNC: 31438] | NA | NA | NA | NA | NA |
| ENSG00000230312 | | | NA | NA | 3.42 | NA | NA |
| ENSG00000230696 | | | NA | NA | 3.16 | NA | NA |
| ENSG00000230706 | | | NA | NA | 3.14 | NA | NA |
| ENSG00000230710 | LINC00332 | long intergenic non-protein coding RNA 332 [Source: HGNC Symbol; Acc: HGNC: 42049] | NA | NA | 3.35 | NA | NA |
| ENSG00000230799 | | | NA | NA | 3.10 | NA | NA |
| ENSG00000231937 | | | NA | NA | 3.43 | NA | NA |
| ENSG00000232015 | HSPE1P25 | heat shock 10 kDa protein 1 pseudogene 25 [Source: HGNC Symbol; Acc: HGNC: 49344] | NA | NA | 3.87 | NA | NA |
| ENSG00000232464 | | | NA | NA | 3.46 | NA | NA |
| ENSG00000232524 | | | NA | NA | 2.80 | NA | NA |
| ENSG00000232591 | | | NA | NA | NA | NA | NA |
| ENSG00000232658 | | | NA | NA | 2.99 | NA | NA |
| ENSG00000232833 | NA | NA | NA | NA | 3.78 | NA | NA |
| ENSG00000233115 | FAM90A11P | family with sequence similarity 90, member A11, pseudogene Source: HGNC Symbol; Acc: HGNC: 32259] | NA | NA | 3.66 | NA | NA |

TABLE 19-continued

Biomarkers differentially expressed when the urine samples of subjects who experienced most frequent head impacts (Max_freq_hits) are compared to the subjects 'baseline, subjects who experienced least forceful head impact (Min_freq_hits), or subjects who are not contact sports athletes (Track_field_control)

| Ensembl_ID | HGNC_symbol | Description | Max_freq_hits_urine_vs_baseline_urine | Ma'_freq_hits_urine_vs_Min_freq_hits_urine | Max_freq_hits_urine_vs_Track_field_control_urine | Max_freq_hits_urine_vs_baseline_urine_previous_day | Max_freq_hits_urine_vs_Track_field_control_urine_previous_day |
|---|---|---|---|---|---|---|---|
| ENSG00000233558 | | | NA | NA | 2.88 | NA | NA |
| ENSG00000234629 | WDR82P1 | WD repeat domain 82 pseudogene 1 [Source: HGNC Symbol; Acc: HGNC: 32447] | NA | NA | 3.54 | NA | NA |
| ENSG00000235573 | | | NA | NA | 3.51 | NA | NA |
| ENSG00000235578 | | | NA | NA | 4.25 | NA | 4.06 |
| ENSG00000235942 | LCE6A | late cornified envelope 6A [Source: HGNC Symbol; Acc: HGNC: 31824] | NA | NA | 2.91 | NA | NA |
| ENSG00000236209 | | | NA | NA | 2.79 | NA | NA |
| ENSG00000236641 | | | NA | NA | 3.67 | NA | NA |
| ENSG00000236751 | LINC01186 | long intergenic non-protein coding RNA 1186 [Source: HGNC Symbol; Acc: HGNC: 49573] | NA | NA | 3.06 | NA | NA |
| ENSG00000236824 | BCYRN1 | brain cytoplasmic RNA 1 [Source: HGNC Symbol; Acc: HGNC: 1022] | NA | NA | −2.33 | NA | NA |
| ENSG00000237213 | RPL23AP22 | ribosomal protein L23a pseudogene 22 [Source: HGNC Symbol; Acc: HGNC: 35505] | NA | NA | 3.15 | NA | NA |
| ENSG00000237979 | | | NA | NA | 3.42 | NA | 3.43 |
| ENSG00000237991 | RPL35P1 | ribosomal protein L35 pseudogene 1 [Source: HGNC Symbol; Acc: HGNC: 36695] | NA | NA | 3.72 | NA | 3.99 |
| ENSG00000238073 | RBMY2HP | RNA binding motif protein, Y-linked, family 2, member H pseudogene [Source: HGNC Symbol; Acc: HGNC: 23893] | NA | NA | 3.34 | NA | NA |
| ENSG00000238337 | NA | NA | NA | NA | 3.37 | NA | NA |
| ENSG00000238609 | RNU7-94P | RNA, U7 small nuclear 94 pseudogene [Source: HGNC Symbol; Acc: HGNC: 45628] | NA | NA | 3.30 | NA | NA |
| ENSG00000239126 | NA | NA | NA | NA | 3.29 | NA | NA |
| ENSG00000239183 | SNORA84 | small nucleolar RNA, H/ACA box 84 [Source: HGNC Symbol; Acc: HGNC: 33615] | NA | NA | 3.73 | NA | NA |
| ENSG00000239196 | NA | NA | NA | NA | 3.81 | NA | NA |
| ENSG00000239272 | RPL21P10 | ribosomal protein L21 pseudogene 10 [Source: HGNC Symbol; Acc: HGNC: 19795] | NA | NA | 3.82 | NA | NA |
| ENSG00000239542 | RN7SL399P | RNA, 7SL, cytoplasmic 399, pseudogene [Source: HGNC Symbol; Acc: HGNC: 46415] | NA | NA | 3.58 | NA | NA |
| ENSG00000239857 | GET4 | golgi to ER traffic protein 4 homolog (*S. cerevisiae*) [Source: HGNC Symbol; Acc: HGNC: 21690] | NA | NA | 2.59 | NA | NA |
| ENSG00000240005 | | | NA | NA | | NA | −3.53 |
| ENSG00000240803 | RN7SL231P | RNA, 7SL, cytoplasmic 231, pseudogene [Source: HGNC Symbol; Acc: HGNC: 46247] | NA | NA | 3.42 | NA | NA |
| ENSG00000242229 | RPS3AP14 | ribosomal protein S3a pseudogene 14 [Source: HGNC Symbol; Acc: HGNC: 35715] | NA | NA | 3.44 | NA | NA |
| ENSG00000242770 | | | NA | NA | 4.06 | NA | NA |
| ENSG00000243004 | | | NA | NA | 2.02 | NA | NA |

TABLE 19-continued

Biomarkers differentially expressed when the urine samples of subjects who experienced most frequent head impacts (Max_freq_hits) are compared to the subjects' baseline, subjects who experienced least forceful head impact (Min_freq_hits), or subjects who are not contact sports athletes (Track_field_control)

| Ensembl_ID | HGNC_symbol | Description | Max_freq_hits_urine_vs_baseline_urine | Ma'_freq_hits_urine_vs_Min_freq_hits_urine | Max_freq_hits_urine_vs_Track_field_control_urine | Max_freq_hits_urine_vs_baseline_urine_previous_day | Max_freq_hits_urine_vs_Track_field_control_urine_previous_day |
|---|---|---|---|---|---|---|---|
| ENSG00000243974 | VTI1BP1 | vesicle transport through interaction with t-SNAREs 1B pseudogene 1 [Source: HGNC Symbol; Acc: HGNC: 43727] | NA | NA | 3.37 | NA | NA |
| ENSG00000244060 | RPS2P41 | ribosomal protein S2 pseudogene 41 [Source: HGNC Symbol; Acc: HGNC: 36357] | NA | NA | | NA | NA |
| ENSG00000244063 | | | NA | NA | 3.33 | NA | NA |
| ENSG00000244260 | | | NA | NA | 2.21 | NA | NA |
| ENSG00000244582 | RPL21P120 | ribosomal protein L21 pseudogene 120 [Source: HGNC Symbol; Acc: HGNC: 35743] | NA | NA | 3.58 | NA | NA |
| ENSG00000244734 | HBB | hemoglobin, beta [Source: HGNC Symbol; Acc: HGNC: 4827] | NA | NA | 3.07 | NA | 3.80 |
| ENSG00000248240 | | | NA | NA | 2.79 | NA | NA |
| ENSG00000248370 | | | NA | NA | 3.64 | NA | NA |
| ENSG00000248834 | MARK2P5 | MAP/microtubule affinity-regulating kinase 2 pseudogene 5 [Source: HGNC Symbol; Acc: HGNC: 39796] | NA | NA | 4.17 | NA | NA |
| ENSG00000248890 | HHIP-AS1 | HHIP antisense RNA 1 [Source: HGNC Symbol; Acc: HGNC: 44182] | NA | NA | 2.96 | NA | NA |
| ENSG00000249014 | HMGN2P4 | high mobility group nucleosomal binding domain 2 pseudogene 4 [Source: HGNC Symbol; Acc: HGNC: 33567] | NA | NA | 3.11 | NA | NA |
| ENSG00000249256 | ATP5LP3 | ATP synthase, H+ transporting, mitochondrial Fo complex, subunit g, pseudogene 3 [Source: HGNC Symbol; Acc: HGNC: 13216] | NA | NA | 3.15 | NA | NA |
| ENSG00000249942 | | | NA | NA | 3.44 | NA | NA |
| ENSG00000250120 | PCDHA10 | protocadherin alpha 10 [Source: HGNC Symbol; Acc: HGNC: 8664] | NA | NA | 2.81 | NA | NA |
| ENSG00000250234 | | | NA | NA | 3.96 | NA | NA |
| ENSG00000250411 | | | NA | NA | 3.28 | NA | NA |
| ENSG00000251048 | | | NA | NA | | NA | −4.21 |
| ENSG00000251445 | | | NA | NA | 3.49 | NA | 3.87 |
| ENSG00000251583 | | | NA | NA | 3.14 | NA | NA |
| ENSG00000252350 | RPPH1-3P | ribonuclease P RNA component H1, 3 pseudogene [Source: HGNC Symbol; Acc: HGNC: 47030] | NA | NA | 3.56 | NA | NA |
| ENSG00000252376 | RNA5SP395 | RNA, 5S ribosomal pseudogene 395 [Source: HGNC Symbol; Acc: HGNC: 43295] | NA | NA | 3.59 | NA | NA |
| ENSG00000252396 | RN7SKP195 | RNA, 7SK small nuclear pseudogene 195 [Source: HGNC Symbol; Acc: HGNC: 45919] | NA | NA | 3.58 | NA | NA |
| ENSG00000252731 | | | NA | NA | 4.20 | NA | NA |
| ENSG00000253112 | | | NA | NA | 3.09 | NA | NA |
| ENSG00000253292 | MIOXP1 | myo-inositol oxygenase pseudogene 1 [Source: HGNC Symbol; Acc: HGNC: 50748] | NA | NA | 3.21 | NA | NA |
| ENSG00000253469 | | | NA | NA | NA | NA | NA |
| ENSG00000253560 | | | NA | NA | 3.30 | NA | NA |
| ENSG00000253597 | NA | NA | NA | NA | 3.64 | NA | NA |

TABLE 19-continued

Biomarkers differentially expressed when the urine samples of subjects who experienced most frequent head impacts (Max_freq_hits) are compared to the subjects' baseline, subjects who experienced least forceful head impact (Min_freq_hits), or subjects who are not contact sports athletes (Track_field_control)

| Ensembl_ID | HGNC_symbol | Description | Max_freq_hits_urine_vs_baseline_urine | Ma'_freq_hits_urine_vs_Min_freq_hits_urine | Max_freq_hits_urine_vs_Track_field_control_urine | Max_freq_hits_urine_vs_baseline_urine_previous_day | Max_freq_hits_urine_vs_Track_field_control_urine_previous_day |
|---|---|---|---|---|---|---|---|
| ENSG00000253759 | IGHV3-57 | immunoglobulin heavy variable 3-57 (pseudogene) [Source: HGNC Symbol; Acc: HGNC: 5612] | NA | NA | 4.36 | NA | 4.47 |
| ENSG00000253882 | | | NA | NA | 3.06 | NA | NA |
| ENSG00000253892 | | | NA | NA | 3.08 | NA | NA |
| ENSG00000253920 | IGLV3-31 | immunoglobulin lambda variable 3-31 (pseudogene) [Source: HGNC Symbol; Acc: HGNC: 5913] | NA | NA | 3.38 | NA | NA |
| ENSG00000254057 | | | NA | NA | 3.36 | NA | NA |
| ENSG00000254082 | | | NA | NA | 3.72 | NA | NA |
| ENSG00000254086 | | | NA | NA | 3.78 | NA | NA |
| ENSG00000254124 | EEF1A1P37 | eukaryotic translation elongation factor 1 alpha 1 pseudogene 37 [Source: HGNC Symbol; Acc: HGNC: 37915] | NA | NA | NA | NA | NA |
| ENSG00000254260 | | | NA | NA | 3.08 | NA | NA |
| ENSG00000254325 | | | NA | NA | 2.96 | NA | NA |
| ENSG00000254389 | RHPN1-AS1 | RHPN1 antisense RNA 1 (head to head) [Source: HGNC Symbol; Acc: HGNC: 28457] | NA | NA | 2.95 | NA | NA |
| ENSG00000254509 | | | NA | NA | 3.07 | NA | NA |
| ENSG00000254624 | OR4R3P | olfactory receptor, family 4, subfamily R, member 3 pseudogene [Source: HGNC Symbol; Acc: HGNC: 15182] | NA | NA | NA | NA | NA |
| ENSG00000254638 | | | NA | NA | 3.94 | NA | NA |
| ENSG00000254832 | OR4A40P | olfactory receptor, family 4, subfamily A, member 40 pseudogene [Source: HGNC Symbol; Acc: HGNC: 31259] | NA | NA | 3.41 | NA | NA |
| ENSG00000255038 | | | NA | NA | 3.09 | NA | NA |
| ENSG00000255040 | | | NA | NA | | NA | NA |
| ENSG00000255079 | | | NA | NA | 3.07 | NA | NA |
| ENSG00000255142 | | | NA | NA | 3.13 | NA | NA |
| ENSG00000256037 | MRPL40P1 | mitochondrial ribosomal protein L40 pseudogene 1 [Source: HGNC Symbol; Acc: HGNC: 44532] | NA | NA | 4.02 | NA | NA |
| ENSG00000256660 | CLEC12B | C-type lectin domain family 12, member B [Source: HGNC Symbol; Acc: HGNC: 31966] | NA | NA | NA | NA | NA |
| ENSG00000256915 | | | NA | NA | NA | NA | NA |
| ENSG00000257022 | | | NA | NA | 3.42 | NA | NA |
| ENSG00000257241 | | | NA | NA | 3.78 | NA | NA |
| ENSG00000257292 | | | NA | NA | 3.88 | NA | NA |
| ENSG00000257476 | | | NA | NA | 2.88 | NA | NA |
| ENSG00000257640 | | | NA | NA | 2.96 | NA | NA |
| ENSG00000257718 | | | NA | NA | 4.18 | NA | 3.76 |
| ENSG00000257803 | | | NA | NA | 4.21 | NA | NA |
| ENSG00000258225 | | | NA | NA | 3.53 | NA | NA |
| ENSG00000258379 | | | NA | NA | 3.11 | NA | NA |
| ENSG00000258486 | RN7SL1 | RNA, 7SL, cytoplasmic 1 [Source: HGNC Symbol; Acc: HGNC: 10038] | NA | NA | −2.17 | NA | NA |
| ENSG00000258590 | NBEAP1 | neurobeachin pseudogene 1 [Source: HGNC Symbol; Acc: HGNC: 1007] | NA | NA | NA | NA | NA |
| ENSG00000258676 | | | NA | NA | 3.04 | NA | 3.13 |
| ENSG00000259035 | | | NA | NA | 2.32 | NA | NA |
| ENSG00000259211 | | | NA | NA | 3.70 | NA | NA |

TABLE 19-continued

Biomarkers differentially expressed when the urine samples of subjects who experienced most frequent head impacts (Max_freq_hits) are compared to the subjects' baseline, subjects who experienced least forceful head impact (Min_freq_hits), or subjects who are not contact sports athletes (Track_field_control)

| Ensembl_ID | HGNC_symbol | Description | Max_freq_hits_urine_vs_baseline_urine | Max_freq_hits_urine_vs_Min_freq_hits_urine | Max_freq_hits_urine_vs_Track_field_control_urine | Max_freq_hits_urine_vs_baseline_urine_previous_day | Max_freq_hits_urine_vs_Track_field_control_urine_previous_day |
|---|---|---|---|---|---|---|---|
| ENSG00000259431 | THTPA | thiamine triphosphatase [Source: HGNC Symbol; Acc: HGNC: 18987] | NA | NA | NA | NA | NA |
| ENSG00000259564 | | | NA | NA | 3.34 | NA | NA |
| ENSG00000259770 | | | NA | NA | 3.97 | NA | 3.53 |
| ENSG00000260077 | | | NA | NA | 2.61 | NA | NA |
| ENSG00000260571 | BNIP3P5 | BCL2/adenovirus E1B 19kDa interacting protein 3 pseudogene 5 [Source: HGNC Symbol; Acc: HGNC: 39658] | NA | NA | 3.48 | NA | NA |
| ENSG00000260601 | | | NA | NA | 3.59 | NA | NA |
| ENSG00000261916 | | | NA | NA | 2.88 | NA | NA |
| ENSG00000261996 | | | NA | NA | 3.15 | NA | NA |
| ENSG00000262001 | DLGAP1-AS2 | DLGAP1 antisense RNA 2 [Source: HGNC Symbol; Acc: HGNC: 28146] | NA | NA | 2.15 | NA | NA |
| ENSG00000262313 | | | NA | NA | 2.82 | NA | NA |
| ENSG00000264280 | NA | NA | NA | NA | 3.54 | NA | NA |
| ENSG00000265713 | | | NA | NA | 2.62 | NA | NA |
| ENSG00000266021 | NA | NA | NA | NA | 3.32 | NA | NA |
| ENSG00000267142 | | | NA | NA | 3.35 | NA | 3.49 |
| ENSG00000267363 | | | NA | NA | 3.48 | NA | NA |
| ENSG00000267493 | CIRBP-AS1 | CIRBP antisense RNA 1 [Source: HGNC Symbol; Acc: HGNC: 28588] | NA | NA | 2.98 | NA | NA |
| ENSG00000267500 | | | NA | NA | | NA | NA |
| ENSG00000267706 | | | NA | NA | 3.50 | NA | NA |
| ENSG00000267762 | | | NA | NA | 3.34 | NA | NA |
| ENSG00000268582 | | | NA | NA | 3.87 | NA | NA |
| ENSG00000268798 | | | NA | NA | 3.10 | NA | NA |
| ENSG00000269364 | LINC01233 | long intergenic non-protein coding RNA 1233 [Source: HGNC Symbol; Acc: HGNC: 49756] | NA | NA | 3.94 | NA | NA |
| ENSG00000269815 | | | NA | NA | 3.60 | NA | NA |
| ENSG00000269900 | RMRP | RNA component of mitochondrial RNA processing endoribonuclease [Source: HGNC Symbol; Acc: HGNC: 10031] | −2.01 | NA | NA | NA | NA |
| ENSG00000270010 | | | NA | NA | 3.57 | NA | NA |
| ENSG00000270103 | RNU11 | RNA, U11 small nuclear [Source: HGNC Symbol; Acc: HGNC: 10108] | −3.06 | −2.54 | NA | −2.77 | NA |
| ENSG00000270188 | MTRNR2L11 | MT-RNR2-like 11 (pseudogene) [Source: HGNC Symbol; Acc: HGNC: 37168] | NA | NA | 2.63 | NA | NA |
| ENSG00000270708 | | | NA | NA | 3.60 | NA | 4.10 |
| ENSG00000270878 | | | NA | NA | 3.74 | NA | 3.58 |
| ENSG00000271029 | | | NA | NA | 3.62 | NA | NA |
| ENSG00000271225 | | | NA | NA | 2.89 | NA | NA |
| ENSG00000271365 | | | NA | NA | 3.66 | NA | NA |
| ENSG00000271581 | | | NA | NA | 2.50 | NA | NA |
| ENSG00000271767 | NA | NA | NA | NA | 3.13 | NA | NA |
| ENSG00000272870 | | | NA | NA | 2.43 | NA | NA |
| ENSG00000273106 | | | NA | NA | 3.33 | NA | NA |
| ENSG00000273327 | OR6L2P | olfactory receptor, family 6, subfamily L, member 2 pseudogene [Source: HGNC Symbol; Acc: HGNC: 15125] | NA | NA | 2.90 | NA | NA |

TABLE 20

Biomarkers differentially expressed when the saliva samples of subjects who experienced most frequent head impact (Max_freq_hits) are compared to the subjects' baseline or subjects who experienced least frequent head impact (Min_freq_hits)

| Ensembl_ID | HGNC_symbol | Description | Max_freq_hits_saliva_vs_baseline_saliva | Max_freq_hits_saliva_vs_Min_freq_hits_saliva |
|---|---|---|---|---|
| ENSG00000120699 | EXOSC8 | exosome component 8 [Source:HGNC Symbol; Acc:HGNC:17035] | −3.24 | NA |
| ENSG00000163577 | EIF5A2 | eukaryotic translation initiation factor 5A2 [Source:HGNC Symbol; Acc:HGNC:3301] | −3.28 | NA |
| ENSG00000164114 | MAP9 | microtubule-associated protein 9 [Source:HGNC Symbol; Acc:HGNC:26118] | −2.96 | NA |
| ENSG00000180708 | OR10K2 | olfactory receptor, family 10, subfamily K, member 2 [Source:HGNC Symbol; Acc:HGNC:14826] | −4.16 | NA |
| ENSG00000221571 | RNU6ATAC35P | RNA, U6atac small nuclear 35, pseudogene [Source:HGNC Symbol; Acc:HGNC:46934] | 4.58 | NA |
| ENSG00000223963 | PRKRIRP8 | protein-kinase, interferon-inducible double stranded RNA dependent inhibitor, repressor of (P58 repressor) pseudogene 8 [Source:HGNC Symbol; Acc:HGNC:39572] | −3.94 | −4.59 |
| ENSG00000224682 | SOCS5P2 | suppressor of cytokine signaling 5 pseudogene 2 [Source:HGNC Symbol; Acc:HGNC:44598] | NA | −3.98 |
| ENSG00000226471 | | | 3.44 | NA |
| ENSG00000228445 | UGT1A2P | UDP glucuronosyltransferase 1 family, polypeptide A2 pseudogene [Source:HGNC Symbol; Acc:HGNC:12534] | −4.43 | NA |
| ENSG00000228695 | CES1P1 | carboxylesterase 1 pseudogene 1 [Source:HGNC Symbol; Acc:HGNC:18546] | 2.37 | NA |
| ENSG00000229571 | PRAMEF26 | PRAME family member 26 [Source:HGNC Symbol; Acc:HGNC:49178] | −4.02 | NA |
| ENSG00000230205 | | | 3.98 | NA |
| ENSG00000250437 | | | NA | 3.98 |
| ENSG00000251634 | | | 4.09 | NA |
| ENSG00000255040 | | | −3.84 | NA |
| ENSG00000256660 | CLEC12B | C-type lectin domain family 12, member B [Source:HGNC Symbol; Acc:HGNC:31966] | −3.31 | NA |
| ENSG00000258590 | NBEAP1 | neurobeachin pseudogene 1 [Source:HGNC Symbol; Acc:HGNC:1007] | NA | −4.25 |
| ENSG00000259431 | THTPA | thiamine triphosphatase [Source:HGNC Symbol; Acc:HGNC:18987] | −4.58 | −4.57 |
| ENSG00000270423 | | | 4.32 | NA |
| ENSG00000272729 | | | −4.11 | NA |

TABLE 21

Biomarkers differentially expressed when the blood samples of subjects who experienced least forceful head impact (Min_HITsp) are compared to the subjects' baseline or subjects who are not contact sports athletes (Track_field_control)

| Ensembl_ID | HGNC_symbol | Description | Min_HITsp_blood_vs_baseline_blood | Min_HITsp_blood_vs_Track_field_control_blood | Min_HITsp_blood_vs_baseline_blood_previous_day | Min_HITsp_blood_vs_Track_field_control_blood_previous_day |
|---|---|---|---|---|---|---|
| ENSG00000096006 | CRISP3 | cysteine-rich secretory protein 3 [Source:HGNC Symbol;Acc:HGNC:16904] | NA | NA | −3.65 | NA |
| ENSG00000165480 | SKA3 | spindle and kinetochore associated complex subunit 3 [Source:HGNC Symbol;Acc:HGNC:20262] | 2.29 | NA | 2.49 | NA |
| ENSG00000210196 | MT-TP | mitochondrially encoded tRNA proline [Source:HGNC Symbol;Acc:HGNC:7494] | NA | 3.21 | NA | 3.03 |
| ENSG00000212297 | RNU6 821P | RNA, U6 small nuclear 821, pseudogene [Source:HGNC Symbol;Acc:HGNC:47784] | NA | 4.09 | NA | 4.58 |
| ENSG00000214114 | MYCBP | MYC binding protein [Source:HGNC Symbol;Acc:HGNC:7554] | NA | 2.58 | NA | |
| ENSG00000230140 | | | NA | 2.93 | NA | 3.11 |
| ENSG00000233690 | EBAG9 P1 | estrogen receptor binding site associated, antigen, 9 pseudogene 1 [Source:HGNC Symbol;Acc:HGNC:45233] | NA | NA | −4.02 | NA |

TABLE 21-continued

Biomarkers differentially expressed when the blood samples of subjects who experienced least forceful head impact (Min_HITsp) are compared to the subjects' baseline or subjects who are not contact sports athletes (Track_field_control)

| Ensembl_ID | HGNC_symbol | Description | Min_HITsp_blood_vs_baseline_blood | Min_HITsp_blood_vs_Track_field_control_blood | Min_HITsp_blood_vs_baseline_blood_previous_day | Min_HITsp_blood_vs_Track_field_control_blood_previous_day |
|---|---|---|---|---|---|---|
| ENSG00000235688 | | | NA | NA | NA | −4.52 |
| ENSG00000254624 | OR4R3P | olfactory receptor, family 4, subfamily R, member 3 pseudogene [Source:HGNC Symbol;Acc:HGNC:15182] | NA | NA | −4.30 | NA |
| ENSG00000259834 | | potassium voltage-gated channel, shaker-related subfamily, member 3 [Source:EntrezGene;Acc:3738] | NA | 4.21 | NA | 4.53 |
| ENSG00000271533 | | | NA | NA | −4.09 | NA |
| ENSG00000271945 | | | NA | NA | −4.87 | NA |

TABLE 22

Biomarkers differentially expressed when the urine sample of subjects who experienced least forceful head impact (Min_HITsp) are compared to subjects who are not contact sports athletes (Track_field_control)

| Ensembl_ID | HGNC_symbol | Description | Min_HITsp_urine_vs_Track_field_control_urine | Min_HITsp_urine_vs_Track_field_control_urine_previous_day |
|---|---|---|---|---|
| ENSG00000007306 | CEACAM7 | carcinoembryonic antigen-related cell adhesion molecule 7 [Source:HGNC Symbol; Acc:HGNC:1819] | 2.71 | 2.68 |
| ENSG00000043462 | LCP2 | lymphocyte cytosolic protein 2 (SH2 domain containing leukocyte protein of 76 kDa) [Source:HGNC Symbol; Acc:HGNC:6529] | 2.25 | 2.13 |
| ENSG00000057657 | PRDM1 | PR domain containing 1, with ZNF domain [Source:HGNC Symbol; Acc:HGNC:9346] | 2.30 | 2.19 |
| ENSG00000059728 | MXD1 | MAX dimerization protein 1 [Source:HGNC Symbol; Acc:HGNC:6761] | 2.45 | 2.33 |
| ENSG00000099985 | OSM | oncostatin M [Source:HGNC Symbol; Acc:HGNC:8506] | NA | 2.89 |
| ENSG00000101336 | HCK | HCK proto-oncogene, Src family tyrosine kinase [Source:HGNC Symbol; Acc:HGNC:4840] | 2.39 | 2.27 |
| ENSG00000103569 | AQP9 | aquaporin 9 [Source:HGNC Symbol; Acc:HGNC:643] | 3.21 | 3.09 |
| ENSG00000116741 | RGS2 | regulator of G-protein signaling 2 [Source:HGNC Symbol; Acc:HGNC:9998] | NA | 2.27 |
| ENSG00000120738 | EGR1 | early growth response 1 [Source:HGNC Symbol; Acc:HGNC:3238] | 2.42 | NA |
| ENSG00000122861 | PLAU | plasminogen activator, urokinase [Source:HGNC Symbol; Acc:HGNC:9052] | 2.70 | 2.56 |
| ENSG00000122862 | SRGN | serglycin [Source:HGNC Symbol; Acc:HGNC:9361] | NA | 3.83 |
| ENSG00000123395 | ATG101 | autophagy related 101 [Source:HGNC Symbol; Acc:HGNC:25679] | 2.09 | NA |
| ENSG00000140279 | DUOX2 | dual oxidase 2 [Source:HGNC Symbol; Acc:HGNC:13273] | 2.50 | 2.39 |
| ENSG00000140678 | ITGAX | integrin, alpha X (complement component 3 receptor 4 subunit) [Source:HGNC Symbol; Acc:HGNC:6152] | 2.24 | NA |
| ENSG00000140749 | IGSF6 | immunoglobulin superfamily, member 6 [Source:HGNC Symbol; Acc:HGNC:5953] | 2.93 | 2.75 |
| ENSG00000145113 | MUC4 | mucin 4, cell surface associated [Source:HGNC Symbol; Acc:HGNC:7514] | 2.48 | 2.38 |
| ENSG00000147180 | ZNF711 | zinc finger protein 711 [Source:HGNC Symbol; Acc:HGNC:13128] | 2.77 | 2.71 |
| ENSG00000150201 | FXYD4 | FXYD domain containing ion transport regulator 4 [Source:HGNC Symbol; Acc:HGNC:4028] | −2.95 | NA |
| ENSG00000153802 | TMPRSS11D | transmembrane protease, serine 11D [Source:HGNC Symbol; Acc:HGNC:24059] | NA | 2.10 |
| ENSG00000163739 | CXCL1 | chemokine (C-X-C motif) ligand 1 (melanoma growth stimulating activity, alpha) [Source:HGNC Symbol; Acc:HGNC:4602] | 3.37 | 3.25 |
| ENSG00000169429 | CXCL8 | chemokine (C-X-C motif) ligand 8 [Source:HGNC Symbol; Acc:HGNC:6025] | 3.66 | 3.71 |
| ENSG00000171223 | JUNB | jun B proto-oncogene [Source:HGNC Symbol; Acc:HGNC:6205] | 2.55 | 2.40 |

TABLE 22-continued

Biomarkers differentially expressed when the urine sample of subjects who experienced least forceful head impact (Min_HITsp) are compared to subjects who are not contact sports athletes (Track_field_control)

| Ensembl_ID | HGNC_symbol | Description | Min_HITsp_urine_vs_Track_field_control_urine | Min_HITsp_urine_vs_Track_field_control_urine_previous_day |
|---|---|---|---|---|
| ENSG00000186831 | KRT17P2 | keratin 17 pseudogene 2 [Source:HGNC Symbol; Acc:HGNC:6429] | NA | 3.57 |
| ENSG00000188215 | DCUN1D3 | DCN1, defective in cullin neddylation 1, domain containing 3 [Source:HGNC Symbol; Acc:HGNC:28734] | 2.06 | NA |
| ENSG00000196352 | CD55 | CD55 molecule, decay accelerating factor for complement (Cromer blood group) [Source:HGNC Symbol; Acc:HGNC:2665] | 2.02 | NA |
| ENSG00000198868 | MIR4461 | microRNA 4461 [Source:HGNC Symbol; Acc:HGNC:41656] | 4.30 | 4.68 |
| ENSG00000200087 | SNORA73B | small nucleolar RNA, H/ACA box 73B [Source:HGNC Symbol; Acc:HGNC:10116] | 3.83 | 4.08 |
| ENSG00000200408 | RNA5SP74 | RNA, 5S ribosomal pseudogene 74 [Source:HGNC Symbol; Acc:HGNC:42851] | NA | 3.84 |
| ENSG00000200785 | SNORD8 | small nucleolar RNA, C/D box 8 [Source:HGNC Symbol; Acc:HGNC:20159] | NA | 4.11 |
| ENSG00000204293 | OR8B2 | olfactory receptor, family 8, subfamily B, member 2 [Source:HGNC Symbol; Acc:HGNC:8471] | NA | 3.47 |
| ENSG00000206172 | HBA1 | hemoglobin, alpha 1 [Source:HGNC Symbol; Acc:HGNC:4823] | 4.09 | 4.19 |
| ENSG00000206634 | SNORA22 | small nucleolar RNA, H/ACA box 22 [Source:HGNC Symbol; Acc:HGNC:32612] | 4.08 | 4.24 |
| ENSG00000211698 | TRGV4 | T cell receptor gamma variable 4 [Source:HGNC Symbol; Acc:HGNC:12289] | 3.45 | 3.83 |
| ENSG00000212443 | SNORA53 | small nucleolar RNA, H/ACA box 53 [Source:HGNC Symbol; Acc:HGNC:32646] | 3.89 | 4.04 |
| ENSG00000213370 | RANP6 | RAN, member RAS oncogene family pseudogene 6 [Source:HGNC Symbol; Acc:HGNC:39861] | NA | 3.95 |
| ENSG00000215004 | MESTP4 | mesoderm specific transcript pseudogene 4 [Source:HGNC Symbol; Acc:HGNC:38554] | 3.31 | 3.30 |
| ENSG00000215043 | GLULP6 | glutamate-ammonia ligase (glutamine synthetase) pseudogene 6 [Source:HGNC Symbol; Acc:HGNC:37990] | NA | 4.31 |
| ENSG00000216966 | | | NA | 4.04 |
| ENSG00000217643 | PTGES3P2 | prostaglandin E synthase 3 (cytosolic) pseudogene 2 [Source:HGNC Symbol; Acc:HGNC:43822] | 3.50 | 3.43 |
| ENSG00000223581 | | | NA | 4.24 |
| ENSG00000223880 | LINC01078 | long intergenic non-protein coding RNA 1078 [Source:HGNC Symbol; Acc:HGNC:49121] | 3.97 | 4.25 |
| ENSG00000225255 | | | NA | 2.73 |
| ENSG00000227056 | RPL6P2 | ribosomal protein L6 pseudogene 2 [Source:HGNC Symbol; Acc:HGNC:35964] | −3.64 | NA |
| ENSG00000227401 | RPL37P1 | ribosomal protein L37 pseudogene 1 [Source:HGNC Symbol; Acc:HGNC:16337] | NA | 3.94 |
| ENSG00000228857 | | | 4.35 | 4.93 |
| ENSG00000230185 | C9orf147 | chromosome 9 open reading frame 147 [Source:HGNC Symbol; Acc:HGNC:31438] | NA | 3.02 |
| ENSG00000230312 | | | 4.17 | 4.85 |
| ENSG00000230799 | | | 3.64 | 3.69 |
| ENSG00000231259 | | | 4.28 | 4.64 |
| ENSG00000232658 | | | NA | 3.68 |
| ENSG00000232833 | | | NA | 4.19 |
| ENSG00000232990 | MTATP6P7 | mitochondrially encoded ATP synthase 6 pseudogene 7 [Source:HGNC Symbol; Acc:HGNC:44581] | 3.91 | 4.69 |
| ENSG00000234629 | WDR82P1 | WD repeat domain 82 pseudogene 1 [Source:HGNC Symbol; Acc:HGNC:32447] | NA | 3.68 |
| ENSG00000235101 | SETP9 | SET pseudogene 9 [Source:HGNC Symbol; Acc:HGNC:42928] | NA | 3.81 |
| ENSG00000238073 | RBMY2HP | RNA binding motif protein, Y-linked, family 2, member H pseudogene [Source:HGNC Symbol; Acc:HGNC:23893] | NA | 4.21 |
| ENSG00000239002 | SCARNA10 | small Cajal body-specific RNA 10 [Source:HGNC Symbol; Acc:HGNC:32567] | 4.64 | 4.53 |
| ENSG00000239272 | RPL21P10 | ribosomal protein L21 pseudogene 10 [Source:HGNC Symbol; Acc:HGNC:19795] | NA | 3.95 |
| ENSG00000240131 | | | NA | 4.11 |
| ENSG00000241397 | LINC00903 | long intergenic non-protein coding RNA 903 [Source:HGNC Symbol; Acc:HGNC:40351] | NA | 4.09 |

TABLE 22-continued

Biomarkers differentially expressed when the urine sample of subjects who experienced least forceful head impact (Min_HITsp) are compared to subjects who are not contact sports athletes (Track_field_control)

| Ensembl_ID | HGNC_symbol | Description | Min_HITsp_urine_vs_Track_field_control_urine | Min_HITsp_urine_vs_Track_field_control_urine_previous_day |
|---|---|---|---|---|
| ENSG00000241983 | RN7SL566P | RNA, 7SL, cytoplasmic 566, pseudogene [Source:HGNC Symbol; Acc:HGNC:46582] | 3.89 | NA |
| ENSG00000242770 | | | 3.67 | 4.30 |
| ENSG00000244063 | | | NA | 4.03 |
| ENSG00000244361 | RPL30P7 | ribosomal protein L30 pseudogene 7 [Source:HGNC Symbol; Acc:HGNC:36402] | NA | 4.26 |
| ENSG00000249019 | | | NA | 3.86 |
| ENSG00000249588 | | | 4.12 | 4.12 |
| ENSG00000253759 | IGHV3-57 | immunoglobulin heavy variable 3-57 (pseudogene) [Source:HGNC Symbol; Acc:HGNC:5612] | 4.13 | 4.52 |
| ENSG00000253882 | | | NA | 3.10 |
| ENSG00000254124 | EEF1A1P37 | eukaryotic translation elongation factor 1 alpha 1 pseudogene 37 [Source:HGNC Symbol; Acc:HGNC:37915] | 4.19 | NA |
| ENSG00000254325 | | | 3.80 | 3.67 |
| ENSG00000254638 | | | 3.77 | 4.46 |
| ENSG00000257241 | | | NA | 4.32 |
| ENSG00000257718 | | | 3.66 | 3.83 |
| ENSG00000257803 | | | NA | 3.91 |
| ENSG00000258676 | | | 3.48 | 3.38 |
| ENSG00000259770 | | | 3.79 | 3.92 |
| ENSG00000261596 | | | NA | 3.50 |
| ENSG00000264280 | | | 3.31 | 3.47 |
| ENSG00000264462 | MIR3648-1 | microRNA 3648-1 [Source:HGNC Symbol; Acc:HGNC:38941] | 3.20 | NA |
| ENSG00000267500 | | | | 4.06 |
| ENSG00000268543 | | | 3.80 | 3.92 |
| ENSG00000270810 | | | NA | 4.33 |
| ENSG00000272870 | | | NA | 2.67 |

TABLE 23

Biomakers differentially expressed when the blood samples of subjects who experienced frequent head impact (Min_freq_hits) are compared to the subjects' baseline or subjects who are not contact sports athletes (Track_field_control).

| Ensembl_ID | HGNC_symbol | Description | Min freq_hits_blood_vs_baseline_blood_previous_day | Min freq_hits_blood_vs_Track_field_control_blood_previous_day |
|---|---|---|---|---|
| ENSG00000040341 | STAU2 | staufen double-stranded RNA binding protein 2 [Source:HGNC Symbol; Acc:HGNC:11371] | NA | 2.21 |
| ENSG00000086666 | ZFAND6 | zinc finger, AN1-type domain 6 [Source:HGNC Symbol; Acc:HGNC:30164] | 2.58 | 2.71 |
| ENSG00000110013 | SIAE | sialic acid acetylesterase [Source:HGNC Symbol; Acc:HGNC:18187] | NA | 2.48 |
| ENSG00000119778 | ATAD2B | ATPase family, AAA domain containing 2B [Source:HGNC Symbol; Acc:HGNC:29230] | NA | 2.11 |
| ENSG00000165480 | SKA3 | spindle and kinetochore associated complex subunit 3 [Source:HGNC Symbol; Acc:HGNC:20262] | 2.42 | NA |
| ENSG00000168461 | RAB31 | RAB31, member RAS oncogene family [Source:HGNC Symbol; Acc:HGNC:9771] | 2.34 | NA |
| ENSG00000198168 | SVIP | small VCP/p97-interacting protein [Source:HGNC Symbol; Acc:HGNC:25238] | 2.26 | NA |
| ENSG00000198886 | MT-ND4 | mitochondrially encoded NADH dehydrogenase 4 [Source:HGNC Symbol; Acc:HGNC:7459] | NA | 3.28 |
| ENSG00000202354 | RNY3 | RNA, Ro-associated Y3 [Source:HGNC Symbol; Acc:HGNC:10243] | 3.35 | NA |
| ENSG00000210196 | MT-TP | mitochondrially encoded tRNA proline [Source:HGNC Symbol; Acc:HGNC:7494] | NA | 3.15 |

TABLE 23-continued

Biomakers differentially expressed when the blood samples of subjects who experienced frequent head impact (Min_freq_hits) are compared to the subjects' baseline or subjects who are not contact sports athletes (Track_field_control).

| Ensembl_ID | HGNC_symbol | Description | Min freq_hits_blood_vs_baseline_blood_previous_day | Min freq_hits_blood_vs_Track_field_control_blood_previous_day |
|---|---|---|---|---|
| ENSG00000271043 | MTRNR2L2 | MT-RNR2-like 2 [Source:HGNC Symbol; Acc:HGNC:37156] | 2.75 | 3.84 |

TABLE 24

Biomarkers differentially expressed when the urine sample of subjects who experienced frequent head impact (Min_freq_hits) are compared to subjects who are not contact sports athletes (Track_field_control)

| Ensembl_ID | HGNC_symbol | Description | Mins_feq_hits_urine_vs_Track_field_control_urine | Mins_freq_hits_urine_vs_Track_field_control_urine_previous_day |
|---|---|---|---|---|
| ENSG00000125652 | ALKBH7 | alkB, alkylation repair homolog 7 (*E. coli*) [Source:HGNC Symbol; Acc:HGNC:21306] | NA | 2.29 |
| ENSG00000198868 | MIR4461 | microRNA 4461 [Source:HGNC Symbol; Acc:HGNC:41656] | 4.15 | NA |
| ENSG00000206172 | HBA1 | hemoglobin, alpha 1 [Source:HGNC Symbol; Acc:HGNC:4823] | 3.81 | 3.84 |
| ENSG00000216629 | OR2W4P | olfactory receptor, family 2, subfamily W, member 4 pseudogene [Source:HGNC Symbol; Acc:HGNC:15071] | −2.91 | NA |
| ENSG00000228857 | | | 4.34 | 4.47 |
| ENSG00000236641 | | | 3.77 | NA |
| ENSG00000244734 | HBB | hemoglobin, beta [Source:HGNC Symbol; Acc:HGNC:4827] | 3.59 | 3.77 |
| ENSG00000254325 | | | 3.26 | NA |
| ENSG00000257718 | | | 3.60 | 3.55 |
| ENSG00000259108 | | | −3.16 | −3.20 |

TABLE 25

Biomarkers differentially expressed when the baseline blood sample of subjects who are contact sport athletes (baseline) are compared to the subjects who are not contact sports athletes (Track_field_control)

| Ensembl_ID | HGNC_symbol | Description | baseline_blood_vs_Track_field_control_blood | baseline_blood_vs_Track_field_control_blood_previous_day |
|---|---|---|---|---|
| ENSG00000178172 | SPINK6 | serine peptidase inhibitor, Kazal type 6 [Source:HGNC Symbol; Acc:HGNC:29486] | 4.24 | 4.78 |
| ENSG00000198022 | | | NA | 2.75 |
| ENSG00000200225 | RNA5SP382 | RNA, 5S ribosomal pseudogene 382 [Source:HGNC Symbol; Acc:HGNC:43282] | NA | 4.26 |
| ENSG00000201704 | RNA5SP396 | RNA, 5S ribosomal pseudogene 396 [Source:HGNC Symbol; Acc:HGNC:43296] | NA | 3.68 |
| ENSG00000204566 | C10orf115 | chromosome 10 open reading frame 115 [Source:HGNC Symbol; Acc:HGNC:31449] | 3.82 | NA |
| ENSG00000212297 | RNU6-821P | RNA, U6 small nuclear 821, pseudogene [Source:HGNC Symbol; Acc:HGNC:47784] | 3.78 | 4.18 |
| ENSG00000223881 | | | 4.42 | NA |
| ENSG00000227675 | | | NA | 3.88 |
| ENSG00000230140 | | | 2.67 | 2.71 |

TABLE 25-continued

Biomarkers differentially expressed when the baseline blood sample of subjects who are contact sport athletes (baseline) are compared to the subjects who are not contact sports athletes (Track_field_control)

| Ensembl_ID | HGNC_symbol | Description | baseline_blood_vs_Track_field_control_blood | baseline_blood_vs_Track_field_control_blood_previous_day |
|---|---|---|---|---|
| ENSG00000230604 | TSEN15P2 | TSEN15 tRNA splicing endonuclease subunit pseudogene 2 [Source:HGNC Symbol; Acc:HGNC:43963] | NA | 4.27 |
| ENSG00000232591 | | | NA | 3.65 |
| ENSG00000236559 | | | 4.52 | 4.65 |
| ENSG00000237027 | | | 3.51 | 3.51 |
| ENSG00000238215 | | | NA | 3.89 |
| ENSG00000238283 | TBC1D3P1 | TBC1 domain family, member 3 pseudogene 1 [Source:HGNC Symbol; Acc:HGNC:27445] | NA | 4.01 |
| ENSG00000242120 | | | NA | 2.89 |
| ENSG00000243075 | RN7SL519P | RNA, 7SL, cytoplasmic 519, pseudogene [Source:HGNC Symbol; Acc:HGNC:46535] | 4.14 | 4.30 |
| ENSG00000248242 | | | NA | 3.71 |
| ENSG00000248498 | ASNSP1 | asparagine synthetase pseudogene 1 [Source:HGNC Symbol; Acc:HGNC:754] | NA | 3.57 |
| ENSG00000249734 | | | NA | 3.41 |
| ENSG00000256721 | CACNA1C-IT3 | CACNA1C intronic transcript 3 (non-protein coding) [Source:HGNC Symbol; Acc:HGNC:41314] | 3.40 | NA |
| ENSG00000256915 | | | 3.73 | 3.94 |
| ENSG00000258406 | | | 3.99 | 4.33 |
| ENSG00000259513 | CYCSP38 | cytochrome c, somatic pseudogene 38 [Source:HGNC Symbol; Acc:HGNC:24411] | NA | 4.26 |
| ENSG00000259790 | ANP32BP1 | acidic (leucine-rich) nuclear phosphoprotein 32 family, member B pseudogene 1 [Source:HGNC Symbol; Acc:HGNC:24267] | NA | 3.85 |
| ENSG00000259834 | | potassium voltage-gated channel, shaker-related subfamily, member 3 [Source:EntrezGene;Acc:3738] | NA | 4.12 |
| ENSG00000260265 | | | 4.41 | 4.08 |
| ENSG00000267167 | | | NA | 3.89 |
| ENSG00000268055 | | | NA | 3.49 |
| ENSG00000268280 | | | 3.82 | 3.91 |
| ENSG00000271945 | | | NA | 4.93 |
| ENSG00000273185 | | | 4.77 | 4.91 |

TABLE 26

Biomarkers differentially expressed when the baseline urine sample of subjects who are contact sport athletes (baseline) are compared to the subjects who are not contact sports athletes (Track_field_control

| Ensembl_ID | HGNC_symbol | Description | baseline_urine_vs_Track_field_control_urine | baseline_urine_vs_Track_field_control_urine_previous_day |
|---|---|---|---|---|
| ENSG00000068366 | ACSL4 | acyl-CoA synthetase long-chain family member 4 [Source:HGNC Symbol; Acc:HGNC:3571] | 2.01 | NA |
| ENSG00000175879 | HOXD8 | homeobox D8 [Source:HGNC Symbol; Acc:HGNC:5139] | 2.50 | 2.48 |
| ENSG00000188536 | HBA2 | hemoglobin, alpha 2 [Source:HGNC Symbol; Acc:HGNC:4824] | NA | 3.44 |
| ENSG00000200087 | SNORA73B | small nucleolar RNA, H/ACA box 73B [Source:HGNC Symbol; Acc:HGNC:10116] | 4.20 | 4.17 |
| ENSG00000200131 | RN7SKP77 | RNA, 7SK small nuclear pseudogene 77 [Source:HGNC Symbol; Acc:HGNC:45801] | NA | 3.96 |
| ENSG00000200785 | SNORD8 | small nucleolar RNA, C/D box 8 [Source:HGNC Symbol; Acc:HGNC:20159] | NA | 5.28 |
| ENSG00000206172 | HBA1 | hemoglobin, alpha 1 [Source:HGNC Symbol; Acc:HGNC:4823] | 3.56 | 3.68 |
| ENSG00000206634 | SNORA22 | small nucleolar RNA, H/ACA box 22 [Source:HGNC Symbol; Acc:HGNC:32612] | 4.23 | 3.97 |
| ENSG00000206652 | RNU1-1 | RNA, U1 small nuclear 1 [Source:HGNC Symbol; Acc:HGNC:10120] | 2.82 | 2.80 |

TABLE 26-continued

Biomarkers differentially expressed when the baseline urine sample of subjects who are contact sport athletes (baseline) are compared to the subjects who are not contact sports athletes (Track_field_control

| Ensembl_ID | HGNC_symbol | Description | baseline_urine_vs_Track_field_control_urine | baseline_urine_vs_Track_field_control_urine_previous_day |
|---|---|---|---|---|
| ENSG00000210194 | MT-TE | mitochondrially encoded tRNA glutamic acid [Source:HGNC Symbol; Acc:HGNC:7479] | 2.74 | 2.73 |
| ENSG00000211698 | TRGV4 | T cell receptor gamma variable 4 [Source:HGNC Symbol; Acc:HGNC:12289] | NA | 3.31 |
| ENSG00000219074 | SOD1P1 | superoxide dismutase 1, soluble pseudogene 1 [Source:HGNC Symbol; Acc:HGNC:45134] | 3.86 | 3.79 |
| ENSG00000228857 | | | 4.05 | 4.07 |
| ENSG00000232015 | HSPE1P25 | heat shock 10 kDa protein 1 pseudogene 25 [Source:HGNC Symbol; Acc:HGNC:49344] | NA | 3.76 |
| ENSG00000232833 | NA | NA | 3.72 | 3.61 |
| ENSG00000234629 | WDR82P1 | WD repeat domain 82 pseudogene 1 [Source:HGNC Symbol; Acc:HGNC:32447] | 3.51 | NA |
| ENSG00000236559 | | | NA | NA |
| ENSG00000236641 | | | 3.46 | 3.43 |
| ENSG00000239002 | SCARNA10 | small Cajal body-specific RNA 10 [Source:HGNC Symbol; Acc:HGNC:32567] | 3.37 | 3.31 |
| ENSG00000244734 | HBB | hemoglobin, beta [Source:HGNC Symbol; Acc:HGNC:4827] | NA | 4.18 |
| ENSG00000251445 | | | NA | 3.76 |
| ENSG00000253759 | IGHV3-57 | immunoglobulin heavy variable 3-57 (pseudogene) [Source:HGNC Symbol; Acc:HGNC:5612] | 3.88 | 3.62 |
| ENSG00000257718 | | | 3.82 | 3.80 |
| ENSG00000259770 | | | 3.22 | NA |
| ENSG00000264280 | NA | NA | 3.33 | 3.30 |
| ENSG00000270878 | | | 3.07 | 3.07 |
| ENSG00000271043 | MTRNR2L2 | MT-RNR2-like 2 [Source:HGNC Symbol; Acc:HGNC:37156] | NA | 3.06 |

TABLE 27

Some biomarkers that are differentially expressed in plasma based on the number of head impact incidents

| Ensembl_ID | hgnc_symbol | description | high_freq_hits_vs_Baseline.x | high_freq_hits_vs_Low_freq_hits.x | low_freq_hits_vs_Baseline.x |
|---|---|---|---|---|---|
| ENSG00000229344 | | | 1.94 | 1.85 | NA |
| ENSG00000212338 | | Small nucleolar RNA SNORA67 [Source:RFAM;Acc:RF00272] | −1.37 | NA | −1.29 |
| ENSG00000186453 | FAM228A | family with sequence similarity 228, member A [Source:HGNC Symbol; Acc:HGNC:34418] | −1.12 | NA | −1.41 |
| ENSG00000234723 | | | −1.08 | NA | NA |
| ENSG00000249072 | | | 1.81 | 1.76 | NA |
| ENSG00000270683 | FAM71BP1 | family with sequence similarity 71, member B pseudogene 1 [Source:HGNC Symbol; Acc:HGNC:49805] | −1.10 | −1.27 | NA |
| ENSG00000227593 | | | −1.39 | NA | −1.33 |
| ENSG00000252596 | NA | NA | −1.41 | NA | −1.36 |
| ENSG00000239011 | NA | NA | −1.12 | NA | −1.37 |
| ENSG00000163993 | S100P | S100 calcium binding protein P [Source:HGNC Symbol; Acc:HGNC:10504] | −1.60 | NA | −1.53 |
| ENSG00000237731 | RNGTTP1 | RNA guanylyltransferase and 5-phosphatase pseudogene 1 [Source:HGNC Symbol; Acc:HGNC:39652] | −1.10 | NA | −1.64 |
| ENSG00000229775 | | | −1.69 | NA | −1.65 |
| ENSG00000237256 | PGAM3P | phosphoglycerate mutase 3, pseudogene [Source:HGNC Symbol; Acc:HGNC:16557] | −1.49 | NA | −1.67 |
| ENSG00000225181 | | | −1.22 | NA | −1.84 |
| ENSG00000200510 | NA | NA | 1.10 | NA | NA |
| ENSG00000264469 | | | −1.07 | NA | NA |
| ENSG00000203691 | NA | NA | −1.13 | NA | NA |
| ENSG00000201271 | RNU1-112P | RNA, U1 small nuclear 112, pseudogene [Source:HGNC Symbol; Acc:HGNC:48454] | −1.21 | NA | NA |

TABLE 27-continued

Some biomarkers that are differentially expressed in plasma based on the number of head impact incidents

| Ensembl_ID | hgnc_symbol | description | high_freq_ hits_vs_ Baseline.x | high_freq_ hits_vs_ Low_freq_ hits.x | low_freq_ hits_vs_ Baseline.x |
|---|---|---|---|---|---|
| ENSG00000242716 | NA | NA | 1.73 | 1.76 | NA |
| ENSG00000215030 | RPL13P12 | ribosomal protein L13 pseudogene 12 [Source:HGNC Symbol; Acc:HGNC:35701] | 1.06 | 1.24 | NA |
| ENSG00000158856 | DMTN | dematin actin binding protein [Source:HGNC Symbol; Acc:HGNC:3382] | 1.81 | 1.20 | NA |
| ENSG00000100345 | MYH9 | myosin, heavy chain 9, non-muscle [Source:HGNC Symbol; Acc:HGNC:7579] | 1.61 | 1.17 | NA |
| ENSG00000175602 | CCDC85B | coiled-coil domain containing 85B [Source:HGNC Symbol; Acc:HGNC:24926] | 1.54 | 1.16 | NA |
| ENSG00000219188 | CACYBPP3 | calcyclin binding protein pseudogene 3 [Source:HGNC Symbol; Acc:HGNC:45124] | −1.19 | −1.08 | NA |
| ENSG00000199287 | NA | NA | −1.28 | −2.02 | NA |
| ENSG00000176043 | | | NA | −1.32 | 1.69 |
| ENSG00000227159 | DDX11L16 | DEAD/H (Asp-Glu-Ala-Asp/His) box helicase 11 like 16 [Source:HGNC Symbol; Acc:HGNC:37115] | 1.06 | NA | 1.32 |
| ENSG00000264386 | MIR4513 | microRNA 4513 [Source:HGNC Symbol; Acc:HGNC:41855] | 1.10 | NA | 1.23 |
| ENSG00000252670 | NA | NA | NA | −1.36 | 1.22 |
| ENSG00000231680 | | | −1.12 | NA | −1.01 |
| ENSG00000253780 | IGHVIII-2-1 | immunoglobulin heavy variable (III)-2-1 (pseudogene) [Source:HGNC Symbol; Acc:HGNC:5695] | −1.36 | NA | −1.07 |
| ENSG00000220505 | EIF4EBP2P3 | eukaryotic translation initiation factor 4E binding protein 2 pseudogene 3 [Source:HGNC Symbol; Acc:HGNC:49318] | −1.48 | NA | −1.09 |
| ENSG00000249941 | | | −1.33 | NA | −1.10 |
| ENSG00000225906 | | | −1.29 | NA | −1.11 |
| ENSG00000232578 | | | −1.17 | NA | −1.13 |
| ENSG00000211967 | IGHV3-53 | immunoglobulin heavy variable 3-53 [Source:HGNC Symbol; Acc:HGNC:5610] | −1.05 | NA | −1.15 |
| ENSG00000235186 | | | NA | NA | −1.15 |
| ENSG00000258088 | | | −1.46 | NA | −1.16 |
| ENSG00000186038 | HTR3E | 5-hydroxytryptamine (serotonin) receptor 3E, ionotropic [Source:HGNC Symbol; Acc:HGNC:24005] | −1.14 | NA | −1.17 |
| ENSG00000206848 | RNU6-890P | RNA, U6 small nuclear 890, pseudogene [Source:HGNC Symbol; Acc:HGNC:47853] | −1.47 | NA | −1.21 |
| ENSG00000270680 | | | NA | 1.35 | −1.23 |
| ENSG00000226272 | ARHGAP26-AS1 | ARHGAP26 antisense RNA 1 [Source:HGNC Symbol; Acc:HGNC:40792] | −1.34 | NA | −1.24 |
| ENSG00000197568 | HHLA3 | HERV-H LTR-associating 3 [Source:HGNC Symbol; Acc:HGNC:4906] | −1.43 | NA | −1.24 |
| ENSG00000256972 | | | −1.15 | NA | −1.25 |
| ENSG00000250392 | | | NA | NA | −1.25 |
| ENSG00000260198 | | | −1.17 | NA | −1.26 |
| ENSG00000249465 | RBMXP4 | RNA binding motif protein, X-linked pseudogene 4 [Source:HGNC Symbol; Acc:HGNC:34028] | −1.54 | NA | −1.27 |
| ENSG00000187689 | AMTN | amelotin [Source:HGNC Symbol; Acc:HGNC:33188] | −1.43 | NA | −1.30 |
| ENSG00000199470 | | Small nucleolar RNA SNORA64/SNORA10 family [Source:RFAM;Acc:RF00264] | −1.10 | NA | −1.31 |
| ENSG00000238763 | NA | NA | −1.25 | NA | −1.33 |
| ENSG00000226939 | | | −1.18 | NA | −1.34 |
| ENSG00000232650 | | | −1.17 | NA | −1.35 |
| ENSG00000217557 | | | −1.11 | NA | −1.36 |
| ENSG00000185296 | | | −1.15 | NA | −1.36 |
| ENSG00000221291 | | | −1.23 | NA | −1.37 |
| ENSG00000265408 | | | −1.21 | NA | −1.43 |
| ENSG00000212564 | RNU6-1326P | RNA, U6 small nuclear 1326, pseudogene [Source:HGNC Symbol; Acc:HGNC:48289] | NA | NA | −1.45 |
| ENSG00000259418 | | | −1.27 | NA | −1.45 |
| ENSG00000261665 | TUBA8P2 | tubulin, alpha 8 pseudogene 2 [Source:HGNC Symbol; Acc:HGNC:44569] | NA | 1.10 | −1.49 |
| ENSG00000250256 | | | −1.20 | NA | −1.51 |
| ENSG00000235902 | | | −1.36 | NA | −1.54 |
| ENSG00000255408 | PCDHA3 | protocadherin alpha 3 [Source:HGNC Symbol; Acc:HGNC:8669] | −1.37 | NA | −1.58 |
| ENSG00000252672 | NA | NA | NA | NA | −1.60 |
| ENSG00000230645 | | | −1.27 | NA | −1.61 |
| ENSG00000229031 | | | −1.52 | NA | −1.62 |
| ENSG00000267670 | | | NA | NA | −1.64 |

TABLE 27-continued

Some biomarkers that are differentially expressed in plasma based on the number of head impact incidents

| Ensembl_ID | hgnc_symbol | description | high_freq_hits_vs_Baseline.x | high_freq_hits_vs_Low_freq_hits.x | low_freq_hits_vs_Baseline.x |
|---|---|---|---|---|---|
| ENSG00000240286 | MEAF6P1 | MYST/Esa1-associated factor 6 pseudogene 1 [Source:HGNC Symbol; Acc:HGNC:42660] | −1.07 | NA | −1.69 |
| ENSG00000168992 | OR7E102P | olfactory receptor, family 7, subfamily E, member 102 pseudogene [Source:HGNC Symbol; Acc:HGNC:15043] | −1.26 | NA | −1.84 |
| ENSG00000182393 | IFNL1 | interferon, lambda 1 [Source:HGNC Symbol; Acc:HGNC:18363] | NA | 2.15 | −1.91 |
| ENSG00000168067 | MAP4K2 | mitogen-activated protein kinase kinase kinase kinase 2 [Source:HGNC Symbol; Acc:HGNC:6864] | 1.59 | NA | NA |
| ENSG00000272468 | | | 1.58 | NA | NA |
| ENSG00000166086 | JAM3 | junctional adhesion molecule 3 [Source:HGNC Symbol; Acc:HGNC:15532] | 1.26 | NA | NA |
| ENSG00000260229 | | | −1.02 | NA | NA |
| ENSG00000222524 | RN7SKP109 | RNA, 7SK small nuclear pseudogene 109 [Source:HGNC Symbol; Acc:HGNC:45833] | −1.05 | NA | NA |
| ENSG00000225785 | | | −1.07 | NA | NA |
| ENSG00000252863 | RNU6-1183P | RNA, U6 small nuclear 1183, pseudogene [Source:HGNC Symbol; Acc:HGNC:48146] | −1.11 | NA | NA |
| ENSG00000230589 | IMP3P1 | IMP3 pseudogene 1 [Source:HGNC Symbol; Acc:HGNC:49385] | −1.12 | NA | NA |
| ENSG00000253849 | | | −1.12 | NA | NA |
| ENSG00000224924 | LINC00320 | long intergenic non-protein coding RNA 320 [Source:HGNC Symbol; Acc:HGNC:19690] | −1.15 | NA | NA |
| ENSG00000233545 | CYCSP33 | cytochrome c, somatic pseudogene 33 [Source:HGNC Symbol; Acc:HGNC:24407] | −1.15 | NA | NA |
| ENSG00000224288 | | | −1.18 | NA | NA |
| ENSG00000239791 | | | −1.20 | NA | NA |
| ENSG00000231957 | GNAI2P2 | guanine nucleotide binding protein (G protein), alpha inhibiting activity polypeptide 2 pseudogene 2 [Source:HGNC Symbol; Acc:HGNC:45110] | −1.21 | NA | NA |
| ENSG00000136872 | ALDOB | aldolase B, fructose-bisphosphate [Source:HGNC Symbol; Acc:HGNC:417] | −1.22 | NA | NA |
| ENSG00000254845 | NA | NA | −1.29 | NA | NA |
| ENSG00000226104 | NA | NA | −1.32 | NA | NA |
| ENSG00000241757 | RN7SL714P | RNA, 7SL, cytoplasmic 714, pseudogene [Source:HGNC Symbol; Acc:HGNC:46730] | −1.33 | NA | NA |
| ENSG00000261340 | | | −1.35 | NA | NA |
| ENSG00000213144 | | | −1.39 | NA | NA |
| ENSG00000219368 | ZNF299P | zinc finger protein 299, pseudogene [Source:HGNC Symbol; Acc:HGNC:13088] | −1.57 | NA | NA |
| ENSG00000244414 | CFHR1 | complement factor H-related 1 [Source:HGNC Symbol; Acc:HGNC:4888] | −1.73 | NA | NA |
| ENSG00000237973 | MIR6723 | microRNA 6723 [Source:HGNC Symbol; Acc:HGNC:50152] | 1.18 | 1.89 | NA |
| ENSG00000223554 | | | 1.37 | 1.53 | NA |
| ENSG00000244921 | | | 1.04 | 1.51 | NA |
| ENSG00000259045 | | | 1.14 | 1.42 | NA |
| ENSG00000133136 | GNG5P2 | guanine nucleotide binding protein (G protein), gammas pseudogene 2 [Source:HGNC Symbol; Acc:HGNC:24826] | 1.32 | 1.23 | NA |
| ENSG00000227468 | | | 1.43 | 1.20 | NA |
| ENSG00000141179 | PCTP | phosphatidylcholine transfer protein [Source:HGNC Symbol; Acc:HGNC:8752] | 1.46 | 1.13 | NA |
| ENSG00000148848 | ADAM12 | ADAM metallopeptidase domain 12 [Source:HGNC Symbol; Acc:HGNC:190] | 1.13 | 1.09 | NA |
| ENSG00000234975 | FTH1P2 | ferritin, heavy polypeptide 1 pseudogene 2 [Source:HGNC Symbol; Acc:HGNC:3989] | 1.01 | 1.07 | NA |
| ENSG00000265565 | MIR3143 | microRNA 3143 [Source:HGNC Symbol; Acc:HGNC:38284] | 1.27 | 1.01 | NA |
| ENSG00000172476 | RAB40A | RAB40A, member RAS oncogene family [Source:HGNC Symbol; Acc:HGNC:18283] | −1.10 | −1.09 | NA |
| ENSG00000120586 | NA | NA | −1.38 | −1.16 | NA |
| ENSG00000230019 | YWHAQP9 | YWHAQ pseudogene 9 [Source:HGNC Symbol; Acc:HGNC:37688] | −1.19 | −1.18 | NA |
| ENSG00000253377 | | | −1.65 | −1.18 | NA |
| ENSG00000243824 | | | −1.32 | −1.22 | NA |
| ENSG00000184674 | NA | NA | −1.15 | −1.22 | NA |
| ENSG00000250461 | | | −1.96 | −1.28 | NA |
| ENSG00000266603 | NA | NA | −1.11 | −1.31 | NA |
| ENSG00000263929 | NA | NA | −1.29 | −1.33 | NA |

TABLE 27-continued

Some biomarkers that are differentially expressed in plasma based on the number of head impact incidents

| Ensembl_ID | hgnc_symbol | description | high_freq_hits_vs_Baseline.x | high_freq_hits_vs_Low_freq_hits.x | low_freq_hits_vs_Baseline.x |
|---|---|---|---|---|---|
| ENSG00000250612 | | | −2.06 | −1.43 | NA |
| ENSG00000259411 | HNRNPA1P45 | heterogeneous nuclear ribonucleoprotein A1 pseudogene 45 [Source:HGNC Symbol; Acc:HGNC:48775] | −1.33 | −1.52 | NA |
| ENSG00000238754 | | Small nucleolar RNA U109 [Source:RFAM;Acc:RF01233] | NA | −1.55 | NA |
| ENSG00000252497 | RPPH1-2P | ribonuclease P RNA component H1, 2 pseudogene [Source:HGNC Symbol; Acc:HGNC:47029] | −1.54 | −1.56 | NA |
| ENSG00000268995 | VN1R82P | vomeronasal 1 receptor 82 pseudogene [Source:HGNC Symbol; Acc:HGNC:37402] | −1.12 | −1.58 | NA |
| ENSG00000235938 | NA | NA | NA | −2.41 | 1.78 |
| ENSG00000268230 | | | NA | −1.39 | 1.52 |
| ENSG00000270457 | | | NA | −1.94 | 1.40 |
| ENSG00000203426 | NA | NA | NA | −1.52 | 1.30 |
| ENSG00000236876 | TMSB4XP1 | thymosin beta 4, X-linked pseudogene 1 [Source:HGNC Symbol; Acc:HGNC:11883] | NA | NA | 1.24 |
| ENSG00000109854 | HTATIP2 | HIV-1 Tat interactive protein 2, 30 kDa [Source:HGNC Symbol; Acc:HGNC:16637] | 1.04 | NA | 1.22 |
| ENSG00000239617 | | | NA | NA | 1.22 |
| ENSG00000200702 | | Y RNA [Source:RFAM;Acc:RF00019] | NA | −1.27 | 1.22 |
| ENSG00000221096 | NA | NA | NA | −1.71 | 1.14 |
| ENSG00000271361 | HTATSF1P2 | HIV-1 Tat specific factor 1 pseudogene 2 [Source:HGNC Symbol; Acc:HGNC:38586] | 1.01 | NA | 1.11 |
| ENSG00000263740 | RN7SL4P | RNA, 7SL, cytoplasmic 4, pseudogene [Source:HGNC Symbol; Acc:HGNC:10039] | NA | NA | 1.10 |
| ENSG00000198829 | SUCNR1 | succinate receptor 1 [Source:HGNC Symbol; Acc:HGNC:4542] | NA | NA | 1.09 |
| ENSG00000248898 | | | NA | −1.34 | 1.08 |
| ENSG00000236090 | LDHAP3 | lactate dehydrogenase A pseudogene 3 [Source:HGNC Symbol; Acc:HGNC:6538] | −1.35 | NA | −1.02 |
| ENSG00000164237 | CMBL | carboxymethylenebutenolidase homolog (Pseudomonas) [Source:HGNC Symbol; Acc:HGNC:25090] | −1.17 | NA | −1.02 |
| ENSG00000159231 | CBR3 | carbonyl reductase 3 [Source:HGNC Symbol; Acc:HGNC:1549] | NA | 1.16 | −1.06 |
| ENSG00000162817 | C1orf115 | chromosome 1 open reading frame 115 [Source:HGNC Symbol; Acc:HGNC:25873] | −1.02 | NA | −1.07 |
| ENSG00000213401 | MAGEA12 | melanoma antigen family A, 12 [Source:HGNC Symbol; Acc:HGNC:6799] | −1.18 | NA | −1.07 |
| ENSG00000266596 | NA | NA | NA | NA | −1.07 |
| ENSG00000263542 | | | −1.13 | NA | −1.08 |
| ENSG00000165841 | CYP2C19 | cytochrome P450, family 2, subfamily C, polypeptide 19 [Source:HGNC Symbol; Acc:HGNC:2621] | −1.13 | NA | −1.09 |
| ENSG00000164124 | TMEM144 | transmembrane protein 144 [Source:HGNC Symbol; Acc:HGNC:25633] | −1.36 | NA | −1.10 |
| ENSG00000230528 | NOS2P3 | nitric oxide synthase 2 pseudogene 3 [Source:HGNC Symbol; Acc:HGNC:35124] | −1.51 | NA | −1.10 |
| ENSG00000252164 | RNA5SP282 | RNA, 5S ribosomal pseudogene 282 [Source:HGNC Symbol; Acc:HGNC:43182] | −1.38 | NA | −1.10 |
| ENSG00000227274 | | | −1.10 | NA | −1.10 |
| ENSG00000225216 | | | −1.25 | NA | −1.11 |
| ENSG00000257519 | | | −1.09 | NA | −1.11 |
| ENSG00000253008 | MIR2355 | microRNA 2355 [Source:HGNC Symbol; Acc:HGNC:38328] | −1.15 | NA | −1.12 |
| ENSG00000136457 | CHAD | chondroadherin [Source:HGNC Symbol; Acc:HGNC:1909] | NA | NA | −1.12 |
| ENSG00000227438 | | | −1.13 | NA | −1.13 |
| ENSG00000200492 | | Small nucleolar RNA U3 [Source:RFAM;Acc:RF00012] | −1.17 | NA | −1.13 |
| ENSG00000239072 | NA | NA | −1.19 | NA | −1.14 |
| ENSG00000222036 | POTEG | POTE ankyrin domain family, member G [Source:HGNC Symbol; Acc:HGNC:33896] | −1.22 | NA | −1.14 |
| ENSG00000254683 | SNRPCP6 | small nuclear ribonucleoprotein polypeptide C pseudogene 6 [Source:HGNC Symbol; Acc:HGNC:49821] | −1.06 | NA | −1.15 |
| ENSG00000266667 | | | −1.47 | NA | −1.15 |
| ENSG00000119888 | EPCAM | epithelial cell adhesion molecule [Source:HGNC Symbol; Acc:HGNC:11529] | −1.01 | NA | −1.15 |
| ENSG00000251983 | RN7SKP157 | RNA, 7SK small nuclear pseudogene 157 [Source:HGNC Symbol; Acc:HGNC:45881] | −1.27 | NA | −1.16 |

TABLE 27-continued

Some biomarkers that are differentially expressed in plasma based on the number of head impact incidents

| Ensembl_ID | hgnc_symbol | description | high_freq_hits_vs_Baseline.x | high_freq_hits_vs_Low_freq_hits.x | low_freq_hits_vs_Baseline.x |
|---|---|---|---|---|---|
| ENSG00000179914 | ITLN1 | intelectin 1 (galactofuranose binding) [Source:HGNC Symbol; Acc:HGNC:18259] | −1.01 | NA | −1.16 |
| ENSG00000197753 | LHFPL5 | lipoma HMGIC fusion partner-like 5 [Source:HGNC Symbol; Acc:HGNC:21253] | −1.30 | NA | −1.16 |
| ENSG00000259588 | | | NA | NA | −1.16 |
| ENSG00000181227 | | | −1.37 | NA | −1.16 |
| ENSG00000141194 | OR4D1 | olfactory receptor, family 4, subfamily D, member 1 [Source:HGNC Symbol; Acc:HGNC:8293] | −1.52 | NA | −1.17 |
| ENSG00000251354 | | | −1.40 | NA | −1.17 |
| ENSG00000267513 | | | −1.38 | NA | −1.17 |
| ENSG00000227790 | | | −1.22 | NA | −1.17 |
| ENSG00000232491 | | | NA | NA | −1.18 |
| ENSG00000171794 | UTF1 | undifferentiated embryonic cell transcription factor 1 [Source:HGNC Symbol; Acc:HGNC:12634] | −1.28 | NA | −1.18 |
| ENSG00000263774 | | | NA | NA | −1.18 |
| ENSG00000177602 | GSG2 | germ cell associated 2 (haspin) [Source:HGNC Symbol; Acc:HGNC:19682] | −1.04 | NA | −1.19 |
| ENSG00000232120 | | | NA | NA | −1.19 |
| ENSG00000264235 | | | NA | 1.26 | −1.19 |
| ENSG00000183346 | C10orf107 | chromosome 10 open reading frame 107 [Source:HGNC Symbol; Acc:HGNC:28678] | −1.24 | NA | −1.19 |
| ENSG00000265946 | | | −1.27 | NA | −1.20 |
| ENSG00000133116 | KL | klotho [Source:HGNC Symbol; Acc:HGNC:6344] | −1.25 | NA | −1.20 |
| ENSG00000200783 | RN7SKP180 | RNA, 7SK small nuclear pseudogene 180 [Source:HGNC Symbol; Acc:HGNC:45904] | −1.01 | NA | −1.20 |
| ENSG00000227011 | C17orf112 | chromosome 17 open reading frame 112 [Source:HGNC Symbol; Acc:HGNC:42963] | −1.54 | NA | −1.21 |
| ENSG00000237621 | OR9A1P | olfactory receptor, family 9, subfamily A, member 1 pseudogene [Source:HGNC Symbol; Acc:HGNC:8486] | −1.05 | NA | −1.21 |
| ENSG00000259761 | | | −1.23 | NA | −1.21 |
| ENSG00000196565 | HBG2 | hemoglobin, gamma G [Source:HGNC Symbol; Acc:HGNC:4832] | −1.40 | NA | −1.21 |
| ENSG00000236852 | | | NA | NA | −1.21 |
| ENSG00000173728 | C1orf100 | chromosome 1 open reading frame 100 [Source:HGNC Symbol; Acc:HGNC:30435] | NA | NA | −1.21 |
| ENSG00000238617 | NA | NA | −1.07 | NA | −1.22 |
| ENSG00000255031 | | | −1.23 | NA | −1.22 |
| ENSG00000204250 | LINC00587 | long intergenic non-protein coding RNA 587 [Source:HGNC Symbol; Acc:HGNC:31372] | −1.69 | NA | −1.22 |
| ENSG00000259047 | | | −1.27 | NA | −1.22 |
| ENSG00000266941 | | | NA | NA | −1.22 |
| ENSG00000258273 | | | −1.17 | NA | −1.23 |
| ENSG00000087494 | PTHLH | parathyroid hormone-like hormone [Source:HGNC Symbol; Acc:HGNC:9607] | −1.30 | NA | −1.23 |
| ENSG00000252343 | RNU2-34P | RNA, U2 small nuclear 34, pseudogene [Source:HGNC Symbol; Acc:HGNC:48527] | −1.16 | NA | −1.23 |
| ENSG00000272626 | | | −1.14 | NA | −1.24 |
| ENSG00000258828 | KRT8P2 | keratin 8 pseudogene 2 [Source:HGNC Symbol; Acc:HGNC:20282] | −1.38 | NA | −1.24 |
| ENSG00000224618 | | | −1.54 | NA | −1.24 |
| ENSG00000234713 | | | −1.39 | NA | −1.24 |
| ENSG00000237356 | | | −1.09 | NA | −1.24 |
| ENSG00000250770 | | | −1.07 | NA | −1.25 |
| ENSG00000238858 | NA | NA | NA | NA | −1.25 |
| ENSG00000234683 | | | −1.39 | NA | −1.25 |
| ENSG00000271415 | | | −1.19 | NA | −1.25 |
| ENSG00000239073 | NA | NA | −1.43 | NA | −1.25 |
| ENSG00000248891 | | | NA | NA | −1.26 |
| ENSG00000251062 | | | −1.33 | NA | −1.26 |
| ENSG00000223783 | | | −1.33 | NA | −1.27 |
| ENSG00000259604 | | | NA | NA | −1.27 |
| ENSG00000226659 | | | −1.43 | NA | −1.27 |
| ENSG00000235147 | | | NA | 1.12 | −1.28 |
| ENSG00000264296 | | | NA | NA | −1.29 |
| ENSG00000223026 | RN7SKP247 | RNA, 7SK small nuclear pseudogene 247 [Source:HGNC Symbol; Acc:HGNC:45971] | −1.22 | NA | −1.29 |
| ENSG00000241656 | UBA52P7 | ubiquitin A-52 residue ribosomal protein fusion product 1 pseudogene 7 [Source:HGNC Symbol; Acc:HGNC:36615] | −1.12 | NA | −1.29 |

TABLE 27-continued

Some biomarkers that are differentially expressed in plasma based on the number of head impact incidents

| Ensembl_ID | hgnc_symbol | description | high_freq_ hits_vs_ Baseline.x | high_freq_ hits_vs_ Low_freq_ hits.x | low_freq_ hits_vs_ Baseline.x |
|---|---|---|---|---|---|
| ENSG00000257777 | | | NA | NA | −1.30 |
| ENSG00000221083 | | Small nucleolar RNA SNORA77 [Source:RFAM;Acc:RF00599] | −2.14 | NA | −1.30 |
| ENSG00000269069 | | | −1.21 | NA | −1.30 |
| ENSG00000241954 | | | NA | NA | −1.30 |
| ENSG00000163793 | DNAJC5G | DnaJ (Hsp40) homolog, subfamily C, member 5 gamma [Source:HGNC Symbol; Acc:HGNC:24844] | −1.39 | NA | −1.32 |
| ENSG00000264910 | RN7SL525P | RNA, 7SL, cytoplasmic 525, pseudogene [Source:HGNC Symbol; Acc:HGNC:46541] | −1.21 | NA | −1.32 |
| ENSG00000211538 | MIR501 | microRNA 501 [Source:HGNC Symbol; Acc:HGNC:32135] | NA | NA | −1.32 |
| ENSG00000256257 | CACNA1C-1T2 | CACNA1C intronic transcript 2 (non-protein coding) [Source:HGNC Symbol; Acc:HGNC:41313] | NA | NA | −1.32 |
| ENSG00000253784 | | | −1.33 | NA | −1.32 |
| ENSG00000226981 | ABHD17AP6 | abhydrolase domain containing 17A pseudogene 6 [Source:HGNC Symbol; Acc:HGNC:34044] | NA | NA | −1.32 |
| ENSG00000134627 | PIWIL4 | piwi-like RNA-mediated gene silencing 4 [Source:HGNC Symbol; Acc:HGNC:18444] | −1.10 | NA | −1.33 |
| ENSG00000197417 | SHPK | sedoheptulokinase [Source:HGNC Symbol; Acc:HGNC:1492] | −1.10 | NA | −1.33 |
| ENSG00000257004 | | | −1.15 | NA | −1.34 |
| ENSG00000215089 | KRT18P11 | keratin 18 pseudogene 11 [Source:HGNC Symbol; Acc:HGNC:6431] | NA | 1.24 | −1.34 |
| ENSG00000255003 | CYCSP28 | cytochrome c, somatic pseudogene 28 [Source:HGNC Symbol; Acc:HGNC:24402] | −1.25 | NA | −1.34 |
| ENSG00000167230 | NA | NA | −1.07 | NA | −1.35 |
| ENSG00000234113 | | | −1.39 | NA | −1.35 |
| ENSG00000121594 | CD80 | CD80 molecule [Source:HGNC Symbol; Acc:HGNC:1700] | −1.29 | NA | −1.35 |
| ENSG00000228648 | | | −1.25 | NA | −1.36 |
| ENSG00000229338 | | | −1.73 | NA | −1.36 |
| ENSG00000226801 | OSTCP8 | oligosaccharyltransferase complex subunit pseudogene 8 [Source:HGNC Symbol; Acc:HGNC:42869] | NA | 1.40 | −1.36 |
| ENSG00000213014 | VN2R17P | vomeronasal 2 receptor 17 pseudogene [Source:HGNC Symbol; Acc:HGNC:33223] | −1.31 | NA | −1.36 |
| ENSG00000227970 | NR1H5P | nuclear receptor subfamily 1, group H, member 5, pseudogene [Source:HGNC Symbol; Acc:HGNC:32673] | −1.21 | NA | −1.37 |
| ENSG00000230495 | | | −1.40 | NA | −1.37 |
| ENSG00000235154 | | | −1.36 | NA | −1.37 |
| ENSG00000253603 | | | −1.68 | NA | −1.37 |
| ENSG00000177685 | CRACR2B | calcium release activated channel regulator 2B [Source:HGNC Symbol; Acc:HGNC:28703] | NA | 1.24 | −1.38 |
| ENSG00000243136 | RN7SL22P | RNA, 7SL, cytoplasmic 22, pseudogene [Source:HGNC Symbol; Acc:HGNC:46038] | −1.62 | NA | −1.39 |
| ENSG00000264439 | | | −1.17 | NA | −1.39 |
| ENSG00000240808 | | | −1.59 | NA | −1.39 |
| ENSG00000263435 | | | −1.35 | NA | −1.39 |
| ENSG00000243290 | IGKV1-12 | immunoglobulin kappa variable 1-12 [Source:HGNC Symbol; Acc:HGNC:5730] | −1.03 | NA | −1.39 |
| ENSG00000258845 | | | −1.26 | NA | −1.41 |
| ENSG00000260282 | EIF4EBP2P2 | eukaryotic translation initiation factor 4E binding protein 2 pseudogene 2 [Source:HGNC Symbol; Acc:HGNC:49317] | −1.22 | NA | −1.42 |
| ENSG00000252904 | | Small nucleolar RNA SNORA76 [Source:RFAM;Acc:RF00598] | −1.48 | NA | −1.42 |
| ENSG00000266187 | RN7SL480P | RNA, 7SL, cytoplasmic 480, pseudogene [Source:HGNC Symbol; Acc:HGNC:46496] | NA | NA | −1.42 |
| ENSG00000258790 | KIAA0391 | KIAA0391 [Source:HGNC Symbol; Acc:HGNC:19958] | −1.27 | NA | −1.44 |
| ENSG00000258642 | | | NA | NA | −1.45 |
| ENSG00000127588 | GNG13 | guanine nucleotide binding protein (G protein), gamma 13 [Source:HGNC Symbol; Acc:HGNC:14131] | NA | 1.36 | −1.45 |
| ENSG00000213048 | OR5S1P | olfactory receptor, family 5, subfamily S, member 1 pseudogene [Source:HGNC Symbol; Acc:HGNC:15040] | −1.12 | NA | −1.46 |

TABLE 27-continued

Some biomarkers that are differentially expressed in plasma based on the number of head impact incidents

| Ensembl_ID | hgnc_symbol | description | high_freq_hits_vs_Baseline.x | high_freq_hits_vs_Low_freq_hits.x | low_freq_hits_vs_Baseline.x |
|---|---|---|---|---|---|
| ENSG00000225112 | | | NA | 1.14 | −1.47 |
| ENSG00000266399 | | | −1.13 | NA | −1.48 |
| ENSG00000184108 | TRIML1 | tripartite motif family-like 1 [Source:HGNC Symbol; Acc:HGNC:26698] | −1.24 | NA | −1.49 |
| ENSG00000254070 | | | −1.40 | NA | −1.50 |
| ENSG00000250360 | | | −1.09 | NA | −1.50 |
| ENSG00000147183 | CPXCR1 | CPX chromosome region, candidate 1 [Source:HGNC Symbol; Acc:HGNC:2332] | −1.37 | NA | −1.51 |
| ENSG00000234724 | HDAC1P1 | histone deacetylase 1 pseudogene 1 [Source:HGNC Symbol; Acc:HGNC:45190] | −1.29 | NA | −1.52 |
| ENSG00000257915 | GLULP5 | glutamate-ammonia ligase (glutamine synthetase) pseudogene 5 [Source:HGNC Symbol; Acc:HGNC:37989] | −1.12 | NA | −1.52 |
| ENSG00000254273 | | | −1.11 | NA | −1.55 |
| ENSG00000230867 | | | −1.31 | NA | −1.55 |
| ENSG00000188060 | RAB42 | RAB42, member RAS oncogene family [Source:HGNC Symbol; Acc:HGNC:28702] | −1.31 | NA | −1.56 |
| ENSG00000200753 | | Small nucleolar RNA SNORD56 [Source:RFAM;Acc:RF00275] | −1.16 | NA | −1.57 |
| ENSG00000230022 | FNTAP2 | farnesyltransferase, CAAX box, alpha pseudogene 2 [Source:HGNC Symbol; Acc:HGNC:3784] | −1.29 | NA | −1.57 |
| ENSG00000259802 | | | NA | 1.12 | −1.57 |
| ENSG00000227676 | LINC01068 | long intergenic non-protein coding RNA 1068 [Source:HGNC Symbol; Acc:HGNC:49106] | −1.33 | NA | −1.59 |
| ENSG00000252180 | NA | NA | −1.43 | NA | −1.59 |
| ENSG00000229485 | KSR1P1 | kinase suppressor of ras 1 pseudogene 1 [Source:HGNC Symbol; Acc:HGNC:44977] | NA | 1.16 | −1.61 |
| ENSG00000233643 | | | −1.06 | NA | −1.61 |
| ENSG00000268357 | VN1R81P | vomeronasal 1 receptor 81 pseudogene [Source:HGNC Symbol; Acc:HGNC:37401] | −1.44 | NA | −1.61 |
| ENSG00000270496 | BNIP3P7 | BCL2/adenovirus E1B 19 kDa interacting protein 3 pseudogene 7 [Source:HGNC Symbol; Acc:HGNC:49101] | −1.68 | NA | −1.63 |
| ENSG00000206637 | | Small nucleolar RNA SNORA70 [Source:RFAM;Acc:RF00156] | −1.26 | NA | −1.64 |
| ENSG00000198787 | OR4D12P | olfactory receptor, family 4, subfamily D, member 12 pseudogene [Source:HGNC Symbol; Acc:HGNC:19587] | −1.48 | NA | −1.66 |
| ENSG00000234619 | RPL7P11 | ribosomal protein L7 pseudogene 11 [Source:HGNC Symbol; Acc:HGNC:35667] | −1.09 | NA | −1.70 |
| ENSG00000230515 | | | −1.29 | NA | −1.71 |
| ENSG00000250347 | | | −1.20 | NA | −1.71 |
| ENSG00000228513 | | | −1.34 | NA | −1.72 |
| ENSG00000207712 | MIR627 | microRNA 627 [Source:HGNC Symbol; Acc:HGNC:32883] | −1.10 | NA | −1.74 |
| ENSG00000270377 | | | −1.20 | NA | −1.85 |
| ENSG00000249429 | | | −1.79 | NA | −1.96 |

TABLE 28

Some biomarkers that are differentially expressed in plasma based on the level of head impact.

| Ensembl_ID | hgnc_symbol | description | Max_hitsp_vs_Baseline.x | Max_hitsp_vs_Min_hitsp.x | Min_hitsp_vs_Baseline.x |
|---|---|---|---|---|---|
| ENSG00000225181 | | | NA | NA | −1.88 |
| ENSG00000264386 | MIR4513 | microRNA 4513 [Source: HGNC Symbol; Acc: HGNC: 41855] | NA | −1.47 | 1.49 |
| ENSG00000252670 | NA | NA | NA | NA | 1.34 |
| ENSG00000235186 | | | NA | NA | −1.33 |
| ENSG00000270680 | | | NA | NA | −1.37 |
| ENSG00000201271 | RNU1-112P | RNA, U1 small nuclear 112, pseudogene [Source: HGNC Symbol; Acc: HGNC: 48454] | NA | NA | −1.39 |
| ENSG00000238763 | NA | NA | NA | NA | −1.41 |
| ENSG00000230645 | | | NA | NA | −1.50 |
| ENSG00000261665 | TUBA8P2 | tubulin, alpha 8 pseudogene 2 [Source: HGNC Symbol; Acc: HGNC: 44569] | NA | NA | −1.62 |

TABLE 28-continued

Some biomarkers that are differentially expressed in plasma based on the level of head impact.

| Ensembl_ID | hgnc_symbol | description | Max_hitsp_vs_Baseline.x | Max_hitsp_vs_Min_hitsp.x | Min_hitsp_vs_Baseline.x |
|---|---|---|---|---|---|
| ENSG00000265408 | | | NA | NA | −1.64 |
| ENSG00000182393 | IFNL1 | interferon, lambda 1 [Source: HGNC Symbol; Acc: HGNC: 18363] | NA | 1.85 | −1.87 |
| ENSG00000237973 | MIR6723 | microRNA 6723 [Source: HGNC Symbol; Acc: HGNC: 50152] | NA | 1.49 | NA |
| ENSG00000221096 | NA | NA | NA | −1.48 | NA |
| ENSG00000259145 | NA | NA | NA | −1.62 | NA |
| ENSG00000268995 | VN1R82P | vomeronasal 1 receptor 82 pseudogene [Source: HGNC Symbol; Acc: HGNC: 37402] | NA | −1.80 | NA |
| ENSG00000238754 | | Small nucleolar RNA U109NA [Source: RFAM; Acc: RF01233] | NA | −1.88 | NA |
| ENSG00000203426 | NA | NA | NA | −1.70 | 1.64 |
| ENSG00000239617 | | | NA | −1.76 | 1.57 |
| ENSG00000200702 | | Y RNA [Source: RFAM; Acc: RF00019] | NA | −1.42 | 1.54 |
| ENSG00000109854 | HTATIP2 | HIV-1 Tat interactive protein 2, 30 kDa [Source: HGNC Symbol; Acc: HGNC: 16637] | NA | NA | 1.45 |
| ENSG00000248898 | | | NA | −1.80 | 1.34 |
| ENSG00000198829 | SUCNR1 | succinate receptor 1 [Source: HGNC Symbol; Acc: HGNC: 4542] | NA | NA | 1.25 |
| ENSG00000269028 | MTRNR2L12 | MT-RNR2-like 12 [Source: HGNC Symbol; Acc: HGNC: 37169] | NA | −1.83 | 1.12 |
| ENSG00000259588 | | | NA | NA | −1.28 |
| ENSG00000196565 | HBG2 | hemoglobin, gamma G [Source: HGNC Symbol; Acc: HGNC: 4832] | NA | NA | −1.30 |
| ENSG00000127588 | GNG13 | guanine nucleotide binding protein (G protein), gamma 13 [Source: HGNC Symbol; Acc: HGNC: 14131] | NA | 2.00 | −1.33 |
| ENSG00000215089 | KRT18P11 | keratin 18 pseudogene 11 [Source: HGNC Symbol; Acc: HGNC: 6431] | NA | NA | −1.33 |
| ENSG00000177685 | CRACR2B | calcium release activated channel regulator 2B [Source: HGNC Symbol; Acc: HGNC: 28703] | NA | 1.94 | −1.36 |
| ENSG00000159231 | CBR3 | carbonyl reductase 3 [Source: HGNC Symbol; Acc: HGNC: 1549] | NA | 1.38 | −1.38 |
| ENSG00000181227 | | | NA | NA | −1.42 |
| ENSG00000204389 | HSPA1A | heat shock 70 kDa protein 1A [Source: HGNC Symbol; Acc: HGNC: 5232] | NA | 1.35 | −1.43 |
| ENSG00000147183 | CPXCR1 | CPXchromosome region, candidate 1 [Source: HGNC Symbol; Acc: HGNC: 2332] | NA | NA | −1.44 |
| ENSG00000233265 | MICF | MHC class I polypeptide-related sequence F (pseudogene) [Source: HGNC Symbol; Acc: HGNC: 16801] | NA | 1.95 | −1.44 |
| ENSG00000236852 | | | NA | NA | −1.45 |
| ENSG00000252343 | RNU2-34P | RNA, U2 small nuclear 34, pseudogene [Source: HGNC Symbol; Acc: HGNC: 48527] | NA | NA | −1.47 |
| ENSG00000229485 | KSR1P1 | kinase suppressor of ras 1 pseudogene 1 [Source: HGNC Symbol; Acc: HGNC: 44977] | NA | 2.02 | −1.52 |
| ENSG00000259802 | | | NA | NA | −1.59 |
| ENSG00000264235 | | | NA | NA | −1.74 |
| ENSG00000158856 | DMTN | dematin actin binding protein [Source: HGNC Symbol; Acc: HGNC: 3382] | 1.99 | 1.31 | NA |
| ENSG00000265565 | MIR3143 | microRNA 3143 [Source: HGNC Symbol; Acc: HGNC: 38284] | 1.94 | 1.47 | NA |
| ENSG00000272468 | | | 1.89 | 1.23 | NA |
| ENSG00000100345 | MYH9 | myosin, heavy chain 9, non-muscle [Source: HGNC Symbol; Acc: HGNC: 7579] | 1.85 | 1.41 | NA |
| ENSG00000268230 | | | 1.82 | 1.24 | NA |
| ENSG00000242716 | NA | NA | 1.82 | 2.01 | NA |
| ENSG00000175602 | CCDC85B | coiled-coil domain containing 85B [Source: HGNC Symbol; Acc: HGNC: 24926] | 1.81 | 1.30 | NA |
| ENSG00000223554 | | | 1.78 | 2.21 | NA |
| ENSG00000235938 | NA | NA | 1.66 | NA | 1.47 |
| ENSG00000133136 | GNG5P2 | guanine nucleotide binding protein (G protein), gamma 5 pseudogene 2 [Source: HGNC Symbol; Acc: HGNC: 24826] | 1.63 | 1.64 | NA |
| ENSG00000227159 | DDX11L16 | DEAD/H (Asp-Glu-Ala-Asp/His) box helicase 11 like 16 [Source: HGNC Symbol; Acc: HGNC: 37115] | 1.62 | NA | 1.20 |
| ENSG00000168067 | MAP4K2 | mitogen-activated protein kinase kinase kinase kinase 2 [Source: HGNC Symbol; Acc: HGNC: 6864] | 1.62 | 1.03 | NA |
| ENSG00000270457 | | | 1.40 | NA | NA |
| ENSG00000215030 | RPL13P12 | ribosomal protein L13 pseudogene 12 [Source: HGNC Symbol; Acc: HGNC: 35701] | 1.39 | 2.18 | NA |
| ENSG00000176043 | | | 1.38 | NA | 1.44 |
| ENSG00000141179 | PCTP | phosphatidylcholine transfer protein [Source: HGNC Symbol; Acc: HGNC: 8752] | 1.36 | 1.22 | NA |

TABLE 28-continued

Some biomarkers that are differentially expressed in plasma based on the level of head impact.

| Ensembl_ID | hgnc_symbol | description | Max_hitsp_vs_Baseline.x | Max_hitsp_vs_Min_hitsp.x | Min_hitsp_vs_Baseline.x |
| --- | --- | --- | --- | --- | --- |
| ENSG00000263740 | RN7SL4P | RNA, 7SL, cytoplasmic 4, pseudogene [Source: HGNC Symbol; Acc: HGNC: 10039] | 1.34 | NA | 1.12 |
| ENSG00000148848 | ADAM12 | ADAM metallopeptidase domain 12 [Source: HGNC Symbol; Acc: HGNC: 190] | 1.30 | 1.17 | NA |
| ENSG00000271361 | HTATSF1P2 | HIV-1 Tat specific factor 1 pseudogene 2 [Source: HGNC Symbol; Acc: HGNC: 38586] | 1.24 | NA | 1.42 |
| ENSG00000229344 | | | 1.23 | 1.27 | NA |
| ENSG00000234975 | FTH1P2 | ferritin, heavy polypeptide 1 pseudogene 2 [Source: HGNC Symbol; Acc: HGNC: 3989] | 1.16 | 1.28 | NA |
| ENSG00000236876 | TMSB4XP1 | thymosin beta 4, X-linked pseudogene 1 [Source: HGNC Symbol; Acc: HGNC: 11883] | 1.16 | NA | NA |
| ENSG00000166086 | JAM3 | junctional adhesion molecule 3 [Source: HGNC Symbol; Acc: HGNC: 15532] | 1.07 | NA | NA |
| ENSG00000162817 | C1orf115 | chromosome 1 open reading frame 115 [Source: HGNC Symbol; Acc: HGNC: 25873] | −1.04 | NA | −1.13 |
| ENSG00000164237 | CMBL | carboxymethylenebutenolidase homolog (Pseudomonas) [Source: HGNC Symbol; Acc: HGNC: 25090] | −1.06 | NA | NA |
| ENSG00000172476 | RAB40A | RAB40A, member RAS oncogene family [Source: HGNC Symbol; Acc: HGNC: 18283] | −1.10 | −1.23 | NA |
| ENSG00000260198 | | | −1.22 | NA | −1.18 |
| ENSG00000237256 | PGAM3P | phosphoglycerate mutase 3, pseudogene [Source: HGNC Symbol; Acc: HGNC: 16557] | −1.23 | NA | −1.87 |
| ENSG00000119888 | EPCAM | epithelial cell adhesion molecule [Source: HGNC Symbol; Acc: HGNC: 11529] | −1.26 | NA | NA |
| ENSG00000230589 | IMP3P1 | IMP3 pseudogene 1 [Source: HGNC Symbol; Acc: HGNC: 49385] | −1.26 | NA | NA |
| ENSG00000230022 | FNTAP2 | farnesyltransferase, CAAX box, alpha pseudogene 2 [Source: HGNC Symbol; Acc: HGNC: 3784] | 1.27 | NA | −1.70 |
| ENSG00000227438 | | | −1.28 | NA | −1.25 |
| ENSG00000227790 | | | −1.29 | NA | −1.31 |
| ENSG00000237356 | | | −1.29 | NA | −1.23 |
| ENSG00000204250 | LINC00587 | long intergenic non-protein coding RNA 587 [Source: HGNC Symbol; Acc: HGNC: 31372] | −1.29 | NA | −1.39 |
| ENSG00000270683 | FAM71BP1 | family with sequence similarity 71, member B pseudogene 1 [Source: HGNC Symbol; Acc: HGNC: 49805] | −1.29 | −1.66 | NA |
| ENSG00000200783 | RN7SKP180 | RNA, 7SK small nuclear pseudogene 180 [Source: HGNC Symbol; Acc: HGNC: 45904] | −1.30 | NA | −1.28 |
| ENSG00000165841 | CYP2C19 | cytochrome P450, family 2, subfamily C, polypeptide 19 [Source: HGNC Symbol; Acc: HGNC: 2621] | −1.33 | NA | −1.28 |
| ENSG00000263542 | | | −1.34 | NA | −1.30 |
| ENSG00000256972 | | | −1.34 | NA | NA |
| ENSG00000250347 | | | −1.34 | NA | −1.83 |
| ENSG00000263929 | NA | NA | −1.35 | −1.65 | NA |
| ENSG00000269069 | | | −1.35 | NA | −1.40 |
| ENSG00000261340 | | | −1.35 | NA | NA |
| ENSG00000197568 | HHLA3 | HERV-H LTR-associating 3 [Source: HGNC Symbol; Acc: HGNC: 4906] | −1.36 | NA | −1.23 |
| ENSG00000227011 | C17orf112 | chromosome 17 open reading frame 112 [Source: HGNC Symbol; Acc: HGNC: 42963] | −1.36 | NA | −1.33 |
| ENSG00000198787 | OR4D12P | olfactory receptor, family 4, subfamily D, member 12 pseudogene [Source: HGNC Symbol; Acc: HGNC: 19587] | −1.36 | NA | −1.69 |
| ENSG00000258088 | | | −1.36 | NA | −1.22 |
| ENSG00000229775 | | | −1.36 | NA | −1.59 |
| ENSG00000258790 | KIAA0391 | KIAA0391 [Source: HGNC Symbol; Acc: HGNC: 19958] | −1.36 | NA | −1.36 |
| ENSG00000223783 | | | −1.36 | NA | −1.18 |
| ENSG00000224924 | LINC00320 | long intergenic non-protein coding RNA 320 [Source: HGNC Symbol; Acc: HGNC: 19690] | −1.36 | NA | NA |
| ENSG00000159186 | | | −1.37 | NA | NA |
| ENSG00000188060 | RAB42 | RAB42, member RAS oncogene family [Source: HGNC Symbol; Acc: HGNC: 28702] | −1.37 | NA | −1.49 |
| ENSG00000257723 | CHCHD3P2 | coiled-coil-helix-coiled-coil-helix domain containing 3 pseudogene 2 [Source: HGNC Symbol; Acc: HGNC: 44698] | −1.38 | −1.42 | NA |
| ENSG00000241656 | UBA52P7 | ubiquitin A-52 residue ribosomal protein fusion product 1 pseudogene 7 [Source: HGNC Symbol; Acc: HGNC: 36615] | −1.39 | NA | −1.35 |
| ENSG00000253008 | MIR2355 | microRNA 2355 [Source: HGNC Symbol; Acc: HGNC: 38328] | −1.39 | NA | −1.36 |
| ENSG00000224618 | | | −1.40 | NA | NA |
| ENSG00000266399 | | | −1.40 | NA | −1.75 |

TABLE 28-continued

Some biomarkers that are differentially expressed in plasma based on the level of head impact.

| Ensembl_ID | hgnc_symbol | description | Max_hitsp_vs_Baseline.x | Max_hitsp_vs_Min_hitsp.x | Min_hitsp_vs_Baseline.x |
|---|---|---|---|---|---|
| ENSG00000167230 | NA | NA | −1.40 | NA | −1.31 |
| ENSG00000200492 | | Small nucleolar RNA U3 [Source: RFAM; Acc: RF00012] | −1.40 | NA | −1.37 |
| ENSG00000239072 | NA | NA | −1.41 | NA | −1.37 |
| ENSG00000222524 | RN7SKP109 | RNA, 7SK small nuclear pseudogene 109 [Source: HGNC Symbol; Acc: HGNC: 45833] | −1.41 | NA | NA |
| ENSG00000226659 | | | −1.41 | NA | NA |
| ENSG00000249465 | RBMXP4 | RNA binding motif protein, X-linked pseudogene 4 [Source: HGNC Symbol; Acc: HGNC: 34028] | −1.41 | NA | NA |
| ENSG00000238460 | | | −1.42 | −1.67 | NA |
| ENSG00000255003 | CYCSP28 | cytochrome c, somatic pseudogene 28 [Source: HGNC Symbol; Acc: HGNC: 24402] | −1.42 | NA | −1.65 |
| ENSG00000255031 | | | −1.42 | NA | −1.45 |
| ENSG00000264439 | | | −1.43 | NA | −1.63 |
| ENSG00000213014 | VN2R17P | vomeronasal 2 receptor 17 pseudogene [Source: HGNC Symbol; Acc: HGNC: 33223] | −1.44 | NA | −1.34 |
| ENSG00000172769 | OR5B3 | olfactory receptor, family 5, subfamily B, member 3 [Source: HGNC Symbol; Acc: HGNC: 8324] | −1.44 | NA | NA |
| ENSG00000225216 | | | −1.44 | NA | NA |
| ENSG00000235147 | | | −1.44 | NA | −1.90 |
| ENSG00000270798 | | | −1.45 | −1.43 | NA |
| ENSG00000233545 | CYCSP33 | cytochrome c, somatic pseudogene 33 [Source: HGNC Symbol; Acc: HGNC: 24407] | −1.45 | NA | NA |
| ENSG00000248891 | | | −1.45 | NA | −1.70 |
| ENSG00000203691 | NA | NA | −1.45 | NA | NA |
| ENSG00000225906 | | | −1.45 | NA | NA |
| ENSG00000184674 | NA | NA | −1.47 | −1.79 | NA |
| ENSG00000168992 | OR7E102P | olfactory receptor, family 7, subfamily E, member 102 pseudogene [Source: HGNC Symbol; Acc: HGNC: 15043] | −1.47 | NA | −2.00 |
| ENSG00000186453 | FAM228A | family with sequence similarity 228, member A [Source: HGNC Symbol; Acc: HGNC: 34418] | −1.47 | NA | −1.29 |
| ENSG00000226981 | ABHD17AP6 | abhydrolase domain containing 17A pseudogene 6 [Source: HGNC Symbol; Acc: HGNC: 34044] | −1.47 | NA | −1.45 |
| ENSG00000183346 | C10orf107 | chromosome 10 open reading frame 107 [Source: HGNC Symbol; Acc: HGNC: 28678] | −1.47 | NA | NA |
| ENSG00000227274 | | | −1.47 | NA | NA |
| ENSG00000212338 | | Small nucleolar RNA SNORA67 [Source: RFAM; Acc: RF00272] | −1.47 | NA | −1.42 |
| ENSG00000255408 | PCDHA3 | protocadherin alpha 3 [Source: HGNC Symbol; Acc: HGNC: 8669] | −1.48 | NA | −1.44 |
| ENSG00000219368 | ZNF299P | zinc finger protein 299, pseudogene [Source: HGNC Symbol; Acc: HGNC: 13088] | −1.48 | NA | NA |
| ENSG00000253849 | | | −1.48 | NA | NA |
| ENSG00000234713 | | | −1.48 | NA | −1.41 |
| ENSG00000263253 | | | −1.48 | NA | NA |
| ENSG00000213401 | MAGEA12 | melanoma antigen family A, 12 [Source: HGNC Symbol; Acc: HGNC: 6799] | −1.48 | NA | NA |
| ENSG00000266603 | NA | NA | −1.48 | −1.95 | NA |
| ENSG00000223026 | RN7SKP247 | RNA, 7SK small nuclear pseudogene 247 [Source: HGNC Symbol; Acc: HGNC: 45971] | −1.49 | NA | −1.39 |
| ENSG00000251062 | | | −1.49 | NA | −1.75 |
| ENSG00000163993 | S100P | S100 calcium binding protein P [Source: HGNC Symbol; Acc: HGNC: 10504] | −1.49 | NA | −1.45 |
| ENSG00000224418 | STK24-AS1 | STK24 antisense RNA 1 [Source: HGNC Symbol; Acc: HGNC: 39935] | −1.49 | −1.34 | NA |
| ENSG00000213144 | | | −1.50 | NA | NA |
| ENSG00000179914 | ITLN1 | intelectin 1 (galactofuranose binding) [Source: HGNC Symbol; Acc: HGNC: 18259] | −1.50 | NA | −1.26 |
| ENSG00000259047 | | | −1.50 | NA | −1.46 |
| ENSG00000237621 | OR9A1P | olfactory receptor, family 9, subfamily A, member 1 pseudogene[Source: HGNC Symbol; Acc: HGNC: 8486] | −1.50 | NA | −1.25 |
| ENSG00000241954 | | | −1.51 | NA | −1.68 |
| ENSG00000231682 | | | −1.51 | −1.32 | NA |
| ENSG00000254070 | | | −1.52 | NA | −1.72 |
| ENSG00000258273 | | | −1.52 | NA | −1.49 |
| ENSG00000251751 | RN7SKP46 | RNA, 7SK small nuclear pseudogene 46 [Source: HGNC Symbol; Acc: HGNC: 45770] | −1.52 | NA | −1.41 |
| ENSG00000228513 | | | −1.52 | NA | −1.96 |
| ENSG00000226272 | ARHGAP26-AS1 | ARHGAP26antisense RNA 1 [Source: HGNC Symbol; Acc: HGNC: 40792] | −1.52 | NA | −1.22 |
| ENSG00000233643 | | | −1.52 | NA | −1.64 |
| ENSG00000258828 | KRT8P2 | keratin 8 pseudogene 2 [Source: HGNC Symbol; Acc: HGNC: 20282] | −1.53 | NA | −1.35 |

TABLE 28-continued

Some biomarkers that are differentially expressed in plasma based on the level of head impact.

| Ensembl_ID | hgnc_symbol | description | Max_hitsp_vs_Baseline.x | Max_hitsp_vs_Min_hitsp.x | Min_hitsp_vs_Baseline.x |
|---|---|---|---|---|---|
| ENSG00000234619 | RPL7P11 | ribosomal protein L7 pseudogene 11 [Source: HGNC Symbol; Acc: HGNC: 35667] | −1.53 | NA | −1.78 |
| ENSG00000234683 | | | −1.53 | NA | NA |
| ENSG00000164124 | TMEM144 | transmembrane protein 144 [Source: HGNC Symbol; Acc: HGNC: 25633] | −1.53 | NA | −1.05 |
| ENSG00000258642 | | | −1.54 | NA | −1.63 |
| ENSG00000197753 | LHFPL5 | lipoma HMGIC fusion partner-like 5 [Source: HGNC Symbol; Acc: HGNC: 21253] | −1.55 | NA | NA |
| ENSG00000252672 | NA | NA | −1.55 | NA | −1.94 |
| ENSG00000271415 | | | −1.55 | NA | −1.52 |
| ENSG00000239791 | | | −1.56 | NA | NA |
| ENSG00000227970 | NR1H5P | nuclear receptor subfamily 1, group H, member 5, pseudogene [Source: HGNC Symbol; Acc: HGNC: 32673] | −1.56 | NA | −1.33 |
| ENSG00000206848 | RNU6-890P | RNA, U6 small nuclear 890, pseudogene [Source: HGNC Symbol; Acc: HGNC: 47853] | −1.56 | NA | NA |
| ENSG00000177602 | GSG2 | germ cell associated 2 (haspin) [Source: HGNC Symbol; Acc: HGNC: 19682] | −1.57 | NA | −1.23 |
| ENSG00000171794 | UTF1 | undifferentiated embryonic cell transcription factor 1 [Source: HGNC Symbol; Acc: HGNC: 12634] | −1.58 | NA | NA |
| ENSG00000226801 | OSTCP8 | oligosaccharyltransferase complex subunit pseudogene 8 [Source: HGNC Symbol; Acc: HGNC: 42869] | −1.58 | NA | −1.87 |
| ENSG00000172594 | SMPDL3A | sphingomyelin phosphodiesterase, acid-like 3A [Source: HGNC Symbol; Acc: HGNC: 17389] | −1.58 | −1.31 | NA |
| ENSG00000254845 | NA | NA | −1.58 | NA | NA |
| ENSG00000263493 | NA | NA | −1.59 | NA | NA |
| ENSG00000243824 | | | −1.59 | −1.64 | NA |
| ENSG00000120586 | NA | NA | −1.60 | −1.55 | NA |
| ENSG00000226104 | NA | NA | −1.60 | NA | NA |
| ENSG00000256257 | CACNA1C-IT2 | CACNA1C intronic transcript 2 (non-protein coding) [Source: HGNC Symbol; Acc: HGNC: 41313] | −1.60 | NA | −1.46 |
| ENSG00000237731 | RNGTTP1 | RNA guanylyltransferase and 5'-phosphatase pseudogene 1 [Source: HGNC Symbol; Acc: HGNC: 39652] | −1.60 | NA | −1.69 |
| ENSG00000225785 | | | −1.60 | −1.33 | NA |
| ENSG00000173728 | C1orf100 | chromosome 1 open reading frame 100 [Source: HGNC Symbol; Acc: HGNC: 30435] | −1.61 | NA | −1.32 |
| ENSG00000232650 | | | −1.61 | NA | −1.48 |
| ENSG00000133116 | KL | klotho [Source: HGNC Symbol; Acc: HGNC: 6344] | −1.61 | NA | −1.14 |
| ENSG00000134627 | PIWIL4 | piwi-like RNA-mediated gene silencing 4 [Source: HGNC Symbol; Acc: HGNC: 18444] | −1.61 | NA | −1.27 |
| ENSG00000257777 | | | −1.62 | NA | −1.32 |
| ENSG00000263774 | | | −1.62 | NA | −1.58 |
| ENSG00000234723 | | | −1.63 | −1.65 | NA |
| ENSG00000232491 | | | −1.63 | NA | −1.59 |
| ENSG00000235902 | | | −1.64 | NA | −1.73 |
| ENSG00000232120 | | | −1.64 | NA | −1.37 |
| ENSG00000186038 | HTR3E | 5-hydroxytryptamine (serotonin) receptor 3E, ionotropic [Source: HGNC Symbol; Acc: HGNC: 24005] | −1.64 | NA | −1.21 |
| ENSG00000228648 | | | −1.65 | NA | −1.39 |
| ENSG00000260282 | EIF4EBP2P2 | eukaryotic translation initiation factor 4E binding protein 2 pseudogene 2 [Source: HGNC Symbol; Acc: HGNC: 49317] | −1.65 | NA | −1.52 |
| ENSG00000252596 | NA | NA | −1.66 | NA | −1.62 |
| ENSG00000270496 | BNIP3P7 | BCL2/adenovirus E1B 19 kDa interacting protein 3 pseudogene 7 [Source: HGNC Symbol; Acc: HGNC: 49101] | −1.66 | NA | −1.85 |
| ENSG00000187689 | AMTN | amelotin [Source: HGNC Symbol; Acc: HGNC: 33188] | −1.67 | NA | −1.26 |
| ENSG00000225112 | | | −1.68 | NA | −1.76 |
| ENSG00000254273 | | | −1.68 | NA | −1.76 |
| ENSG00000266596 | NA | NA | −1.69 | NA | NA |
| ENSG00000232578 | | | −1.69 | NA | NA |
| ENSG00000200753 | | Small nucleolar RNA SNORD56 [Source: RFAM;Acc: RF00275] | −1.69 | NA | −1.74 |
| ENSG00000239011 | NA | NA | −1.69 | NA | −1.64 |
| ENSG00000258845 | | | −1.70 | NA | −1.64 |
| ENSG00000238858 | NA | NA | −1.70 | NA | −1.67 |
| ENSG00000252180 | NA | NA | −1.70 | NA | −1.86 |
| ENSG00000267670 | | | −1.71 | NA | −1.80 |
| ENSG00000212564 | RNU6-1326P | RNA, U6 small nuclear 1326, pseudogene [Source: HGNC Symbol; Acc: HGNC: 48289] | −1.71 | NA | −1.88 |
| ENSG00000211967 | IGHV3-53 | immunoglobulin heavy variable 3-53 [Source: HGNC Symbol; Acc: HGNC: 5610] | −1.71 | NA | −1.15 |

TABLE 28-continued

Some biomarkers that are differentially expressed in plasma based on the level of head impact.

| Ensembl_ID | hgnc_symbol | description | Max_hitsp_vs_Baseline.x | Max_hitsp_vs_Min_hitsp.x | Min_hitsp_vs_Baseline.x |
|---|---|---|---|---|---|
| ENSG00000249429 | | | −1.71 | NA | −2.03 |
| ENSG00000266187 | RN7SL480P | RNA, 7SL, cytoplasmic 480, pseudogene [Source: HGNC Symbol; Acc: HGNC: 46496] | −1.72 | NA | −2.01 |
| ENSG00000265946 | | | −1.72 | NA | NA |
| ENSG00000252904 | | Small nucleolar RNA SNORA76 [Source: RFAM;Acc: RF00598] | −1.72 | NA | −1.68 |
| ENSG00000241757 | RN7SL714P | RNA, 7SL, cytoplasmic 714, pseudogene [Source: HGNC Symbol; Acc: HGNC: 46730] | −1.73 | NA | NA |
| ENSG00000222036 | POTEG | POTE ankyrin domain family, member G [Source: HGNC Symbol; Acc: HGNC: 33896] | −1.73 | NA | −1.08 |
| ENSG00000230495 | | | −1.73 | NA | −1.32 |
| ENSG00000257519 | | | −1.73 | NA | NA |
| ENSG00000221291 | | | −1.74 | NA | −1.70 |
| ENSG00000223881 | | | −1.74 | −1.53 | NA |
| ENSG00000251983 | RN7SKP157 | RNA, 7SK small nuclear pseudogene 157 [Source: HGNC Symbol; Acc: HGNC: 45881] | −1.74 | NA | NA |
| ENSG00000240545 | RN7SL492P | RNA, 7SL, cytoplasmic 492, pseudogene [Source: HGNC Symbol; Acc: HGNC: 46508] | −1.74 | −1.56 | NA |
| ENSG00000230867 | | | −1.75 | NA | −1.61 |
| ENSG00000235154 | | | −1.75 | NA | −1.28 |
| ENSG00000197417 | SHPK | sedoheptulokinase [Source: HGNC Symbol; Acc: HGNC: 1492] | −1.76 | NA | −1.33 |
| ENSG00000266941 | | | −1.77 | NA | −1.57 |
| ENSG00000234113 | | | −1.77 | NA | −1.37 |
| ENSG00000163793 | DNAJC5G | DnaJ (Hsp40) homolog, subfamily C, member 5 gamma [Source: HGNC Symbol; Acc: HGNC: 24844] | −1.79 | NA | −1.26 |
| ENSG00000240286 | MEAF6P1 | MYST/Esa1-associated factor 6 pseudogene 1 [Source: HGNC Symbol; Acc: HGNC: 42660] | −1.79 | NA | −2.10 |
| ENSG00000207712 | MIR627 | microRNA 627 [Source: HGNC Symbol; Acc: HGNC: 32883] | −1.80 | NA | −2.13 |
| ENSG00000121594 | CD80 | CD80 molecule [Source: HGNC Symbol; Acc: HGNC: 1700] | −1.80 | NA | −1.34 |
| ENSG00000199470 | | Small nucleolar RNASNORA64/SNORA10 family [Source: RFAM;Acc: RF00264] | −1.81 | NA | −1.40 |
| ENSG00000240808 | | | −1.82 | NA | −1.43 |
| ENSG00000264469 | | | −1.82 | NA | NA |
| ENSG00000257915 | GLULP5 | glutamate-ammonia ligase (glutamine synthetase) pseudogene 5 [Source: HGNC Symbol; Acc: HGNC: 37989] | −1.82 | NA | −1.65 |
| ENSG00000270377 | | | −1.83 | NA | −2.22 |
| ENSG00000227593 | | | −1.84 | NA | −1.31 |
| ENSG00000220505 | EIF4EBP2P3 | eukaryotic translation initiation factor 4E binding protein 2 pseudogene 3 [Source: HGNC Symbol; Acc: HGNC: 49318] | −1.85 | NA | NA |
| ENSG00000230515 | | | −1.85 | NA | −1.78 |
| ENSG00000250770 | | | −1.86 | NA | −1.25 |
| ENSG00000226939 | | | −1.86 | NA | −1.33 |
| ENSG00000239073 | NA | NA | −1.87 | NA | −1.40 |
| ENSG00000251354 | | | −1.87 | NA | NA |
| ENSG00000231957 | GNAI2P2 | guanine nucleotide binding protein (G protein), alpha inhibiting activity polypeptide 2 pseudogene 2 [Source: HGNC Symbol; Acc: HGNC: 45110] | −1.89 | −1.43 | NA |
| ENSG00000141194 | OR4D1 | olfactory receptor, family 4, subfamily D, member 1 [Source: HGNC Symbol; Acc: HGNC: 8293] | −1.90 | NA | NA |
| ENSG00000250256 | | | −1.90 | NA | −1.60 |
| ENSG00000259761 | | | −1.91 | NA | −1.28 |
| ENSG00000257004 | | | −1.93 | NA | −1.65 |
| ENSG00000259418 | | | −1.94 | NA | −1.44 |
| ENSG00000266667 | | | −1.95 | NA | |
| ENSG00000264910 | RN7SL525P | RNA, 7SL, cytoplasmic 525, pseudogene [Source: HGNC Symbol; Acc: HGNC: 46541] | −1.95 | NA | −1.62 |
| ENSG00000252164 | RNA5SP282 | RNA, 5S ribosomal pseudogene 282 [Source: HGNC Symbol; Acc: HGNC: 43182] | −1.96 | NA | NA |
| ENSG00000239547 | RN7SL843P | RNA, 7SL, cytoplasmic 843, pseudogene [Source: HGNC Symbol; Acc: HGNC: 46859] | −1.96 | NA | NA |
| ENSG00000211538 | MIR501 | microRNA 501 [Source: HGNC Symbol; Acc: HGNC: 32135] | −1.99 | NA | −1.58 |
| ENSG00000231680 | | | −1.99 | NA | NA |
| ENSG00000250392 | | | −2.00 | NA | −1.35 |
| ENSG00000087494 | PTHLH | parathyroid hormone-like hormone [Source: HGNC Symbol; Acc: HGNC: 9607] | −2.00 | NA | −1.18 |
| ENSG00000217557 | | | −2.02 | NA | −1.59 |
| ENSG00000267513 | | | −2.03 | NA | NA |
| ENSG00000263435 | | | −2.04 | NA | −1.43 |

TABLE 28-continued

Some biomarkers that are differentially expressed in plasma based on the level of head impact.

| Ensembl_ID | hgnc_symbol | description | Max_hitsp_vs_Baseline.x | Max_hitsp_vs_Min_hitsp.x | Min_hitsp_vs_Baseline.x |
|---|---|---|---|---|---|
| ENSG00000184108 | TRIML1 | tripartite motif family-like 1 [Source: HGNC Symbol; Acc: HGNC: 26698] | −2.05 | NA | −1.50 |
| ENSG00000229338 | | | −2.06 | NA | −1.36 |
| ENSG00000243290 | IGKV1-12 | immunoglobulin kappa variable 1-12 [Source: HGNC Symbol; Acc: HGNC: 5730] | −2.07 | NA | −1.37 |
| ENSG00000272626 | | | −2.07 | NA | −1.36 |
| ENSG00000253603 | | | −2.08 | NA | −1.40 |
| ENSG00000249941 | | | −2.11 | NA | NA |
| ENSG00000260229 | | | −2.13 | −1.41 | NA |
| ENSG00000243136 | RN7SL22P | RNA, 7SL, cytoplasmic 22, pseudogene [Source: HGNC Symbol; Acc: HGNC: 46038] | −2.17 | NA | −1.47 |
| ENSG00000206637 | | Small nucleolar RNA SNORA70 [Source: RFAM;Acc: RF00156] | −2.17 | NA | −2.13 |
| ENSG00000229031 | | | −2.19 | NA | −1.59 |
| ENSG00000268357 | VN1R81P | vomeronasal 1 receptor 81 pseudogene [Source: HGNC Symbol; Acc: HGNC: 37401] | −2.20 | NA | −1.89 |
| ENSG00000227676 | LINC01068 | long intergenic non-protein coding RNA 1068 [Source: HGNC Symbol; Acc: HGNC: 49106] | −2.20 | NA | −1.76 |
| ENSG00000234724 | HDAC1P1 | histone deacetylase 1 pseudogene 1 [Source: HGNC Symbol; Acc: HGNC: 45190] | −2.22 | NA | −1.51 |
| ENSG00000264296 | | | −2.23 | NA | −1.58 |
| ENSG00000185296 | | | −2.24 | NA | −1.45 |
| ENSG00000250612 | | | −2.25 | −1.79 | NA |
| ENSG00000253784 | | | −2.27 | NA | −1.59 |
| ENSG00000236090 | LDHAP3 | lactate dehydrogenase A pseudogene 3 [Source: HGNC Symbol; Acc: HGNC: 6538] | −2.29 | −1.32 | NA |
| ENSG00000244414 | CFHR1 | complement factor H-related 1 [Source: HGNC Symbol; Acc: HGNC: 4888] | −2.50 | −1.41 | NA |
| ENSG00000253780 | IGHVIII-2-1 | immunoglobulin heavy variable (III)-2-1 (pseudogene) [Source: HGNC Symbol; Acc: HGNC: 5695] | −2.57 | −1.47 | NA |
| ENSG00000238617 | NA | NA | −2.65 | NA | −1.30 |
| ENSG00000250360 | | | −2.66 | NA | −1.62 |
| ENSG00000213048 | OR5S1P | olfactory receptor, family 5, subfamily S, member 1 pseudogene [Source: HGNC Symbol; Acc: HGNC: 15040] | −2.81 | NA | −1.70 |

TABLE 29

Biomarkers that are differentially expressed in urine based on the number of head impact incidents

| Ensembl_ID | hgnc_symbol | description | High_freq_hits_vs_Baseline.y | High_freq_hits_vs_Low_freq_hits.y | Low_freq_hits_vs_Baseline.y |
|---|---|---|---|---|---|
| ENSG00000210140 | MT-TC | mitochondrially encoded tRNA cysteine [Source: HGNC Symbol; Acc: HGNC: 7477] | NA | 1.17 | −1.16 |
| ENSG00000229344 | | | 1.58 | 2.02 | NA |
| ENSG00000225972 | MTND1P23 | MT-ND1 pseudogene 23 [Source: HGNC Symbol; Acc: HGNC: 42092] | 1.06 | 1.22 | NA |
| ENSG00000122585 | NPY | neuropeptide Y [Source: HGNC Symbol; Acc: HGNC: 7955] | NA | NA | 1.07 |
| ENSG00000198840 | MT-ND3 | mitochondrially encoded NADH dehydrogenase 3 [Source: HGNC Symbol; Acc: HGNC: 7458] | NA | 1.54 | −1.01 |
| ENSG00000210174 | MT-TR | mitochondrially encoded tRNA arginine [Source: HGNC Symbol; Acc: HGNC: 7496] | NA | 1.67 | −1.01 |
| ENSG00000210191 | MT-TL2 | mitochondrially encoded tRNA leucine 2 (CUN) [Source: HGNC Symbol; Acc: HGNC: 7491] | NA | 1.36 | −1.02 |
| ENSG00000210156 | MT-TK | mitochondrially encoded tRNA lysine [Source: HGNC Symbol; Acc: HGNC: 7489] | NA | 1.65 | −1.02 |
| ENSG00000210049 | MT-TF | mitochondrially encoded tRNA phenylalanine [Source: HGNC Symbol; Acc: HGNC: 7481] | NA | 1.44 | −1.08 |
| ENSG00000210107 | MT-TQ | mitochondrially encoded tRNA glutamine [Source: HGNC Symbol; Acc: HGNC: 7495] | NA | 1.31 | −1.10 |
| ENSG00000210196 | MT-TP | mitochondrially encoded tRNA proline [Source: HGNC Symbol; Acc: HGNC: 7494] | NA | 1.43 | −1.11 |
| ENSG00000210100 | MT-TI | mitochondrially encoded tRNA isoleucine [Source: HGNC Symbol; Acc: HGNC: 7488] | NA | 1.72 | −1.21 |
| ENSG00000210194 | MT-TE | mitochondrially encoded tRNA glutamic acid [Source: HGNC Symbol; Acc: HGNC: 7479] | NA | 1.63 | NA |
| ENSG00000209082 | MT-TL1 | mitochondrially encoded tRNA leucine 1 (UUA/G) [Source: HGNC Symbol; Acc: HGNC: 7490] | NA | 1.60 | NA |

TABLE 29-continued

Biomarkers that are differentially expressed in urine based on the number of head impact incidents

| Ensembl_ID | hgnc_symbol | description | High_freq_hits_vs_Baseline.y | High_freq_hits_vs_Low_freq_hits.y | Low_freq_hits_vs_Baseline.y |
|---|---|---|---|---|---|
| ENSG00000210127 | MT-TA | mitochondrially encoded tRNA alanine [Source: HGNC Symbol; Acc: HGNC: 7475] | NA | 1.55 | NA |
| ENSG00000210195 | MT-TT | mitochondrially encoded tRNA threonine [Source: HGNC Symbol; Acc: HGNC: 7499] | NA | 1.54 | NA |
| ENSG00000210117 | MT-TW | mitochondrially encoded tRNA tryptophan [Source: HGNC Symbol; Acc: HGNC: 7501] | NA | 1.54 | NA |
| ENSG00000210077 | MT-TV | mitochondrially encoded tRNA valine [Source: HGNC Symbol; Acc: HGNC: 7500] | NA | 1.41 | NA |
| ENSG00000210176 | MT-TH | mitochondrially encoded tRNA histidine [Source: HGNC Symbol; Acc: HGNC: 7487] | NA | 1.41 | NA |
| ENSG00000198763 | MT-ND2 | mitochondrially encoded NADH dehydrogenase 2 [Source: HGNC Symbol; Acc: HGNC: 7456] | NA | 1.41 | NA |
| ENSG00000198938 | MT-CO3 | mitochondrially encoded cytochrome c oxidase III [Source: HGNC Symbol; Acc: HGNC: 7422] | NA | 1.35 | NA |
| ENSG00000198786 | MT-ND5 | mitochondrially encoded NADH dehydrogenase 5 [Source: HGNC Symbol; Acc: HGNC: 7461] | NA | 1.34 | NA |
| ENSG00000225630 | MTND2P28 | MT-ND2 pseudogene 28 [Source: HGNC Symbol; Acc: HGNC: 42129] | NA | 1.34 | NA |
| ENSG00000198712 | MT-CO2 | mitochondrially encoded cytochrome c oxidase II [Source: HGNC Symbol; Acc: HGNC: 7421] | NA | 1.32 | NA |
| ENSG00000198727 | MT-CYB | mitochondrially encoded cytochrome b [Source: HGNC Symbol; Acc: HGNC: 7427] | NA | 1.31 | NA |
| ENSG00000198888 | MT-ND1 | mitochondrially encoded NADH dehydrogenase 1 [Source: HGNC Symbol; Acc: HGNC: 7455] | NA | 1.25 | NA |
| ENSG00000198804 | MT-001 | mitochondrially encoded cytochrome c oxidase I [Source: HGNC Symbol; Acc: HGNC: 7419] | NA | 1.23 | NA |
| ENSG00000198886 | MT-ND4 | mitochondrially encoded NADH dehydrogenase 4 [Source: HGNC Symbol; Acc: HGNC: 7459] | NA | 1.23 | NA |
| ENSG00000198899 | MT-ATP6 | mitochondrially encoded ATP synthase 6 [Source: HGNC Symbol; Acc: HGNC: 7414] | NA | 1.22 | NA |
| ENSG00000210184 | MT-TS2 | mitochondrially encoded tRNA serine 2 (AGU/C) [Source: HGNC Symbol; Acc: HGNC: 7498] | NA | 1.15 | NA |
| ENSG00000198695 | MT-ND6 | mitochondrially encoded NADH dehydrogenase 6 [Source: HGNC Symbol; Acc: HGNC: 7462] | NA | 1.12 | NA |
| ENSG00000210144 | MT-TY | mitochondrially encoded tRNA tyrosine [Source: HGNC Symbol; Acc: HGNC: 7502] | NA | 1.09 | NA |
| ENSG00000228253 | MT-ATP8 | mitochondrially encoded ATP synthase 8 [Source: HGNC Symbol; Acc: HGNC: 7415] | NA | 1.05 | NA |
| ENSG00000258696 | | | NA | 1.03 | NA |
| ENSG00000175646 | PRM1 | protamine 1 [Source: HGNC Symbol; Acc: HGNC: 9447] | NA | NA | 1.01 |

TABLE 30

Biomarkers that are differentially expressed in urine based on the level of head impact

| Ensembl_ID | hgnc_symbol | description | Min_hitsp_vs_Baseline.y |
|---|---|---|---|
| ENSG00000210140 | MT-TC | mitochondrially encoded tRNA cysteine [Source: HGNC Symbol; Acc: HGNC: 7477] | −1.00 |
| ENSG00000122585 | NPY | neuropeptide Y [Source: HGNC Symbol; Acc: HGNC: 7955] | 1.13 |

TABLE 31

Some biomarkers that are differentially expressed in plasma based on subjects' probability score for the risk of concussion

| Ensembl_ID | hgnc_symbol | description | X1_vs_0.x | X2_vs_0.x | X2_vs_1.x | X3_vs_0.x | X3_vs_1.x | X3_vs_2.x |
|---|---|---|---|---|---|---|---|---|
| ENSG00000229344 | | | 1.20 | 1.39 | NA | NA | −1.25 | −1.43 |
| ENSG00000212338 | | Small nucleolar RNA SNORA67 [Source:RFAM;Acc:RF00272] | −1.07 | −1.09 | NA | −1.15 | NA | NA |
| ENSG00000186453 | FAM228A | family with sequence similarity 228, member A [Source:HGNC Symbol;Acc:HGNC:34418] | −1.13 | NA | NA | NA | 1.37 | 1.07 |

TABLE 31-continued

Some biomarkers that are differentially expressed in plasma based on subjects' probability score for the risk of concussion

| Ensembl_ID | hgnc_symbol | description | X1_vs_0.x | X2_vs_0.x | X2_vs_1.x | X3_vs_0.x | X3_vs_1.x | X3_vs_2.x |
|---|---|---|---|---|---|---|---|---|
| ENSG00000239011 | NA | NA | −1.02 | −1.06 | NA | NA | NA | NA |
| ENSG00000229775 | | | −1.10 | −1.15 | NA | NA | NA | NA |
| ENSG00000252596 | NA | NA | −1.36 | −1.23 | NA | NA | NA | NA |
| ENSG00000237731 | RNGTTP1 | RNA guanylyltransferase and 5'-phosphatase pseudogene 1 [Source:HGNC Symbol;Acc:HGNC:39652] | −1.24 | −1.48 | NA | NA | NA | NA |
| ENSG00000270683 | FAM71BP1 | family with sequence similarity 71, member B pseudogene 1 [Source:HGNC Symbol;Acc:HGNC:49805] | NA | −1.07 | NA | −1.02 | NA | NA |
| ENSG00000225181 | | | −1.22 | −1.07 | NA | −1.07 | NA | NA |
| ENSG00000163993 | S100P | S100 calcium binding protein P [Source:HGNC Symbol;Acc:HGNC:10504] | −1.26 | NA | NA | −1.29 | NA | NA |
| ENSG00000237256 | PGAM3P | phosphoglycerate mutase 3, pseudogene [Source:HGNC Symbol;Acc:HGNC:16557] | −1.37 | NA | NA | NA | 1.13 | NA |
| ENSG00000227593 | | | −1.20 | NA | NA | NA | 1.02 | NA |
| ENSG00000234723 | | | NA | −1.16 | NA | NA | 1.02 | 1.80 |
| ENSG00000249072 | | | 1.30 | 1.27 | NA | NA | −1.06 | −1.03 |
| ENSG00000252670 | NA | NA | 1.01 | 1.25 | NA | NA | NA | NA |
| ENSG00000264386 | MIR4513 | microRNA 4513 [Source:HGNC Symbol;Acc:HGNC:41855] | NA | 1.07 | NA | NA | NA | NA |
| ENSG00000185296 | | | NA | −1.01 | NA | NA | NA | NA |
| ENSG00000221291 | | | NA | −1.04 | NA | NA | NA | NA |
| ENSG00000256972 | | | −1.09 | −1.10 | NA | NA | NA | NA |
| ENSG00000197568 | HHLA3 | HERV-H LTR-associating 3 [Source:HGNC Symbol;Acc:HGNC:4906] | NA | −1.12 | NA | NA | NA | NA |
| ENSG00000230645 | | | −1.47 | −1.16 | NA | NA | NA | NA |
| ENSG00000229031 | | | NA | −1.18 | NA | NA | NA | NA |
| ENSG00000232578 | | | −1.18 | −1.18 | NA | NA | NA | NA |
| ENSG00000231680 | | | −1.25 | −1.21 | NA | NA | NA | NA |
| ENSG00000226939 | | | NA | −1.27 | NA | NA | NA | NA |
| ENSG00000258088 | | | NA | −1.29 | NA | NA | NA | NA |
| ENSG00000250392 | | | −1.26 | −1.35 | NA | NA | NA | NA |
| ENSG00000215030 | RPL13P12 | ribosomal protein L13 pseudogene 12 [Source:HGNC Symbol;Acc:HGNC:35701] | NA | NA | 1.13 | NA | NA | NA |
| ENSG00000220505 | EIF4EBP2P3 | eukaryotic translation initiation factor 4E binding protein 2 pseudogene 3 [Source:HGNC Symbol;Acc:HGNC:49318] | NA | −1.55 | −1.06 | NA | NA | NA |
| ENSG00000158856 | DMTN | dematin actin binding protein [Source:HGNC Symbol;Acc:HGNC:3382] | NA | NA | NA | 1.31 | NA | NA |
| ENSG00000100345 | MYH9 | myosin, heavy chain 9, non-muscle [Source:HGNC Symbol;Acc:HGNC:7579] | NA | NA | NA | 1.08 | NA | NA |
| ENSG00000242716 | NA | NA | NA | NA | NA | 1.07 | NA | NA |
| ENSG00000175602 | CCDC85B | coiled-coil domain containing 85B [Source:HGNC Symbol;Acc:HGNC:24926] | NA | NA | NA | 1.03 | NA | NA |
| ENSG00000225906 | | | −1.01 | NA | NA | −1.02 | NA | NA |
| ENSG00000201271 | RNU1-112P | RNA, U1 small nuclear 112, pseudogene [Source:HGNC Symbol;Acc:HGNC:48454] | −1.14 | −1.21 | NA | −1.04 | NA | NA |
| ENSG00000265408 | | | −1.10 | NA | NA | −1.05 | NA | NA |
| ENSG00000172594 | SMPDL3A | sphingomyelin phosphodiesterase, acid-like 3A [Source:HGNC Symbol;Acc:HGNC:17389] | −1.07 | −1.24 | NA | −1.06 | NA | NA |
| ENSG00000203691 | NA | NA | −1.49 | −1.37 | NA | −1.13 | NA | NA |
| ENSG00000212564 | RNU6-1326P | RNA, U6 small nuclear 1326, pseudogene [Source:HGNC Symbol;Acc:HGNC:48289] | NA | −1.17 | NA | −1.13 | NA | NA |
| ENSG00000199470 | | Small nucleolar RNA SNORA64/SNORA10 family [Source:RFAM;Acc:RF00264] | NA | NA | NA | −1.17 | NA | NA |
| ENSG00000264469 | | | −1.01 | −1.13 | NA | −1.18 | NA | NA |
| ENSG00000267670 | | | −1.47 | NA | NA | −1.20 | NA | NA |
| ENSG00000238763 | NA | NA | −1.11 | NA | NA | −1.35 | NA | NA |
| ENSG00000270680 | | | −1.13 | NA | NA | NA | 1.15 | NA |
| ENSG00000182393 | IFNL1 | interferon, lambda 1 [Source:HGNC Symbol;Acc:HGNC:18363] | NA | NA | NA | NA | 1.14 | NA |
| ENSG00000249941 | | | −1.12 | NA | NA | NA | 1.09 | NA |
| ENSG00000261665 | TUBA8P2 | tubulin, alpha 8 pseudogene 2 [Source:HGNC Symbol;Acc:HGNC:44569] | NA | NA | 1.00 | NA | 1.06 | NA |
| ENSG00000235186 | | | −1.02 | NA | 1.04 | NA | 1.05 | NA |
| ENSG00000249465 | RBMXP4 | RNA binding motif protein, X-linked pseudogene 4 [Source:HGNC Symbol;Acc:HGNC:34028] | −1.24 | NA | NA | NA | 1.05 | NA |
| ENSG00000219188 | CACYBPP3 | calcyclin binding protein pseudogene 3 [Source:HGNC Symbol;Acc:HGNC:45124] | NA | −1.05 | NA | NA | 1.06 | 1.31 |
| ENSG00000199287 | NA | NA | NA | −1.27 | −1.10 | NA | NA | 1.03 |
| ENSG00000206848 | RNU6-890P | RNA, U6 small nuclear 890, pseudogene [Source:HGNC Symbol;Acc:HGNC:47853] | NA | NA | NA | NA | 1.01 | 1.01 |
| ENSG00000252672 | NA | NA | NA | NA | 1.33 | NA | NA | −1.26 |
| ENSG00000200510 | NA | NA | 1.95 | 2.01 | NA | NA | −1.67 | −1.72 |

TABLE 31-continued

Some biomarkers that are differentially expressed in plasma based on subjects' probability score for the risk of concussion

| Ensembl_ID | hgnc_symbol | description | X1_vs_0.x | X2_vs_0.x | X2_vs_1.x | X3_vs_0.x | X3_vs_1.x | X3_vs_2.x |
|---|---|---|---|---|---|---|---|---|
| ENSG00000263740 | RN7SL4P | RNA, 7SL, cytoplasmic 4, pseudogene [Source:HGNC Symbol;Acc:HGNC:10039] | NA | 1.42 | NA | NA | NA | NA |
| ENSG00000166086 | JAM3 | junctional adhesion molecule 3 [Source:HGNC Symbol;Acc:HGNC:15532] | 1.18 | 1.05 | NA | NA | NA | NA |
| ENSG00000272468 | | | NA | 1.02 | NA | NA | NA | NA |
| ENSG00000232120 | | | NA | −1.01 | NA | NA | NA | NA |
| ENSG00000251354 | | | NA | −1.01 | NA | NA | NA | NA |
| ENSG00000183346 | C10orf107 | chromosome 10 open reading frame 107 [Source:HGNC Symbol;Acc:HGNC:28678] | NA | −1.01 | NA | NA | NA | NA |
| ENSG00000234683 | | | NA | −1.02 | NA | NA | NA | NA |
| ENSG00000263774 | | | NA | −1.03 | NA | NA | NA | NA |
| ENSG00000265946 | | | NA | −1.03 | NA | NA | NA | NA |
| ENSG00000260229 | | | NA | −1.03 | NA | NA | NA | NA |
| ENSG00000225785 | | | NA | −1.05 | NA | NA | NA | NA |
| ENSG00000252164 | RNA5SP282 | RNA, 5S ribosomal pseudogene 282 [Source:HGNC Symbol;Acc:HGNC:43182] | NA | −1.07 | NA | NA | NA | NA |
| ENSG00000226659 | | | NA | −1.07 | NA | NA | NA | NA |
| ENSG00000266596 | NA | NA | −1.05 | −1.07 | NA | NA | NA | NA |
| ENSG00000221083 | | Small nucleolar RNA SNORA77 [Source:RFAM;Acc:RF00599] | −1.03 | −1.09 | NA | NA | NA | NA |
| ENSG00000219368 | ZNF299P | zinc finger protein 299, pseudogene [Source:HGNC Symbol;Acc:HGNC:13088] | −1.06 | −1.10 | NA | NA | NA | NA |
| ENSG00000251751 | RN7SKP46 | RNA, 7SK small nuclear pseudogene 46 [Source:HGNC Symbol;Acc:HGNC:45770] | −1.00 | −1.12 | NA | NA | NA | NA |
| ENSG00000213144 | | | −1.11 | −1.12 | NA | NA | NA | NA |
| ENSG00000147183 | CPXCR1 | CPX chromosome region, candidate 1 [Source:HGNC Symbol;Acc:HGNC:2332] | NA | −1.12 | NA | NA | NA | NA |
| ENSG00000266941 | | | NA | −1.12 | NA | NA | NA | NA |
| ENSG00000231957 | GNAI2P2 | guanine nucleotide binding protein (G protein), alpha inhibiting activity polypeptide 2 pseudogene 2 [Source:HGNC Symbol;Acc:HGNC:45110] | NA | −1.13 | NA | NA | NA | NA |
| ENSG00000224924 | LINC00320 | long intergenic non-protein coding RNA 320 [Source:HGNC Symbol;Acc:HGNC:19690] | −1.06 | −1.13 | NA | NA | NA | NA |
| ENSG00000225216 | | | NA | −1.14 | NA | NA | NA | NA |
| ENSG00000266667 | | | NA | −1.14 | NA | NA | NA | NA |
| ENSG00000224618 | | | NA | −1.16 | NA | NA | NA | NA |
| ENSG00000241954 | | | NA | −1.18 | NA | NA | NA | NA |
| ENSG00000253849 | | | −1.04 | −1.20 | NA | NA | NA | NA |
| ENSG00000230589 | IMP3P1 | IMP3 pseudogene 1 [Source:HGNC Symbol;Acc:HGNC:49385] | −1.37 | −1.21 | NA | NA | NA | NA |
| ENSG00000254845 | NA | NA | −1.16 | −1.24 | NA | NA | NA | NA |
| ENSG00000204389 | HSPA1A | heat shock 70 kDa protein 1A [Source:HGNC Symbol;Acc:HGNC:5232] | −1.07 | −1.29 | NA | NA | NA | NA |
| ENSG00000224418 | STK24-AS1 | STK24 antisense RNA 1 [Source:HGNC Symbol;Acc:HGNC:39935] | −1.00 | −1.30 | NA | NA | NA | NA |
| ENSG00000258642 | | | NA | −1.35 | NA | NA | NA | NA |
| ENSG00000239791 | | | −1.51 | −1.50 | NA | NA | NA | NA |
| ENSG00000171794 | UTF1 | undifferentiated embryonic cell transcription factor 1 [Source:HGNC Symbol;Acc:HGNC:12634] | NA | NA | 1.19 | NA | NA | NA |
| ENSG00000232491 | | | NA | NA | 1.12 | NA | NA | NA |
| ENSG00000226981 | ABHD17AP6 | abhydrolase domain containing 17A pseudogene 6 [Source:HGNC Symbol;Acc:HGNC:34044] | NA | NA | 1.06 | NA | NA | NA |
| ENSG00000215089 | KRT18P11 | keratin 18 pseudogene 11 [Source:HGNC Symbol;Acc:HGNC:6431] | NA | NA | 1.04 | NA | NA | NA |
| ENSG00000222524 | RN7SKP109 | RNA, 7SK small nuclear pseudogene 109 [Source:HGNC Symbol;Acc:HGNC:45833] | −1.27 | NA | 1.02 | NA | NA | NA |
| ENSG00000250461 | | | NA | −1.13 | −1.03 | NA | NA | NA |
| ENSG00000252497 | RPPH1-2P | ribonuclease P RNA component H1, 2 pseudogene [Source:HGNC Symbol;Acc:HGNC:47029] | NA | −1.26 | −1.09 | NA | NA | NA |
| ENSG00000221096 | NA | NA | NA | NA | −1.12 | NA | NA | NA |
| ENSG00000168067 | MAP4K2 | mitogen-activated protein kinase kinase kinase kinase 2 [Source:HGNC Symbol;Acc:HGNC:6864] | NA | NA | NA | 1.06 | NA | NA |
| ENSG00000239617 | | | NA | NA | NA | 1.01 | NA | NA |
| ENSG00000230528 | NOS2P3 | nitric oxide synthase 2 pseudogene 3 [Source:HGNC Symbol;Acc:HGNC:35124] | −1.22 | NA | NA | −1.01 | NA | NA |
| ENSG00000236852 | | | NA | −1.09 | NA | −1.02 | NA | NA |
| ENSG00000267513 | | | NA | NA | NA | −1.03 | NA | NA |
| ENSG00000254683 | SNRPCP6 | small nuclear ribonucleoprotein polypeptide C pseudogene 6 [Source:HGNC Symbol;Acc:HGNC:49821] | −1.02 | NA | NA | −1.04 | NA | NA |
| ENSG00000230019 | YWHAQP9 | YWHAQ pseudogene 9 [Source:HGNC Symbol;Acc:HGNC:37688] | NA | −1.25 | NA | −1.04 | NA | NA |
| ENSG00000253377 | | | NA | −1.04 | NA | −1.04 | NA | NA |

TABLE 31-continued

Some biomarkers that are differentially expressed in plasma based on subjects' probability score for the risk of concussion

| Ensembl_ID | hgnc_symbol | description | X1_vs_0.x | X2_vs_0.x | X2_vs_1.x | X3_vs_0.x | X3_vs_1.x | X3_vs_2.x |
|---|---|---|---|---|---|---|---|---|
| ENSG00000266187 | RN7SL480P | RNA, 7SL, cytoplasmic 480, pseudogene [Source:HGNC Symbol;Acc:HGNC:46496] | NA | NA | NA | −1.07 | NA | NA |
| ENSG00000264296 | | | NA | NA | NA | −1.09 | NA | NA |
| ENSG00000261340 | | | NA | −1.02 | NA | −1.10 | NA | NA |
| ENSG00000172769 | OR5B3 | olfactory receptor, family 5, subfamily B, member 3 [Source:HGNC Symbol;Acc:HGNC:8324] | −1.06 | −1.09 | NA | −1.14 | NA | NA |
| ENSG00000238858 | NA | NA | NA | NA | NA | −1.15 | NA | NA |
| ENSG00000257519 | | | NA | NA | NA | −1.24 | NA | NA |
| ENSG00000224288 | | | −1.01 | −1.25 | NA | −1.25 | NA | NA |
| ENSG00000270798 | | | NA | −1.28 | NA | −1.28 | NA | NA |
| ENSG00000252863 | RNU6-1183P | RNA, U6 small nuclear 1183, pseudogene [Source:HGNC Symbol;Acc:HGNC:48146] | −1.03 | −1.12 | NA | −1.31 | NA | NA |
| ENSG00000223881 | | | NA | −1.45 | NA | −1.32 | NA | NA |
| ENSG00000263253 | | | −1.01 | −1.24 | NA | −1.39 | NA | NA |
| ENSG00000248891 | | | NA | NA | NA | −1.43 | NA | NA |
| ENSG00000136872 | ALDOB | aldolase B, fructose-bisphosphate [Source:HGNC Symbol;Acc:HGNC:417] | −1.66 | −1.42 | NA | −1.48 | NA | NA |
| ENSG00000270371 | | | NA | 1.16 | 1.09 | 1.19 | 1.12 | NA |
| ENSG00000273154 | | | NA | 1.21 | 1.11 | 1.18 | 1.08 | NA |
| ENSG00000233545 | CYCSP33 | cytochrome c, somatic pseudogene 33 [Source:HGNC Symbol;Acc:HGNC:24407] | −1.38 | NA | NA | NA | 1.06 | NA |
| ENSG00000231682 | | | −1.14 | NA | NA | NA | 1.05 | NA |
| ENSG00000238460 | | | NA | NA | NA | −1.06 | −1.00 | NA |
| ENSG00000270457 | | | NA | NA | NA | NA | −1.12 | NA |
| ENSG00000268995 | VN1R82P | vomeronasal 1 receptor 82 pseudogene [Source:HGNC Symbol;Acc:HGNC:37402] | NA | NA | NA | NA | −1.12 | NA |
| ENSG00000198829 | SUCNR1 | succinate receptor 1 [Source:HGNC Symbol;Acc:HGNC:4542] | 1.02 | NA | NA | NA | −1.21 | NA |
| ENSG00000248538 | | | NA | −1.05 | −1.03 | −1.24 | −1.22 | NA |
| ENSG00000243370 | RN7SL775P | RNA, 7SL, cytoplasmic 775, pseudogene [Source:HGNC Symbol;Acc:HGNC:46791] | −1.01 | −1.41 | NA | NA | 1.04 | 1.44 |
| ENSG00000259588 | | | NA | −1.19 | NA | NA | NA | 1.34 |
| ENSG00000263493 | NA | NA | NA | −1.26 | −1.09 | NA | NA | 1.27 |
| ENSG00000233265 | MICF | MHC class I polypeptide-related sequence F (pseudogene) [Source:HGNC Symbol;Acc:HGNC:16801] | NA | NA | NA | NA | 1.42 | 1.24 |
| ENSG00000239547 | RN7SL843P | RNA, 7SL, cytoplasmic 843, pseudogene [Source:HGNC Symbol;Acc:HGNC:46859] | −1.08 | NA | NA | NA | 1.34 | 1.20 |
| ENSG00000240545 | RN7SL492P | RNA, 7SL, cytoplasmic 492, pseudogene [Source:HGNC Symbol;Acc:HGNC:46508] | NA | −1.16 | NA | NA | NA | 1.16 |
| ENSG00000226104 | NA | NA | NA | −1.12 | NA | NA | NA | 1.11 |
| ENSG00000257723 | CHCHD3P2 | coiled-coil-helix-coiled-coil-helix domain containing 3 pseudogene 2 [Source:HGNC Symbol;Acc:HGNC:44698] | NA | −1.16 | NA | NA | NA | 1.10 |
| ENSG00000259411 | HNRNPA1P45 | heterogeneous nuclear ribonucleoprotein A1 pseudogene 45 [Source:HGNC Symbol;Acc:HGNC:48775] | NA | −1.10 | NA | NA | NA | 1.06 |
| ENSG00000136457 | CHAD | chondroadherin [Source:HGNC Symbol;Acc:HGNC:1909] | −1.02 | NA | NA | NA | 1.35 | 1.06 |
| ENSG00000265334 | | | −1.14 | −1.01 | NA | NA | 1.17 | 1.03 |
| ENSG00000241757 | RN7SL714P | RNA, 7SL, cytoplasmic 714, pseudogene [Source:HGNC Symbol;Acc:HGNC:46730] | NA | −1.02 | NA | NA | NA | 1.03 |
| ENSG00000159186 | | | −1.02 | −1.12 | NA | NA | NA | 1.03 |
| ENSG00000238754 | | Small nucleolar RNA U109 [Source: RFAM ;Acc:RF01233] | NA | NA | −1.11 | NA | NA | 1.01 |
| ENSG00000229196 | | | −1.19 | −1.17 | NA | NA | 1.04 | 1.01 |
| ENSG00000259604 | | | −1.31 | −1.35 | NA | NA | NA | 1.01 |
| ENSG00000236876 | TMSB4XP1 | thymosin beta 4, X-linked pseudogene 1 [Source:HGNC Symbol;Acc:HGNC:11883] | NA | 1.24 | NA | NA | NA | −1.11 |
| ENSG00000244921 | | | NA | 1.03 | NA | NA | NA | −1.16 |
| ENSG00000259145 | NA | NA | NA | NA | NA | −1.25 | −1.01 | −1.17 |
| ENSG00000227468 | | | NA | 1.04 | NA | NA | NA | −1.20 |
| ENSG00000269028 | MTRNR2L12 | MT-RNR2-like 12 [Source:HGNC Symbol;Acc:HGNC:37169] | NA | NA | NA | NA | −1.26 | −1.22 |
| ENSG00000201955 | RNY3P1 | RNA, Ro-associated Y3 pseudogene 1 [Source:HGNC Symbol;Acc:HGNC:42477] | 1.00 | 1.06 | NA | NA | −1.19 | −1.24 |
| ENSG00000237973 | MIR6723 | microRNA 6723 [Source:HGNC Symbol;Acc:HGNC:50152] | NA | NA | NA | NA | NA | −1.27 |
| ENSG00000259045 | | | NA | 1.06 | NA | NA | NA | −1.37 |

TABLE 32

Biomarkers that are differentially expressed in urine based on subjects' probability score for the risk of concussion

| Ensembl_ID | hgnc_symbol | description | X1_vs_0.y | X2_vs_0.y | X2_vs_1.y | X3_vs_0.y | X3_vs_1.y | X3_vs_2.y |
|---|---|---|---|---|---|---|---|---|
| ENSG00000136689 | IL1RN | interleukin 1 receptor antagonist [Source:HGNC Symbol;Acc:HGNC:6000] | NA | NA | NA | 1.03 | NA | 1.11 |
| ENSG00000124233 | SEMG1 | semenogelin I [Source:HGNC Symbol;Acc:HGNC:10742] | 1.02 | NA | NA | NA | NA | NA |
| ENSG00000134240 | HMGCS2 | 3-hydroxy-3-methylglutaryl-CoA synthase 2 (mitochondrial) [Source:HGNC Symbol;Acc:HGNC:5008] | NA | NA | NA | 1.06 | NA | NA |
| ENSG00000242082 | | | NA | NA | NA | 1.00 | NA | NA |
| ENSG00000181617 | FDCSP | follicular dendritic cell secreted protein [Source:HGNC Symbol;Acc:HGNC:19215] | NA | NA | NA | −1.04 | NA | NA |
| ENSG00000214049 | UCA1 | urothelial cancer associated 1 (non-protein coding) [Source:HGNC Symbol;Acc:HGNC:37126] | NA | NA | NA | NA | NA | 1.10 |
| ENSG00000153071 | DAB2 | Dab, mitogen-responsive phosphoprotein, homolog 2 (Drosophila) [Source:HGNC Symbol;Acc:HGNC:2662] | NA | NA | NA | NA | NA | 1.00 |
| ENSG00000224203 | RPS23P10 | ribosomal protein S23 pseudogene 10 [Source:HGNC Symbol;Acc:HGNC:48342] | NA | NA | NA | NA | NA | −1.01 |
| ENSG00000212930 | | | NA | NA | NA | NA | NA | −1.01 |
| ENSG00000240863 | RN7SL645P | RNA, 7SL, cytoplasmic 645, pseudogene [Source:HGNC Symbol;Acc:HGNC:46661 ] | NA | NA | NA | NA | NA | −1.02 |
| ENSG00000237460 | | | NA | NA | NA | NA | NA | −1.02 |
| ENSG00000236495 | | | NA | NA | NA | NA | NA | −1.02 |
| ENSG00000226197 | | | NA | NA | NA | NA | NA | −1.02 |

TABLE 33

The markers listed discriminate between a subject who is exposed to frequent head impact (e.g. an athlete who plays contact sports) and subject with normal exposure to head impact (e.g. an athlete who does not play contact sports, like track and field) using blood samples.

| Ensembl_ID | HGNC_symbol | Description |
|---|---|---|
| ENSG00000001626 | CFTR | cystic fibrosis transmembrane conductance regulator (ATP-binding cassette sub-family C, member 7) [Source: HGNC Symbol; Acc: HGNC: 1884] |
| ENSG00000003249 | DBNDD1 | dysbindin (dystrobrevin binding protein 1) domain containing 1 [Source: HGNC Symbol; Acc: HGNC: 28455] |
| ENSG00000106018 | VIPR2 | vasoactive intestinal peptide receptor 2 [Source: HGNC Symbol; Acc: HGNC: 12695] |
| ENSG00000117411 | B4GALT2 | UDP-Gal: betaGlcNAc beta 1,4- galactosyltransferase, polypeptide 2 [Source: HGNC Symbol; Acc: HGNC: 925] |
| ENSG00000119614 | VSX2 | visual system homeobox 2 [Source: HGNC Symbol; Acc: HGNC: 1975] |
| ENSG00000122254 | HS3ST2 | heparan sulfate (glucosamine) 3-O-sulfotransferase 2 [Source: HGNC Symbol; Acc: HGNC: 5195] |
| ENSG00000122584 | NXPH1 | neurexophilin 1 [Source: HGNC Symbol; Acc: HGNC: 20693] |
| ENSG00000124089 | MC3R | melanocortin 3 receptor [Source: HGNC Symbol; Acc: HGNC: 6931] |
| ENSG00000130545 | CRB3 | crumbs family member 3 [Source: HGNC Symbol; Acc: HGNC: 20237] |
| ENSG00000160161 | CILP2 | cartilage intermediate layer protein 2 [Source: HGNC Symbol; Acc: HGNC: 24213] |
| ENSG00000169174 | PCSK9 | proprotein convertase subtilisin/kexin type 9 [Source: HGNC Symbol; Acc: HGNC: 20001] |
| ENSG00000172780 | RAB43 | RAB43, member RAS oncogene family [Source: HGNC Symbol; Acc: HGNC: 19983] |
| ENSG00000184154 | LRTOMT | leucine rich transmembrane and O-methyltransferase domain containing [Source: HGNC Symbol; Acc: HGNC: 25033] |
| ENSG00000185915 | KLHL34 | kelch-like family member 34 [Source: HGNC Symbol; Acc: HGNC: 26634] |
| ENSG00000188833 | ENTPD8 | ectonucleoside triphosphate diphosphohydrolase 8 [Source: HGNC Symbol; Acc: HGNC: 24860] |
| ENSG00000205765 | C5orf51 | chromosome 5 open reading frame 51 [Source: HGNC Symbol; Acc: HGNC: 27750] |
| ENSG00000233421 | | |
| ENSG00000234944 | | |
| ENSG00000256463 | SALL3 | spalt-like transcription factor 3 [Source: HGNC Symbol; Acc: HGNC: 10527] |
| ENSG00000258991 | DUX4L19 | double homeobox 4 like 19 [Source: HGNC Symbol; Acc: HGNC: 37718] |
| ENSG00000266947 | | |
| ENSG00000184194 | GPR173 | G protein-coupled receptor 173 [Source: HGNC Symbol; Acc: HGNC: 18186] |

TABLE 33-continued

The markers listed discriminate between a subject who is exposed to frequent head impact (e.g. an athlete who plays contact sports) and subject with normal exposure to head impact (e.g. an athlete who does not play contact sports, like track and field) using blood samples.

| Ensembl_ID | HGNC_symbol | Description |
| --- | --- | --- |
| ENSG00000176956 | LY6H | lymphocyte antigen 6 complex, locus H [Source: HGNC Symbol; Acc: HGNC: 6728] |
| ENSG00000171606 | ZNF274 | zinc finger protein 274 [Source: HGNC Symbol; Acc: HGNC: 13068] |

TABLE 34

The markers listed discriminate between a subject who is exposed to frequent head impact (e.g. an athlete who plays contact sports) and subject with normal exposure to head impact (e.g. an athlete who does not play contact sports, like track and field) using urine samples.

| Ensembl_ID | HGNC_symbol | Description |
| --- | --- | --- |
| ENSG00000065675 | PRKCQ | protein kinase C, theta [Source: HGNC Symbol; Acc: HGNC: 9410] |
| ENSG00000105948 | TTC26 | tetratricopeptide repeat domain 26 [Source: HGNC Symbol; Acc: HGNC: 21882] |
| ENSG00000116273 | PHF13 | PHD finger protein 13 [Source: HGNC Symbol; Acc: HGNC: 22983] |
| ENSG00000138050 | THUMPD2 | THUMP domain containing 2 [Source: HGNC Symbol; Acc: HGNC: 14890] |
| ENSG00000151093 | OXSM | 3-oxoacyl-ACP synthase, mitochondrial [Source: HGNC Symbol; Acc: HGNC: 26063] |
| ENSG00000151623 | NR3C2 | nuclear receptor subfamily 3, group C, member 2 [Source: HGNC Symbol; Acc: HGNC: 7979] |
| ENSG00000168491 | CCDC110 | coiled-coil domain containing 110 [Source: HGNC Symbol; Acc: HGNC: 28504] |
| ENSG00000170989 | S1PR1 | sphingosine-1-phosphate receptor 1 [Source: HGNC Symbol; Acc: HGNC: 3165] |
| ENSG00000175857 | GAPT | GRB2-binding adaptor protein, transmembrane [Source: HGNC Symbol; Acc: HGNC: 26588] |
| ENSG00000188488 | SERPINA5 | serpin peptidase inhibitor, clade A (alpha-1 antiproteinase, antitrypsin), member 5 [Source: HGNC Symbol; Acc: HGNC: 8723] |
| ENSG00000198077 | CYP2A7 | cytochrome P450, family 2, subfamily A, polypeptide 7 [Source: HGNC Symbol; Acc: HGNC: 2611] |
| ENSG00000198889 | DCAF12L1 | DDB1 and CUL4 associated factor 12-like 1 [Source: HGNC Symbol; Acc: HGNC: 29395] |
| ENSG00000204666 | | FLJ26850 protein [Source: EntrezGene; Acc: 400710] |
| ENSG00000228506 | | |
| ENSG00000229356 | LRRC3-AS1 | LRRC3 antisense RNA 1 (head to head) [Source: HGNC Symbol; Acc: HGNC: 43636] |
| ENSG00000249465 | RBMXP4 | RNA binding motif protein, X-linked pseudogene 4 [Source: HGNC Symbol; Acc: HGNC: 34028] |
| ENSG00000257242 | C12orf79 | chromosome 12 open reading frame 79 [Source: HGNC Symbol; Acc: HGNC: 27409] |
| ENSG00000125630 | POLR1B | polymerase (RNA) I polypeptide B, 128 kDa [Source: HGNC Symbol; Acc: HGNC: 20454] |
| ENSG00000198142 | SOWAHC | sosondowah ankyrin repeat domain family member C [Source: HGNC Symbol; Acc: HGNC: 26149] |
| ENSG00000113360 | DROSHA | drosha, ribonuclease type III [Source: HGNC Symbol; Acc: HGNC: 17904] |
| ENSG00000174899 | C3orf55 | chromosome 3 open reading frame 55 [Source: HGNC Symbol; Acc: HGNC: 25146] |
| ENSG00000141034 | GID4 | GID complex subunit 4 [Source: HGNC Symbol; Acc: HGNC: 28453] |

TABLE 35

The markers listed discriminate between a subject who is a contact sport athlete and experienced the most frequent head impact and the subject's baseline using blood samples.

| Ensembl_ID | HGNC_symbol | Description |
|---|---|---|
| ENSG00000006114 | NA | NA |
| ENSG00000074582 | BCS1L | BC1 (ubiquinol-cytochrome c reductase) synthesis-like [Source: HGNC Symbol; Acc: HGNC: 1020] |
| ENSG00000084764 | MAPRE3 | microtubule-associated protein, RP/EB family, member 3 [Source: HGNC Symbol; Acc: HGNC: 6892] |
| ENSG00000101098 | RIMS4 | regulating synaptic membrane exocytosis 4 [Source: HGNC Symbol; Acc: HGNC: 16183] |
| ENSG00000128512 | DOCK4 | dedicator of cytokinesis 4 [Source: HGNC Symbol; Acc: HGNC: 19192] |
| ENSG00000132535 | DLG4 | discs, large homolog 4 (*Drosophila*) [Source: HGNC Symbol; Acc: HGNC: 2903] |
| ENSG00000163704 | PRRT3 | proline-rich transmembrane protein 3 [Source: HGNC Symbol; Acc: HGNC: 26591] |
| ENSG00000164093 | PITX2 | paired-like homeodomain 2 [Source: HGNC Symbol; Acc: HGNC: 9005] |
| ENSG00000172071 | EIF2AK3 | eukaryotic translation initiation factor 2-alpha kinase 3 [Source: HGNC Symbol; Acc: HGNC: 3255] |
| ENSG00000182552 | RWDD4 | RWD domain containing 4 [Source: HGNC Symbol; Acc: HGNC: 23750] |
| ENSG00000182973 | CNOT10 | CCR4-NOT transcription complex, subunit 10 [Source: HGNC Symbol; Acc: HGNC: 23817] |
| ENSG00000213414 | | |
| ENSG00000228215 | | |
| ENSG00000228327 | | |
| ENSG00000232900 | | |
| ENSG00000236540 | | |
| ENSG00000243772 | KIR2DL3 | killer cell immunoglobulin-like receptor, two domains, long cytoplasmic tail, 3 [Source: HGNC Symbol; Acc: HGNC: 6331] |
| ENSG00000243916 | | |
| ENSG00000261398 | | |
| ENSG00000266677 | | |
| ENSG00000270696 | | |
| ENSG00000272645 | | |
| ENSG00000196268 | ZNF493 | zinc finger protein 493 [Source: HGNC Symbol; Acc: HGNC: 23708] |
| ENSG00000181773 | GPR3 | G protein-coupled receptor 3 [Source: HGNC Symbol; Acc: HGNC: 4484] |

TABLE 36

The markers listed discriminate between a subject who is a contact sport athlete and experienced the most frequent head impact and a subject who is a contact sport athlete and experienced the least frequent head impact using a blood sample.

| Ensembl_ID | HGNC_symbol | Description |
|---|---|---|
| ENSG00000100012 | SEC14L3 | SEC14-like 3 (*S. cerevisiae*) [Source: HGNC Symbol; Acc: HGNC: 18655] |
| ENSG00000112852 | PCDHB2 | protocadherin beta 2 [Source: HGNC Symbol; Acc: HGNC: 8687] |
| ENSG00000125734 | GPR108 | G protein-coupled receptor 108 [Source: HGNC Symbol; Acc: HGNC: 17829] |
| ENSG00000130489 | SCO2 | SCO2 cytochrome c oxidase assembly protein [Source: HGNC Symbol; Acc: HGNC: 10604] |
| ENSG00000143337 | TOR1AIP1 | torsin A interacting protein 1 [Source: HGNC Symbol; Acc: HGNC: 29456] |
| ENSG00000151240 | DIP2C | DIP2 disco-interacting protein 2 homolog C (*Drosophila*) [Source: HGNC Symbol; Acc: HGNC: 29150] |
| ENSG00000154764 | WNT7A | wingless-type MMTV integration site family, member 7A [Source: HGNC Symbol; Acc: HGNC: 12786] |
| ENSG00000166167 | BTRC | beta-transducin repeat containing E3 ubiquitin protein ligase [Source: HGNC Symbol; Acc: HGNC: 1144] |
| ENSG00000168280 | KIF5C | kinesin family member 5C [Source: HGNC Symbol; Acc: HGNC: 6325] |
| ENSG00000172116 | CD8B | CD8b molecule [Source: HGNC Symbol; Acc: HGNC: 1707] |
| ENSG00000180902 | D2HGDH | D-2-hydroxyglutarate dehydrogenase [Source: HGNC Symbol; Acc: HGNC: 28358] |
| ENSG00000181722 | ZBTB20 | zinc finger and BTB domain containing 20 [Source: HGNC Symbol; Acc: HGNC: 13503] |

TABLE 36-continued

The markers listed discriminate between a subject who is a contact sport athlete and experienced the most frequent head impact and a subject who is a contact sport athlete and experienced the least frequent head impact using a blood sample.

| Ensembl_ID | HGNC_symbol | Description |
| --- | --- | --- |
| ENSG00000187556 | NANOS3 | nanos homolog 3 (*Drosophila*) [Source: HGNC Symbol; Acc: HGNC: 22048] |
| ENSG00000196268 | ZNF493 | zinc finger protein 493 [Source: HGNC Symbol; Acc: HGNC: 23708] |
| ENSG00000225492 | GBP1P1 | guanylate binding protein 1, interferon-inducible pseudogene 1 [Source: HGNC Symbol; Acc: HGNC: 39561] |
| ENSG00000227892 | OR5P4P | olfactory receptor, family 5, subfamily P, member 4 pseudogene [Source: HGNC Symbol; Acc: HGNC: 15295] |
| ENSG00000236445 | LINC00608 | long intergenic non-protein coding RNA 608 [Source: HGNC Symbol; Acc: HGNC: 27179] |
| ENSG00000249831 | | |
| ENSG00000257943 | | |
| ENSG00000260288 | | |
| ENSG00000261770 | | |
| ENSG00000270275 | | |
| ENSG00000270948 | | |
| ENSG00000258071 | ARL2BPP2 | ADP-ribosylation factor-like 2 binding protein pseudogene 2 [Source: HGNC Symbol; Acc: HGNC: 31036] |

TABLE 37

The markers listed discriminate between a subject who is a contact sport athlete and experienced the most frequent head impact and a subject with normal exposure to head impact (e.g. an athlete who does not play contact sports, like track and field) using blood samples.

| Ensembl_ID | HGNC_symbol | Description |
| --- | --- | --- |
| ENSG00000131759 | RARA | retinoic acid receptor, alpha [Source: HGNC Symbol; Acc: HGNC: 9864] |
| ENSG00000140995 | DEF8 | differentially expressed in FDCP 8 homolog (mouse) [Source: HGNC Symbol; Acc: HGNC: 25969] |
| ENSG00000143595 | AQP10 | aquaporin 10 [Source: HGNC Symbol; Acc: HGNC: 16029] |
| ENSG00000177728 | KIAA0195 | KIAA0195 [Source: HGNC Symbol; Acc: HGNC: 28983] |
| ENSG00000180613 | GSX2 | GS homeobox 2 [Source: HGNC Symbol; Acc: HGNC: 24959] |
| ENSG00000181773 | GPR3 | G protein-coupled receptor 3 [Source: HGNC Symbol; Acc: HGNC: 4484] |
| ENSG00000182636 | NDN | necdin, melanoma antigen (MAGE) family member [Source: HGNC Symbol; Acc: HGNC: 7675] |
| ENSG00000183921 | SDR42E2 | short chain dehydrogenase/reductase family 42E, member 2 [Source: HGNC Symbol; Acc: HGNC: 35414] |
| ENSG00000184194 | GPR173 | G protein-coupled receptor 173 [Source: HGNC Symbol; Acc: HGNC: 18186] |
| ENSG00000184502 | GAST | gastrin [Source: HGNC Symbol; Acc: HGNC: 4164] |
| ENSG00000186868 | MAPT | microtubule-associated protein tau [Source: HGNC Symbol; Acc: HGNC: 6893] |
| ENSG00000189223 | PAX8-AS1 | PAX8 antisense RNA 1 [Source: HGNC Symbol; Acc: HGNC: 49271] |
| ENSG00000213152 | RPL7AP60 | ribosomal protein L7a pseudogene 60 [Source: HGNC Symbol; Acc: HGNC: 35859] |
| ENSG00000221844 | | |
| ENSG00000230989 | HSBP1 | heat shock factor binding protein 1 [Source: HGNC Symbol; Acc: HGNC: 5203] |
| ENSG00000235979 | | |
| ENSG00000237753 | | uncharacterized LOC400999 [Source: EntrezGene; Acc: 400999] |
| ENSG00000244122 | UGT1A7 | UDP glucuronosyltransferase 1 family, polypeptide A7 [Source: HGNC Symbol; Acc: HGNC: 12539] |
| ENSG00000244280 | ECEL1P2 | endothelin converting enzyme-like 1, pseudogene 2 [Source: HGNC Symbol; Acc: HGNC: 14019] |
| ENSG00000251624 | UNC93B7 | unc-93 homolog B7 pseudogene (*C. elegans*) [Source: HGNC Symbol; Acc: HGNC: 44036] |
| ENSG00000253318 | TMCC1P1 | transmembrane and coiled-coil domain family 1 pseudogene 1 [Source: HGNC Symbol; Acc: HGNC: 31901] |

TABLE 37-continued

The markers listed discriminate between a subject who is a contact sport athlete and experienced the most frequent head impact and a subject with normal exposure to head impact (e.g. an athlete who does not play contact sports, like track and field) using blood samples.

| Ensembl_ID | HGNC_symbol | Description |
|---|---|---|
| ENSG00000254966 | | |
| ENSG00000258071 | ARL2BPP2 | ADP-ribosylation factor-like 2 binding protein pseudogene 2 [Source: HGNC Symbol; Acc: HGNC: 31036] |
| ENSG00000273382 | | |
| ENSG00000260288 | | |

TABLE 38

The markers listed discriminate between a subject who is a contact sport athlete and experienced the most frequent head impact and the subject's baseline using urine samples.

| Ensembl_ID | HGNC_symbol | Description |
|---|---|---|
| ENSG00000061273 | HDAC7 | histone deacetylase 7 [Source: HGNC Symbol; Acc: HGNC: 14067] |
| ENSG00000102287 | GABRE | gamma-aminobutyric acid (GABA) A receptor, epsilon [Source: HGNC Symbol; Acc: HGNC: 4085] |
| ENSG00000103152 | MPG | N-methylpurine-DNA glycosylase [Source: HGNC Symbol; Acc: HGNC: 7211] |
| ENSG00000116984 | MTR | 5-methyltetrahydrofolate-homocysteine methyltransferase [Source: HGNC Symbol; Acc: HGNC: 7468] |
| ENSG00000130349 | C6orf203 | chromosome 6 open reading frame 203 [Source: HGNC Symbol; Acc: HGNC: 17971] |
| ENSG00000130829 | DUSP9 | dual specificity phosphatase 9 [Source: HGNC Symbol; Acc: HGNC: 3076] |
| ENSG00000134215 | VAV3 | vav 3 guanine nucleotide exchange factor [Source: HGNC Symbol; Acc: HGNC: 12659] |
| ENSG00000138639 | ARHGAP24 | Rho GTPase activating protein 24 [Source: HGNC Symbol; Acc: HGNC: 25361] |
| ENSG00000144283 | PKP4 | plakophilin 4 [Source: HGNC Symbol; Acc: HGNC: 9026] |
| ENSG00000169894 | MUC3A | mucin 3A, cell surface associated [Source: HGNC Symbol; Acc: HGNC: 7513] |
| ENSG00000184454 | NCMAP | noncompact myelin associated protein [Source: HGNC Symbol; Acc: HGNC: 29332] |
| ENSG00000188987 | NA | NA |
| ENSG00000205927 | OLIG2 | oligodendrocyte lineage transcription factor 2 [Source: HGNC Symbol; Acc: HGNC: 9398] |
| ENSG00000215070 | XRCC6P5 | X-ray repair complementing defective repair in Chinese hamster cells 6 pseudogene 5 [Source: HGNC Symbol; Acc: HGNC: 45187] |
| ENSG00000234500 | | |
| ENSG00000260896 | | |
| ENSG00000264016 | | |
| ENSG00000151623 | NR3C2 | nuclear receptor subfamily 3, group C, member 2 [Source: HGNC Symbol; Acc: HGNC: 7979] |
| ENSG00000085415 | SEH1L | SEH1-like (S. cerevisiae) [Source: HGNC Symbol; Acc: HGNC: 30379] |
| ENSG00000112679 | DUSP22 | dual specificity phosphatase 22 [Source: HGNC Symbol; Acc: HGNC: 16077] |

TABLE 39

The markers listed discriminate between a subject who is a contact sport athlete and experienced the most frequent head impact and a subject who is a contact sport athlete and experienced the least frequent head impact using a urine sample.

| Ensembl_ID | HGNC_symbol | Description |
|---|---|---|
| ENSG00000085415 | SEH1L | SEH1-like (S. cerevisiae) [Source:HGNC Symbol;Acc:HGNC:30379] |
| ENSG00000088882 | CPXM1 | carboxypeptidase X (M14 family), member 1 [Source:HGNC Symbol;Acc:HGNC:15771] |

TABLE 39-continued

The markers listed discriminate between a subject who is a contact sport athlete and experienced the most frequent head impact and a subject who is a contact sport athlete and experienced the least frequent head impact using a urine sample.

| Ensembl_ID | HGNC_symbol | Description |
|---|---|---|
| ENSG00000101276 | SLC52A3 | solute carrier family 52 (riboflavin transporter), member 3 [Source:HGNC Symbol;Acc:HGNC:16187] |
| ENSG00000105865 | DUS4L | dihydrouridine synthase 4-like (*S. cerevisiae*) [Source:HGNC Symbol;Acc:HGNC:21517] |
| ENSG00000110448 | CD5 | CD5 molecule [Source:HGNC Symbol;Acc:HGNC:1685] |
| ENSG00000112941 | PAPD7 | PAP associated domain containing 7 [Source:HGNC Symbol;Acc:HGNC:16705] |
| ENSG00000126500 | FLRT1 | fibronectin leucine rich transmembrane protein 1 [Source:HGNC Symbol;Acc:HGNC:3760] |
| ENSG00000127511 | SIN3B | SIN3 transcription regulator family member B [Source:HGNC Symbol;Acc:HGNC:19354] |
| ENSG00000137802 | MAPKBP1 | mitogen-activated protein kinase binding protein 1 [Source:HGNC Symbol;Acc:HGNC:29536] |
| ENSG00000164978 | NUDT2 | nudix (nucleoside diphosphate linked moiety X)-type motif 2 [Source:HGNC Symbol;Acc:HGNC:8049] |
| ENSG00000170929 | OR1M1 | olfactory receptor, family 1, subfamily M, member 1 [Source:HGNC Symbol;Acc:HGNC:8220] |
| ENSG00000186318 | BACE1 | beta-site APP-cleaving enzyme 1 [Source:HGNC Symbol;Acc:HGNC:933] |
| ENSG00000188508 | KRTDAP | keratinocyte differentiation-associated protein [Source:HGNC Symbol;Acc:HGNC:16313] |
| ENSG00000197177 | GPR123 | G protein-coupled receptor 123 [Source:HGNC Symbol;Acc:HGNC:13838] |
| ENSG00000203620 | | |
| ENSG00000225365 | | |
| ENSG00000226070 | | |
| ENSG00000235816 | PRELID1P3 | PRELI domain containing 1 pseudogene 3 [Source:HGNC Symbol;Acc:HGNC:43888] |
| ENSG00000236969 | GGT8P | gamma-glutamyltransferase 8 pseudogene [Source:HGNC Symbol;Acc:HGNC:33438] |
| ENSG00000242159 | ABCF2P1 | ATP-binding cassette, sub-family F (GCN20), member 2 pseudogene 1 [Source:HGNC Symbol;Acc:HGNC:48841] |
| ENSG00000243810 | | |
| ENSG00000260664 | | |
| ENSG00000267028 | | |
| ENSG00000184454 | NCMAP | noncompact myelin associated protein [Source:HGNC Symbol;Acc:HGNC:29332] |

TABLE 40

The markers listed discriminate between a subject who is a contact sport athlete and experienced the most forceful head impact and the subject's baseline using blood samples.

| Ensembl_ID | HGNC_symbol | Description |
|---|---|---|
| ENSG00000091181 | IL5RA | interleukin 5 receptor, alpha [Source:HGNC Symbol;Acc:HGNC:6017] |
| ENSG00000103429 | BFAR | bifunctional apoptosis regulator [Source:HGNC Symbol;Acc:HGNC:17613] |
| ENSG00000124256 | ZBP1 | Z-DNA binding protein 1 [Source:HGNC Symbol;Acc:HGNC:16176] |
| ENSG00000136274 | NACAD | NAC alpha domain containing [Source:HGNC Symbol;Acc:HGNC:22196] |
| ENSG00000138081 | FBXO11 | F-box protein 11 [Source:HGNC Symbol;Acc:HGNC:13590] |
| ENSG00000146242 | TPBG | trophoblast glycoprotein [Source:HGNC Symbol;Acc:HGNC:12004] |
| ENSG00000151689 | INPP1 | inositol polyphosphate-1-phosphatase [Source:HGNC Symbol;Acc:HGNC:6071] |
| ENSG00000163497 | FEV | FEV (ETS oncogene family) [Source:HGNC Symbol;Acc:HGNC:18562] |
| ENSG00000164022 | AIMP1 | aminoacyl tRNA synthetase complex-interacting multifunctional protein 1 [Source:HGNC Symbol;Acc:HGNC:10648] |
| ENSG00000164616 | FBXL21 | F-box and leucine-rich repeat protein 21 (gene/pseudogene) [Source:HGNC Symbol;Acc:HGNC:13600] |
| ENSG00000166987 | MBD6 | methyl-CpG binding domain protein 6 [Source:HGNC Symbol;Acc:HGNC:20445] |
| ENSG00000168032 | ENTPD3 | ectonucleoside triphosphate diphosphohydrolase 3 [Source:HGNC Symbol;Acc:HGNC:3365] |

TABLE 40-continued

The markers listed discriminate between a subject who is a contact sport athlete and experienced the most forceful head impact and the subject's baseline using blood samples.

| Ensembl_ID | HGNC_symbol | Description |
| --- | --- | --- |
| ENSG00000181837 | OR5D17P | olfactory receptor, family 5, subfamily D, member 17 pseudogene [Source:HGNC Symbol;Acc:HGNC:15284] |
| ENSG00000197322 | C17orf102 | chromosome 17 open reading frame 102 [Source:HGNC Symbol;Acc:HGNC:34412] |
| ENSG00000204682 | CASC10 | cancer susceptibility candidate 10 [Source:HGNC Symbol;Acc:HGNC:31448] |
| ENSG00000213759 | UGT2B11 | UDP glucuronosyltransferase 2 family, polypeptide B11 [Source:HGNC Symbol;Acc:HGNC:12545] |
| ENSG00000226149 | | |
| ENSG00000250391 | | |
| ENSG00000254537 | | |
| ENSG00000255189 | GLYATL1P1 | glycine-N-acyltransferase-like 1 pseudogene 1 [Source:HGNC Symbol;Acc:HGNC:37866] |
| ENSG00000259675 | | |
| ENSG00000261351 | | |
| ENSG00000264515 | | |
| ENSG00000138286 | FAM149B1 | family with sequence similarity 149, member B1 [Source:HGNC Symbol;Acc:HGNC:29162] |

TABLE 41

The markers listed discriminate between a subject who is a contact sport athlete and experienced the most forceful head impact and a subject who is a contact sport athlete and experienced the least forceful head impact using blood samples.

| Ensembl_ID | HGNC_symbol | Description |
| --- | --- | --- |
| ENSG00000091138 | SLC26A3 | solute carrier family 26 (anion exchanger), member 3 [Source:HGNC Symbol;Acc:HGNC:3018] |
| ENSG00000107262 | BAG1 | BCL2-associated athanogene [Source:HGNC Symbol;Acc:HGNC:937] |
| ENSG00000117501 | MROH9 | maestro heat-like repeat family member 9 [Source:HGNC Symbol;Acc:HGNC:26287] |
| ENSG00000128606 | LRRC17 | leucine rich repeat containing 17 [Source:HGNC Symbol;Acc:HGNC:16895] |
| ENSG00000132507 | EIF5A | eukaryotic translation initiation factor 5A [Source:HGNC Symbol;Acc:HGNC:3300] |
| ENSG00000136155 | SCEL | sciellin [Source:HGNC Symbol;Acc:HGNC:10573] |
| ENSG00000138286 | FAM149B1 | family with sequence similarity 149, member B1 [Source:HGNC Symbol;Acc:HGNC:29162] |
| ENSG00000143341 | HMCN1 | hemicentin 1 [Source:HGNC Symbol;Acc:HGNC:19194] |
| ENSG00000152034 | MCHR2 | melanin-concentrating hormone receptor 2 [Source:HGNC Symbol;Acc:HGNC:20867] |
| ENSG00000173250 | GPR151 | G protein-coupled receptor 151 [Source:HGNC Symbol;Acc:HGNC:23624] |
| ENSG00000175164 | ABO | ABO blood group (transferase A, alpha 1-3-N-acetylgalactosaminyltransferase; transferase B, alpha 1-3-galactosyltransferase) [Source:HGNC Symbol;Acc:HGNC:79] |
| ENSG00000177106 | EPS8L2 | EPS8-like 2 [Source:HGNC Symbol;Acc:HGNC:21296] |
| ENSG00000177352 | CCDC71 | coiled-coil domain containing 71 [Source:HGNC Symbol;Acc:HGNC:25760] |
| ENSG00000215853 | RPTN | repetin [Source:HGNC Symbol;Acc:HGNC:26809] |
| ENSG00000225361 | PPP1R26-AS1 | PPP1R26 antisense RNA 1 [Source:HGNC Symbol;Acc:HGNC:48717] |
| ENSG00000227036 | LINC00511 | long intergenic non-protein coding RNA 511 [Source:HGNC Symbol;Acc:HGNC:43564] |
| ENSG00000230173 | | |
| ENSG00000230925 | | |
| ENSG00000231852 | CYP21A2 | cytochrome P450, family 21, subfamily A, polypeptide 2 [Source:HGNC Symbol;Acc:HGNC:2600] |
| ENSG00000236596 | | |
| ENSG00000247381 | PDX1-AS1 | PDX1 antisense RNA 1 [Source:HGNC Symbol;Acc:HGNC:43698] |
| ENSG00000253374 | | |
| ENSG00000253706 | | |
| ENSG00000259293 | | |

TABLE 42

The markers listed discriminate between a subject who is a contact sport athlete and experienced the most forceful head impact and a subject with normal exposure to head impact (e.g. an athlete who does not play contact sports, like track and field) using blood samples.

| Ensembl_ID | HGNC_symbol | description |
|---|---|---|
| ENSG00000028203 | VEZT | vezatin, adherens junctions transmembrane protein [Source:HGNC Symbol;Acc:HGNC:18258] |
| ENSG00000063169 | GLTSCR1 | glioma tumor suppressor candidate region gene 1 [Source:HGNC Symbol;Acc:HGNC:4332] |
| ENSG00000100258 | LMF2 | lipase maturation factor 2 [Source:HGNC Symbol;Acc:HGNC:25096] |
| ENSG00000113396 | SLC27A6 | solute carrier family 27 (fatty acid transporter), member 6 [Source:HGNC Symbol;Acc:HGNC:11000] |
| ENSG00000113946 | CLDN16 | claudin 16 [Source:HGNC Symbol;Acc:HGNC:2037] |
| ENSG00000120322 | PCDHB8 | protocadherin beta 8 [Source:HGNC Symbol;Acc:HGNC:8693] |
| ENSG00000136021 | SCYL2 | SCY1-like 2 (*S. cerevisiae*) [Source:HGNC Symbol;Acc:HGNC:19286] |
| ENSG00000157322 | CLEC18A | C-type lectin domain family 18, member A [Source:HGNC Symbol;Acc:HGNC:30388] |
| ENSG00000161912 | ADCY10P1 | adenylate cyclase 10 (soluble) pseudogene 1 [Source:HGNC Symbol;Acc:HGNC:44143] |
| ENSG00000162040 | HS3ST6 | heparan sulfate (glucosamine) 3-O-sulfotransferase 6 [Source:HGNC Symbol;Acc:HGNC:14178] |
| ENSG00000166313 | APBB1 | amyloid beta (A4) precursor protein-binding, family B, member 1 (Fe65) [Source:HGNC Symbol;Acc:HGNC:581] |
| ENSG00000166348 | USP54 | ubiquitin specific peptidase 54 [Source:HGNC Symbol;Acc:HGNC:23513] |
| ENSG00000186625 | KATNA1 | katanin p60 (ATPase containing) subunit A 1 [Source:HGNC Symbol;Acc:HGNC:6216] |
| ENSG00000188626 | GOLGA8M | golgin A8 family, member M [Source:HGNC Symbol;Acc:HGNC:44404] |
| ENSG00000197582 | GPX1P1 | glutathione peroxidase pseudogene 1 [Source:HGNC Symbol;Acc:HGNC:4560] |
| ENSG00000198468 | FLVCR1-AS1 | FLVCR1 antisense RNA 1 (head to head) [Source:HGNC Symbol;Acc:HGNC:39077] |
| ENSG00000198964 | SGMS1 | sphingomyelin synthase 1 [Source:HGNC Symbol;Acc:HGNC:29799] |
| ENSG00000226820 | | |
| ENSG00000236301 | MRGPRG-AS1 | MRGPRG antisense RNA 1 [Source:HGNC Symbol;Acc:HGNC:26691] |
| ENSG00000254449 | SF3A3P2 | splicing factor 3a, subunit 3 pseudogene 2 [Source:HGNC Symbol;Acc:HGNC:23277] |
| ENSG00000260423 | | |
| ENSG00000260704 | LINC00543 | long intergenic non-protein coding RNA 543 [Source:HGNC Symbol;Acc:HGNC:43678] |
| ENSG00000263551 | | |
| ENSG00000266172 | NA | NA |
| ENSG00000205765 | C5orf51 | chromosome 5 open reading frame 51 [Source:HGNC Symbol;Acc:HGNC:27750] |

TABLE 43

The markers listed discriminate between a subject who is a contact sport athlete and experienced the most forceful head impact and the subject's baseline using urine samples.

| Ensembl_ID | HGNC_symbol | Description |
|---|---|---|
| ENSG00000101544 | ADNP2 | ADNP homeobox 2 [Source:HGNC Symbol;Acc:HGNC:23803] |
| ENSG00000109133 | TMEM33 | transmembrane protein 33 [Source:HGNC Symbol;Acc:HGNC:25541] |
| ENSG00000112679 | DUSP22 | dual specificity phosphatase 22 [Source:HGNC Symbol;Acc:HGNC:16077] |
| ENSG00000128165 | ADM2 | adrenomedullin 2 [Source:HGNC Symbol;Acc:HGNC:28898] |
| ENSG00000134779 | TPGS2 | tubulin polyglutamylase complex subunit 2 [Source:HGNC Symbol;Acc:HGNC:24561] |
| ENSG00000137819 | PAQR5 | progestin and adipoQ receptor family member V [Source:HGNC Symbol;Acc:HGNC:29645] |
| ENSG00000143190 | POU2F1 | POU class 2 homeobox 1 [Source:HGNC Symbol;Acc:HGNC:9212] |
| ENSG00000161281 | COX7A1 | cytochrome c oxidase subunit VIIa polypeptide 1 (muscle) [Source:HGNC Symbol;Acc:HGNC:2287] |
| ENSG00000161929 | SCIMP | SLP adaptor and CSK interacting membrane protein [Source:HGNC Symbol;Acc:HGNC:33504] |

TABLE 43-continued

The markers listed discriminate between a subject who is a contact sport athlete and experienced the most forceful head impact and the subject's baseline using urine samples.

| Ensembl_ID | HGNC_symbol | Description |
| --- | --- | --- |
| ENSG00000165699 | TSC1 | tuberous sclerosis 1 [Source:HGNC Symbol;Acc:HGNC:12362] |
| ENSG00000166225 | FRS2 | fibroblast growth factor receptor substrate 2 [Source:HGNC Symbol;Acc:HGNC:16971] |
| ENSG00000178053 | MLF1 | myeloid leukemia factor 1 [Source:HGNC Symbol;Acc:HGNC:7125] |
| ENSG00000179242 | CDH4 | cadherin 4, type 1, R-cadherin (retinal) [Source:HGNC Symbol;Acc:HGNC:1763] |
| ENSG00000180818 | HOXC10 | homeobox C10 [Source:HGNC Symbol;Acc:HGNC:5122] |
| ENSG00000183495 | EP400 | E1A binding protein p400 [Source:HGNC Symbol;Acc:HGNC:11958] |
| ENSG00000183580 | FBXL7 | F-box and leucine-rich repeat protein 7 [Source:HGNC Symbol;Acc:HGNC:13604] |
| ENSG00000203482 | NA | NA |
| ENSG00000251192 | ZNF674 | zinc finger protein 674 [Source:HGNC Symbol;Acc:HGNC:17625] |
| ENSG00000255306 | | |
| ENSG00000130349 | C6orf203 | chromosome 6 open reading frame 203 [Source:HGNC Symbol;Acc:HGNC:17971] |
| ENSG00000138639 | ARHGAP24 | Rho GTPase activating protein 24 [Source:HGNC Symbol;Acc:HGNC:25361] |
| ENSG00000164327 | RICTOR | RPTOR independent companion of MTOR, complex 2 [Source:HGNC Symbol;Acc:HGNC:28611] |

TABLE 44

The markers listed discriminate between a subject who is a contact sport athlete and experienced the most forceful head impact and a subject who is a contact sport athlete and experienced the least forceful head impact using urine samples.

| Ensembl_ID | HGNC_symbol | Description |
| --- | --- | --- |
| ENSG00000102786 | INTS6 | integrator complex subunit 6 [Source:HGNC Symbol;Acc:HGNC:14879] |
| ENSG00000103811 | CTSH | cathepsin H [Source:HGNC Symbol;Acc:HGNC:2535] |
| ENSG00000108785 | HSD17B1P1 | hydroxysteroid (17-beta) dehydrogenase 1 pseudogene 1 [Source:HGNC Symbol;Acc:HGNC:5216] |
| ENSG00000120910 | PPP3CC | protein phosphatase 3, catalytic subunit, gamma isozyme [Source:HGNC Symbol;Acc:HGNC:9316] |
| ENSG00000156398 | SFXN2 | sideroflexin 2 [Source:HGNC Symbol;Acc:HGNC:16086] |
| ENSG00000168209 | DDIT4 | DNA-damage-inducible transcript 4 [Source:HGNC Symbol;Acc:HGNC:24944] |
| ENSG00000178229 | ZNF543 | zinc finger protein 543 [Source:HGNC Symbol;Acc:HGNC:25281] |
| ENSG00000185880 | TRIM69 | tripartite motif containing 69 [Source:HGNC Symbol;Acc:HGNC:17857] |
| ENSG00000198108 | CHSY3 | chondroitin sulfate synthase 3 [Source:HGNC Symbol;Acc:HGNC:24293] |
| ENSG00000198690 | FAN1 | FANCD2/FANCI-associated nuclease 1 [Source:HGNC Symbol;Acc:HGNC:29170] |
| ENSG00000205002 | AARD | alanine and arginine rich domain containing protein [Source:HGNC Symbol;Acc:HGNC:33842] |
| ENSG00000221972 | C3orf36 | chromosome 3 open reading frame 36 [Source:HGNC Symbol;Acc:HGNC:26170] |
| ENSG00000224238 | WARS2-IT1 | WARS2 intronic transcript 1 (non-protein coding) [Source:HGNC Symbol;Acc:HGNC:41393] |
| ENSG00000225944 | RIOK3P1 | RIO kinase 3 pseudogene 1 [Source:HGNC Symbol;Acc:HGNC:39714] |
| ENSG00000228794 | LINC01128 | long intergenic non-protein coding RNA 1128 [Source:HGNC Symbol;Acc:HGNC:49377] |
| ENSG00000229774 | | |
| ENSG00000238040 | SALL4P2 | spalt-like transcription factor 4 pseudogene 2 [Source:HGNC Symbol;Acc:HGNC:39819] |
| ENSG00000245060 | LINC00847 | long intergenic non-protein coding RNA 847 [Source:HGNC Symbol;Acc:HGNC:45050] |
| ENSG00000249307 | LINC01088 | long intergenic non-protein coding RNA 1088 [Source:HGNC Symbol;Acc:HGNC:49148] |
| ENSG00000253522 | MIR146A | microRNA 146a [Source:HGNC Symbol;Acc:HGNC:31533] |
| ENSG00000257135 | | |
| ENSG00000258120 | KRT128P | keratin 128 pseudogene [Source:HGNC Symbol;Acc:HGNC:48882] |

TABLE 44-continued

The markers listed discriminate between a subject who is a contact sport athlete and experienced the most forceful head impact and a subject who is a contact sport athlete and experienced the least forceful head impact using urine samples.

| Ensembl_ID | HGNC_symbol | Description |
| --- | --- | --- |
| ENSG00000164978 | NUDT2 | nudix (nucleoside diphosphate linked moiety X)-type motif 2 [Source:HGNC Symbol;Acc:HGNC:8049] |
| ENSG00000128165 | ADM2 | adrenomedullin 2 [Source:HGNC Symbol;Acc:HGNC:28898] |
| ENSG00000128534 | LSM8 | LSM8 homolog, U6 small nuclear RNA associated (*S. cerevisiae*) [Source:HGNC Symbol;Acc:HGNC:20471] |

TABLE 45

The markers listed discriminate between a subject who is a contact sport athlete and experienced the most forceful head impact and a subject with normal exposure to head impact (e.g. an athlete who does not play contact sports, like track and field) using urine samples.

| Ensembl_ID | HGNC_symbol | Description |
| --- | --- | --- |
| ENSG00000101951 | PAGE4 | P antigen family, member 4 (prostate associated) [Source:HGNC Symbol;Acc:HGNC:4108] |
| ENSG00000116701 | NCF2 | neutrophil cytosolic factor 2 [Source:HGNC Symbol;Acc:HGNC:7661] |
| ENSG00000120068 | HOXB8 | homeobox B8 [Source:HGNC Symbol;Acc:HGNC:5119] |
| ENSG00000121680 | PEX16 | peroxisomal biogenesis factor 16 [Source:HGNC Symbol;Acc:HGNC:8857] |
| ENSG00000125630 | POLR1B | polymerase (RNA) I polypeptide B, 128 kDa [Source:HGNC Symbol;Acc:HGNC:20454] |
| ENSG00000126790 | L3HYPDH | L-3-hydroxyproline dehydratase (trans-) [Source:HGNC Symbol;Acc:HGNC:20488] |
| ENSG00000134962 | KLB | klotho beta [Source:HGNC Symbol;Acc:HGNC:15527] |
| ENSG00000150433 | TMEM218 | transmembrane protein 218 [Source:HGNC Symbol;Acc:HGNC:27344] |
| ENSG00000157884 | CIB4 | calcium and integrin binding family member 4 [Source:HGNC Symbol;Acc:HGNC:33703] |
| ENSG00000163161 | ERCC3 | excision repair cross-complementation group 3 [Source:HGNC Symbol;Acc:HGNC:3435] |
| ENSG00000167548 | KMT2D | lysine (K)-specific methyltransferase 2D [Source:HGNC Symbol;Acc:HGNC:7133] |
| ENSG00000167552 | TUBA1A | tubulin, alpha 1a [Source:HGNC Symbol;Acc:HGNC:20766] |
| ENSG00000170890 | PLA2G1B | phospholipase A2, group IB (pancreas) [Source:HGNC Symbol;Acc:HGNC:9030] |
| ENSG00000171401 | KRT13 | keratin 13 [Source:HGNC Symbol;Acc:HGNC:6415] |
| ENSG00000174083 | NA | NA |
| ENSG00000176136 | MC5R | melanocortin 5 receptor [Source:HGNC Symbol;Acc:HGNC:6933] |
| ENSG00000183199 | HSP90AB3P | heat shock protein 90 kDa alpha (cytosolic), class B member 3, pseudogene [Source:HGNC Symbol;Acc:HGNC:5259] |
| ENSG00000198142 | SOWAHC | sosondowah ankyrin repeat domain family member C [Source:HGNC Symbol;Acc:HGNC:26149] |
| ENSG00000204584 | | |
| ENSG00000204622 | HLA-J | major histocompatibility complex, class I, J (pseudogene) [Source:HGNC Symbol;Acc:HGNC:4967] |
| ENSG00000229248 | WBP2P1 | WW domain binding protein 2 pseudogene 1 [Source:HGNC Symbol;Acc:HGNC:31695] |
| ENSG00000261337 | NA | NA |
| ENSG00000263731 | | |
| ENSG00000221972 | C3orf36 | chromosome 3 open reading frame 36 [Source:HGNC Symbol;Acc:HGNC:26170] |

TABLE 46

The markers listed discriminate between a subject who is a contact sport athlete and experienced the least frequent head impact and the subject's baseline using blood samples.

| Ensembl_ID | HGNC_symbol | Description |
| --- | --- | --- |
| ENSG00000002745 | WNT16 | wingless-type MMTV integration site family, member 16 [Source:HGNC Symbol;Acc:HGNC:16267] |
| ENSG00000006788 | MYH13 | myosin, heavy chain 13, skeletal muscle [Source:HGNC Symbol;Acc:HGNC:7571] |

TABLE 46-continued

The markers listed discriminate between a subject who is a contact sport athlete and experienced the least frequent head impact and the subject's baseline using blood samples.

| Ensembl_ID | HGNC_symbol | Description |
|---|---|---|
| ENSG00000054654 | SYNE2 | spectrin repeat containing, nuclear envelope 2 [Source:HGNC Symbol;Acc:HGNC:17084] |
| ENSG00000101460 | MAP1LC3A | microtubule-associated protein 1 light chain 3 alpha [Source:HGNC Symbol;Acc:HGNC:6838] |
| ENSG00000106261 | ZKSCAN1 | zinc finger with KRAB and SCAN domains 1 [Source:HGNC Symbol;Acc:HGNC:13101] |
| ENSG00000115073 | ACTR1B | ARP1 actin-related protein 1 homolog B, centractin beta (yeast) [Source:HGNC Symbol;Acc:HGNC:168] |
| ENSG00000137392 | CLPS | colipase, pancreatic [Source:HGNC Symbol;Acc:HGNC:2085] |
| ENSG00000138650 | PCDH10 | protocadherin 10 [Source:HGNC Symbol;Acc:HGNC:13404] |
| ENSG00000149136 | SSRP1 | structure specific recognition protein 1 [Source:HGNC Symbol;Acc:HGNC:11327] |
| ENSG00000160446 | ZDHHC12 | zinc finger, DHHC-type containing 12 [Source:HGNC Symbol;Acc:HGNC:19159] |
| ENSG00000160613 | PCSK7 | proprotein convertase subtilisin/kexin type 7 [Source:HGNC Symbol;Acc:HGNC:8748] |
| ENSG00000164430 | MB21D1 | Mab-21 domain containing 1 [Source:HGNC Symbol;Acc:HGNC:21367] |
| ENSG00000176034 | CHDC2 | calponin homology domain containing 2 [Source:HGNC Symbol;Acc:HGNC:26708] |
| ENSG00000176956 | LY6H | lymphocyte antigen 6 complex, locus H [Source:HGNC Symbol;Acc:HGNC:6728] |
| ENSG00000188107 | EYS | eyes shut homolog (Drosophila) [Source:HGNC Symbol;Acc:HGNC:21555] |
| ENSG00000196228 | SULT1C3 | sulfotransferase family, cytosolic, 1C, member 3 [Source:HGNC Symbol;Acc:HGNC:33543] |
| ENSG00000196295 | | |
| ENSG00000196549 | MME | membrane metallo-endopeptidase [Source:HGNC Symbol;Acc:HGNC:7154] |
| ENSG00000197594 | ENPP1 | ectonucleotide pyrophosphatase/phosphodiesterase 1 [Source:HGNC Symbol;Acc:HGNC:3356] |
| ENSG00000228823 | | |
| ENSG00000229622 | MTND5P2 | MT-ND5 pseudogene 2 [Source:HGNC Symbol;Acc:HGNC:41919] |
| ENSG00000249066 | | |
| ENSG00000261437 | | |
| ENSG00000266998 | | |
| ENSG00000257943 | | |

TABLE 47

The markers listed discriminate between a subject who is a contact sport athlete and experienced the least frequent head impact and a subject with normal exposure to head impact (e.g. an athlete who does not play contact sports, like track and field) using blood samples.

| Ensembl_ID | HGNC_symbol | Description |
|---|---|---|
| ENSG00000049239 | H6PD | hexose-6-phosphate dehydrogenase (glucose 1-dehydrogenase) [Source:HGNC Symbol;Acc:HGNC:4795] |
| ENSG00000107937 | GTPBP4 | GTP binding protein 4 [Source:HGNC Symbol;Acc:HGNC:21535] |
| ENSG00000115844 | DLX2 | distal-less homeobox 2 [Source:HGNC Symbol;Acc:HGNC:2915] |
| ENSG00000118162 | KPTN | kaptin (actin binding protein) [Source:HGNC Symbol;Acc:HGNC:6404] |
| ENSG00000139352 | ASCL1 | achaete-scute family bHLH transcription factor 1 [Source:HGNC Symbol;Acc:HGNC:738] |
| ENSG00000141316 | SPACA3 | sperm acrosome associated 3 [Source:HGNC Symbol;Acc:HGNC:16260] |
| ENSG00000144339 | TMEFF2 | transmembrane protein with EGF-like and two follistatin-like domains 2 [Source:HGNC Symbol;Acc:HGNC:11867] |
| ENSG00000149179 | C11orf49 | chromosome 11 open reading frame 49 [Source:HGNC Symbol;Acc:HGNC:28720] |
| ENSG00000166822 | TMEM170A | transmembrane protein 170A [Source:HGNC Symbol;Acc:HGNC:29577] |
| ENSG00000169474 | SPRR1A | small proline-rich protein 1A [Source:HGNC Symbol;Acc:HGNC:11259] |
| ENSG00000171606 | ZNF274 | zinc finger protein 274 [Source:HGNC Symbol;Acc:HGNC:13068] |

TABLE 47-continued

The markers listed discriminate between a subject who is a contact sport athlete and experienced the least frequent head impact and a subject with normal exposure to head impact (e.g. an athlete who does not play contact sports, like track and field) using blood samples.

| Ensembl_ID | HGNC_symbol | Description |
|---|---|---|
| ENSG00000182173 | TSEN54 | TSEN54 tRNA splicing endonuclease subunit [Source:HGNC Symbol;Acc:HGNC:27561] |
| ENSG00000187730 | GABRD | gamma-aminobutyric acid (GABA) A receptor, delta [Source:HGNC Symbol;Acc:HGNC:4084] |
| ENSG00000197536 | C5orf56 | chromosome 5 open reading frame 56 [Source:HGNC Symbol;Acc:HGNC:33838] |
| ENSG00000213780 | GTF2H4 | general transcription factor IIH, polypeptide 4, 52 kDa [Source:HGNC Symbol;Acc:HGNC:4658] |
| ENSG00000213930 | GALT | galactose-1-phosphate uridylyltransferase [Source:HGNC Symbol;Acc:HGNC:4135] |
| ENSG00000228876 | | |
| ENSG00000238021 | ARMC4P1 | armadillo repeat containing 4 pseudogene 1 [Source:HGNC Symbol;Acc:HGNC:44937] |
| ENSG00000240040 | | |
| ENSG00000244291 | NA | NA |
| ENSG00000249215 | | |
| ENSG00000269758 | | |
| ENSG00000270127 | | protein kinase, X-linked, pseudogene 1 [Source:EntrezGene;Acc:441733] |
| ENSG00000162040 | HS3ST6 | heparan sulfate (glucosamine) 3-O-sulfotransferase 6 [Source:HGNC Symbol;Acc:HGNC:14178] |
| ENSG00000120875 | DUSP4 | dual specificity phosphatase 4 [Source:HGNC Symbol;Acc:HGNC:3070] |

TABLE 48

The markers listed discriminate between a subject who is a contact sport athlete and experienced the least frequent head impact and the subject's baseline using urine samples.

| Ensembl_ID | HGNC_symbol | Description |
|---|---|---|
| ENSG00000066185 | ZMYND12 | zinc finger, MYND-type containing 12 [Source:HGNC Symbol;Acc:HGNC:21192] |
| ENSG00000073169 | | selenoprotein 0 [Source:EntrezGene;Acc:83642] |
| ENSG00000074590 | NUAK1 | NUAK family, SNF1-like kinase, 1 [Source:HGNC Symbol;Acc:HGNC:14311] |
| ENSG00000115241 | PPM1G | protein phosphatase, Mg2+/Mn2+ dependent, 1G [Source:HGNC Symbol;Acc:HGNC:9278] |
| ENSG00000124839 | RAB17 | RAB17, member RAS oncogene family [Source:HGNC Symbol;Acc:HGNC:16523] |
| ENSG00000125827 | TMX4 | thioredoxin-related transmembrane protein 4 [Source:HGNC Symbol;Acc:HGNC:25237] |
| ENSG00000136295 | TTYH3 | tweety family member 3 [Source:HGNC Symbol;Acc:HGNC:22222] |
| ENSG00000143061 | IGSF3 | immunoglobulin superfamily, member 3 [Source:HGNC Symbol;Acc:HGNC:5950] |
| ENSG00000144481 | TRPM8 | transient receptor potential cation channel, subfamily M, member 8 [Source:HGNC Symbol;Acc:HGNC:17961] |
| ENSG00000156853 | ZNF689 | zinc finger protein 689 [Source:HGNC Symbol;Acc:HGNC:25173] |
| ENSG00000164327 | RICTOR | RPTOR independent companion of MTOR, complex 2 [Source:HGNC Symbol;Acc:HGNC:28611] |
| ENSG00000166173 | LARP6 | La ribonucleoprotein domain family, member 6 [Source:HGNC Symbol;Acc:HGNC:24012] |
| ENSG00000166426 | CRABP1 | cellular retinoic acid binding protein 1 [Source:HGNC Symbol;Acc:HGNC:2338] |
| ENSG00000168002 | POLR2G | polymerase (RNA) II (DNA directed) polypeptide G [Source:HGNC Symbol;Acc:HGNC:9194] |
| ENSG00000169499 | PLEKHA2 | pleckstrin homology domain containing, family A (phosphoinositide binding specific) member 2 [Source:HGNC Symbol;Acc:HGNC:14336] |
| ENSG00000196335 | STK31 | serine/threonine kinase 31 [Source:HGNC Symbol;Acc:HGNC:11407] |
| ENSG00000196409 | NA | NA |
| ENSG00000196532 | NA | NA |
| ENSG00000213963 | | |
| ENSG00000226935 | LINC00161 | long intergenic non-protein coding RNA 161 [Source:HGNC Symbol;Acc:HGNC:17138] |

TABLE 48-continued

The markers listed discriminate between a subject who is a contact sport athlete and experienced the least frequent head impact and the subject's baseline using urine samples.

| Ensembl_ID | HGNC_symbol | Description |
|---|---|---|
| ENSG00000242732 | RGAG4 | retrotransposon gag domain containing 4 [Source:HGNC Symbol;Acc:HGNC:29430] |
| ENSG00000247363 | | |
| ENSG00000260163 | | |
| ENSG00000140043 | PTGR2 | prostaglandin reductase 2 [Source:HGNC Symbol;Acc:HGNC:20149] |
| ENSG00000253688 | | |

TABLE 49

The markers listed discriminate between a subject who is a contact sport athlete and experienced the least frequent head impact and a subject with normal exposure to head impact (e.g. an athlete who does not play contact sports, like track and field) using urine samples.

| Ensembl_ID | HGNC_symbol | Description |
|---|---|---|
| ENSG00000082515 | MRPL22 | mitochondrial ribosomal protein L22 [Source:HGNC Symbol;Acc:HGNC:14480] |
| ENSG00000100197 | CYP2D6 | cytochrome P450, family 2, subfamily D, polypeptide 6 [Source:HGNC Symbol;Acc:HGNC:2625] |
| ENSG00000103528 | SYT17 | synaptotagmin XVII [Source:HGNC Symbol;Acc:HGNC:24119] |
| ENSG00000105197 | TIMM50 | translocase of inner mitochondrial membrane 50 homolog (S. cerevisiae) [Source:HGNC Symbol;Acc:HGNC:23656] |
| ENSG00000105989 | WNT2 | wingless-type MMTV integration site family member 2 [Source:HGNC Symbol;Acc:HGNC:12780] |
| ENSG00000113360 | DROSHA | drosha, ribonuclease type III [Source:HGNC Symbol;Acc:HGNC:17904] |
| ENSG00000122644 | ARL4A | ADP-ribosylation factor-like 4A [Source:HGNC Symbol;Acc:HGNC:695] |
| ENSG00000124006 | OBSL1 | obscurin-like 1 [Source:HGNC Symbol;Acc:HGNC:29092] |
| ENSG00000129003 | VPS13C | vacuolar protein sorting 13 homolog C (S. cerevisiae) [Source:HGNC Symbol;Acc:HGNC:23594] |
| ENSG00000131435 | PDLIM4 | PDZ and LIM domain 4 [Source:HGNC Symbol;Acc:HGNC:16501] |
| ENSG00000140043 | PTGR2 | prostaglandin reductase 2 [Source:HGNC Symbol;Acc:HGNC:20149] |
| ENSG00000143493 | INTS7 | integrator complex subunit 7 [Source:HGNC Symbol;Acc:HGNC:24484] |
| ENSG00000174899 | C3orf55 | chromosome 3 open reading frame 55 [Source:HGNC Symbol;Acc:HGNC:25146] |
| ENSG00000182831 | C16orf72 | chromosome 16 open reading frame 72 [Source:HGNC Symbol;Acc:HGNC:30103] |
| ENSG00000187626 | ZKSCAN4 | zinc finger with KRAB and SCAN domains 4 [Source:HGNC Symbol;Acc:HGNC:13854] |
| ENSG00000198373 | WWP2 | WW domain containing E3 ubiquitin protein ligase 2 [Source:HGNC Symbol;Acc:HGNC:16804] |
| ENSG00000205832 | C16orf96 | chromosome 16 open reading frame 96 [Source:HGNC Symbol;Acc:HGNC:40031] |
| ENSG00000226067 | | long intergenic non-protein coding RNA 869 [Source:EntrezGene;Acc:57234] |
| ENSG00000233896 | | |
| ENSG00000242498 | ARPIN | actin-related protein 2/3 complex inhibitor [Source:HGNC Symbol;Acc:HGNC:28782] |
| ENSG00000248445 | SEMA6A-AS1 | SEMA6A antisense RNA 1 [Source:HGNC Symbol;Acc:HGNC:51110] |
| ENSG00000270020 | | |
| ENSG00000257242 | C12orf79 | chromosome 12 open reading frame 79 [Source:HGNC Symbol;Acc:HGNC:27409] |

TABLE 50

The markers listed discriminate between a subject who is a contact sport athlete and experienced the least forceful head impact and the subject's baseline using blood samples.

| Ensembl_ID | HGNC_symbol | Description |
|---|---|---|
| ENSG00000073067 | CYP2W1 | cytochrome P450, family 2, subfamily W, polypeptide 1 [Source:HGNC Symbol;Acc:HGNC:20243] |
| ENSG00000127329 | PTPRB | protein tyrosine phosphatase, receptor type, B [Source:HGNC Symbol;Acc:HGNC:9665] |
| ENSG00000134138 | MEIS2 | Meis homeobox 2 [Source:HGNC Symbol;Acc:HGNC:7001] |
| ENSG00000141524 | TMC6 | transmembrane channel-like 6 [Source:HGNC Symbol;Acc:HGNC:18021] |
| ENSG00000148795 | CYP17A1 | cytochrome P450, family 17, subfamily A, polypeptide 1 [Source:HGNC Symbol;Acc:HGNC:2593] |
| ENSG00000151502 | VPS26B | vacuolar protein sorting 26 homolog B (*S. pombe*) [Source:HGNC Symbol;Acc:HGNC:28119] |
| ENSG00000152128 | TMEM163 | transmembrane protein 163 [Source:HGNC Symbol;Acc:HGNC:25380] |
| ENSG00000164237 | CMBL | carboxymethylenebutenolidase homolog (Pseudomonas) [Source:HGNC Symbol;Acc:HGNC:25090] |
| ENSG00000166049 | PASD1 | PAS domain containing 1 [Source:HGNC Symbol;Acc:HGNC:20686] |
| ENSG00000173638 | SLC19A1 | solute carrier family 19 (folate transporter), member 1 [Source:HGNC Symbol;Acc:HGNC:10937] |
| ENSG00000173699 | SPATA3 | spermatogenesis associated 3 [Source:HGNC Symbol;Acc:HGNC:17884] |
| ENSG00000174705 | SH3PXD2B | SH3 and PX domains 2B [Source:HGNC Symbol;Acc:HGNC:29242] |
| ENSG00000181007 | ZFP82 | ZFP82 zinc finger protein [Source:HGNC Symbol;Acc:HGNC:28682] |
| ENSG00000196970 | NXF4 | nuclear RNA export factor 4 pseudogene [Source:HGNC Symbol;Acc:HGNC:8074] |
| ENSG00000201148 | RNA5SP42 | RNA, 5S ribosomal pseudogene 42 [Source:HGNC Symbol;Acc:HGNC:42818] |
| ENSG00000230484 | OR51A10P | olfactory receptor, family 51, subfamily A, member 10 pseudogene [Source:HGNC Symbol;Acc:HGNC:15185] |
| ENSG00000231682 | | |
| ENSG00000239670 | | |
| ENSG00000250274 | | |
| ENSG00000259358 | | |
| ENSG00000259870 | | |
| ENSG00000260721 | | |
| ENSG00000196268 | ZNF493 | zinc finger protein 493 [Source:HGNC Symbol;Acc:HGNC:23708] |
| ENSG00000236596 | | |
| ENSG00000249066 | | |

TABLE 51

The markers listed discriminate between a subject who is a contact sport athlete and experienced the least forceful head impact and a subject with normal exposure to head impact (e.g. an athlete who does not play contact sports, like track and field) using blood samples.

| Ensembl_ID | HGNC_symbol | Description |
|---|---|---|
| ENSG00000075945 | KIFAP3 | kinesin-associated protein 3 [Source:HGNC Symbol;Acc:HGNC:17060] |
| ENSG00000099326 | MZF1 | myeloid zinc finger 1 [Source:HGNC Symbol;Acc:HGNC:13108] |
| ENSG00000104047 | DTWD1 | DTW domain containing 1 [Source:HGNC Symbol;Acc:HGNC:30926] |
| ENSG00000118705 | RPN2 | ribophorin II [Source:HGNC Symbol;Acc:HGNC:10382] |
| ENSG00000120875 | DUSP4 | dual specificity phosphatase 4 [Source:HGNC Symbol;Acc:HGNC:3070] |
| ENSG00000167110 | GOLGA2 | golgin A2 [Source:HGNC Symbol;Acc:HGNC:4425] |
| ENSG00000170262 | MRAP | melanocortin 2 receptor accessory protein [Source:HGNC Symbol;Acc:HGNC:1304] |
| ENSG00000170689 | HOXB9 | homeobox B9 [Source:HGNC Symbol;Acc:HGNC:5120] |
| ENSG00000180316 | PNPLA1 | patatin-like phospholipase domain containing 1 [Source:HGNC Symbol;Acc:HGNC:21246] |
| ENSG00000182057 | OGFRP1 | opioid growth factor receptor pseudogene 1 [Source:HGNC Symbol;Acc:HGNC:50511] |
| ENSG00000187166 | H1FNT | H1 histone family, member N, testis-specific [Source:HGNC Symbol;Acc:HGNC:24893] |

TABLE 51-continued

The markers listed discriminate between a subject who is a contact sport athlete and experienced the least forceful head impact and a subject with normal exposure to head impact (e.g. an athlete who does not play contact sports, like track and field) using blood samples.

| Ensembl_ID | HGNC_symbol | Description |
|---|---|---|
| ENSG00000197863 | ZNF790 | zinc finger protein 790 [Source:HGNC Symbol;Acc:HGNC:33114] |
| ENSG00000198814 | GK | glycerol kinase [Source:HGNC Symbol;Acc:HGNC:4289] |
| ENSG00000214063 | TSPAN4 | tetraspanin 4 [Source:HGNC Symbol;Acc:HGNC:11859] |
| ENSG00000215305 | VPS16 | vacuolar protein sorting 16 homolog (S. cerevisiae) [Source:HGNC Symbol;Acc:HGNC:14584] |
| ENSG00000225972 | MTND1P23 | MT-ND1 pseudogene 23 [Source:HGNC Symbol;Acc:HGNC:42092] |
| ENSG00000250986 | | |
| ENSG00000253973 | | |
| ENSG00000256612 | CYP2B7P | cytochrome P450, family 2, subfamily B, polypeptide 7, pseudogene [Source:HGNC Symbol;Acc:HGNC:2616] |
| ENSG00000259011 | | |
| ENSG00000267023 | LRRC37A16P | leucine rich repeat containing 37, member A16, pseudogene [Source:HGNC Symbol;Acc:HGNC:43820] |
| ENSG00000273096 | | |
| ENSG00000166049 | PASD1 | PAS domain containing 1 [Source:HGNC Symbol;Acc:HGNC:20686] |

TABLE 52

The markers listed discriminate between a subject who is a contact sport athlete and experienced the least forceful head impact and the subject's baseline using urine samples.

| Ensembl_ID | HGNC_symbol | description |
|---|---|---|
| ENSG00000080839 | RBL1 | retinoblastoma-like 1 [Source:HGNC Symbol;Acc:HGNC:9893] |
| ENSG00000106948 | AKNA | AT-hook transcription factor [Source:HGNC Symbol;Acc:HGNC:24108] |
| ENSG00000119737 | GPR75 | G protein-coupled receptor 75 [Source:HGNC Symbol;Acc:HGNC:4526] |
| ENSG00000120051 | CFAP58 | cilia and flagella associated protein 58 [Source:HGNC Symbol;Acc:HGNC:26676] |
| ENSG00000125810 | CD93 | CD93 molecule [Source:HGNC Symbol;Acc:HGNC:15855] |
| ENSG00000128534 | LSM8 | LSM8 homolog, U6 small nuclear RNA associated (S. cerevisiae) [Source:HGNC Symbol;Acc:HGNC:20471] |
| ENSG00000132640 | BTBD3 | BTB (POZ) domain containing 3 [Source:HGNC Symbol;Acc:HGNC:15854] |
| ENSG00000137871 | ZNF280D | zinc finger protein 280D [Source:HGNC Symbol;Acc:HGNC:25953] |
| ENSG00000138621 | PPCDC | phosphopantothenoylcysteine decarboxylase [Source:HGNC Symbol;Acc:HGNC:28107] |
| ENSG00000141034 | GID4 | GID complex subunit 4 [Source:HGNC Symbol;Acc:HGNC:28453] |
| ENSG00000153015 | CWC27 | CWC27 spliceosome-associated protein homolog (S. cerevisiae) [Source:HGNC Symbol;Acc:HGNC:10664] |
| ENSG00000160959 | LRRC14 | leucine rich repeat containing 14 [Source:HGNC Symbol;Acc:HGNC:20419] |
| ENSG00000170873 | MTSS1 | metastasis suppressor 1 [Source:HGNC Symbol;Acc:HGNC:20443] |
| ENSG00000182093 | WRB | tryptophan rich basic protein [Source:HGNC Symbol;Acc:HGNC:12790] |
| ENSG00000184210 | DGAT2L6 | diacylglycerol O-acyltransferase 2-like 6 [Source:HGNC Symbol;Acc:HGNC:23250] |
| ENSG00000188266 | HYKK | hydroxylysine kinase [Source:HGNC Symbol;Acc:HGNC:34403] |
| ENSG00000189433 | GJB4 | gap junction protein, beta 4, 30.3 kDa [Source:HGNC Symbol;Acc:HGNC:4286] |
| ENSG00000198836 | OPA1 | optic atrophy 1 (autosomal dominant) [Source:HGNC Symbol;Acc:HGNC:8140] |
| ENSG00000229323 | DLEU1-AS1 | DLEU1 antisense RNA 1 [Source:HGNC Symbol;Acc:HGNC:50496] |
| ENSG00000233527 | ZNF529-AS1 | ZNF529 antisense RNA 1 [Source:HGNC Symbol;Acc:HGNC:51275] |
| ENSG00000235524 | | |
| ENSG00000253688 | | |
| ENSG00000257531 | | |

TABLE 52-continued

The markers listed discriminate between a subject who is a contact sport athlete and experienced the least forceful head impact and the subject's baseline using urine samples.

| Ensembl_ID | HGNC_symbol | description |
|---|---|---|
| ENSG00000172071 | EIF2AK3 | eukaryotic translation initiation factor 2-alpha kinase 3 [Source:HGNC Symbol;Acc:HGNC:3255] |
| ENSG00000124839 | RAB17 | RAB17, member RAS oncogene family [Source:HGNC Symbol;Acc:HGNC:16523] |

TABLE 53

Markers with expression that is significant different across the different biological samples

| Ensembl_ID | HGNC_symbol | Description | Change in Expression |
|---|---|---|---|
| ENSG00000113889 | KNG1 | kininogen 1 [Source:HGNC Symbol;Acc:HGNC:6383] | Decrease |
| ENSG00000164825 | DEFB1 | defensin, beta 1 [Source:HGNC Symbol;Acc:HGNC:2766] | Decrease |
| ENSG00000165685 | TMEM52B | transmembrane protein 52B [Source:HGNC Symbol;Acc:HGNC:26438] | Decrease |
| ENSG00000169344 | UMOD | uromodulin [Source:HGNC Symbol;Acc:HGNC:12559] | Decrease |
| ENSG00000184908 | CLCNKB | chloride channel, voltage-sensitive Kb [Source:HGNC Symbol;Acc:HGNC:2027] | Decrease |
| ENSG00000270103 | RNU11 | RNA, U11 small nuclear [Source:HGNC Symbol;Acc:HGNC:10108] | Decrease |
| ENSG00000125652 | ALKBH7 | alkB, alkylation repair homolog 7 (*E. coli*) [Source:HGNC Symbol;Acc:HGNC:21306] | Increase |
| ENSG00000145113 | MUC4 | mucin 4, cell surface associated [Source:HGNC Symbol;Acc:HGNC:7514] | increase |
| ENSG00000153802 | TMPRSS11D | transmembrane protease, serine 11D [Source:HGNC Symbol;Acc:HGNC:24059] | Increase |
| ENSG00000196352 | CD55 | CD55 molecule, decay accelerating factor for complement (Cromer blood group) [Source:HGNC Symbol;Acc:HGNC:2665] | Increase |
| ENSG00000197674 | OR51C1P | olfactory receptor, family 51, subfamily C, member 1 pseudogene [Source:HGNC Symbol;Acc:HGNC:15191] | Increase |
| ENSG00000206652 | RNU1-1 | RNA, U1 small nuclear 1 [Source:HGNC Symbol;Acc:HGNC:10120] | Increase |
| ENSG00000210194 | MT-TE | mitochondrially encoded tRNA glutamic acid [Source:HGNC Symbol;Acc:HGNC:7479] | Increase |
| ENSG00000230140 | | | Increase |
| ENSG00000254325 | | | Increase |
| ENSG00000258406 | | | Increase |
| ENSG00000267706 | | | Increase |
| ENSG00000269364 | LINC01233 | long intergenic non-protein coding RNA 1233 [Source:HGNC Symbol;Acc:HGNC:49756] | Increase |
| ENSG00000271043 | MTRNR2L2 | MT-RNR2-like 2 [Source:HGNC Symbol;Acc:HGNC:37156] | Increase |

What is claimed is:

1. A method for determining the risk of a subject for developing mild traumatic brain injuries (mTBI) or the fitness of a subject for participating in an activity with increased chances of receiving a head impact, comprising:
    obtaining a biological sample from the subject after a head injury;
    obtaining a control biological sample, wherein the control biological sample is selected from the group consisting of: the baseline sample of the subject, a matched sample from a different subject that plays non-contact sports, and a predicted control sample calculated from the general population;
    measuring the biological sample with RNASeq for an amount of at least one extracellular RNA (exRNA) biomarker transcribed from a gene selected from the group consisting of ENSG00000163346, ENSG00000112941, ENSG00000087589, and ENSG00000160917;
    measuring the control biological sample with RNASeq for an amount of the at least one exRNA biomarker; and
    comparing the amount of the at least one exRNA biomarker in the biological sample with the amount of the at least one exRNA biomarker in the control biological sample, wherein a change in the amount of the at least one exRNA biomarker from the subject compared with the control biological sample is indicative of the subject having an increased risk for mTBI or being unfit for participating in the activity with increased chances of receiving a head impact;

wherein decreased amounts of exRNA transcribed from the gene of ENSG00000112941 in a urine sample and/or ENSG00000087589 in a plasma sample and increased amounts of exRNA transcribed from the gene of ENSG00000160917 in a urine sample and/or ENSG00000163346 in a urine sample are indicative of the subject being at increased risk for mTBI or unfit for participating in the activity with increased chances of receiving a head impact.

2. The method of claim 1, wherein the control biological sample is a matched sample from a different subject that plays non-contact sports.

3. The method of claim 1, wherein the control biological sample is from the subject's baseline sample.

4. The method of claim 1, wherein the biological sample from the subject is obtained within 48 hours after the subject received a head impact or is suspected of having a head impact.

5. The method of claim 1, wherein at least two exRNA biomarkers are measured and compared, wherein a change in the amount of the at least two exRNA biomarkers from the subject compared with the control is indicative of the subject having an increased risk for mTBI or being unfit for participating in the activity with increased chances of receiving a head impact.

6. The method of claim 1, wherein the at least one exRNA biomarker comprises exRNA transcribed from the gene of ENSG00000163346.

7. The method of claim 1, wherein the biological sample from the subject is obtained within 24 hours after the subject received a head impact or is suspected of having a head impact.

* * * * *